(12) United States Patent
Jolidon et al.

(10) Patent No.: US 7,557,114 B2
(45) Date of Patent: Jul. 7, 2009

(54) HETEROCYCLIC-SUBSTITUTED PHENYL METHANONES

(75) Inventors: Synese Jolidon, Blauen (CH); Robert Narquizian, St. Louis (FR); Roger David Norcross, Olsberg (CH); Emmanuel Pinard, Linsdorf (FR)

(73) Assignee: Hoffman-La Roche Inc., Nutley, NJ (US)

( * ) Notice: Subject to any disclaimer, the term of this patent is extended or adjusted under 35 U.S.C. 154(b) by 79 days.

(21) Appl. No.: 11/343,365

(22) Filed: Jan. 31, 2006

(65) Prior Publication Data
US 2006/0178381 A1 Aug. 10, 2006

(30) Foreign Application Priority Data
Feb. 7, 2005 (EP) .................................. 05100813

(51) Int. Cl.
| | |
|---|---|
| *A01N 43/90* | (2006.01) |
| *A01N 43/42* | (2006.01) |
| *A61K 31/519* | (2006.01) |
| *A61K 31/44* | (2006.01) |
| *A01N 43/52* | (2006.01) |
| *A01N 43/56* | (2006.01) |
| *A61K 31/40* | (2006.01) |
| *C07D 471/02* | (2006.01) |
| *C07D 491/02* | (2006.01) |
| *C07D 498/02* | (2006.01) |
| *C07D 513/02* | (2006.01) |
| *C07D 515/02* | (2006.01) |

(52) U.S. Cl. .................... 514/265.1; 514/300; 514/406; 514/394; 514/419; 514/416; 546/113

(58) Field of Classification Search ............... None
See application file for complete search history.

(56) References Cited

U.S. PATENT DOCUMENTS

| | | | |
|---|---|---|---|
| 2,767,191 A * | 10/1956 | Wright, Jr. .................. 546/113 |
| 3,933,802 A | 1/1976 | Ferrini et al. |
| 4,244,871 A | 1/1981 | Kosary et al. |
| 6,001,854 A | 12/1999 | Ognyanov et al. |
| 2005/0059668 A1 | 3/2005 | Alberati-Giani et al. |
| 2005/0070539 A1 | 3/2005 | Alberati-Giani et al. |
| 2005/0209241 A1 | 9/2005 | Jolidon et al. |

FOREIGN PATENT DOCUMENTS

| | | |
|---|---|---|
| EP | 0 171 636 | 2/1985 |
| EP | 0 624 584 | 11/1994 |
| WO | WO 99/44596 | 9/1999 |
| WO | WO 99/45011 | 9/1999 |
| WO | WO 01/81308 | 11/2001 |
| WO | WO 02/00602 | 1/2002 |
| WO | WO 02/22612 | 3/2002 |
| WO | WO 02/074774 | 9/2002 |
| WO | WO 03/004480 | 1/2003 |
| WO | WO 03/035602 | 5/2003 |
| WO | WO 2004/037800 | 5/2004 |
| WO | WO 2005/058882 | 6/2005 |
| WO | WO 2005/110983 | 11/2005 |

OTHER PUBLICATIONS

Dorwald F. A. Side Reactions in Organic Synthesis, 2005, Wiley: VCH, Weinheim p. IX of Preface.*
Wright, et. al., Journal of the American Chemical Society, (1957), 79, 2199-203.*
Lewis D.A. & Lieberman J.A., Neuron. vol. 28, pp. 325-334 (2000).
Vandenberg R. J. & Aubrey K. R., Exp. Opin. Ther. Targets vol. 5(4) pp. 507-518 (2001).
Nakazato A. & Okuyama S., Exp. Opin. Ther. Patents vol. 10(1) pp. 75-98 (2000).
Sharma T., Br. J. Psychiatry, vol. 174 (Suppl. 38) pp. 44-51 (1999).
Javitt D. C. et al., Biol. Psychiatry, vol. 45 pp. 668-679 (1999).
Mohn A. R. et al., Cell, vol. 98 pp. 427-436 (1999).
Bliss, T. V. & Collingridge G. L., Nature, vol. 361 pp. 31-39 (1993).
Tang J. P. et al., Nature, vol. 401, pp. 63-69 (1999).
Gainetdinov R. R. et al., Trends in Pharm. Sci. vol. 23(8) pp. 367-373 (2002).
Lopez-Corcuera B, et al., Mol. Mem. Biol. vol. 18 pp. 13-20 (2001).
Bergeron R. et al., Proc. Natl. Acad. Sci. USA vol. 95, pp. 15730-15734 (1998).
Chen et al., J. Neurophysiol. vol. 89(2) pp. 691-703 (2003).
Armer R. E. & Miller D. J., Exp. Opin. Ther. Patents vol. 11(4) pp. 563-572 (2001).
Pralong E. et al., Prog. in Neurobiol. vol. 67, pp. 173-202 (2002).
Carlsson M. L., J. Neural Trans. vol. 105, pp. 525-535 (1998).
Kwong et al., Org. Lett. 4, pp. 581-584 (2002).
Kuwano et al., JOC 67, pp. 6479-6486 (2002).
Chem. Abstract XP-002299148.
Caulfield W. L. et al., Journal of Med. Chem. vol. 44(17) pp. 2679-2682 (2001).
Chem. Abstract XP-002299149.
Chemical Abstracts Service, Apr. 23, 2003, XP002308402, Database accession No. 2003: 2142911 Chemcats & Catalog: AsInExExpress Gold.

(Continued)

*Primary Examiner*—James O Wilson
*Assistant Examiner*—Jeffrey H Murray
(74) *Attorney, Agent, or Firm*—George W. Johnston; Patricia S. Rocha-Tramaloni; Kimberly J. Prior

(57) ABSTRACT

The present invention relates to compounds of formula I

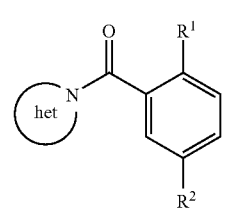

wherein $R^1$ and $R^2$ are defined in the specification and to pharmaceutically acceptable acid addition salts thereof. Compounds of the invention are GlyT-1 inhibitors and are useful for the treatment of CNS disorders such as psychoses, dysfunction in memory and learning, schizophrenia, dementia, attention deficit disorders, or Alzheimer's disease.

6 Claims, No Drawings

OTHER PUBLICATIONS

Chemical Abstracts Service, Jun. 6, 2003, XP002308481 & Database Chemcats.
Chemical Abstracts Service, Jan. 1, 2004, XP002308405, Database accession No. 2003:2872406 Chemcats & Catalog: Ambinter Stock Screening Collection.
Chemical Abstracts Service, Jan. 1, 2004, XP002308403, Database accession No. 2004:591813 & Catalog: Ambinter Stock Screening Collection.
Chemical Abstracts Service, Jan. 1, 2004, XP002308404, Database accession No. 2004:660630 & Catalog: Ambinter Screening Library.
Chemical Abstracts Service, XP002308978.
Chemical Abstracts Service, XP002308979; Chemcats No. 2003:1026314.
Chemical Abstracts Service, XP002308980; Chemcats No. 2001;2814605.
Chemical Abstracts Service, XP002308981; Chemcats No. 2002:2063001.
Chemical Abstracts Service, XP002308983; Chemcats No. 2003:1026533.
Chemical Abstracts Service, XP002308984; Chemcats No. 2002:2288893.
Chemical Abstracts Service, XP002308985; Chemcats No. 2003:709504.
Chemical Abstracts Service, XP002308986; Chemcats No. 2003:709503.
Chemical Abstracts Service, XP002308987; Chemcats No. 2003:709505.
Chemical Abstracts Service, XP002308988; Chemcats No. 2004:1498769.
Chemical Abstracts Service, XP002308989; Chemcats No. 2002:2386068.
Chemical Abstracts Service, XP002308990; Chemcats No. 2002:2894607.
Chemical Abstracts Service, XP002308991; Chemcats No. 2003:3342164.
Chemical Abstracts Service, XP002308992; Chemcats No. 2003:3345505.
Chemical Abstracts Service, XP002308993; Chemcats No. 2003:3346187.
Chemical Abstracts Service, XP002309007; Chemcats No. 2004:660630.
Cabiddu et al., Journal of Organometallic Chemistry, 1991, 419(1-2) 1-8.
Collins, et al., J. Med. Chem. 1998, 41, p. 5037-5054.
Yamanaka et al., Tetrahedron Lett., 1996, vol. 37, p. 1829-1832.
Guisado et al., Tetrahedron Lett., 2002, vol. 43, p. 7105-7109.
Souers et al., Bioorganic & Medicinal Chem. Letters, vol. 14(19) pp. 4883-4886 (2004).
Wolin et al., Bioorganic & Medicinal Chem. vol. 12, pp. 4511-4532 (2004).
Lowe, John A., III, Expert Opin. Ther. Patents vol. 15 (11) pp. 1657-1662 (2005).
Wolfe et al., J. Am. Chem. Soc. 1996, vol. 118(30), pp. 7215-7216.
Kwong, et al., Org. Lett. 2002, vol. 4(20), pp. 3517-3520.
Wolter, et al., Org. Lett. 2002, vol. 4(6), pp. 973-976.
Murata et al., Tetrahedron 2004, vol. 60, pp. 7397-7403.
El-Ghandour et al., Egypt. J. Pharm. Sci. vol. 29, No. 1-4, pp. 545-551 (1988).
Ghiusoli et al, *Transition Metal Chemistry*, 14(3):235-40 (1989) Caplus 1989:534023.
Wright et al, *Jour. of the Amer. Chem. Soc*, 2199-2203 (1957) Caplus 1957:71484.
Forbes et al, *Tetrahedron* 24:6223-9 (1968).

* cited by examiner

HETEROCYCLIC-SUBSTITUTED PHENYL METHANONES

PRIORITY TO RELATED APPLICATIONS

This application claims the benefit of European Application No. 05100813.4, filed Feb. 7, 2005, which is hereby incorporated by reference in its entirety.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, *Neuron*, 2000, 28:325-33). For decades research has focused on the "dopaminergic hyperactivity" hypothesis which has led to therapeutic interventions involving blockade of the dopaminergic system (Vandenberg R J and Aubrey K R., *Exp. Opin. Ther. Targets*, 2001, 5(4): 507-518; Nakazato A and Okuyama S, et al., 2000, *Exp. Opin. Ther. Patents*, 10(1): 75-98). This pharmacological approach poorly address negative and cognitive symptoms which are the best predictors of functional outcome (Sharma T., *Br. J. Psychiatry*, 1999, 174(suppl. 28): 44-51).

A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly in healthy volunteers, PCP-induced psychotomimetic action incorporates positive and negative symptoms as well as cognitive dysfunction, thus closely resembling schizophrenia in patients (Javitt D C et al., 1999, *Biol. Psychiatry*, 45: 668-679 and refs. herein). Furthermore transgenic mice expressing reduced levels of the NMDAR1 subunit displays behavioral abnormalities similar to those observed in pharmacologically induced models of schizophrenia, supporting a model in which reduced NMDA receptor activity results in schizophrenia-like behavior (Mohn A R et al., 1999, *Cell*, 98: 427-236).

Glutamate neurotransmission, in particular NMDA receptor activity, plays a critical role in synaptic plasticity, learning and memory, such as the NMDA receptors appears to serve as a graded switch for gating the threshold of synaptic plasticity and memory formation (Hebb D O, 1949, *The organization of behavior*, Wiley, NY; Bliss T V and Collingridge G L, 1993, *Nature*, 361: 31-39). Transgenic mice overexpressing the NMDA NR2B subunit exhibit enhanced synaptic plasticity and superior ability in learning and memory (Tang J P et al., 1999, *Nature:* 401-63-69).

Thus, if a glutamate deficit is implicated in the pathophysiology of schizophrenia, enhancing glutamate transmission, in particular via NMDA receptor activation, would be predicted to produce both anti-psychotic and cognitive enhancing effects.

The amino acid glycine is known to have at least two important functions in the CNS. It acts as an inhibitory amino acid, binding to strychnine sensitive glycine receptors, and it also influences excitatory activity, acting as an essential co-agonist with glutamate for N-methyl-D-aspartate (NMDA) receptor function. While glutamate is released in an activity-dependent manner from synaptic terminals, glycine is apparently present at a more constant level and seems to modulate/control the receptor for its response to glutamate.

One of the most effective ways to control synaptic concentrations of neurotransmitter is to influence their re-uptake at the synapses. Neurotransmitter transporters by removing neurotransmitters from the extracellular space, can control their extracellular lifetime and thereby modulate the magnitude of the synaptic transmission (Gainetdinov R R et al, 2002, Trends in Pharm. Sci., 23(8): 367-373).

Glycine transporters, which form part of the sodium and chloride family of neurotransmitter transporters, play an important role in the termination of post-synaptic glycinergic actions and maintenance of low extracellular glycine concentration by re-uptake of glycine into presynaptic nerve terminals and surrounding fine glial processes.

Two distinct glycine transporter genes have been cloned (GlyT-1 and GlyT-2) from mammalian brain, which give rise to two transporters with ~50% amino acid sequence homology. GlyT-1 presents four isoforms arising from alternative splicing and alternative promoter usage (1a, 1b, 1c and 1d). Only two of these isoforms have been found in rodent brain (GlyT-1a and GlyT-1b). GlyT-2 also presents some degree of heterogeneity. Two GlyT-2 isoforms (2a and 2b) have been identified in rodent brains. GlyT-1 is known to be located in CNS and in peripheral tissues, whereas GlyT-2 is specific to the CNS. GlyT-1 has a predominantly glial distribution and is found not only in areas corresponding to strychnine sensitive glycine receptors but also outside these areas, where it has been postulated to be involved in modulation of NMDA receptor function (Lopez-Corcuera B et al., 2001, *Mol. Mem. Biol.*, 18: 13-20). Thus, one strategy to enhance NMDA receptor activity is to elevate the glycine concentration in the local microenvironment of synaptic NMDA receptors by inhibition of GlyT-1 transporter (Bergereon R. Et al., 1998, *Proc. Natl. Acad. Sci. USA*, 95: 15730-15734; Chen L et al., 2003, *J. Neurophysiol.*, 89 (2): 691-703).

Glycine transporter inhibitors are suitable for the treatment of neurological and neuropsychiatric disorders. The majority of diseases states implicated are psychoses, schizophrenia (Armer R E and Miller D J, 2001, *Exp. Opin. Ther. Patents*, 11 (4): 563-572), psychotic mood disorders such as severe major depressive disorder, mood disorders associated with psychotic disorders such as acute mania or depression associated with bipolar disorders and mood disorders associated with schizophrenia, (Pralong E T et al., 2002, *Prog. Neurobiol.*, 67: 173-202), autistic disorders (Carlsson M L, 1998, *J. Neural Transm.* 105: 525-535), cognitive disorders such as dementias, including age related dementia and senile dementia of the Alzheimer type, memory disorders in a mammal, including a human, attention deficit disorders and pain (Armer R E and Miller D J, 2001, *Exp. Opin. Ther. Patents*, 11 (4): 563-572).

Thus, increasing activation of NMDA receptors via GlyT-1 inhibition may lead to agents that treat psychosis, schizophrenia, dementia and other diseases in which cognitive processes are impaired, such as attention deficit disorders or Alzheimer's disease.

SUMMARY OF THE INVENTION

The present invention provides compounds of formula I

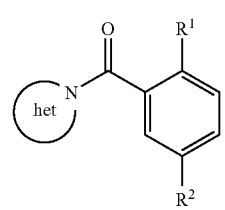

wherein
$R^1$ is halogen, —$OR^{1'}$, —$SR^{1'}$, cycloalkyl, cyclic amide, heterocycloalkyl, aryl or 5- or 6-membered heteroaryl containing one, two or three heteroatoms selected from the group consisting of oxygen, sulphur and nitrogen;

R¹' and R¹'" are each independently hydrogen, lower alkyl, lower alkyl substituted by halogen, —(CH₂)ₓ-cycloalkyl or —(CH₂)ₓ-aryl;

R² is —S(O)₂-lower alkyl, —S(O)₂NH-lower alkyl, NO₂ or CN;

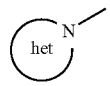

is an aromatic or partially aromatic bicyclic amine, having one or two additional N-atoms selected from the group consisting of a) 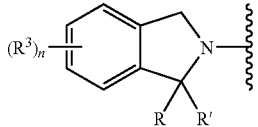

b) 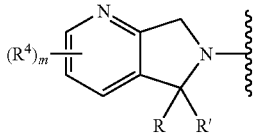

c) 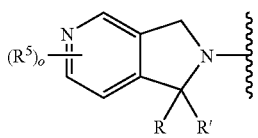

d) 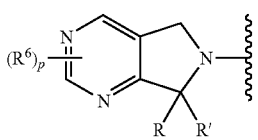

e) 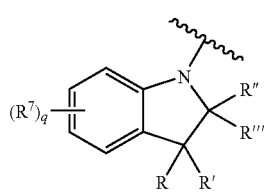

f) 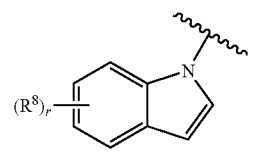

g) 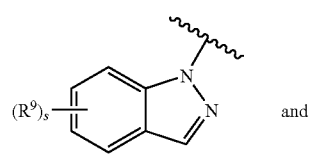

and h) 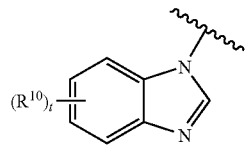

and wherein one of the additional N-ring atoms of the aromatic or partially aromatic bicyclic amine can be available in form of its oxide

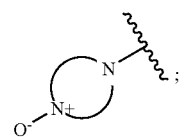

R³ to R¹⁰ are each independently hydrogen, hydroxy, halogen, =O, lower alkyl, cycloalkyl, heterocycloalkyl, lower alkoxy, CN, NO₂, NH₂, aryl, 5- or 6-membered heteroaryl containing one, two or three heteroatoms selected from the group consisting of oxygen, sulphur or nitrogen, —NH-lower alkyl, —N(lower alkyl)₂, cyclic amide, —C(O)-cyclic amide, S-lower alkyl, —S(O)₂-lower alkyl, lower alkyl substituted by halogen, lower alkoxy substituted by halogen, lower alkyl substituted by hydroxy, —O—(CH₂)ᵧ-lower alkoxy, —O(CH₂)ᵧC(O)N(lower alkyl)₂, —C(O)-lower alkyl, —O—(CH₂)ₓ-aryl, —O—(CH₂)ₓ-cycloalkyl, —O—(CH₂)ₓ-heterocycloalkyl, —C(O)O-lower alkyl, —C(O)—NH-lower alkyl, —C(O)—N(lower alkyl)₂, 2-oxy-5-aza-bicyclo[2.2.1]hept-5-yl or 3-oxa-8-aza-bicyclo[3.2.1]oct-8-yl;

R, R', R" and R'" are each independently hydrogen or lower alkyl; or

R' and R'" in group e) together with —(CH₂)₄— form a six membered ring;

and wherein all aryl-, cycloalkyl-, cyclic amide, heterocycloalkyl- or 5 or 6 membered heteroaryl groups as defined for R¹, R¹', R¹'" and R³ to R¹⁰ are unsubstituted or substituted by one or more substituents selected from the group consisting of hydroxy, =O, halogen, lower alkyl, phenyl, lower alkyl substituted by halogen and lower alkoxy, n, m, o, p, q, r, s and t are each independently 1 or 2;
x is 0, 1 or 2; and
y is 1 or 2;

and pharmaceutically acceptable acid addition salts thereof.

The invention includes all racemic mixtures, all their corresponding enantiomers and/or optical isomers. The present invention also provides pharmaceutical compositions containing compounds of the invention and a pharmaceutically acceptable carrier. The invention also provides methods for manufacturing compounds of the invention and compositions containing them.

Compounds of formula I are good inhibitors of the glycine transporter 1 (GlyT-1), and have a good selectivity to glycine transporter 2 (GlyT-2) inhibitors. The present invention further provides methods for the treatment of diseases related to activation of NMDA receptors via GlyT-1 inhibition, such as psychoses, dysfunction in memory and learning, schizophrenia, dementia and other diseases in which cognitive processes are impaired, such as attention deficit disorders or Alzheimer's disease. The preferred indications using the compounds of the present invention are schizophrenia, cognitive impairment and Alzheimer's disease.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-carbon chain containing from 1 to 6 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "cycloalkyl" denotes a saturated carbon ring containing from 3 to 6 carbon atoms.

As used herein, the term "heterocycloalkyl" denotes a saturated carbon ring, containing from 3 to 6 carbon atoms as defined above wherein at least one of the carbon atoms is replaced by a heteroatom, selected from the group consisting of N, O or S. Examples of such groups are tetrahydropyran-2, 3 or 4-yl, tetrahydrofuran-2 or 3-yl, oxetan-3-yl, [1,4]dioxin-2-yl and the like.

The term "halogen" denotes fluorine, chlorine, bromine, and iodine.

The term "lower alkyl substituted by halogen" denotes a lower alkyl group as defined above wherein at least one hydrogen atom is replaced by a halogen atom, for example the following groups: $CF_3$, $CHF_2$, $CH_2F$, $CH_2CF_3$, $CH_2CHF_2$, $CH_2CH_2F$, $CH_2CH_2CF_3$, $CH_2CH_2CH_2CF_3$, $CH(CF_3)CH_2CH_3$, $C[(CH_3)_2]—CF_3$, $CH_2CH_2Cl$, $CH_2CF_2CF_3$, $CH_2CF_2CHF_2$, $CF_2CHFCF_3$, $C(CH_3)_2CF_3$, $CH(CH_3)CF_3$ or $CH(CH_2F)CH_2F$. Preferred are $CH_2CF_3$, $CF_3$ or $CH(CH_3)CF_3$.

The term "lower alkoxy" denotes a saturated straight- or branched-carbon chain containing from 1 to 6 carbon atoms as described above which is connected via an oxygen atom.

The term "lower alkoxy substituted by halogen" denotes a lower alkoxy group as defined above wherein at least one hydrogen atom is replaced by a halogen atom.

The term "aryl" denotes a mono or bicyclic aromatic carbon ring system, for example phenyl, benzyl or naphthyl.

The term "cyclic amide" denotes a heterocycloalkyl group as defined above wherein the heterocycloalkyl group contains at least one N atom, and the N-atom is linked to an aromatic or partially aromatic bicyclic group or to a phenyl ring as described herein, for example piperidine, piperazine, morpholine, thiomorpholine, di-oxo-thiomorpholine, pyrrolidine, pyrazoline, imidazolidine, azetidine, and the like. Such groups can be substituted by one or more substituents, selected from the group consisting of halogen, hydroxy, phenyl, lower alkyl, lower alkoxy or =O.

"An aromatic or partially aromatic bicyclic amine" is a group having one of the following formulae

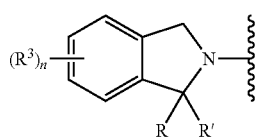
a)

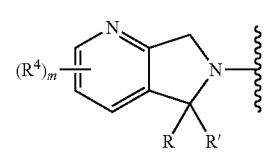
b)

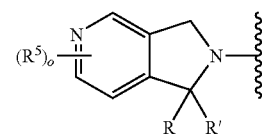
c)

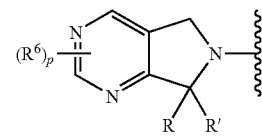
d)

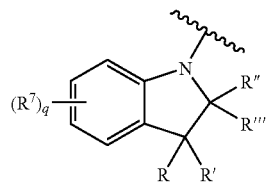
e)

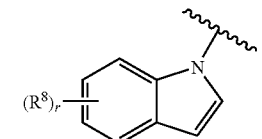
f)

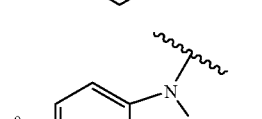
g)

or

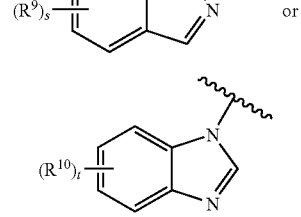
h)

wherein each of the substituents is as defined herein and wherein, when there are two or more nitrogen atoms, one of the N-ring atoms of the aromatic or partially aromatic bicyclic amine can be available in form of its oxide

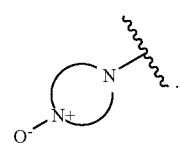

The term "5 or 6-membered heteroaryl" denotes an aromatic 5- or 6-membered ring or one or more fused rings containing one or more heteroatoms selected from nitrogen, oxygen or sulphur, for example furanyl, thienyl, pyrrolyl, imidazolyl, pyrazolyl, triazolyl, thiazolyl, isothiazolyl, isoxazolyl, pyridinyl, pyrazinyl, pyrimidinyl or the like.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

The present invention provides compounds of formula I

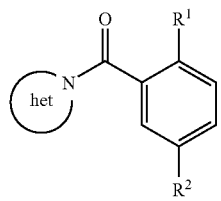

I wherein
$R^1$ is halogen, —$OR^{1'}$, —$SR^{1'''}$, cycloalkyl, cyclic amide, heterocycloalkyl, aryl or 5- or 6-membered heteroaryl containing one, two or three heteroatoms selected from the group consisting of oxygen, sulphur and nitrogen;
$R^{1'}$ and $R^{1'''}$ are each independently hydrogen, lower alkyl, lower alkyl substituted by halogen, —$(CH_2)_x$-cycloalkyl or —$(CH_2)_x$-aryl;
$R^2$ is —$S(O)_2$-lower alkyl, —$S(O)_2NH$-lower alkyl, $NO_2$ or CN;

is an aromatic or partially aromatic bicyclic amine, having one or two additional N-atoms selected from the group consisting of

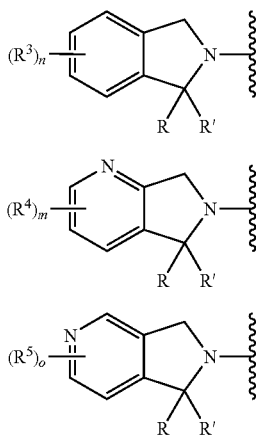

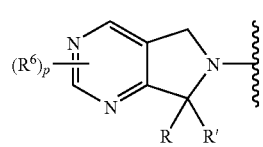

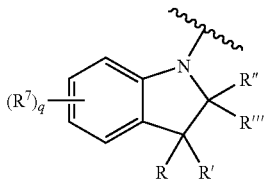

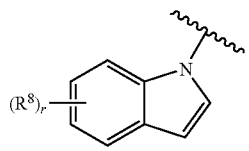

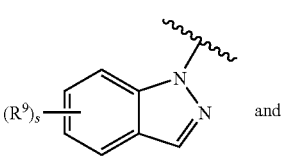

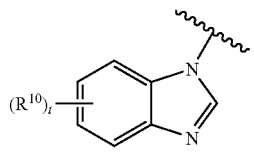

and wherein one of the additional N-ring atoms of the aromatic or partially aromatic bicyclic amine can be available in form of its oxide

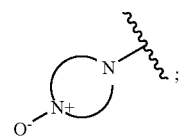

$R^3$ to $R^{10}$ are each independently hydrogen, hydroxy, halogen, =O, lower alkyl, cycloalkyl, heterocycloalkyl, lower alkoxy, CN, $NO_2$, $NH_2$, aryl, 5- or 6-membered heteroaryl containing one, two or three heteroatoms selected from the group consisting of oxygen, sulphur and nitrogen, —NH-lower alkyl, —N(lower alkyl)$_2$, cyclic amide, —C(O)-cyclic amide, S-lower alkyl, —$S(O)_2$-lower alkyl, lower alkyl substituted by halogen, lower alkoxy substituted by halogen, lower alkyl substituted by hydroxy, —O—$(CH_2)_y$-lower alkoxy, —$O(CH_2)_yC(O)N$(lower alkyl)$_2$, —C(O)-lower alkyl, —O—$(CH_2)_x$-aryl, —O—$(CH_2)_x$-cycloalkyl, —O—$(CH_2)_x$-heterocycloalkyl, —C(O)O-lower alkyl, —C(O)—NH-lower alkyl, —C(O)—N(lower alkyl)$_2$, 2-oxy-5-aza-bicyclo[2.2.1]hept-5-yl or 3-oxa-8-aza-bicyclo[3.2.1]oct-8-yl;
R, R', R" and R'" are each independently hydrogen or lower alkyl; or
R' and R'" in group e) together with —$(CH_2)_4$— form a six membered ring;

and wherein all aryl-, cycloalkyl-, cyclic amide, heterocycloalkyl- or 5 or 6 membered heteroaryl groups as defined for $R^1$, $R^{1'}$, $R^{1''}$ and $R^3$ to $R^{10}$ are unsubstituted or substituted by one or more substituents selected from the group consisting of hydroxy, =O, halogen, lower alkyl, phenyl, lower alkyl substituted by halogen and lower alkoxy, n, m, o, p, q, r, s and t are each independently 1 or 2;

x is 0, 1 or 2; and y is 1 or 2;

and pharmaceutically acceptable acid addition salts thereof.

Compounds encompassed by the present invention include those of the following structure:

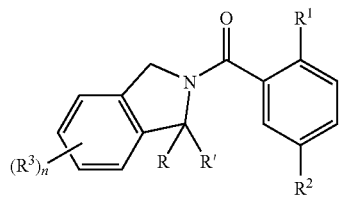
IA

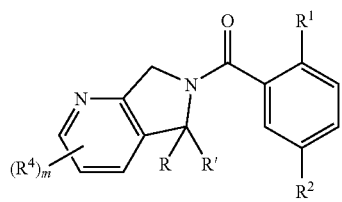
IB

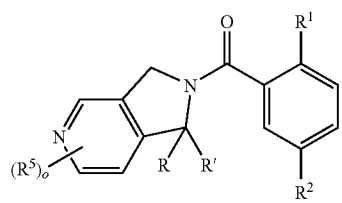
IC

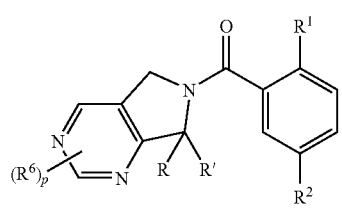
ID

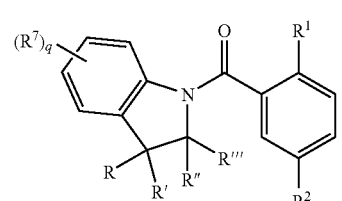
IE

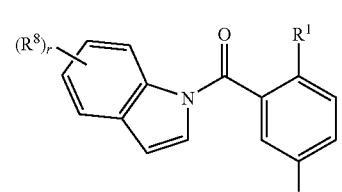
IF

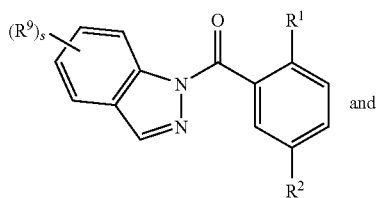
IG and

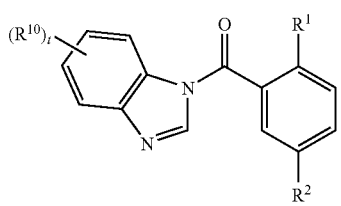
IH wherein the definitions are described above.

The invention includes all racemic mixtures, all their corresponding enantiomers and/or optical isomers.

In one embodiment, the invention provides compounds of formula I A

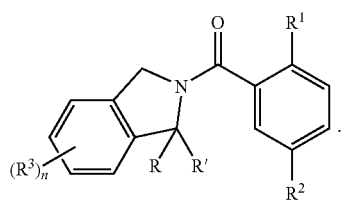

Especially preferred compounds of formula I A are those, wherein $R^1$ is $OR^{1'}$ and $R^{1'}$ is as described above.

The following specific compounds relate to this group:

(5,6-dichloro-1,3-dihydro-isoindol-2-yl)-(2-isopropoxy-5-methanesulfonyl-phenyl)-methanone, rac-(5,6-dichloro-1,3-dihydro-isoindol-2-yl)-[5-methanesulfonyl-2-(2,2,2-trifluoro-1-methyl-ethoxy)-phenyl]-methanone,

[5-methanesulfonyl-2-((S)-2,2,2-trifluoro-1-methyl-ethoxy)-phenyl]-(5-trifluoromethyl-1,3-dihydro-isoindol-2-yl)-methanone, (5,6-dichloro-1,3-dihydro-isoindol-2-yl)-(2-isopropylsulfanyl-5-methanesulfonyl-phenyl)-methanone,

[5-methanesulfonyl-2-((R)-2,2,2-trifluoro-1-methyl-ethoxy)-phenyl]-(5-trifluoromethyl-1,3-dihydro-isoindol-2-yl)-methanone, (5-chloro-6-methyl-1,3-dihydro-isoindol-2-yl)-[5-methanesulfonyl-2-((S)-2,2,2-trifluoro-1-methyl-ethoxy)-phenyl]-methanone, (5-chloro-6-methoxy-1,3-dihydro-isoindol-2-yl)-[5-methanesulfonyl-2-((S)-2,2,2-trifluoro-1-methyl-ethoxy)-phenyl]-methanone, (5-ethylsulfanyl-1,3-dihydro-isoindol-2-yl)-[5-methanesulfonyl-2-((S)-2,2,2-trifluoro-1-methyl-ethoxy)-phenyl]-methanone, (2-isobutoxy-5-methanesulfonyl-phenyl)-(5-trifluoromethyl-1,3-dihydro-isoindol-2-yl)-methanone, 4-isopropoxy-N-methyl-3-(5-trifluoromethyl-1,3-dihydro-isoindole-2-carbonyl)-benzenesulfonamide, (5-chloro-6-methyl-1,3-dihydro-isoindol-2-yl)-[5-methanesulfonyl-2-((R)-2,2,2-trifluoro-1-methyl-ethoxy)-phenyl]-methanone, (5-chloro-6-methyl-1,3-dihydro-isoindol-2-yl)-(2-isobutoxy-5-methanesulfonyl-phenyl)-methanone,
(5-chloro-6-ethylsulfanyl-1,3-dihydro-isoindol-2-yl)-[5-methanesulfonyl-2-((R)-2,2,2-trifluoro-1-methylethoxy)-phenyl]-methanone,
(2-isopropoxy-5-methanesulfonyl-phenyl)-(5-methoxy-1,3-dihydro-isoindol-2-yl)-methanone,
[[5-methanesulfonyl-2-((S)-2,2,2-trifluoro-1-methylethoxy)-phenyl]-(5-methyl-6-trifluoromethyl-1,3-dihydro-isoindol-2-yl)-methanone,
[[5-methanesulfonyl-2-((S)-2,2,2-trifluoro-1-methylethoxy)-phenyl]-(5-methoxy-6-trifluoromethyl-1,3-dihydro-isoindol-2-yl)-methanone,
[5-methanesulfonyl-2-((S)-2,2,2-trifluoro-1-methylethoxy)-phenyl]-(5-trifluoromethoxy-1,3-dihydro-isoindol-2-yl)-methanone,
[5-methanesulfonyl-2-((S)-2,2,2-trifluoro-1-methylethoxy)-phenyl]-[5-(4-methyl-thiazol-2-yl)-1,3-dihydro-isoindol-2-yl]-methanone,
[5-methanesulfonyl-2-((S)-2,2,2-trifluoro-1-methylethoxy)-phenyl]-[5-(2-methyl-pyridin-4-yl)-1,3-dihydro-isoindol-2-yl]-methanone,
[5-methanesulfonyl-2-((S)-2,2,2-trifluoro-1-methylethoxy)-phenyl]-[5-(5-methyl-thiophen-3-yl)-1,3-dihydro-isoindol-2-yl]-methanone,
[5-methanesulfonyl-2-((S)-2,2,2-trifluoro-1-methylethoxy)-phenyl]-(5-thiazol-2-yl-1,3-dihydro-isoindol-2-yl)-methanone,
(5-ethylsulfanyl-6-trifluoromethyl-1,3-dihydro-isoindol-2-yl)-[5-methanesulfonyl-2-((S)-2,2,2-trifluoro-1-methylethoxy)-phenyl]-methanone,
(5-chloro-6-methoxy-1,3-dihydro-isoindol-2-yl)-[5-methanesulfonyl-2-((R)-2,2,2-trifluoro-1-methyl-ethoxy)-phenyl]-methanone
(5-chloro-6-methoxy-1,3-dihydro-isoindol-2-yl)-(2-isobutoxy-5-methanesulfonyl-phenyl)-methanone,
(5-fluoro-6-trifluoromethyl-1,3-dihydro-isoindol-2-yl)-[5-methanesulfonyl-2-((S)-2,2,2-trifluoro-1-methylethoxy)-phenyl]-methanone,
(5-ethoxy-6-trifluoromethyl-1,3-dihydro-isoindol-2-yl)-(2-isopropoxy-5-methanesulfonyl-phenyl)-methanone,
(5-chloro-6-morpholin-4-yl-1,3-dihydro-isoindol-2-yl)-(2-isobutoxy-5-methanesulfonyl-phenyl)-methanone,
(5-chloro-6-morpholin-4-yl-1,3-dihydro-isoindol-2-yl)-(2-cyclobutylmethoxy-5-methanesulfonyl-phenyl)-methanone,
(2-isopropoxy-5-methanesulfonyl-phenyl)-[5-(tetrahydro-pyran-4-yl)-1,3-dihydro-isoindol-2-yl]-methanone,
[5-methanesulfonyl-2-((S)-2,2,2-trifluoro-1-methylethoxy)-phenyl]-[5-(tetrahydro-pyran-4-yl)-1,3-dihydro-isoindol-2-yl]-methanone,
(2-isobutoxy-5-methanesulfonyl-phenyl)-[5-(tetrahydro-pyran-4-yl)-1,3-dihydro-isoindol-2-yl]-methanone,
(2-cyclopropylmethoxy-5-methanesulfonyl-phenyl)-[5-(tetrahydro-pyran-4-yl)-1,3-dihydro-isoindol-2-yl]-methanone,
(2-cyclobutylmethoxy-5-methanesulfonyl-phenyl)-[5-(tetrahydro-pyran-4-yl)-1,3-dihydro-isoindol-2-yl]-methanone,
[2-(2,2-dimethyl-propoxy)-5-methanesulfonyl-phenyl]-[5-(tetrahydro-pyran-4-yl)-1,3-dihydro-isoindol-2-yl]-methanone,
[5-(3,3-difluoro-piperidin-1-yl)-1,3-dihydro-isoindol-2-yl]-[5-methanesulfonyl-2-((S)-2,2,2-trifluoro-1-methylethoxy)-phenyl]-methanone,
[5-methanesulfonyl-2-((S)-2,2,2-trifluoro-1-methylethoxy)-phenyl]-[5-(2,2,2-trifluoro-ethyl)-1,3-dihydro-isoindol-2-yl]-methanone,
[5-methanesulfonyl-2-((S)-2,2,2-trifluoro-1-methylethoxy)-phenyl]-[(1R,5S)-5-(3-oxa-8-aza-bicyclo [3.2.1] oct-8-yl)-1,3-dihydro-isoindol-2-yl]-methanone,
[5-methanesulfonyl-2-((S)-2,2,2-trifluoro-1-methylethoxy)-phenyl]-[5-methyl-6-(tetrahydro-pyran-4-yl)-1,3-dihydro-isoindol-2-yl]-methanone,
[5-methanesulfonyl-2-((S)-2,2,2-trifluoro-1-methylethoxy)-phenyl]-[5-(tetrahydro-furan-3-yl)-1,3-dihydro-isoindol-2-yl]-methanone,
[5-chloro-6-(tetrahydro-pyran-4-yl)-1,3-dihydro-isoindol-2-yl]-[5-methanesulfonyl-2-((S)-2,2,2-trifluoro-1-methylethoxy)-phenyl]-methanone,
[5-methanesulfonyl-2-((S)-2,2,2-trifluoro-1-methylethoxy)-phenyl]-[5-(tetrahydro-pyran-3-yl)-1,3-dihydro-isoindol-2-yl]-methanone,
[5-methanesulfonyl-2-((S)-2,2,2-trifluoro-1-methylethoxy)-phenyl]-(5-pyridin-4-yl-1,3-dihydro-isoindol-2-yl)-methanone,
[5-methanesulfonyl-2-((S)-2,2,2-trifluoro-1-methylethoxy)-phenyl]-(5-pyridin-3-yl-1,3-dihydro-isoindol-2-yl)-methanone,
[5-methanesulfonyl-2-((S)-2,2,2-trifluoro-1-methylethoxy)-phenyl]-(5-phenyl-1,3-dihydro-isoindol-2-yl)-methanone,
[5-(2-chloro-phenyl)-1,3-dihydro-isoindol-2-yl]-[5-methanesulfonyl-2-(2,2,2-trifluoro-1-methyl-ethoxy)-phenyl]-methanone,
[5-methanesulfonyl-2-(2,2,2-trifluoro-1-methyl-ethoxy)-phenyl]-(5-thiophen-3-yl-1,3-dihydro-isoindol-2-yl)-methanone,
[5-methanesulfonyl-2-(2,2,2-trifluoro-1-methyl-ethoxy)-phenyl]-[5-(4-methyl-thiophen-2-yl)-1,3-dihydro-isoindol-2-yl]-methanone,
[5-methanesulfonyl-2-(2,2,2-trifluoro-1-methyl-ethoxy)-phenyl]-[5-(3-methyl-thiophen-2-yl)-1,3-dihydro-isoindol-2-yl]-methanone,
[5-(4-fluoro-phenyl)-1,3-dihydro-isoindol-2-yl]-[5-methanesulfonyl-2-(2,2,2-trifluoro-1-methyl-ethoxy)-phenyl]-methanone,
[5-(3-fluoro-phenyl)-1,3-dihydro-isoindol-2-yl]-[5-methanesulfonyl-2-(2,2,2-trifluoro-1-methyl-ethoxy)-phenyl]-methanone,
[5-(2-fluoro-phenyl)-1,3-dihydro-isoindol-2-yl]-[5-methanesulfonyl-2-(2,2,2-trifluoro-1-methyl-ethoxy)-phenyl]-methanone,
[5-(3,5-difluoro-phenyl)-1,3-dihydro-isoindol-2-yl]-[5-methanesulfonyl-2-(2,2,2-trifluoro-1-methyl-ethoxy)-phenyl]-methanone,
[5-methanesulfonyl-2-(2,2,2-trifluoro-1-methyl-ethoxy)-phenyl]-[5-(3-methoxy-phenyl)-1,3-dihydro-isoindol-2-yl]-methanone,
[5-methanesulfonyl-2-((S)-2,2,2-trifluoro-1-methylethoxy)-phenyl]-(5-thiophen-2-yl-1,3-dihydro-isoindol-2-yl)-methanone,
[5-methanesulfonyl-2-((S)-2,2,2-trifluoro-1-methylethoxy)-phenyl]-[5-(4-methyl-thiophen-3-yl)-1,3-dihydro-isoindol-2-yl]-methanone,
[5-methanesulfonyl-2-((S)-2,2,2-trifluoro-1-methylethoxy)-phenyl]-(5-pyrazol-1-yl-1,3-dihydro-isoindol-2-yl)-methanone,
[5-methanesulfonyl-2-((S)-2,2,2-trifluoro-1-methylethoxy)-phenyl]-[5-(2,2,2-trifluoro-ethoxy)-1,3-dihydro-isoindol-2-yl]-methanone,

[5-chloro-6-(tetrahydro-furan-3-yl)-1,3-dihydro-isoindol-2-yl]-[5-methanesulfonyl-2-((S)-2,2,2-trifluoro-1-methyl-ethoxy)-phenyl]-methanone, rac-(2-isopropoxy-5-methanesulfonyl-phenyl)-[5-(tetrahydro-furan-3-yl)-1,3-dihydro-isoindol-2-yl]-methanone,
rac-[5-methanesulfonyl-2-(2,2,3,3,3-pentafluoro-propoxy)-phenyl]-[5-(tetrahydro-furan-3-yl)-1,3-dihydro-isoindol-2-yl]-methanone,
rac-(2-isopropoxy-5-methanesulfonyl-phenyl)-[5-(tetrahydro-pyran-3-yl)-1,3-dihydro-isoindol-2-yl]-methanone,
[5-chloro-6-(3-oxa-8-aza-bicyclo[3.2.1]oct-8-yl)-1,3-dihydro-isoindol-2-yl]-[5-methanesulfonyl-2-(2,2,3,3,3-pentafluoro-propoxy)-phenyl]-methanone,
rac-[5-methanesulfonyl-2-(2,2,3,3,3-pentafluoro-propoxy)-phenyl]-[5-(tetrahydro-pyran-3-yl)-1,3-dihydro-isoindol-2-yl]-methanone,
((1S,4S)-5-chloro-6-2-oxa-5-aza-bicyclo[2.2.1]hept-5-yl-1,3-dihydro-isoindol-2-yl)-[5-methanesulfonyl-2-((S)-2,2,2-trifluoro-1-methyl-ethoxy)-phenyl]-methanone,
[5-fluoro-6-(tetrahydro-pyran-4-yl)-1,3-dihydro-isoindol-2-yl]-[5-methanesulfonyl-2-((S)-2,2,2-trifluoro-1-methyl-ethoxy)-phenyl]-methanone,
[5-methanesulfonyl-2-((S)-2,2,2-trifluoro-1-methyl-ethoxy)-phenyl]-[5-(tetrahydro-pyran-4-yloxy)-1,3-dihydro-isoindol-2-yl]-methanone,
[5-(3-fluoro-oxetan-3-yl)-1,3-dihydro-isoindol-2-yl]-[5-methanesulfonyl-2-((S)-2,2,2-trifluoro-1-methyl-ethoxy)-phenyl]-methanone,
[5-methanesulfonyl-2-((S)-2,2,2-trifluoro-1-methyl-ethoxy)-phenyl]-[5-(3,3,3-trifluoro-propoxy)-1,3-dihydro-isoindol-2-yl]-methanone,
(5-fluoro-6-morpholin-4-yl-1,3-dihydro-isoindol-2-yl)-[5-methanesulfonyl-2-((S)-2,2,2-trifluoro-1-methyl-ethoxy)-phenyl]-methanone,
(5-fluoro-6-morpholin-4-yl-1,3-dihydro-isoindol-2-yl)-[5-methanesulfonyl-2-(2,2,3,3,3-pentafluoro-propoxy)-phenyl]-methanone,
(2-isopropoxy-5-methanesulfonyl-phenyl)-[5-(tetrahydro-pyran-4-yloxy)-1,3-dihydro-isoindol-2-yl]-methanone,
[5-methanesulfonyl-2-(2,2,3,3,3-pentafluoro-propoxy)-phenyl]-[5-(tetrahydro-pyran-4-yloxy)-1,3-dihydro-isoindol-2-yl]-methanone,
[5-chloro-6-(tetrahydro-pyran-4-yloxy)-1,3-dihydro-isoindol-2-yl]-[5-methanesulfonyl-2-((S)-2,2,2-trifluoro-1-methyl-ethoxy)-phenyl]-methanone,
[5-chloro-6-(tetrahydro-pyran-4-yloxy)-1,3-dihydro-isoindol-2-yl]-(2-isopropoxy-5-methanesulfonyl-phenyl)-methanone,
[5-fluoro-6-(tetrahydro-pyran-4-yloxy)-1,3-dihydro-isoindol-2-yl]-[5-methanesulfonyl-2-((S)-2,2,2-trifluoro-1-methyl-ethoxy)-phenyl]-methanone,
[5-fluoro-6-(tetrahydro-pyran-4-yloxy)-1,3-dihydro-isoindol-2-yl]-(2-isopropoxy-5-methanesulfonyl-phenyl)-methanone,
[5-fluoro-6-(tetrahydro-pyran-4-yloxy)-1,3-dihydro-isoindol-2-yl]-[5-methanesulfonyl-2-(2,2,3,3,3-pentafluoro-propoxy)-phenyl]-methanone and [5-chloro-6-(tetrahydro-pyran-4-yloxy)-1,3-dihydro-isoindol-2-yl]-[5-methanesulfonyl-2-(2,2,3,3,3-pentafluoro-propoxy)-phenyl]-methanone.

Preferred compounds of formula I A are further those, wherein $R^1$ is unsubstituted or substituted phenyl, for example the following compounds:
(5-chloro-6-morpholin-4-yl-1,3-dihydro-isoindol-2-yl)-(4-methanesulfonyl-biphenyl-2-yl)-methanone,
(5-chloro-6-morpholin-4-yl-1,3-dihydro-isoindol-2-yl)-(3'-fluoro-4-methanesulfonyl-biphenyl-2-yl)-methanone,
(5-chloro-6-morpholin-4-yl-1,3-dihydro-isoindol-2-yl)-(4'-fluoro-4-methanesulfonyl-biphenyl-2-yl)-methanone and
(4'-fluoro-4-methanesulfonyl-biphenyl-2-yl)-[5-(tetrahydro-pyran-4-yl)-1,3-dihydro-isoindol-2-yl]-methanone.

In another embodiment the invention provides compounds of formula IB

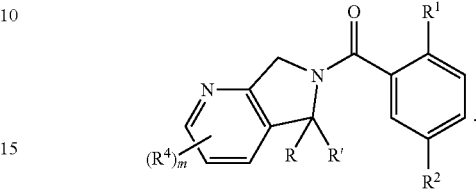

The following compounds of formula I B are preferred:
(2-cyclobutylmethoxy-5-methanesulfonyl-phenyl)-(3-trifluoromethyl-5,7-dihydro-pyrrolo[3,4-b]pyridin-6-yl)-methanone,
(2-isobutoxy-5-methanesulfonyl-phenyl)-(3-trifluoromethyl-5,7-dihydro-pyrrolo[3,4-b]pyridin-6-yl)-methanone,
[5-methanesulfonyl-2-((R)-2,2,2-trifluoro-1-methyl-ethoxy)-phenyl]-(3-trifluoromethyl-5,7-dihydro-pyrrolo[3,4-b]pyridin-6-yl)-methanone,
(4'-fluoro-4-methanesulfonyl-biphenyl-2-yl)-(3-trifluoromethyl-5,7-dihydro-pyrrolo[3,4-b]pyridin-6-yl)-methanone,
(3',4'-difluoro-4-methanesulfonyl-biphenyl-2-yl)-(3-trifluoromethyl-5,7-dihydro-pyrrolo[3,4-b]pyridin-6-yl)-methanone,
[5-methanesulfonyl-2-(2,2,3,3,3-pentafluoro-propoxy)-phenyl]-(3-trifluoromethyl-5,7-dihydro-pyrrolo [3,4-b]pyridin-6-yl)-methanone,
[5-methanesulfonyl-2-(2,2,3,3-tetrafluoro-propoxy)-phenyl]-(3-trifluoromethyl-5,7-dihydro-pyrrolo[3,4-b]pyridin-6-yl)-methanone,
[5-methanesulfonyl-2-((S)-2,2,2-trifluoro-1-methyl-ethoxy)-phenyl]-(2-methyl-3-trifluoromethyl-5,7-dihydro-pyrrolo[3,4-b]pyridin-6-yl)-methanone,
[3-(4-fluoro-phenyl)-5,7-dihydro-pyrrolo[3,4-b]pyridin-6-yl]-[5-methanesulfonyl-2-((S)-2,2,2-trifluoro-1-methyl-ethoxy)-phenyl]-methanone,
[5-methanesulfonyl-2-((S)-2,2,2-trifluoro-1-methyl-ethoxy)-phenyl]-(3-trifluoromethyl-5,7-dihydro-pyrrolo [3,4-b]pyridin-6-yl)-methanone and
[2-(4-fluoro-phenyl)-5,7-dihydro-pyrrolo[3,4-b]pyridin-6-yl]-[5-methanesulfonyl-2-((S)-2,2,2-trifluoro-1-methyl-ethoxy)-phenyl]-methanone In another embodiment the invention provides compounds of formula IC

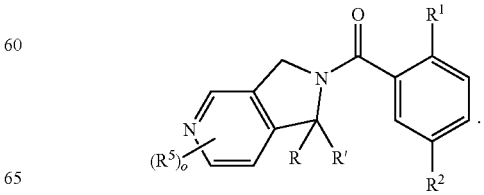

Preferred compounds of formula I C include
(2-cyclobutylmethoxy-5-methanesulfonyl-phenyl)-(6-trifluoromethyl-1,3-dihydro-pyrrolo[3,4-c]pyridin-2-yl)-methanone,
(4'-fluoro-4-methanesulfonyl-biphenyl-2-yl)-(6-trifluoromethyl-1,3-dihydro-pyrrolo[3,4-c]pyridin-2-yl)-methanone,
(3',4'-difluoro-4-methanesulfonyl-biphenyl-2-yl)-(6-trifluoromethyl-1,3-dihydro-pyrrolo[3,4-c]pyridin-2-yl)-methanone,
[5-methanesulfonyl-2-(2,2,3,3,3-pentafluoro-propoxy)-phenyl]-(6-trifluoromethyl-1,3-dihydro-pyrrolo [3,4-c]pyridin-2-yl)-methanone,
[5-methanesulfonyl-2-(2,2,3,3-tetrafluoro-propoxy)-phenyl]-(6-trifluoromethyl-1,3-dihydro-pyrrolo [3,4-c]pyridin-2-yl)-methanone,
[6-(4-fluoro-phenyl)-1,3-dihydro-pyrrolo[3,4-c]pyridin-2-yl]-[5-methanesulfonyl-2-((S)-2,2,2-trifluoro-1-methyl-ethoxy)-phenyl]-methanone and
[5-methanesulfonyl-2-((S)-2,2,2-trifluoro-1-methyl-ethoxy)-phenyl]-(6-morpholin-4-yl-1,3-dihydro-pyrrolo [3,4-c]pyridin-2-yl)-methanone.

In yet another embodiment the invention provides compounds of formula ID

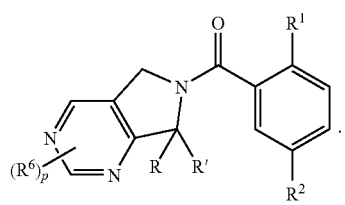

ID

Specific compounds of formula ID include the following
[5-methanesulfonyl-2-((S)-2,2,2-trifluoro-1-methyl-ethoxy)-phenyl]-(2-trifluoromethyl-5,7-dihydro-pyrrolo [3,4-d]pyrimidin-6-yl)-methanone,
(2-isopropoxy-5-methanesulfonyl-phenyl)-(2-trifluoromethyl-5,7-dihydro-pyrrolo[3,4-d]pyrimidin-6-yl)-methanone,
(4-methanesulfonyl-biphenyl-2-yl)-(2-trifluoromethyl-5,7-dihydro-pyrrolo[3,4-d]pyrimidin-6-yl)-methanone,
(2-isopropoxy-5-methanesulfonyl-phenyl)-(2-methyl-5,7-dihydro-pyrrolo[3,4-d]pyrimidin-6-yl)-methanone and
[5-methanesulfonyl-2-((S)-2,2,2-trifluoro-1-methyl-ethoxy)-phenyl]-(2-methyl-5,7-dihydro-pyrrolo[3,4-d]pyrimidin-6-yl)-methanone.

In one embodiment the invention provides compounds of formula IE

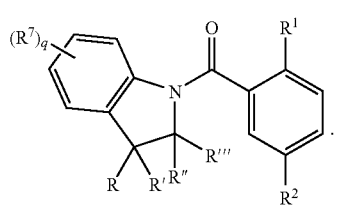

IE

Preferred compounds of formula I E include
1-(4-methanesulfonyl-biphenyl-2-carbonyl)-2,3-dihydro-1H-indole-4-carbonitrile,
1-[5-methanesulfonyl-2-((S)-2,2,2-trifluoro-1-methyl-ethoxy)-benzoyl]-2,3-dihydro-1H-indole-4-carboxylic acid methyl ester,
1-(2-isopropoxy-5-methanesulfonyl-benzoyl)-2,3-dihydro-1H!-indole-4-carboxylic acid methyl ester and
(4-bromo-2,3-dihydro-indol-1-yl)-[5-methanesulfonyl-2-((S)-2,2,2-trifluoro-1-methyl-ethoxy)-phenyl]-methanone.

In another embodiment the present invention provides compounds of formula IF

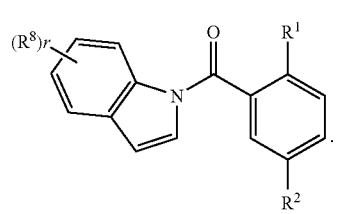

IF

Specific compounds of formula I F include the following
(5-bromo-indol-1-yl)-[5-methanesulfonyl-2-((S)-2,2,2-trifluoro-1-methyl-ethoxy)-phenyl]-methanone,
1-[5-methanesulfonyl-2-((S)-2,2,2-trifluoro-1-methyl-ethoxy)-benzoyl]-1H-indole-6-carbonitrile,
(6-chloro-indol-1-yl)-[5-methanesulfonyl-2-((S)-2,2,2-trifluoro-1-methyl-ethoxy)-phenyl]-methanone and
(4-bromo-indol-1-yl)-[5-methanesulfonyl-2-(2,2,2-trifluoro-1-methyl-ethoxy)-phenyl]-methanone.

In a further embodiment the invention provides compounds of formula IG

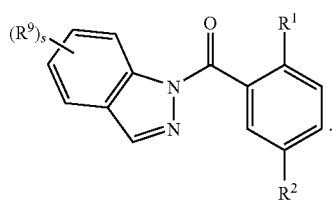

IG

Specific compounds of formula I G include the following
[5-methanesulfonyl-2-((S)-2,2,2-trifluoro-1-methyl-ethoxy)-phenyl]-(5-nitro-indazol-1-yl)-methanone,
(5-chloro-indazol-1-yl)-[5-methanesulfonyl-2-((S)-2,2,2-trifluoro-1-methyl-ethoxy)-phenyl]-methanone and
(5,7-Dichloro-indazol-1-yl)-[5-methanesulfonyl-2-((S)-2,2,2-trifluoro-1-methyl-ethoxy)-phenyl]-methanone.

In another embodiment the invention provides compounds of formula IH

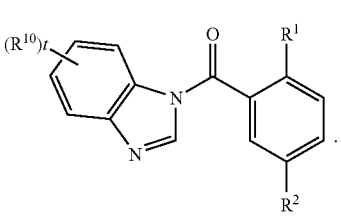

IH

A specific compound of formula I H is the following (5,6-dimethyl-benzoimidazol-1-yl)-[5-methanesulfonyl-2-((S)-2,2,2-trifluoro-1-methyl-ethoxy)-phenyl]-methanone.

The present compounds of formula I and their pharmaceutically acceptable salts can be prepared by methods known in the art, for example, by a process described below, which process consists in a) reacting a compound of formula

II selected from the group consisting of

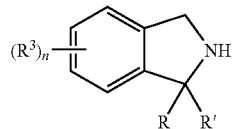

IIA

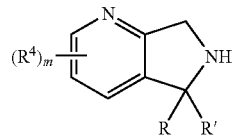

IIB

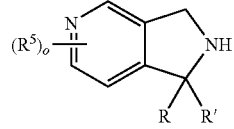

IIC

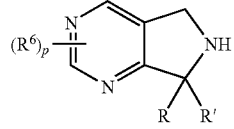

IID

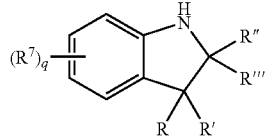

IIE

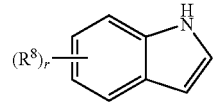

IIF

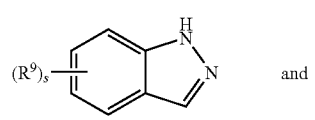  and

IIG

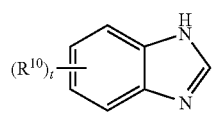

IIH with a compound of formula

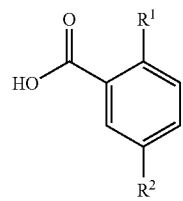

III in the presence of an activating agent, such as TBTU, to obtain a compound of formula

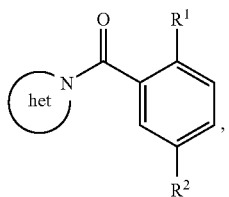

I which includes the following structures

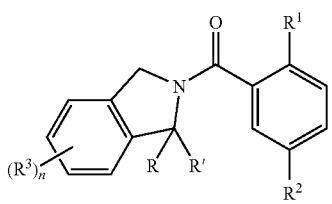

IA

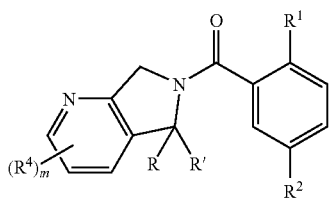

IB

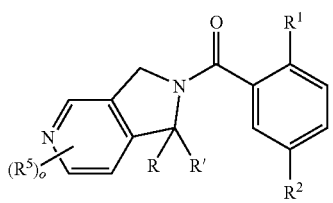

IC

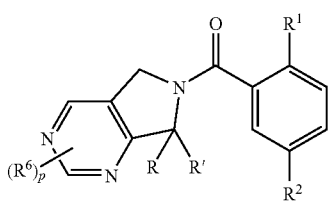

ID

-continued

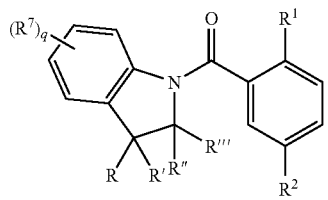
IE

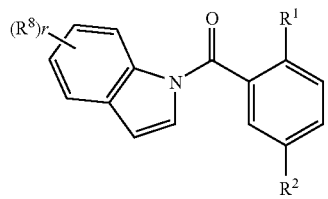
IF

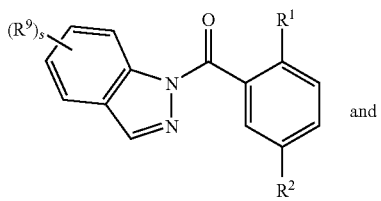
IG
and

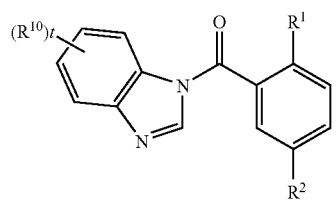
IH wherein the definitions are given above, or
b) reacting a compound of formula

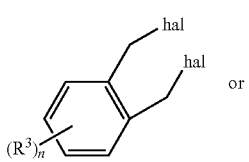
IVA
or

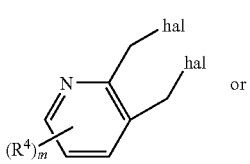
IVB
or

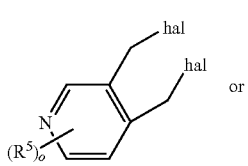
IVC
or

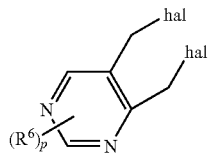
IVD wherein hal is an halogen group such as Br or Cl
with a compound of formula

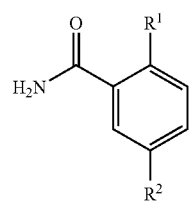
V in the presence of a base, such as sodium hydride,
to obtain a compound of formulas

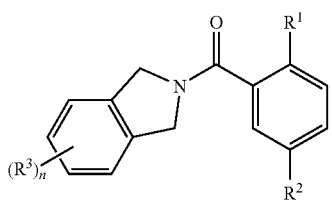
IA
or

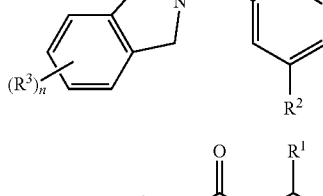
IB
or

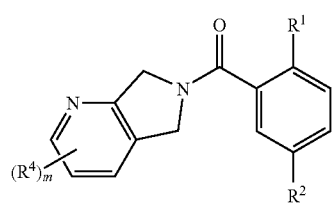
IC
or

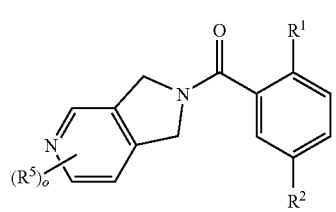
ID

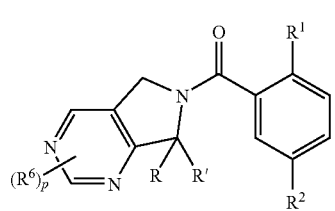

wherein the substituents are as defined above, and,
if desired, converting the compounds obtained into pharmaceutically acceptable acid addition salts.

The compounds of formula I can be prepared in accordance with the process variant as described above and with the following schemes 1-2. The starting materials are either commercially available, are otherwise known in the chemical literature, or can be prepared in accordance with methods well known in the art.
The following abbreviation has been used: TBTU=(2-(1H-benzotriazole-1-yl)-1,1,3,3-tetramethyluroniumtetrafluoroborate)
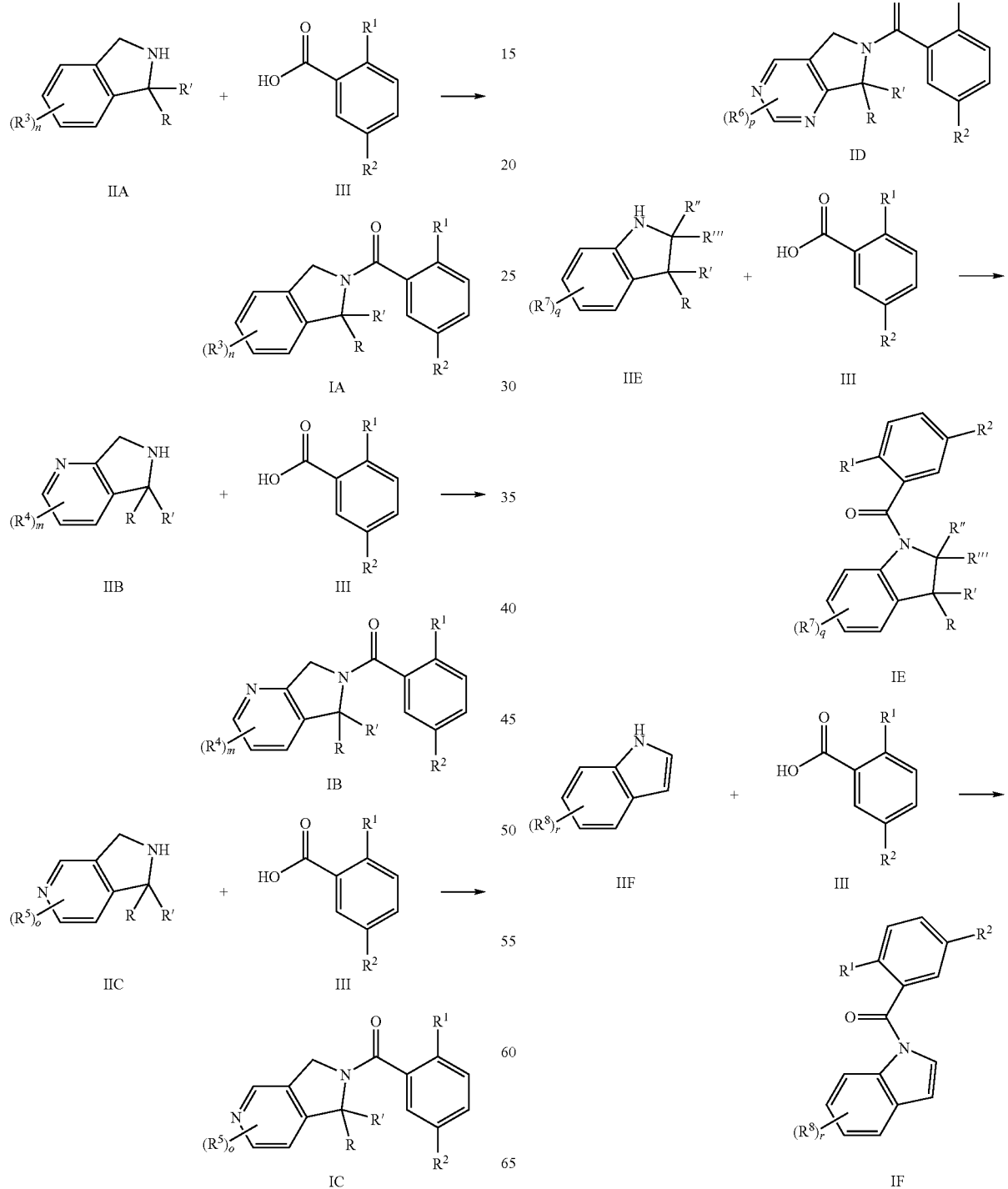

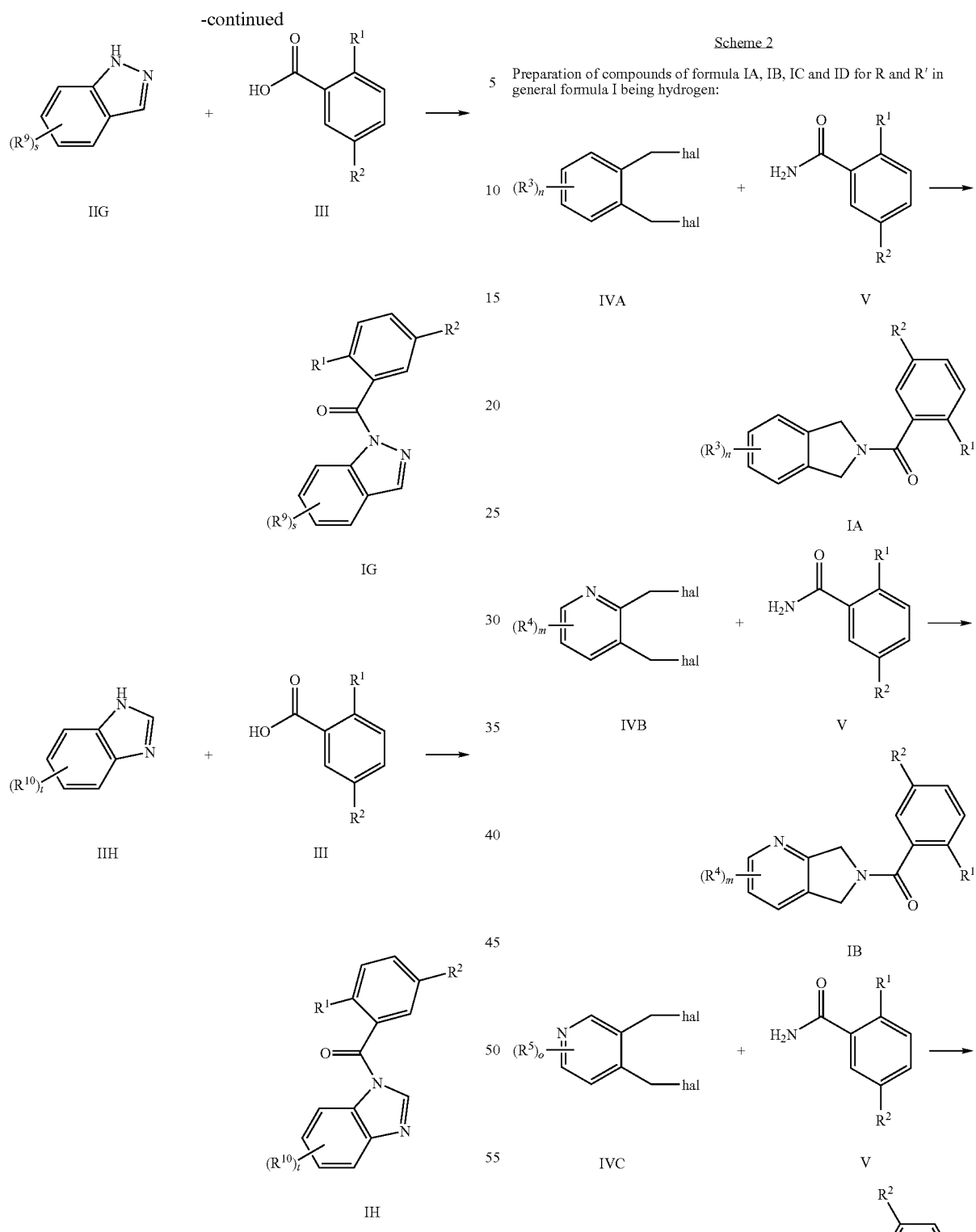
wherein substituents are as defined above.
A compound of formula II (II A, II B, II C, II D, II E, II F, II G and II H) is treated with a compound of formula III in the presence of TBTU and a base, such as N-ethyldiisopropylamine, to obtain a compound of formula I (I A, I B, I C, I D, I E, I F, I G and I H).

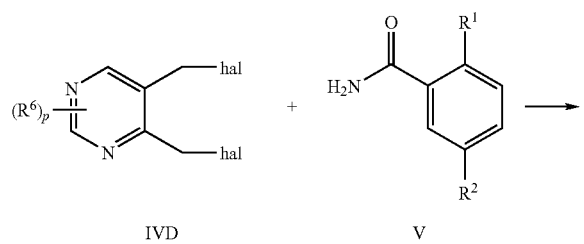

IVD  V

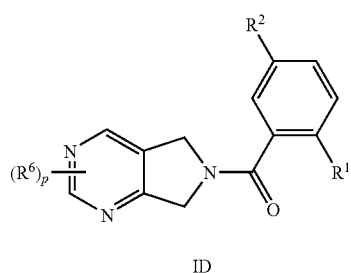

ID wherein the substituents are as defined above.

A compound of formula IV (A, B, C and D) is treated with a compound of formula V in the presence of sodium hydride to obtain a compound of formula I (A, B, C and D). The acids of formula III can be prepared by various routes as shown in Schemes 3-7.

Scheme 3

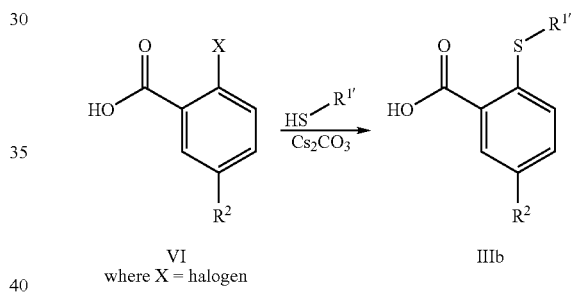

VI
where X = halogen

IIIa

For example, compounds of formula IIIa where $R^{1'}$ is lower alkyl, lower alkyl substituted by halogen or —$(CH_2)_x$-cycloalkyl can be prepared by reaction of a halogen compound of formula VI with an alcohol of formula $R^{1'}$OH, optionally in the presence of a copper salt, like Cu(I)Br, and a base, such as triethylamine (Scheme 3), at elevated temperature.

Scheme 4

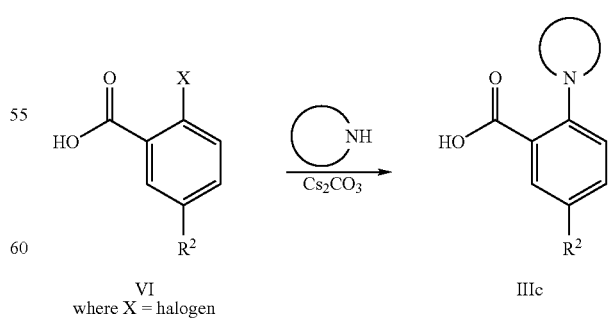

VII

VIII  IIIa

Alternatively, compounds of formula IIIa, where $R^{1'}$ is lower alkyl, lower alkyl substituted by halogen or —$(CH_2)_x$-cycloalkyl can be prepared by reacting a hydroxy compound of formula VII with an alcohol of formula $R^{1'}$OH, under Mitsunobu reaction conditions in the presence of a phosphine, like triphenylphosphine or diphenyl-2-pyridylphosphine, and a dialkylazadicarboxylate, like diethylazadicarboxylate or di-tert-butyl azodicarboxylate, to afford intermediate compounds of formula VIII, followed by hydrolysis in the presence of an aqueous base, such as potassium hydroxide, sodium hydroxide or lithium hydroxide (Scheme 4).

Scheme 5

VI
where X = halogen

IIIb

Compounds of formula IIIb where $R^{1'}$ is lower alkyl, lower alkyl substituted by halogen or —$(CH_2)_x$-cycloalkyl can be prepared by reaction of a halogen compound of formula VI with a thiol of formula $R^{1'}$SH, optionally in the presence of a base, such as caesium carbonate, potassium carbonate or sodium carbonate (Scheme 5), at elevated temperature.

Scheme 6

VI
where X = halogen

IIIc

Compounds of formula IIIc where $R^1$ is a heterocycloalkyl group, containing a N atom, can be prepared by reaction of a halogen compound of formula VI with an amine of formula

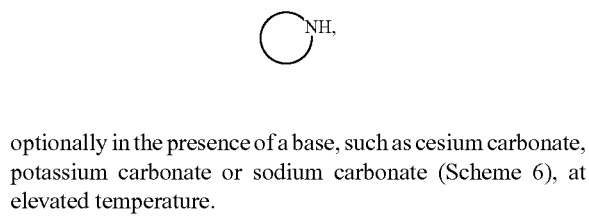

optionally in the presence of a base, such as cesium carbonate, potassium carbonate or sodium carbonate (Scheme 6), at elevated temperature.

Scheme 7

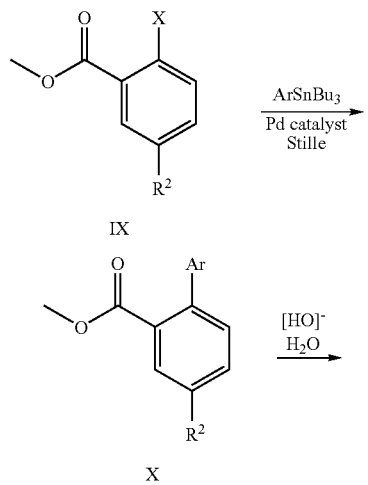

Compounds of formula IIId can be prepared by reacting a halogen compound of formula IX with aryltributyltin under Stille reaction conditions in the presence of a palladium catalyst, like tris(dibenzylideneacetone)dipalladium(0), to afford intermediate compounds of formula X, followed by hydrolysis in the presence of an aqueous base, such as potassium hydroxide, sodium hydroxide or lithium hydroxide (Scheme 7).

The halogen-substituted and hydroxyl-substituted starting materials of formula VI, VII and IX (as shown in Schemes 3-7) are either commercially available, are otherwise known in the chemical literature, or can be prepared using a variety of methods well known in the art.

The bis-halogenated compounds of formula IVa, where $R^3$ and $R^4$ are H can be prepared by methods well known in the art.

Scheme 8

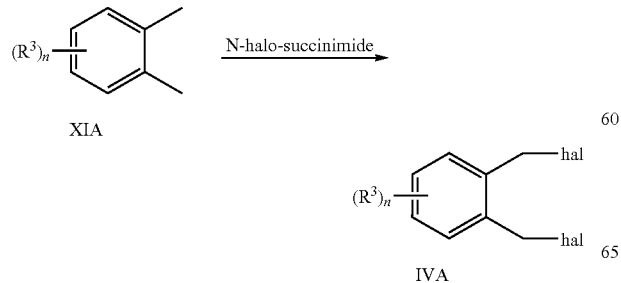

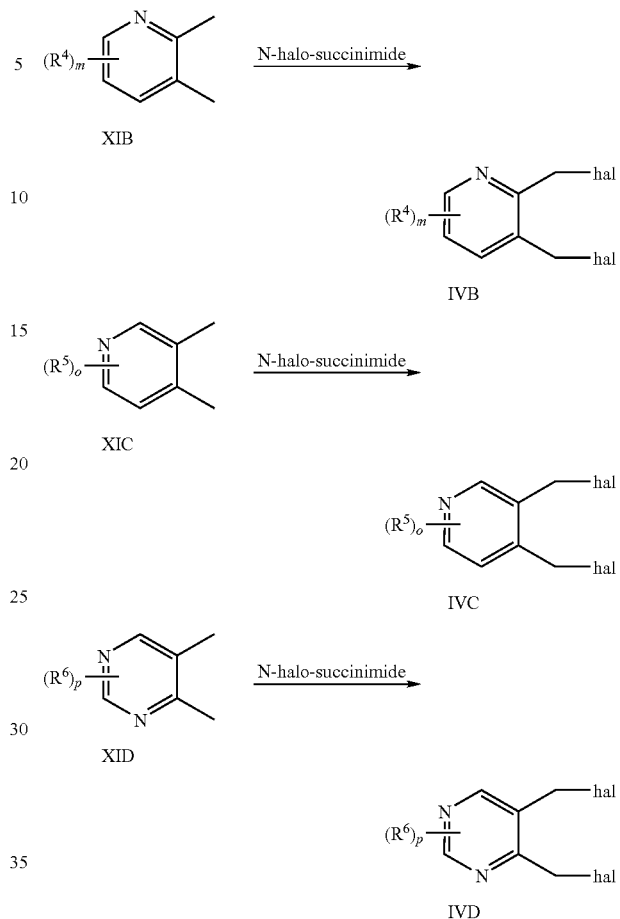

For example, compounds of formula IV A, IV B, IV C and IV D, can be prepared by reaction of an ortho-dimethylated compound of formulas XI A, XI B, XI C and XI D, respectively, with an N-halo-succinimide such as N-bromo-succinimide (Scheme 8).

Scheme 9

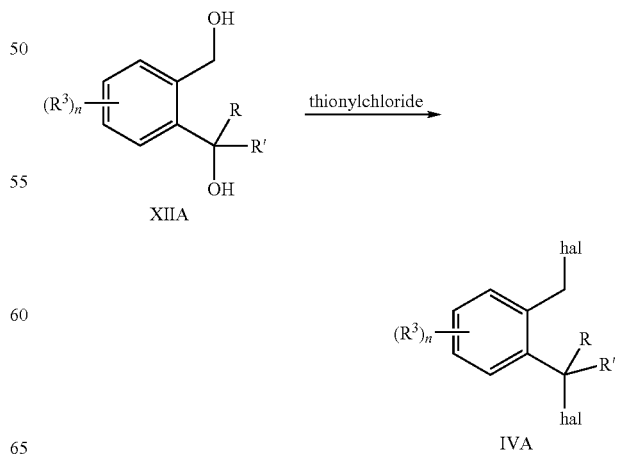

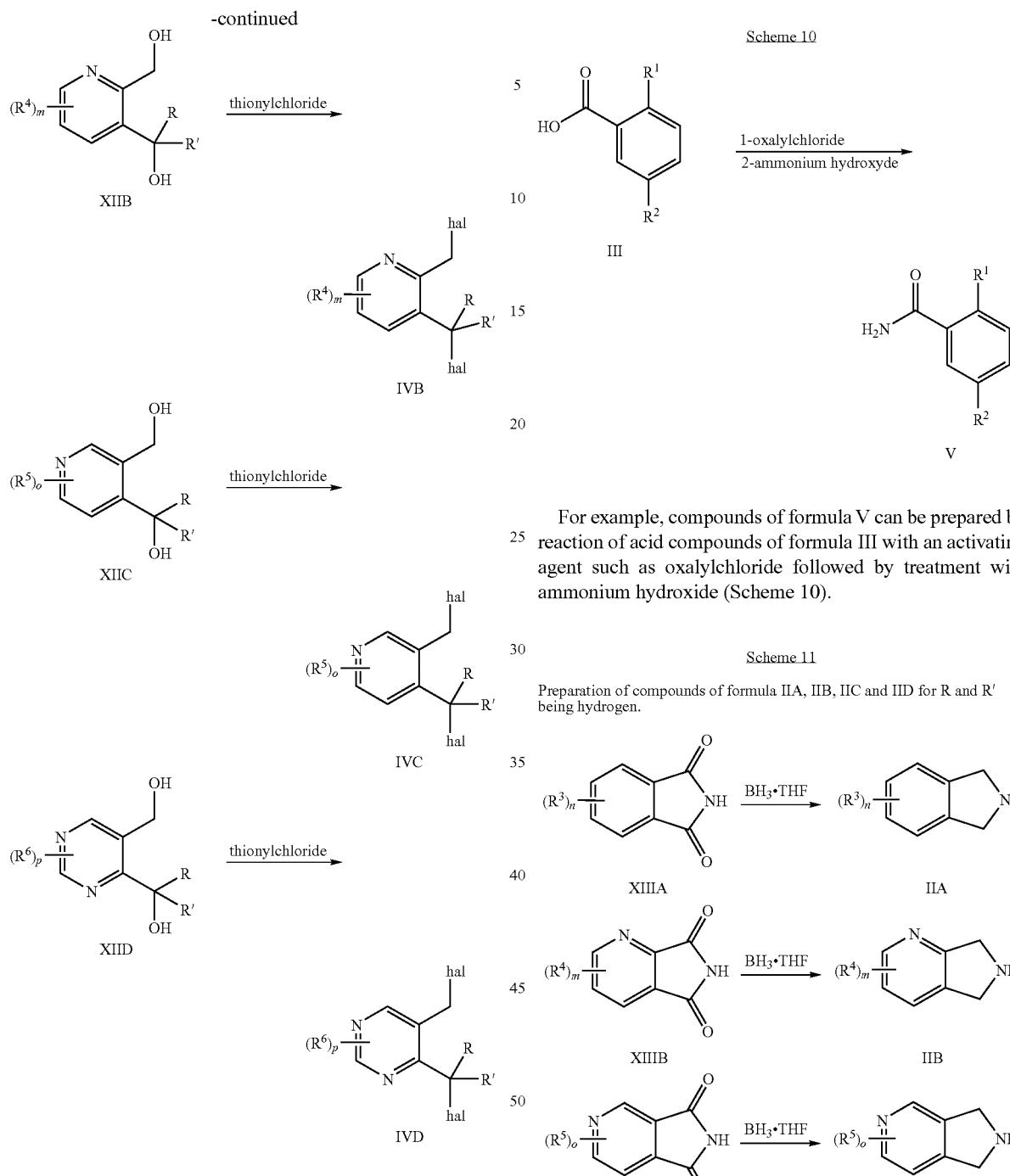

For example, compounds of formula V can be prepared by reaction of acid compounds of formula III with an activating agent such as oxalylchloride followed by treatment with ammonium hydroxide (Scheme 10).

Scheme 11

Preparation of compounds of formula IIA, IIB, IIC and IID for R and R' being hydrogen.

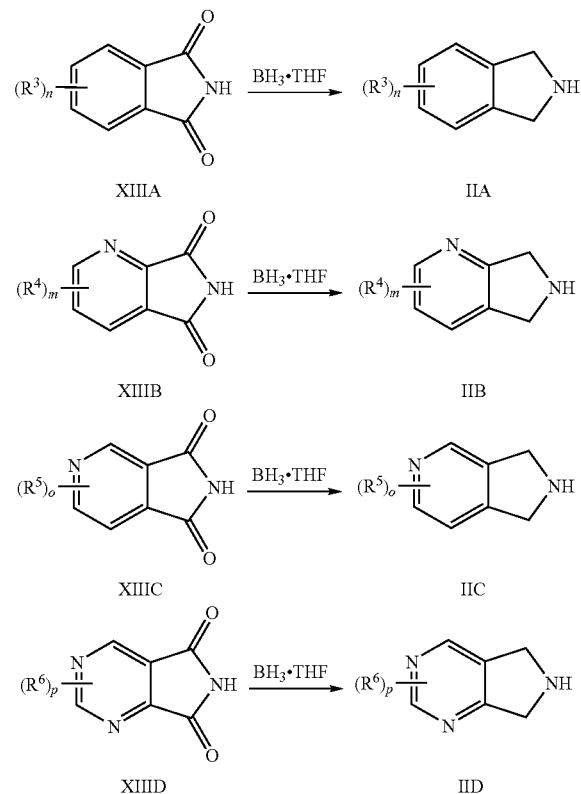

Alternatively, compounds of formulas IV A, IV B, IV C and IV D can be prepared by reaction of an ortho-dihydroxymethylated compound of formula XII (XII A, XII B, XII C and XII D) with a chlorinating agent such as thionylchloride (Scheme 9).

The ortho-dimethylated and -dihydroxymethylated compound of formula XI (A, B, C and D) and XII (A, B, C and D) as shown in Schemes 8 and 9 are either commercially available, are otherwise known in the chemical literature, or can be prepared using a variety of methods well known in the art.

The amide compounds of formula V can be prepared by methods well known in the art.

For example, compounds of formula II A, II B, II C and II D can be prepared by reaction of phtalimide compounds of formula XIII (A, B, C and D) in the presence of a reducing agent, such as borane THF complex (Scheme 11).

The phtalimide compounds of formula XIII (A, B, C and D) (as shown in Scheme 11) are either commercially available, are otherwise known in the chemical literature, or can be prepared using a variety of methods well known in the art.

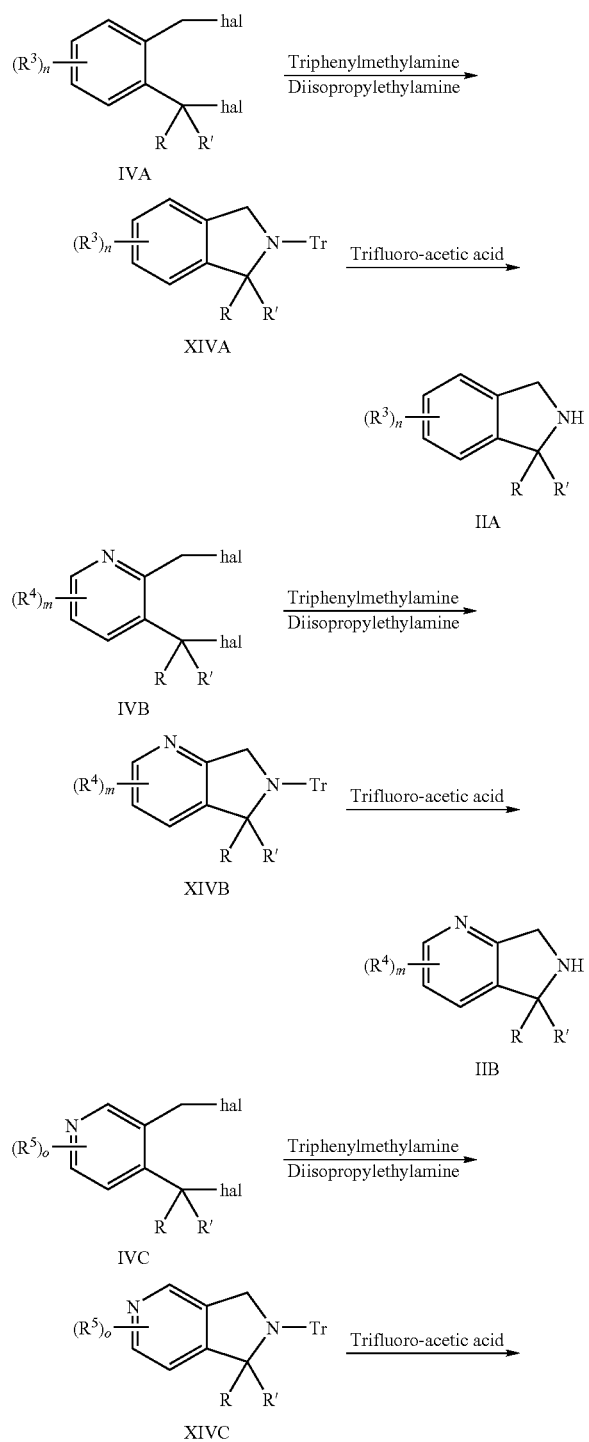

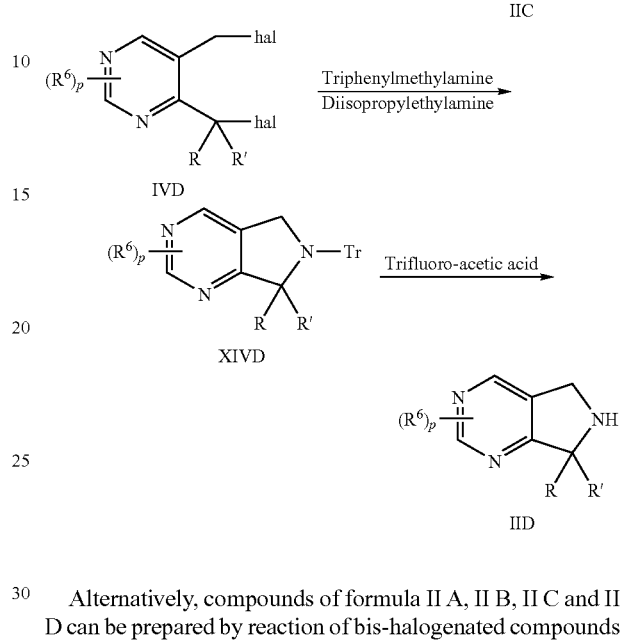

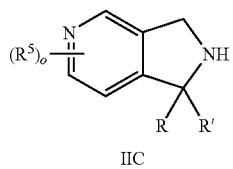

Alternatively, compounds of formula II A, II B, II C and II D can be prepared by reaction of bis-halogenated compounds of formula IV (A, B, C and D) in the presence of triphenylmethylamine and a base, such as diisopropylethylamine, to afford intermediate compounds of formula XIV (A, B, C and D) followed by deprotection in the presence of an acid, such as trifluoroacetic acid (Scheme 12).

In the case where compounds of general formula II contain a reactive functionality (e.g. halogen substituents or thioether substituents) in $R^3$, $R^4$ or $R^5$, further reactions can be performed on either the compounds of formula II (A, B, C, D) or the compounds of formula II in which the nitrogen atom is protected (i.e. Boc or Trityl) or the compounds of formula I so as to modify the substituents $R^3$ to $R^6$. Examples of such reactions include functional group interconversions (e.g. change of oxidation state, such as thioether to sulphone substituent), coupling reactions mediated by organometallic (palladium, copper) catalysts (e.g. Stille, Suzuki or Buchwald coupling reactions, in case where there is a reactive halogen substituent). Such reactions can be performed using a variety of methods well known in the art and specific examples can be had by reference to the Examples hereunder described. In cases where such reactions are performed on compounds of formula II in which the nitrogen atom is protected (i.e. Boc or Trityl), deprotection of the protective groups in acidic media (i.e. HCl, or trifluoroacetic acid) is subsequently performed Furthermore, aromatic or partially aromatic bicyclic amines in form of their oxides

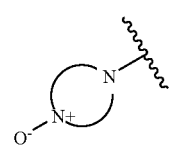

can be prepared by oxidizing a compound of formula I with 3-chloroperbenzoic acid in dichloromethane and stirring the mixture at room temperature for about 72 hours.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used Racemic mixtures of chiral compounds of formula I can be separated using chiral HPLC.

The acid addition salts of the basic compounds of formula I can be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, compounds of the present invention are good inhibitors of the glycine transporter 1 (GlyT-1).

The compounds were investigated in accordance with the test given hereinafter.

Solutions and Materials

DMEM complete medium: Nutrient mixture F-12 (Gibco Life-technologies), fetal bovine serum (FBS) 5%, (Gibco life-technologies), Penicillin/Streptomycin 1% (Gibco life technologies), Hygromycin 0.6 mg/ml (Gibco life technologies), Glutarine 1 mM (Gibco life technologies)

Uptake buffer (UB): 150 mM NaCl, 10 mM Hepes-Tris, pH 7.4, 1 mM $CaCl_2$, 2.5 mM KCl, 2.5 mM $MgSO_4$, 10 mM (+) D-glucose.

Flp-in™-CHO (Invitrogen Cat No. R758-07) cells stably transfected with mGlyTlb cDNA.

Glycine Uptake Inhibition Assay (mGlyT-1b)

On day 1 mammalian cells, (Flp-in™-CHO), transfected with mGlyT-1b cDNA, were plated at the density of 40,000 cells/well in complete F-12 medium, without hygromycin in 96-well culture plates. On day 2, the medium was aspirated, and the cells were washed twice with uptake buffer (UB). The cells were then incubated for 20 min at 22° C. with either (i) no potential competitor, (ii) 10 mM non-radioactive glycine, (iii) a concentration of a potential inhibitor. A range of concentrations of the potential inhibitor was used to generate data for calculating the concentration of inhibitor resulting in 50% of the effect (e.g. $IC_{50}$, the concentration of the competitor inhibiting glycine uptake of 50%). A solution was then immediately added containing [$^3$H]-glycine 60 nM (11-16 Ci/mmol) and 25 µM non-radioactive glycine. The plates were incubated with gentle shaking, and the reaction was stopped by aspiration of the mixture and washing (three times) with ice-cold UB. The cells were lysed with scintillation liquid, shaken 3 hours, and the radioactivity in the cells was counted using a scintillation counter.

The most preferred compounds show an $IC_{50}$ (µM) at GlyT-1<0.05. Representative $IC_{50}$s are shown in the table below.

| Example | $IC_{50}$ (µM) |
| --- | --- |
| 5 | 0.042 |
| 9 | 0.031 |
| 15 | 0.021 |
| 16 | 0.048 |
| 17 | 0.012 |
| 24 | 0.019 |
| 27 | 0.022 |
| 32 | 0.037 |
| 35 | 0.028 |
| 43 | 0.034 |
| 49 | 0.034 |
| 56 | 0.016 |
| 59 | 0.036 |
| 71 | 0.049 |
| 74 | 0.031 |
| 99 | 0.042 |
| 100 | 0.045 |
| 103 | 0.046 |
| 118 | 0.038 |
| 121 | 0.047 |
| 124 | 0.03 |
| 125 | 0.03 |
| 139 | 0.014 |
| 140 | 0.036 |
| 146 | 0.047 |
| 148 | 0.032 |
| 155 | 0.044 |
| 156 | 0.047 |
| 157 | 0.025 |
| 158 | 0.024 |
| 163 | 0.045 |
| 168 | 0.033 |
| 169 | 0.003 |
| 170 | 0.048 |
| 172 | 0.03 |
| 204 | 0.019 |
| 205 | 0.046 |
| 206 | 0.041 |
| 211 | 0.034 |
| 217 | 0.037 |
| 218 | 0.04 |
| 221 | 0.022 |
| 224 | 0.019 |
| 240 | 0.0456 |
| 248 | 0.026 |
| 249 | 0.022 |
| 252 | 0.033 |
| 255 | 0.017 |
| 256 | 0.032 |
| 268 | 0.028 |
| 269 | 0.014 |
| 270 | 0.035 |
| 271 | 0.029 |
| 272 | 0.034 |
| 273 | 0.047 |
| 283 | 0.016 |
| 287 | 0.043 |
| 290 | 0.022 |
| 295 | 0.04 |
| 300 | 0.017 |
| 304 | 0.008 |
| 305 | 0.037 |
| 306 | 0.087 |
| 312 | 0.032 |
| 315 | 0.017 |
| 317 | 0.024 |
| 321 | 0.034 |
| 322 | 0.012 |
| 323 | 0.013 |
| 324 | 0.045 |
| 330 | 0.02 |
| 331 | 0.022 |
| 332 | 0.041 |
| 333 | 0.047 |
| 334 | 0.02 |
| 335 | 0.031 |
| 337 | 0.022 |

-continued

| Example | IC$_{50}$ (μM) |
|---------|----------------|
| 340 | 0.025 |
| 344 | 0.02 |
| 345 | 0.034 |
| 347 | 0.043 |
| 356 | 0.013 |
| 357 | 0.03 |
| 359 | 0.01 |
| 360 | 0.022 |
| 361 | 0.002 |
| 363 | 0.004 |
| 364 | 0.005 |
| 365 | 0.033 |
| 366 | 0.002 |
| 367 | 0.0015 |
| 368 | 0.005 |
| 370 | 0.047 |
| 371 | 0.006 |
| 372 | 0.004 |
| 373 | 0.015 |
| 374 | 0.003 |
| 375 | 0.015 |
| 376 | 0.016 |
| 377 | 0.007 |
| 378 | 0.035 |
| 379 | 0.007 |
| 380 | 0.005 |
| 382 | 0.024 |

The present invention also provides pharmaceutical compositions containing compounds of the invention, for example compounds of formula I and their pharmaceutically acceptable acid addition salts, and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions moreover can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts thereof and, if desired, one or more other therapeutically valuable substances into a galenical administration form together with one or more therapeutically inert carriers.

Compounds of formula I are good inhibitors of the glycine transporter 1 (GlyT-1), and have good selectivity to glycine transporter 2 (GlyT-2) inhibitors. The invention further provides methods for the treatment of diseases related to activation of NMDA receptors via GlyT-1 inhibition, such as psychoses, dysfunction in memory and learning, schizophrenia, dementia and other diseases in which cognitive processes are impaired, such as attention deficit disorders or Alzheimer's disease. In particular, the present invention provides a method for treating schizophrenia, which comprises administering a therapeutically effective amount of a compound of formula I or a pharmaceutically acceptable salt thereof. The invention also provides a method of treating cognitive impairment, which comprises administering a therapeutically effective amount of a compound of formula I or a pharmaceutically acceptable salt thereof. The invention further provides a method for the treatment of Alzheimer's disease, which comprises administering a therapeutically effective amount of a compound of formula I or a pharmaceutically acceptable salt thereof.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The following examples illustrate the invention but are not intended to limit its scope. The following abbreviations were used in the examples:

n-Boc-piperazine: tert-Butyl 1-piperazinecarboxylate,
Oxone®: (potassium peroxymonosulfate) 2 $KHSO_5 \cdot KHSO_4 \cdot K_2SO_4$,
TBTU: 2-(1H-benzotriazole-1-yl)-1,1,3,3-tetramethyluroniumtetrafluoroborate;

Preparation of Intermediates

EXAMPLE A1

6-Chloro-2,3-dihydro-1H-isoindol-5-ylamine

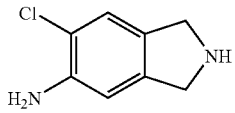

To 25.4 mmol 5-amino-6-chloroisoindoline-1,3-dione (commercial, CAS: 5566-48-3) was added 127 mmol borane-THF complex and the resulting mixture was stirred at 80° C. for 16 h. The reaction mixture was then cooled to room temperature and quenched by dropwise addition of 50 ml methanol. After stirring at room temperature for 30 min, 50 ml concentrated hydrochloric acid was added and the resulting mixture was stirred at 80° C. for 30 min before being cooled to room temperature and concentrated in vacuo. The residue was made basic by addition of concentrated aqueous sodium hydroxide. The resulting crystals were collected by filtration, washed sequentially with water, a small amount of acetone, and a small amount of ether, and then dried in vacuo to yield the title compound as an off-white solid. MS (m/e): 171.1 ($\{^{37}Cl\}$M+H+, 40%), 169.2 ($\{^{35}Cl\}$M+H+, 100%).

EXAMPLE A2

3-Bromo-6,7-dihydro-5H-pyrrolo[3,4-b]pyridine a) 5-Bromo-2,3-bis-bromomethyl-pyridine

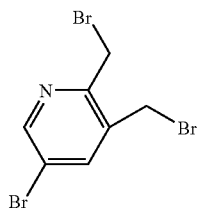

A mixture of 2.8 mmol 5-Bromo-2,3-dimethyl-pyridine (CAS: 27063-90-7), 5.61 mmol N-bromosuccinimide and 0.06 mmol AIBN in 5 ml tetrachloromethane was refluxed for 4 hours. The mixture was then cooled to RT, filtered and the filtrate was concentrated in vacuo to provide the title compound as yellow oil which was used in the next reaction without further purification.

b) 3-Bromo-6-trityl-6,7-dihydro-5H-pyrrolo[3,4-b]pyridine

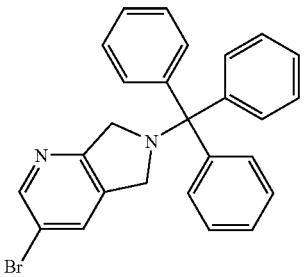

A mixture of 0.87 mmol 5-Bromo-2,3-bis-bromomethyl-pyridine, 1.1 mmol tritylamine, and 2.61 mmol DIPEA in 3 ml DMF was stirred at 60° C. for 2 h. The reaction mixture was evaporated in vacuo. The residue was taken in water and extracted with ethylacetate. The combined organic phases were washed with water, dried over sodium sulfate, filtered and concentrated in vacuo. The residue was purified by chromatography (SiO$_2$, heptane/dichloromethane) to yield the title compound as a light brown solid. MS (m/e): 243.4 (tritylion, 100%)

(c) 3-Bromo-6,7-dihydro-5H-pyrrolo[3,4-b]pyridine

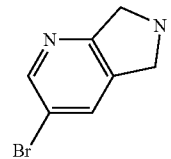

To a 0° C. solution of 0.18 mmol 3-bromo-6-trityl-6,7-dihydro-5H-pyrrolo[3,4-b]pyridine in 0.5 ml chloroform and 0.5 ml methanol was added dropwise 1 ml trifluoroacetic acid. After 5 minutes stirring at 0° C. and 30 minutes at RT, the reaction mixture was concentrated. The residue was taken in water/ether and 1 ml 1N HCl was added. The aqueous phase was extracted with ether (2 times), then basified with 5N NaOH and extracted with dichloromethane (3 times). Combined organic phases were dried over sodium sulfate, filtered and concentrated in vacuo to yield the title compound as a light yellow solid. MS (m/e): 199.0 (M+, 100%)

EXAMPLE A3

5-Chloro-6-pyrrolidin-1-yl-2,3-dihydro-1H-isoindole-hydrochloride (a) 5-Chloro-6-iodo-isoindole-1,3-dione

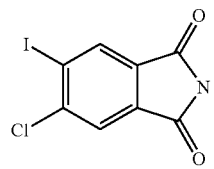

To a stirred suspension of 96.1 mmol 5-amino-6-chloroisoindoline-1,3-dione (commercial, CAS: 5566-48-3) in 170 ml water was added dropwise at 10° C. a solution of 11 ml concentrated sulfuric acid in 50 ml water. After cooling the mixture to 5° C., a solution of 120 mmol sodium nitrite in 40 ml water was added dropwise and stirring continued at 0° C. for 90 min. A solution of 327 mmol potassium iodide in 80 ml water was then added dropwise over 40 min while maintaining the reaction temperature between 0 and 5° C. The reaction mixture was then warmed to room temperature and subsequently heated at 35° C. for 45 min and then 60° C. for 30 min before being recooled to room temperature and diluted with tetrahydrofuran/ethyl acetate (1/2). The phases were separated and the organic phase washed sequentially with aqueous sodium thiosulphite and brine and then dried over sodium sulfate and concentrated in vacuo. The residue was resuspended in 300 ml dichloromethane, stirred for 10 min at room temperature, and the resulting crystals collected by filtration to yield the title compound as a light brown solid. MS (m/e): 308.9 ({$^{37}$Cl}M$^+$, 35%), 306.9 ({$^{35}$Cl}M$^+$, 100%).

(b) 5-Chloro-6-iodo-2,3-dihydro-1H-isoindole

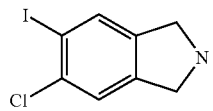

Prepared in analogy to Example A1 from 5-chloro-6-iodo-isoindole-1,3-dione and borane-THF complex. Off-white solid. MS (m/e): 282.0 ({$^{37}$Cl}M+H$^+$, 35%), 279.9 ({$^{35}$Cl}M+H$^+$, 100%).

(c) 5-Chloro-6-iodo-1,3-dihydro-isoindole-2-carboxylic acid tert-butyl ester

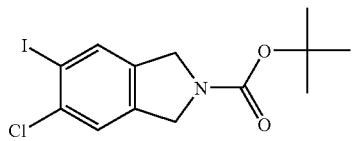

To a stirred suspension of 10.4 mmol 5-chloro-6-iodo-2,3-dihydro-1H-isoindole in 30 ml dichloromethane was added 12.5 ml (Boc)$_2$O and the mixture stirred at room temperature for 16 h. The resulting solution was concentrated in vacuo and the residue purified by chromatography (SiO$_2$, heptane/ethyl acetate) to yield the title compound as an off-white solid. MS (m/e): 326.0 ({$^{37}$Cl}[M+H− Me$_2$C═CH$_2$]$^+$, 35%), 324.0 ({$^{35}$Cl}[M+H− Me$_2$C═CH$_2$]$^+$, 100%).

(d) 5-Chloro-6-pyrrolidin-1-yl-1,3-dihydro-isoindole-2-carboxylic acid tert-butyl ester

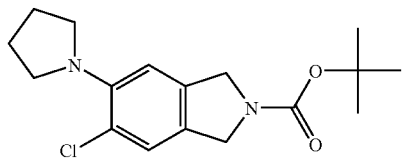

Lit. *J. Am. Chem. Soc.* 1996, 118 (30), 7215-7218. To a stirred suspension of 2.63 mmol 5-chloro-6-iodo-1,3-dihydro-isoindole-2-carboxylic acid tert-butyl ester in 20 ml toluene were added 0.24 mmol 2-(dicyclohexylphosphino)biphenyl, 0.08 mmol tris(dibenzylidene-acetone)dipalladium chloroform complex and 3.68 mmol sodium tert-butoxide and the mixture was stirred at 110° C. for 2 h. The reaction mixture was then cooled to room temperature, diluted with ethyl acetate and washed twice with brine. The organic phase was dried over sodium sulfate and concentrated in vacuo. The residue was purified by chromatography (SiO$_2$, heptane/ethyl acetate) to yield the title compound as a yellow oil. MS (m/e): 325.2 ({$^{37}$Cl}M+H$^+$, 35%), 323.2 ({$^{35}$Cl}M+H$^+$, 100%).

(e) 5-Chloro-6-pyrrolidin-1-yl-2,3-dihydro-1H-isoindole-hydrochloride

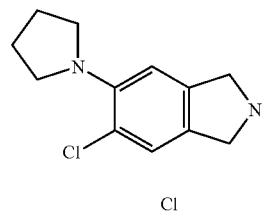

To a stirred suspension of 0.12 mmol 5-chloro-6-pyrrolidin-1-yl-1,3-dihydro-isoindole-2-carboxylic acid tert-butyl ester in 1 ml dioxane was added 1.86 mmol hydrogen chloride solution (4 M in dioxane) and the mixture was stirred at 90° C. for 2 h. The reaction mixture was then concentrated in vacuo to yield the title compound as a brown solid which was used in the next step without further purification. MS (m/e): 325.2 ({$^{37}$Cl}M+H$^+$, 35%), 323.2 ({$^{35}$Cl}M+H$^+$, 100%).

EXAMPLE A4

5-Chloro-6-methyl-2,3-dihydro-1H-isoindole hydrochloride (a) 5-Chloro-6-methyl-1,3-dihydro-isoindole-2-carboxylic acid tert-butyl ester

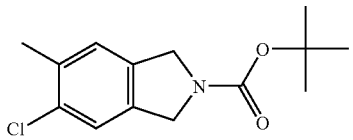

Lit. *Tetrahedron Lett.* 1999, 40, 2719-2722. To a stirred suspension of 1.58 mmol 5-chloro-6-iodo-1,3-dihydro-isoindole-2-carboxylic acid tert-butyl ester (Example A3(c)) in 3 ml N-methylpyrolidone were added 0.05 mmol tris(dibenzylideneacetone)dipalladium chloroform complex and 0.32 mmol triphenylphosphine and the mixture was stirred at 50° C. for 10 min. 0.16 mmol copper(I) iodide was then added and the mixture stirred at 50° C. for a further 10 min. Finally, 3.48 mmol tetramethyl tin was added and the reaction mixture was stirred at 80° C. for 16 h. The mixture was then cooled to room temperature, diluted with ethyl acetate and washed twice with brine. The organic phase was dried over sodium sulfate and concentrated in vacuo. The residue was purified by chromatography (SiO$_2$, heptane/ethyl acetate) to yield the title compound as a yellow solid. MS (m/e): 214.1 ($\{^{37}Cl\}$[M+H– Me$_2$C=CH$_2$]$^+$, 35%), 212.0 ($\{^{35}Cl\}$[M+H– Me$_2$C=CH$_2$]$^+$, 100%).

(b) 5-Chloro-6-methyl-2,3-dihydro-1H-isoindole hydrochloride

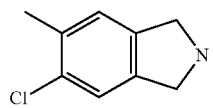

Prepared in analogy to Example A3(e) from 5-chloro-6-methyl-1,3-dihydro-isoindole-2-carboxylic acid tert-butyl ester and HCl. Grey solid. MS (m/e): 170.1 ($\{^{37}Cl\}$M+H$^+$, 35%), 168.3 ($\{^{35}Cl\}$M+H$^+$, 100%).

EXAMPLE A5

5-Chloro-6-ethylsulfanyl-2,3-dihydro-1H-isoindole hydrochloride (a) 5-Chloro-6-ethylsulfanyl-1,3-dihydro-isoindole-2-carboxylic acid tert-butyl ester

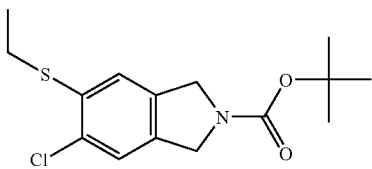

Lit. *Org. Lett.* 2002, 4(20), 3517-3520. To a stirred suspension of 0.66 mmol 5-chloro-6-iodo-1,3-dihydro-isoindole-2-carboxylic acid tert-butyl ester (Example A3(c)) in 5 ml isopropanol were added 1.32 mmol ethylene glycol, 0.07 mmol copper(I) iodide, 1.32 mmol cesium carbonate, 0.13 mmol 1,20-phenanthroline and 3.29 mmol ethyl mercaptan and the reaction mixture was stirred at 120° C. for 1 h. The mixture was then cooled to room temperature and concentrated in vacuo. The residue was purified by chromatography (SiO$_2$, heptane/ethyl acetate) to yield the title compound as a white solid. MS (m/e): 260.0 ($\{^{37}Cl\}$[M+H– Me$_2$C=CH$_2$]$^+$, 42%), 258.1 ($\{^{35}Cl\}$[M+H– Me$_2$C=CH$_2$]$^+$, 100%).

(b) 5-Chloro-6-ethylsulfanyl-2,3-dihydro-1H-isoindole hydrochloride

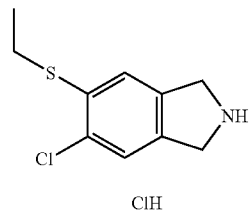

Prepared in analogy to Example A3(e) from 5-Chloro-6-ethylsulfanyl-1,3-dihydro-isoindole-2-carboxylic acid tert-butyl ester and HCl. Off-white solid. MS (m/e): 216.2 ($\{^{37}Cl\}$M+H$^+$, 42%), 214.2 ($\{^{35}Cl\}$M+H$^+$, 100%).

EXAMPLE A6

5-Chloro-6-methoxy-2,3-dihydro-1H-isoindole hydrochloride (a) 5-Chloro-6-methoxy-1,3-dihydro-isoindole-2-carboxylic acid tert-butyl ester

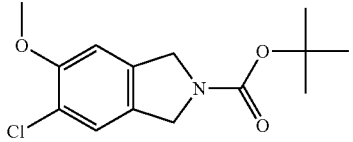

Lit. *Org. Lett.* 2002, 4(6), 973-976. To a stirred suspension of 1.84 mmol 5-chloro-6-iodo-1,3-dihydro-isoindole-2-carboxylic acid tert-butyl ester (Example A3(c)) in 7 ml methanol were added 0.18 mmol copper(I) iodide, 3.69 mmol cesium carbonate and 0.37 mmol 1,20-phenanthroline and the reaction mixture was stirred at 140° C. for 16 h. The mixture was then cooled to room temperature and concentrated in vacuo. The residue was purified by chromatography (SiO$_2$, heptane/ethyl acetate) to yield the title compound as a light red solid. MS (m/e): 230.2 ($\{^{37}Cl\}$[M+H– Me$_2$C=CH$_2$]$^+$, 42%), 228.2 ($\{^{35}Cl\}$[M+H– Me$_2$C=CH$_2$]$^+$, 100%).

(b) 5-Chloro-6-methoxy-2,3-dihydro-1H-isoindole hydrochloride

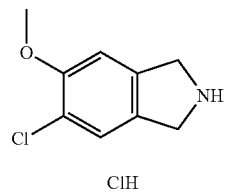

Prepared in analogy to Example A3(e) from 5-chloro-6-methoxy-1,3-dihydro-isoindole-2-carboxylic acid tert-butyl ester and HCl. Off-white solid. MS (m/e): 186.1 ($\{^{37}Cl\}$M+H$^+$, 30%), 184.1 ($\{^{35}Cl\}$M+H$^+$, 100%).

EXAMPLE A7

5-Chloro-6-ethanesulfonyl-2,3-dihydro-1H-isoindole hydrochloride (a) 5-Chloro-6-ethanesulfonyl-1,3-dihydro-isoindole-2-carboxylic acid tert-butyl ester

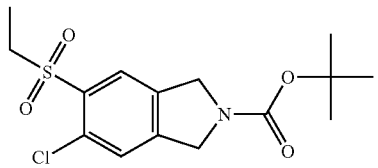

To a stirred solution of 0.61 mmol 5-chloro-6-ethylsulfanyl-1,3-dihydro-isoindole-2-carboxylic acid tert-butyl ester (Example A5(a)) in 5 ml dichloromethane was added 1.51 mmol 3-chloroperoxybenzoic acid and the reaction mixture was stirred at 50° C. for 90 min. The mixture was then cooled to room temperature, diluted with dichloromethane and washed sequentially with aq. sodium carbonate solution and with water. The organic phase was dried over sodium sulfate and concentrated in vacuo to yield the title compound as a yellow oil which was used in the next step without further purification. MS (m/e): 292.0 ($\{^{37}Cl\}[M+H-Me_2C=CH_2]^+$, 44%), 290.0 ($\{^{35}Cl\}[M+H-Me_2C=CH_2]^+$, 100%).

(b) 5-Chloro-6-ethanesulfonyl-2,3-dihydro-1H-isoindole hydrochloride

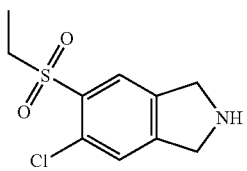

Prepared in analogy to Example A3(e) from 5-chloro-6-ethanesulfonyl-1,3-dihydro-isoindole-2-carboxylic acid tert-butyl ester and HCl. Grey solid. MS (m/e): 248.1 ($\{^{37}Cl\}M+H^+$, 30%), 246.2 ($\{^{35}Cl\}M+H^+$, 100%).

EXAMPLE A8

2-Chloro-6,7-dihydro-5H-pyrrolo[3,4-b]pyridine (a) 2-Chloro-6-trityl-6,7-dihydro-5H-pyrrolo[3,4-b]pyridine

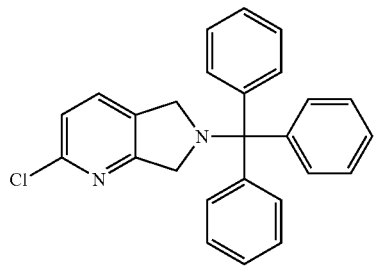

Prepared in analogy to Example A2(b) from 6-chloro-2,3-bis-chloromethyl-pyridine (CAS: 220001-94-5) and triphenylmethylamine. Light yellow foam. MS (m/e): 397.0 ([MH$^+$, 100%).

(b) 2-Chloro-6,7-dihydro-5H-pyrrolo[3,4-b]pyridine

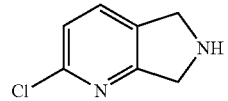

Prepared in analogy to Example A2(c) from 2-chloro-6-trityl-6,7-dihydro-5H-pyrrolo[3,4-b]pyridine and trifluoroacetic acid. Light brown solid. MS (m/e): 154.9 ([M$^+$, 100%).

EXAMPLE A9

2,3-Dihydro-1H-isoindole-4-carbonitrile (a) 2-Trityl-2,3-dihydro-1H-isoindole-4-carbonitrile

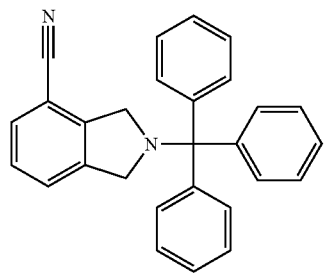

Prepared in analogy to Example A2(b) from 2,3-Bis-bromomethyl-benzonitrile (CAS: 66126-18-9) and triphenylmethylamine. Yellow foam.

(b) 2,3-Dihydro-1H-isoindole-4-carbonitrile

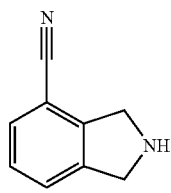

Prepared in analogy to Example A2(c) from 2-trityl-2,3-dihydro-1H-isoindole-4-carbonitrile and trifluoroacetic acid. Light brown solid.

EXAMPLE A10

5-Pyrrolidin-1-yl-2,3-dihydro-1H-isoindole (a) 5-Pyrrolidin-1-yl-1,3-dihydro-isoindole-2-carboxylic acid tert-butyl ester

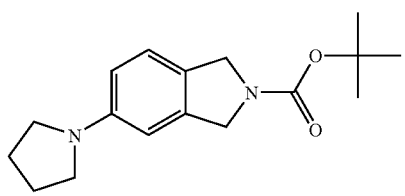

Prepared in analogy to Example A3(d) from 5-Bromo-1,3-dihydro-isoindole-2-carboxylic acid tert-butyl ester (CAS: 201940-08-1) and pyrrolidine. Orange solid. MS (m/e): 289.2 (M+H$^+$, 100%).

(b) 5-Pyrrolidin-1-yl-2,3-dihydro-1H-isoindole

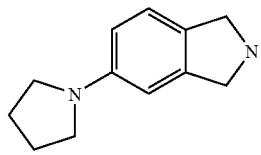

Prepared in analogy to Example A3(e) from 5-Pyrrolidin-1-yl-1,3-dihydro-isoindole-2-carboxylic acid tert-butyl ester and HCl. Brown oil. MS (m/e): 189.6 (M+H$^+$, 100%).

EXAMPLE A11

5-Ethylsulfanyl-2,3-dihydro-1H-isoindole hydrochloride (a) 5-Ethylsulfanyl-1,3-dihydro-isoindole-2-carboxylic acid tert-butyl ester

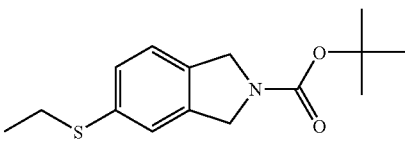

Lit. *Tetrahedron* 2004, 60, 7397-7403. To a stirred suspension of 1.34 mmol 5-bromo-1,3-dihydro-isoindole-2-carboxylic acid tert-butyl ester (CAS: 201940-08-1) in 2 ml dioxane were added 0.03 mmol 1,1'-bis(diisopropylphosphino)ferrocene, 0.03 mmol palladium acetate, 1.61 mmol sodium tert-butoxide and 2.68 mmol ethanethiol and the mixture was stirred at 100° C. for 16 h. The reaction mixture was then cooled to room temperature, diluted with ethyl acetate/tetrahydrofuran and washed with brine. The organic phase was dried over sodium sulfate and concentrated in vacuo to yield the title compound as a brown oil which was used in the next step without further purification.

(b) 5-Ethylsulfanyl-2,3-dihydro-1H-isoindole hydrochloride

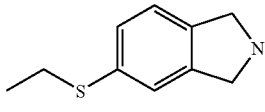

Prepared in analogy to Example A3(e) from 5-Ethylsulfanyl-1,3-dihydro-isoindole-2-carboxylic acid tert-butyl ester and HCl. Light Brown solid. MS (m/e): 216.3 ([M+H$^+$, 100%).

EXAMPLE A12

5-Chloro-6-fluoro-2,3-dihydro-1H-isoindole (a) 1,2-Bis-bromomethyl-4-chloro-5-fluoro-benzene

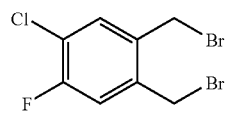

Prepared in analogy to Example A2(a) from 1-Chloro-2-fluoro-4,5-dimethyl-benzene (CAS: 116850-30-7) and NBS. Brown oil.

(b) 5-chloro-6-fluoro-2-trityl-2,3-dihydro-1H-isoindole

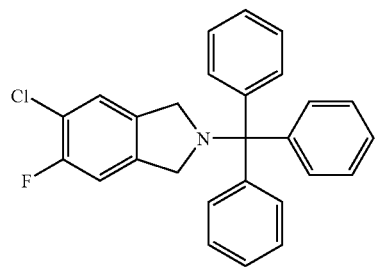

Prepared in analogy to Example A2(b) from 1,2-Bis-bromomethyl-4-chloro-5-fluoro-benzene and triphenylmethylamine. Brown oil.

(c) 5-Chloro-6-fluoro-2,3-dihydro-1H-isoindole

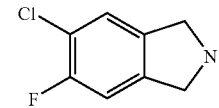

Prepared in analogy to Example A2(c) from 5-chloro-6-fluoro-2-trityl-2,3-dihydro-1H-isoindole and trifluoroacetic acid. Light brown solid.

EXAMPLE A13

6-Trifluoromethyl-2,3-dihydro-1H-pyrrolo[3,4-c]pyridine (a) 4,5-Bis-chloromethyl-2-trifluoromethyl-pyridine

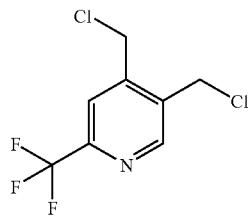

To a room temperature suspension of 2.5 mmol (5-Hydroxymethyl-2-trifluoromethyl-pyridin-4-yl)-methanol (CAS: 765298-25-7) in 3 ml dichloromethane was added dropwise 12.5 mmol thionylchloride. After 1 hour, the reaction mixture was evaporated in vacuo. The residue was dissolved in dichloromethane and washed with saturated sodium bicarbonate solution, dried over sodium sulfate, filtered and concentrated in vacuo. The residue was purified by chromatography ($SiO_2$, heptane/ethyl acetate) to yield the title compound as a light yellow oil (66% yield). MS (m/e): 243.0 (M−H, 100%)

(b) 6-Trifluoromethyl-2-trityl-2,3-dihydro-1H-pyrrolo[3,4-c]pyridine

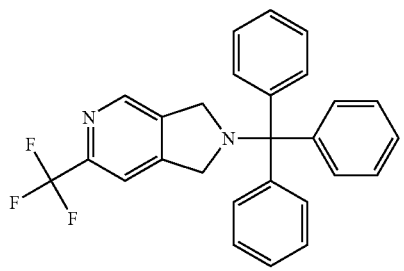

Prepared in analogy to Example A2(b) from 4,5-Bis-chloromethyl-2-trifluoromethyl-pyridine and triphenylmethylamine. White solid.

(c) 6-Trifluoromethyl-2,3-dihydro-1H-pyrrolo[3,4-c]pyridine

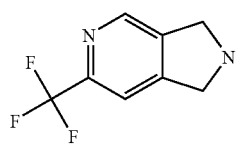

Prepared in analogy to Example A2(c) from 6-Trifluoromethyl-2-trityl-2,3-dihydro-1H-pyrrolo[3,4-c]pyridine and trifluoroacetic acid. Off white solid.

EXAMPLE A14

2-Trifluoromethyl-6,7-dihydro-5H-pyrrolo[3,4-b]pyridine (a) 6-Trifluoromethyl-pyridine-2,3-dicarboxylic acid dimethyl ester

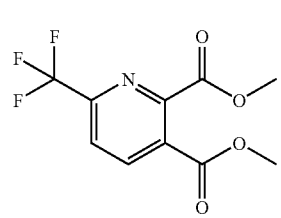

A mixture of 245 mmol periodic acid and 1.1 mmol ruthenium trichloride hydrate in 40 ml acetonitrile and 40 ml carbon tetrachloride was stirred at room temperature for 10 minutes. 17 mmol of 2-trifluoromethyl-quinoline (CAS: 1701-38-8), was added portionwise during 2.5 hours. The temperature was kept below 45° C. by occasional cooling with an ice-bath. After addition, the reaction mixture was cooled to 0° C. and extracted 3 times with ethyl acetate, dried over magnesium sulfate, filtered and concentrated. The residue was dissolved in 65 ml N,N-dimethylformamide. 48 mmol of cesium carbonate was added, followed by 97 mmol of methyl iodide. After stirring at room temperature overnight, the reaction mixture is diluted with water and extracted with ethyl acetate. The crude compound obtained after concentration is purified by chromatography ($SiO_2$; ethyl acetate/n-heptane 1:4) to give the title compound as a yellow liquid. Yield: 37%. MS (m/e): 264.0 (MH+, 44%).

(b) (3-Hydroxymethyl-6-trifluoromethyl-pyridin-2-yl)-methanol

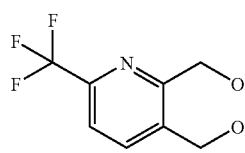

A solution of 6 mmol 6-trifluoromethyl-pyridine-2,3-dicarboxylic acid dimethyl ester in 10 ml methanol was cooled to 0° C. 12 mmol of sodium borohydride and 6 mmol of calcium chloride were added and the resulting mixture stirred overnight at room temperature. After cooling again to 0° the reaction mixture was neutralized by addition of 5 ml 3M aqueous hydrochloric acid. The mixture is concentrated, diluted with water and extracted 3 times with ethyl acetate. The crude compound is purified by chromatography ($SiO_2$; ethyl acetate/n-heptane 1:1) to give the title compound as a yellow oil. Yield: 72%. MS (m/e): 208.1 (MH+, 100%).

(c) 2-Trifluoromethyl-6-trityl-6,7-dihydro-5H-pyrrolo[3,4-b]pyridine

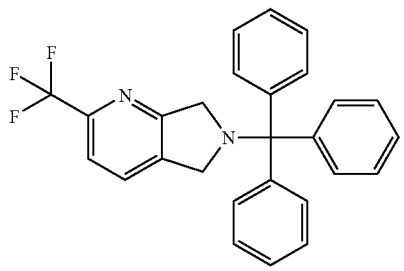

A solution of 7 mmol (3-hydroxymethyl-6-trifluoromethyl-pyridin-2-yl)-methanol in 20 ml dichloromethane was cooled to 0° C. 0.15 mmol 4-(N,N-dimethylamino)-pyridine and 15 mmol of mesyl chloride was added, followed by careful addition of 28 mmol triethyl amine. After stirring for 1 hour at 0° C., the reaction mixture was extracted with dichloromethane, dried and concentrated. The crude mesylate was dissolved in 10 ml N,N-dimethyl formamide, treated with 21 mmol DIPEA and 9 mmol triphenyl methylamine and hold overnight at 60° C. The resulting mixture was concentrated, diluted with water and extracted 3 times with ethyl acetate. The crude compound was purified by chromatography (SiO₂; ethyl acetate/n-heptane 1:4) to give the title compound as a viscous yellow oil. Yield: 37%.

(d) 2-Trifluoromethyl-6,7-dihydro-5H-pyrrolo[3,4-b]pyridine

Prepared in analogy to Example A2(c) from 2-Trifluoromethyl-6-trityl-6,7-dihydro-5H-pyrrolo[3,4-b]pyridine and trifluoroacetic acid. Light yellow solid. MS (m/e): 189.3 ([M+H]⁺, 100%).

EXAMPLE A15

6-Trifluoromethyl-2,3-dihydro-1H-isoindol-5-ylamine (a) 4-Fluoro-5-trifluoromethyl-phthalic acid

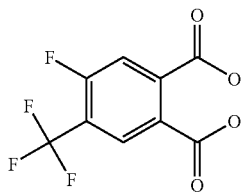

To a stirred solution of 234 mmol 1-fluoro-4,5-dimethyl-2-trifluoromethyl-benzene (CAS: 116850-000) in 14 ml glacial acetic acid was added dropwise 2.5 ml concentrated sulfuric acid. 16.4 mmol Chromium(VI) oxide was then added in small portions while the reaction mixture was cooled in an ice bath. The cooling bath was then removed and stirring continued at room temperature for 16 h. The reaction mixture was then poured onto water and the mixture extracted twice with tetrahydrofuran. The combined organic phases were washed with brine, dried over sodium sulfate, and concentrated in vacuo to yield the title compound as a grey solid which was used in the next step without further purification. MS (m/e): 250.9 ([M−H]⁻, 100%)

(b) 5-Amino-6-trifluoromethyl-isoindole-1,3-dione

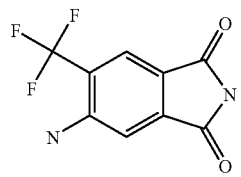

To a stirred solution of 2.14 mmol 4-fluoro-5-trifluoromethyl-phthalic acid in 7 ml N-methylpyrolidone was added 4.28 mmol urea and the mixture was at 140° C. for 2 h, and then at 160° C. for 4 h. The reaction mixture was then cooled to room temperature, diluted with ethyl acetate and washed sequentially with water and brine. The organic phase was dried over sodium sulfate and concentrated in vacuo. The residue was triturated in ether/penane (1/1) to yield the title compound as a yellow solid. MS (m/e): 229.1 ([M−H]⁻, 100%)

(c) 6-Trifluoromethyl-2,3-dihydro-1H-isoindol-5-ylamine

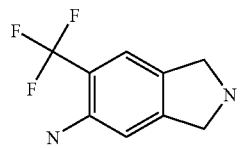

Prepared in analogy to Example A1 from 5-amino-6-trifluoromethyl-isoindole-1,3-dione and borane tetrahydrofuran complex. Yellow solid. MS (m/e): 203.3 ([M+H⁺, 100%).

EXAMPLE A16

3-Trifluoromethyl-6,7-dihydro-5H-pyrrolo[3,4-b]pyridine (a) (3-Hydroxymethyl-5-trifluoromethyl-pyridin-2-yl)-methanol

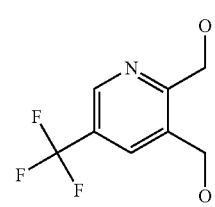

To a room temperature suspension of 9.06 mmol 3-Trifluoromethyl-5H-furo[3,4-b]pyridin-7-onel (CAS: 765298-32-6) in 40 ml ethanol was added portionwise 19.9 mmol sodium borohydride. After 30 minutes, the reaction mixture was cooled to 0° C., 2N HCl was added to pH 1 and the solvent was removed in vacuo. The residue was taken in water, the mixture was neutralized with 1N NaOH and then saturated with NaCl. The aqueous phase was extracted 6 times with dichloromethane. The combined extracts were dried over sodium sulfate, filtered and concentrated in vacuo to yield the title compound as a yellow oil (92% yield). MS (m/e): 230.1 (M+Na, 100%)

(b) 2,3-Bis-chloromethyl-5-trifluoromethyl-pyridine

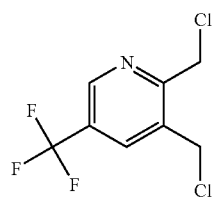

Prepared in analogy to Example A13(a) from (3-Hydroxymethyl-5-trifluoromethyl-pyridin-2-yl)-methanol and thionylchloride. Red oil. MS (m/e): 243.1 ([M−H⁺, 100%).

(c) 3-Trifluoromethyl-6-trityl-6,7-dihydro-5H-pyrrolo[3,4-b]pyridine

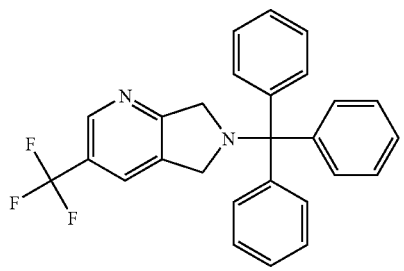

Prepared in analogy to Example A2(b) from 2,3-Bis-chloromethyl-5-trifluoromethyl-pyridine and triphenylmethylamine. White solid. MS (m/e): 431.3 ([MH⁺, 100%).

(d) 3-Trifluoromethyl-6,7-dihydro-5H-pyrrolo[3,4-b]pyridine

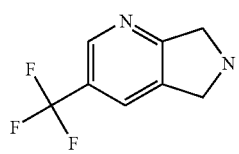

Prepared in analogy to Example A2(c) from 3-Trifluoromethyl-6-trityl-6,7-dihydro-5H-pyrrolo[3,4-b]pyridine and trifluoroacetic acid. Yellow oil. MS (m/e): 189.4 ([M+H⁺, 100%).

EXAMPLE A17

4-Fluoro-6-trifluoromethyl-2,3-dihydro-1H-isoindole (a) 3-Fluoro-N,N-diisopropyl-5-trifluoromethyl-benzamide

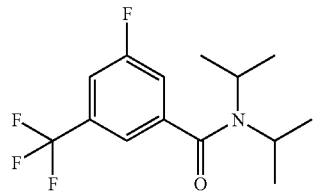

To a suspension of 15.9 mmol 3-Fluoro-5-(Trifluoromethyl) benzoic acid in 20 ml toluene containing 2 drops of DMF was added 79.7 mmol thionylchloride at 0° C. The mixture was heated at 85° C. for 5 hours. The solvent was carefully removed in vacuo. The colorless liquid was dissolved in 25 ml dichloromethane and cooled to 0° C. 63.8 mmol diisopropylamine was added dropwise. The mixture was allowed to warm to RT. After 1 hour the solvent was removed in vacuo. The residue was taken in ethyl acetate and washed twice with water. The washings were extracted once with ethyl acetate. The combined organic phases were dried over sodium sulfate, filtered and concentrated in vacuo. The residue was purified by chromatography (SiO₂, heptane/ethyl acetate) to yield the title compound as a light yellow solid (85% yield). MS (m/e): 291.9 (M⁺, 100%)

(b) 3-Fluoro-2-formyl-N,N-diisopropyl-5-trifluoromethyl-benzamide

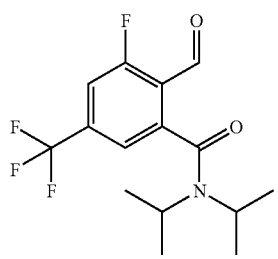

A dried 200 ml round-bottomed flask containing 20 ml diethylether was cooled to −75° C. then 22.15 mmol diisopropylamine, 22.15 mmol 1.6M n-butyllithium in hexane, and a solution of 14.77 mmol 3-fluoro-N,N-diisopropyl-5-trifluoromethyl-benzamide in 20 ml diethylether were added sequentially. The mixture was stirred at −75° C. for 2 hours. 2.9 ml DMF was added dropwise. After the reaction was stirred for another hour, the mixture was warmed and stirred at room temperature for 30 minutes. The mixture was quenched with 100 ml 10% citric acid and extracted 3 times with ether. The combined organic phases were dried over sodium sulfate, filtered and concentrated in vacuo. The residue was purified by chromatography (SiO₂, heptane/ethyl acetate) to yield the title compound as a light yellow solid (90% yield). MS (m/e): 320.1 (M+H$^+$, 100%)

(c) 4-Fluoro-6-trifluoromethyl-3H-isobenzofuran-1-one

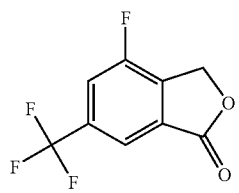

To a solution of 5.39 mmol 3-fluoro-2-formyl-N,N-diisopropyl-5-trifluoromethyl-benzamide in 17 ml ethanol was added portionwise 5.39 mmol sodium borohydride. The temperature was maintained at 30° C. with a water bath. The mixture was then stirred at room temperature for 50 minutes then cooled in an ice-water bath. Excess sodium borohydride was destroyed by adding HCl 2N. Ethanol was removed in vacuo. The residue was taken in 25 ml HCl 6N and refluxed at 120° C. for 2 hours. The mixture was cooled to room temperature and extracted 3 times with dichloromethane. The combined organic phases were dried over sodium sulfate, filtered and concentrated in vacuo. The residue was purified by chromatography (SiO$_2$, heptane/ethyl acetate) to yield the title compound as a white solid (71% yield). MS (m/e): 220.2 (M$^+$, 100%)

(d) (2-Fluoro-6-hydroxymethyl-4-trifluoromethyl-phenyl)-methanol

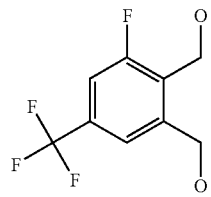

Prepared in analogy to Example A16(a) from 4-Fluoro-6-trifluoromethyl-3H-isobenzofuran-1-one e and sodium borohydride. Colorless oil. MS (m/e): 225.1 ([M+H$^+$, 100%).

(e) 4-Fluoro-6-trifluoromethyl-2-trityl-2,3-dihydro-1H-isoindole

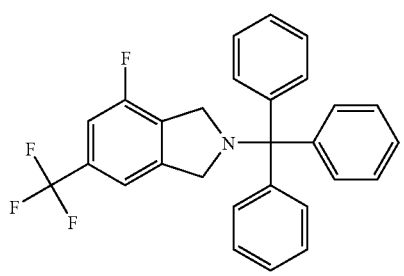

Prepared in analogy to Example A14(c) from (2-Fluoro-6-hydroxymethyl-4-trifluoromethyl-phenyl)-methanol. Yellow oil.

(f) 4-Fluoro-6-trifluoromethyl-2,3-dihydro-1H-isoindole

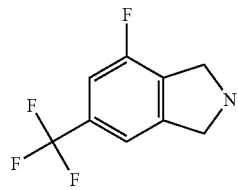

Prepared in analogy to Example A2(c) from 4-Fluoro-6-trifluoromethyl-2-trityl-2,3-dihydro-1H-isoindole and trifluoroacetic acid. Yellow oil. MS (m/e): 206.1 ([M+H$^+$, 100%).

EXAMPLE A18

5-Trifluoromethoxy-2,3-dihydro-1H-isoindole (a) N,N-Diisopropyl-4-trifluoromethoxy-benzamide

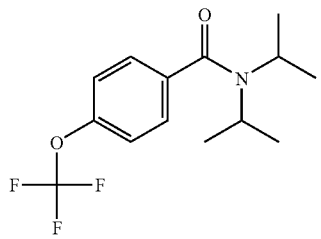

Prepared in analogy to Example A17(a) from 4-(trifuoromethoxy)-benzoic acid. Yellow oil. MS (m/e): 290.2 ([M+H]$^+$, 100%)

(b) 2-Formyl-N,N-diisopropyl-4-trifluoromethoxy-benzamide

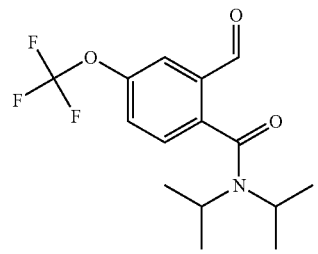

Prepared in analogy to Example A17(b) from N,N-Diisopropyl-4-trifluoromethoxy-benzamide. Yellow oil. MS (m/e): 318.1 ([M+H]$^+$, 100%)

(c) 5-Trifluoromethoxy-3H-isobenzofuran-1-one

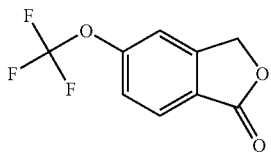

Prepared in analogy to Example A17(c) from 2-Formyl-N,N-diisopropyl-4-trifluoromethoxy-benzamide. White needle. MS (m/e): 219.1 ([M+H]$^+$, 100%)

(d) (2-Hydroxymethyl-5-trifluoromethoxy-phenyl)-methanol

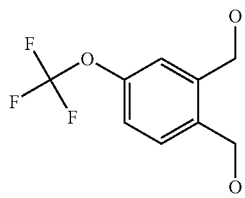

Prepared in analogy to Example A16(a) from 5-Trifluoromethoxy-3H-isobenzofuran-1-one. Colorless oil.

(e) 5-Trifluoromethoxy-2-trityl-2,3-dihydro-1H-isoindole

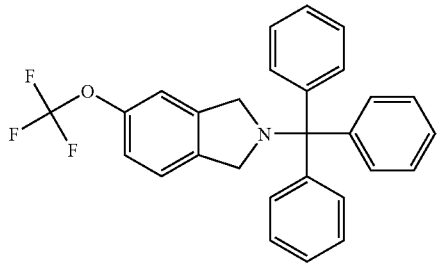

Prepared in analogy to Example A14(c) from (2-Hydroxymethyl-5-trifluoromethoxy-phenyl)-methanol. Light red oil.

(f) 5-Trifluoromethoxy-2,3-dihydro-1H-isoindole

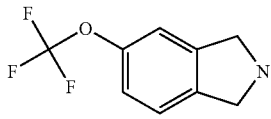

Prepared in analogy to Example A2(c) from 5-Trifluoromethoxy-2-trityl-2,3-dihydro-1H-isoindole. Dark brown oil.

EXAMPLE A19

5-difluoromethoxy-2,3-dihydro-1H-isoindoline trifluoroacetic acid (a) 5-Difluoromethoxy-1,3-dihydro-isoindole-2-carboxylic acid tert-butyl ester

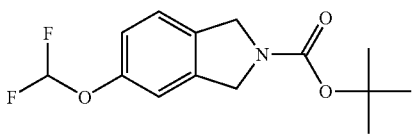

A mixture containing 0.68 mmol 5-Hydroxy-1,3-dihydro-isoindole-2-carboxylic acid tert-butyl ester (CAS: 226070-47-9), 0.68 mmol potassium carbonate and 0.68 mmol ethyl chlorodifluoroacetate in 1.5 ml DMF was stirred overnight at 65° C. The mixture was then partitioned between ethyl acetate and water and the organic phase was then separated, dried over sodium sulfate, and concentrated in vacuo. The residue was purified by chromatography on silica gel (eluant: n-heptane/ethylacetate) to afford the title compound as a white solid (40% yield).

(b) 5-difluoromethoxy-2,3-dihydro-1H-isoindoline trifluoroacetic acid

Prepared in analogy to Example A3(e) from 5-Difluoromethoxy-1,3-dihydro-isoindole-2-carboxylic acid tert-butyl ester by using trifluoroacetic acid instead of hydrochloride acid. Dark brown oil.

EXAMPLE A20

2-Methyl-3-trifluoromethyl-6,7-dihydro-5H-pyrrolo[3,4-b]pyridine (a) 6-Methyl-5-trifluoromethyl-pyridine-2-carboxylic acid diisopropylamide Prepared in analogy to Example A17(a) from 6-Methyl-5-trifluoromethyl-pyridine-2-carboxylic acid (CAS: 855916-28-8). Yellow oil. MS (m/e): 289.1 ([M+H]$^+$, 100%)

(b) 3-Formyl-6-methyl-5-trifluoromethyl-pyridine-2-carboxylic acid diisopropylamide

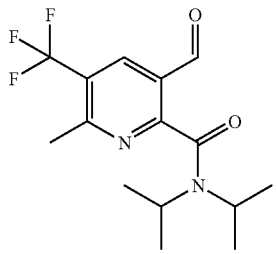

Prepared in analogy to Example A17(b) from 6-Methyl-5-trifluoromethyl-pyridine-2-carboxylic acid diisopropylamide. Yellow oil. MS (m/e): 316.9 ([M+H]$^+$, 100%).

(c) 2-Methyl-3-trifluoromethyl-5H-furo[3,4-b]pyridin-7-one

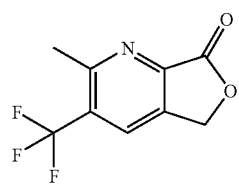

Prepared in analogy to Example A17(c) from 3-Formyl-6-methyl-5-trifluoromethyl-pyridine-2-carboxylic acid diisopropylamide. White solid. MS (m/e): 218.1 ([M+H]$^+$, 100%)

(d) (3-Hydroxymethyl-6-methyl-5-trifluoromethyl-pyridin-2-yl)-methanol

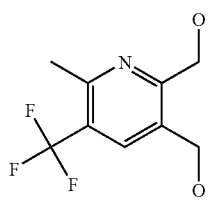

Prepared in analogy to Example A16(a) from 2-Methyl-3-trifluoromethyl-5H-furo[3,4-b]pyridin-7-one. White solid. MS (m/e): 222.1 ([M+H]$^+$, 100%)

(e) 2,3-Bis-chloromethyl-6-methyl-5-trifluoromethyl-pyridine

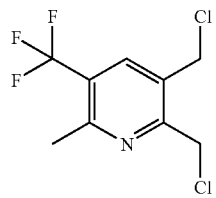

Prepared in analogy to Example A13(a) from (3-Hydroxymethyl-6-methyl-5-trifluoromethyl-pyridin-2-yl)-methanol. Colorless oil. MS (m/e): 257.0 ([M+H]$^+$, 100%)

(f) 2-Methyl-3-trifluoromethyl-6-trityl-6,7-dihydro-5H-pyrrolo[3,4-b]pyridine

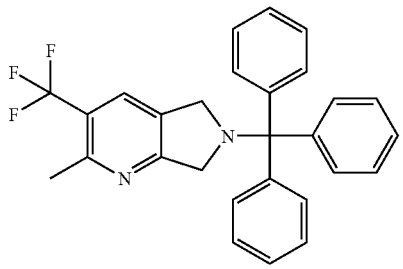

Prepared in analogy to Example A2(b) from 2,3-Bis-chloromethyl-6-methyl-5-trifluoromethyl-pyridine. Light yellow solid. MS (m/e): 445.1 ([M+H]$^+$, 100%)

(g) 2-Methyl-3-trifluoromethyl-6,7-dihydro-5H-pyrrolo[3,4-b]pyridine

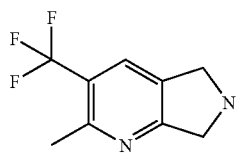

Prepared in analogy to Example A2(c) from 2-Methyl-3-trifluoromethyl-6-trityl-6,7-dihydro-5H-pyrrolo[3,4-b]pyridine. Light yellow oil. MS (m/e): 202.8 ([M+H]$^+$, 100%)

EXAMPLE A21

Rac-5-Methyl-3-trifluoromethyl-6,7-dihydro-5H-pyrrolo[3,4-b]pyridine (a) 3-Acetyl-5-trifluoromethyl-pyridine-2-carboxylic acid diisopropylamide

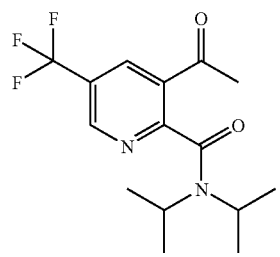

Prepared in analogy to Example A17(b) from 5-Trifluoromethyl-pyridine-2-carboxylic acid diisopropylamide (CAS: 765298-31-5) and N-methoxy-N-methylacetamide instead of dimethylformamide. Orange solid. MS (m/e): 317.1 ([M+H]$^+$, 100%)

(b) rac-5-Methyl-3-trifluoromethyl-5H-furo[3,4-b]pyridin-7-one

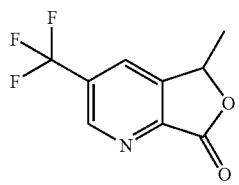

Prepared in analogy to Example A17(c) from 3-Acetyl-5-trifluoromethyl-pyridine-2-carboxylic acid diisopropylamide. White solid. MS (m/e): 217.1 ([M+H]$^+$, 100%)

(c) rac-1-(2-Hydroxymethyl-5-trifluoromethyl-pyridin-3-yl)-ethanol

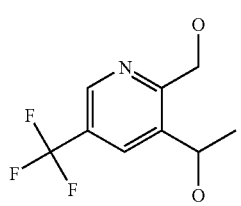

Prepared in analogy to Example A16(a) from rac-5-Methyl-3-trifluoromethyl-5H-furo[3,4-b]pyridin-7-one. Colorless oil. MS (m/e): 222.2 ([M+H]$^+$, 100%)

(d) rac-5-Methyl-3-trifluoromethyl-6-trityl-6,7-dihydro-5H-pyrrolo[3,4-b]pyridine

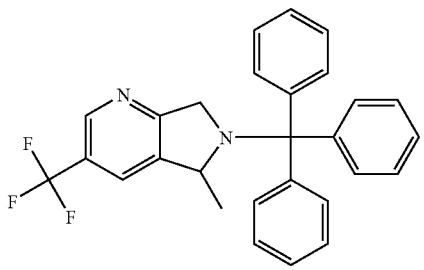

Prepared in analogy to Example A14(c) from rac-1-(2-Hydroxymethyl-5-trifluoromethyl-pyridin-3-yl)-ethanol. Yellow oil.

(e) rac-5-Methyl-3-trifluoromethyl-6,7-dihydro-5H-pyrrolo[3,4-b]pyridine

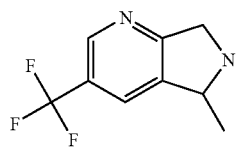

Prepared in analogy to Example A2(c) from rac-5-Methyl-3-trifluoromethyl-6-trityl-6,7-dihydro-5H-pyrrolo[3,4-b]pyridine. Yellow oil. MS (m/e): 203.3 ([M+H]$^+$, 100%).

EXAMPLE A22

6-Chloro-2,3-dihydro-1H-pyrrolo[3,4-c]pyridine (a) 6-Chloro-N,N-diisopropyl-nicotinamide

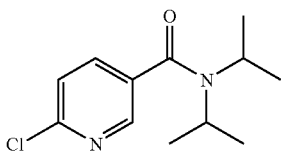

Prepared in analogy to Example A17(a) from 2-chlorpyridine-5-carboxylic acid. Yellow oil. MS (m/e): 241.3 ([M+H]$^+$, 100%).

(b) 6-Chloro-4-formyl-N,N-diisopropyl-nicotinamide

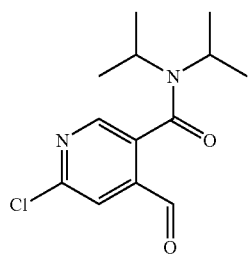

Prepared in analogy to Example A17(b) from N,N-Diisopropyl-4-trifluoromethoxy-benzamide. Yellow oil. MS (m/e): 269.2 ([M+H]$^+$, 100%).

(c) 6-Chloro-1H-furo[3,4-c]pyridin-3-one

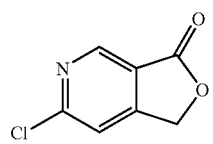

Prepared in analogy to Example A17(c) from 6-Chloro-4-formyl-N,N-diisopropyl-nicotinamide. White solid.

(d) (6-Chloro-4-hydroxymethyl-pyridin-3-yl)-methanol

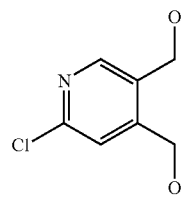

Prepared in analogy to Example A16(a) from 6-Chloro-1H-furo[3,4-c]pyridin-3-one. White solid. MS (m/e): 172.0 ([M−H], 100%).

(e) 6-Chloro-2-trityl-2,3-dihydro-1H-pyrrolo[3,4-c]pyridine

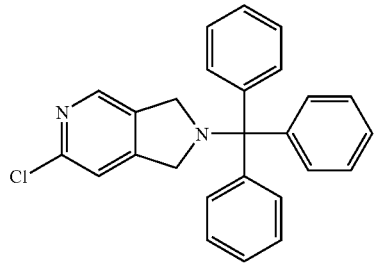

Prepared in analogy to Example A14(c) from (6-Chloro-4-hydroxymethyl-pyridin-3-yl)-methanol. White foam.

(f) 6-Chloro-2,3-dihydro-1H-pyrrolo[3,4-c]pyridine

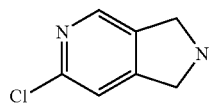

Prepared in analogy to Example A2(c) from 6-Chloro-2-trityl-2,3-dihydro-1H-pyrrolo[3,4-c]pyridine. White solid. MS (m/e): 155.1 ([M+H]$^+$, 100%)

EXAMPLE A23

5-(4-Methyl-thiazol-2-yl)-2,3-dihydro-1H-isoindole (a) 5-(4,4,5,5-Tetramethyl-[1,3,2]dioxaborolan-2-yl)-1,3-dihydro-isoindole-2-carboxylic acid tert-butyl ester

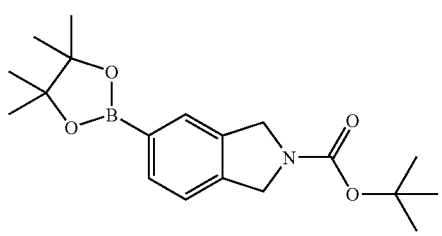

A mixture containing 5.03 mmol 5-Bromo-1,3-dihydro-isoindole-2-carboxylic acid tert-butyl ester (CAS: 201940-08-1), 16.6 mmol potassium carbonate, 5.5 mmol bis(pinacolato)diboron and 0.15 mmol 1,1-bis(diphenylphosphino)ferrocene dichloro palladium (II) dichloromethane adduct in 15 ml deglazed DMF was stirred at 70° C. for 6 hours. The solvent was removed in vacuo. The residue was stirred in 30 ml dichloromethane. The mixture was filtered and the filtrate concentrated in vacuo. The crude oil was purified on a 50 g Flashpack cartridge (Eluent: Heptane/AcOEt) to afford the title compound as a white solid (63% yield). MS (m/e): 346.1 ([M+H]$^+$, 100%)

(b) 5-(4-Methyl-thiazol-2-yl)-1,3-dihydro-isoindole-2-carboxylic acid tert-butyl ester

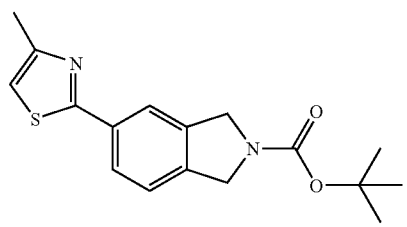

A mixture containing 3.2 mmol 5-(4,4,5,5-Tetramethyl-[1,3,2]dioxaborolan-2-yl)-1,3-dihydro-isoindole-2-carboxylic acid tert-butyl ester, 15.9 mmol potassium carbonate, 3.8 mmol 2-Iodo-4-methyl-thiazole (CAS: 34203-25-3) and 0.1 mmol tetrakistriphenylphosphine in 11 ml deglazed DMF was stirred at 90° C. for 43 hours. The solvent was removed in vacuo. The residue was taken in ethyl acetate. The mixture was washed twice with water. The aqueous layer was extracted once with ethyl acetate. The combined organic layers were dried over Na$_2$SO$_4$, filtered and the solvent was removed in vacuo. The crude oil was purified on a 50 g Flashpack cartridge (Eluent: Heptane/AcOEt) to afford the title compound as a white solid (36% yield). MS (m/e): 316.1 (M$^+$, 100%)

(c) 5-(4-Methyl-thiazol-2-yl)-2,3-dihydro-1H-isoindole

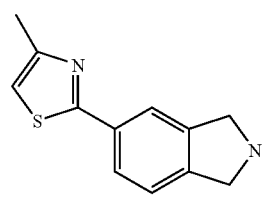

Prepared in analogy to Example A3(e) from 5-(4-Methyl-thiazol-2-yl)-1,3-dihydro-isoindole-2-carboxylic acid tert-butyl ester and using trifluoacetic acid instead of hydrochloride acid. Brown solid. MS (m/e): 217.1 ([M+H]$^+$, 100%)

EXAMPLE A24

5-(2-Methyl-pyridin-4-yl)-2,3-dihydro-1H-isoindole (a) 5-(2-Methyl-pyridin-4-yl)-1,3-dihydro-isoindole-2-carboxylic acid tert-butyl ester

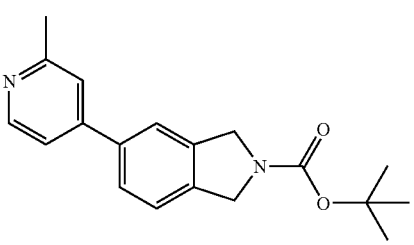

A mixture containing 1.4 mmol 5-(4,4,5,5-Tetramethyl-[1,3,2]dioxaborolan-2-yl)-1,3-dihydro-isoindole-2-carboxylic acid tert-butyl ester, 4.8 mmol potassium fluoride, 1.4 mmol 4-chloro-2-picoline (commercial) and 0.03 mmol bis(tri-tert.-butylphosphine)palladium in 5 ml deglazed dioxane was stirred at 100° C. for 1.5 hours. The solvent was removed in vacuo. The residue was taken in ethyl acetate. The mixture was washed twice with water. The aqueous layer was extracted once with ethyl acetate. The combined organic layers were dried over $Na_2SO_4$, filtered and the solvent was removed in vacuo. The crude oil was purified on a 20 g Flashpack cartridge (Eluent: Heptane/AcOEt) to afford the title compound as a yellow oil (69% yield). MS (m/e): 311.2 ([M+H]$^+$, 100%)

(b) 5-(2-Methyl-pyridin-4-yl)-2,3-dihydro-1H-isoindole

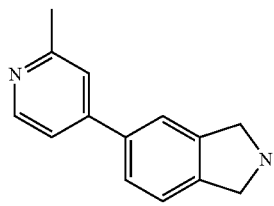

Prepared in analogy to Example A3(e) from 5-(2-Methyl-pyridin-4-yl)-1,3-dihydro-isoindole-2-carboxylic acid tert-butyl ester and using trifluoacetic acid instead of hydrochloride acid. Brown solid. MS (m/e): 211.0 ([M+H]$^+$, 100%)

EXAMPLE A25

5-(5-Methyl-thiophen-3-yl)-2,3-dihydro-1H-isoindole (a) 5-(5-Methyl-thiophen-3-yl)-1,3-dihydro-isoindole-2-carboxylic acid tert-butyl ester

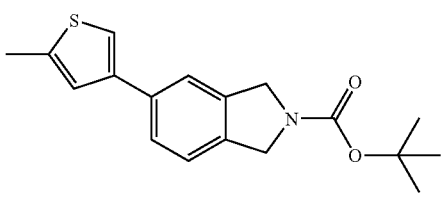

Prepared in analogy to Example A23(b) from 5-(4,4,5,5-Tetramethyl-[1,3,2]dioxaborolan-2-yl)-1,3-dihydro-isoindole-2-carboxylic acid tert-butyl ester and 4-bromo-2-methylthiophene (commercial). Light yellow solid. MS (m/e): 315.2 ([M]$^+$, 100%)

(b) 5-(5-Methyl-thiophen-3-yl)-2,3-dihydro-1H-isoindole

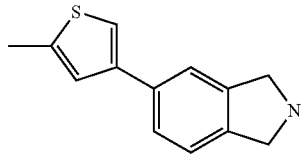

Prepared in analogy to Example A3(e) from 5-(5-Methyl-thiophen-3-yl)-1,3-dihydro-isoindole-2-carboxylic acid tert-butyl ester and using trifluoacetic acid instead of hydrochloride acid. Light yellow solid. MS (m/e): 216.1 ([M+H]$^+$, 100%)

EXAMPLE A26

5-(5-Methyl-thiazol-2-yl)-2,3-dihydro-1H-isoindole (a) 5-(5-Methyl-thiazol-2-yl)-1,3-dihydro-isoindole-2-carboxylic acid tert-butyl ester

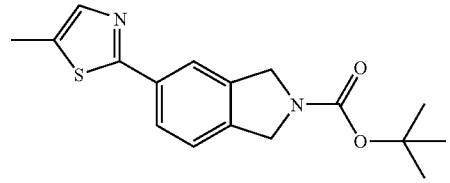

Prepared in analogy to Example A23(b) from 5-(4,4,5,5-Tetramethyl-[1,3,2]dioxaborolan-2-yl)-1,3-dihydro-isoindole-2-carboxylic acid tert-butyl ester and 2-Iodo-5-methyl-thiazole (CAS: 847547-16-4). Yellow solid. MS (m/e): 317.0 ([M]$^+$, 100%)

(b) 5-(5-Methyl-thiazol-2-yl)-2,3-dihydro-1H-isoindole

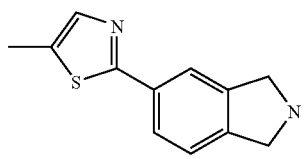

Prepared in analogy to Example A3(e) from 5-(5-Methyl-thiazol-2-yl)-1,3-dihydro-isoindole-2-carboxylic acid tert-butyl ester and using trifluoacetic acid instead of hydrochloride acid. Brown gum. MS (m/e): 217.0 ([M+H]$^+$, 100%)

EXAMPLE A27

5-Thiazol-2-yl-2,3-dihydro-1H-isoindole (a) 5-Thiazol-2-yl-1,3-dihydro-isoindole-2-carboxylic acid tert-butyl ester

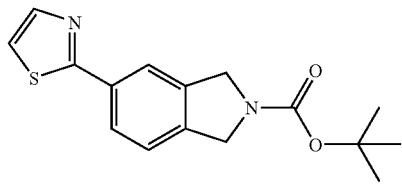

Prepared in analogy to Example A23(b) from 5-(4,4,5,5-Tetramethyl-[1,3,2]dioxaborolan-2-yl)-1,3-dihydro-isoindole-2-carboxylic acid tert-butyl ester and 2-Iodo-thiazole (CAS: 3034-54-6). Yellow oil. MS (m/e): 303.1 ([M+H]$^+$, 100%)

(b) 5-Thiazol-2-yl-2,3-dihydro-1H-isoindole

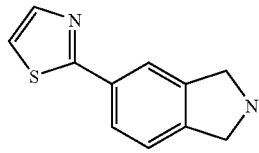

Prepared in analogy to Example A3(e) from 5-Thiazol-2-yl-1,3-dihydro-isoindole-2-carboxylic acid tert-butyl ester and using trifluoacetic acid instead of hydrochloride acid. Yellow gum. MS (m/e): 202.8 ([M+H]$^+$, 100%)

EXAMPLE A28

2-Trifluoromethyl-6,7-dihydro-5H-pyrrolo[3,4-d]pyrimidine a) 3-[1-Dimethylamino-meth-(Z)-ylidene]-4-oxo-pyrrolidine-1-carboxylic acid tert.-butyl ester

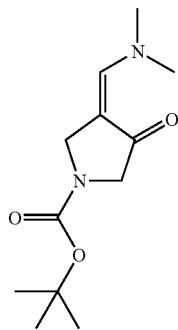

A solution of 13.5 mmol N-BOC-3-pyrrolidone and 13.5 mmol N,N-dimethylformamide-dimethylacetal in 50 ml N,N-dimethylformamide was hold overnight at 60° C. The reaction mixture was quenched by addition of 50 ml water and extracted 3 times with ethyl acetate. The extract was dried over magnesium sulfate and concentrated to give the crude title compound as a yellowish oil. Yield=90%. MS (m/e): 241.4 ([M+H]$^+$, 100%).

b) 2-Trifluoromethyl-5,7-dihydro-pyrrolo[3,4-d]pyrimidine-6-carboxylic acid tert-butyl ester A fresh solution of sodium ethanolate was prepared by dissolving 182 mg of sodium in 50 ml of ethanol. To this solution was added 7.9 mmol) 3-[1-Dimethylamino-meth-(Z)-ylidene]-4-oxo-pyrrolidine-1-carboxylic acid tert.-butyl ester and 7.9 mmol trifluoroacetamidine and the mixture refluxed overnight. The resulting solution was concentrated, hydrolysed and extracted 3 times with ethyl acetate. Chromatography (silica gel; ethyl acetate/heptane) gave the title compound in a yield of 44%. MS (m/e): 290.3 ([M+H]$^+$, 40%).

c) 2-Trifluoromethyl-6,7-dihydro-5H-pyrrolo[3,4-d]pyrimidine trifluoroacetate

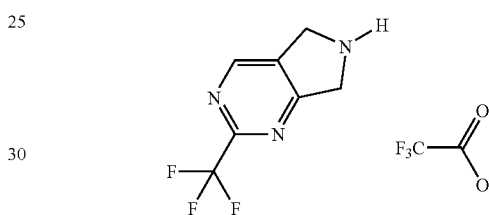

3.4 mmol of 2-Trifluoromethyl-5,7-dihydro-pyrrolo[3,4-d]pyrimidine-6-carboxylic acid tert-butyl ester was dissolved in a mixture of 20 ml dichloromethane and 3 g trifluoroacetic acid. The mixture was hold at 45° C. for 3 hours and concentrated to give the title compound as a waxy solid. Yield=100%. MS (m/e): 190.3 ([M+H]$^+$, 100%).

EXAMPLE A29

4-Trifluoromethyl-2,3-dihydro-1H-indole a) Dimethyl-[(E)-2-(2-nitro-6-trifluoromethyl-phenyl)-vinyl]-amine

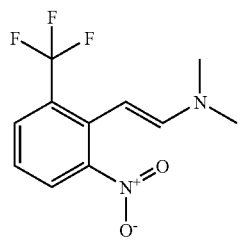

A solution of 17 mmol 2-methyl-3-nitrobenzotrifluoride and 43 mmol N,N-dimethylformamide-dimethylacetal in 30 ml N,N-dimethylformamide was held at 120° C. overnight. The reaction mixture is concentrated in vacuo to give the crude title compound. Yield=83%. MS (m/e): 261.1 ([M+H]$^+$, 90%).

b) 4-Trifluoromethyl-1H-indole

7.7 mmol Dimethyl-[(E)-2-(2-nitro-6-trifluoromethyl-phenyl)-vinyl]-amine was dissolved in 20 ml methanol. 200 mg of palladium 5% on charcoal was added and the reaction mixture hydrogenated at room temperature and atmospheric pressure. When no further hydrogen is absorbed (ca. 3 hours), the reaction mixture is filtered, concentrated and dissolved in diethyl ether. The organic phase is washed with 2 M hydrochloric acid and brine and concentrated to yield the title compound as a yellowish solid. Yield=58%. MS (m/e): 184.9 ([M+H]$^+$, 100%).

c) 4-Trifluoromethyl-2,3-dihydro-1H-indole

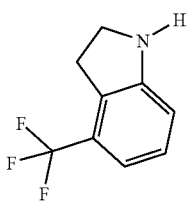

4.4 mmol of 4-trifluoromethyl-1H-indole were dissolved in 8 ml acetic acid. 8.8 mmol of sodium cyanoborohydride were added at once and the reaction mixture stirred at room temperature for 3.5 hours. 20 ml of water were added. The reaction mixture is treated with aqueous sodium hydroxide 40% until basic. Extraction with ethyl acetate yields the crude title compound as a yellowish waxy solid. Yield=76%. MS (m/e): 188.4 ([M+H]$^+$, 97%).

EXAMPLE A30

2,3-Dihydro-1H-indole-4-carbonitrile

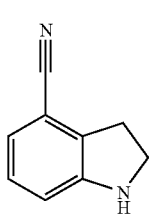

This compound was prepared in analogy to example A29c), starting from 4-cyanoindole. Yield=15%. MS (m/e): 144.1 ([M]$^+$, 53%).

EXAMPLE A31 rac-5-Chloro-3-methyl-2,3-dihydro-1H-indole

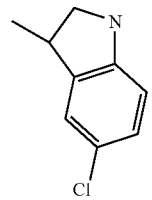

This compound was prepared in analogy to example A29c), starting from 4-methylindole. Yield=49%. MS (m/e): 133.1 ([M]$^+$, 80%).

EXAMPLE A32

2-(2,3-Dihydro-1H-indol-4-yloxy)-N,N-dimethyl-acetamide

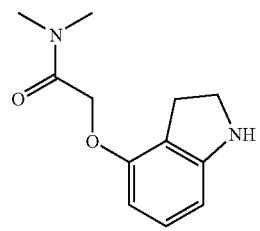

This compound was prepared in analogy to example A29c), starting from 2-(1H-Indol-4-yloxy)-N,N-dimethyl-acetamide. Yield=36%. MS (m/e): 221.1 ([M+H]$^+$, 100%).

EXAMPLE A33

4-Chloro-5-methoxy-2,3-dihydro-1H-indole

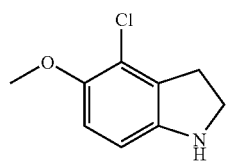

This compound was prepared in analogy to example A29c), starting from 4-Chloro-5-methoxy-2,3-dihydro-1H-indole (CA=[68935-48-8]). Yield=42%. MS (m/e): 184.1 ([M+H]$^+$, 100%).

EXAMPLE A34

(2,3-Dihydro-1H-indol-4-yl)-methanol

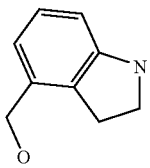

This compound was prepared in analogy to example A29c), starting from 4-formyl-indole. Yield=81%. MS (m/e): 150.3 ([M+H]$^+$, 100%).

EXAMPLE A35

5-Ethylsulfanyl-6-trifluoromethyl-2,3-dihydro-1H-isoindole hydrochloride (a) 4-Iodo-5-trifluoromethyl-phthalic acid

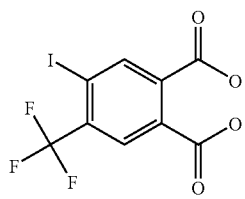

Prepared in analogy to Example A15(a) from 1-iodo-4,5-dimethyl-2-trifluoromethyl-benzene (CAS: 165323-73-9) and chromium(VI) oxide. Grey solid. MS (m/e): 359.0 ([M−H]$^-$, 100%)

(b) 5-Iodo-6-trifluoromethyl-isoindole-1,3-dione

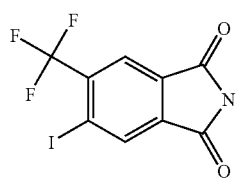

Prepared in analogy to Example A15(b) from 4-iodo-5-trifluoromethyl-phthalic acid and urea. Brown solid. MS (m/e): 339.9 ([M−H]$^-$, 100%)

(c) 5-Iodo-6-trifluoromethyl-2,3-dihydro-1H-isoindole

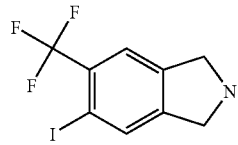

Prepared in analogy to Example A1 from 5-iodo-6-trifluoromethyl-isoindole-1,3-dione and borane tetrahydrofuran complex. Brown solid. MS (m/e): 314.0 ([M+H$^+$, 100%).

(d) 5-Iodo-6-trifluoromethyl-1,3-dihydro-isoindole-2-carboxylic acid tert-butyl ester

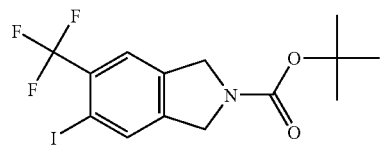

Prepared in analogy to Example A3(c) from 5-iodo-6-trifluoromethyl-2,3-dihydro-1H-isoindole and di-tert-butyl dicarbonate. White solid. MS (m/e): 358.0 ([M+H−Me$_2$C=CH$_2$]$^+$, 100%).

(e) 5-Ethylsulfanyl-6-trifluoromethyl-1,3-dihydro-isoindole-2-carboxylic add tert-butyl ester

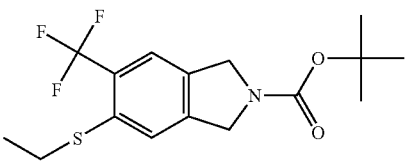

Prepared in analogy to Example A5(a) from 5-iodo-6-trifluoromethyl-1,3-dihydro-isoindole-2-carboxylic acid tert-butyl ester and ethyl mercaptan. White solid. MS (m/e): 292.1 ([M+H−Me$_2$C=CH$_2$]$^+$, 100%).

(f) 5-Ethylsulfanyl-6-trifluoromethyl-2,3-dihydro-1H-isoindole hydrochloride

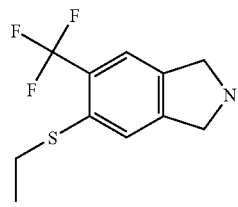

Prepared in analogy to Example A3(e) from 5-ethylsulfanyl-6-trifluoromethyl-1,3-dihydro-isoindole-2-carboxylic acid tert-butyl ester and hydrochloric acid. Yellow solid. MS (m/e): 284.3 ([M+H]⁺, 100%).

EXAMPLE A36

5-Fluoro-6-trifluoromethyl-2,3-dihydro-1H-isoindole trifluoroacetate (a) 4-Fluoro-5-trifluoromethyl-phthalic acid dimethyl ester

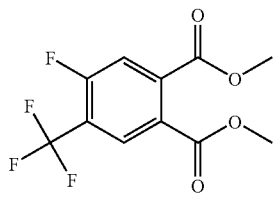

To 7.93 mmol 4-fluoro-5-trifluoromethyl-phthalic acid (Example A15(a)) in 20 ml methanol was added 1.19 mmol conc. sulphuric acid and the mixture was heated at reflux for 2 days. The mixture was then cooled to room temperature, diluted with ethyl acetate, and washed sequentially with 0.5 M aq. sodium hydroxide solution and brine. The organic phase was then separated, dried over sodium sulfate, and concentrated in vacuo to afford the title compound as a yellow solid (54% yield). EI-MS (m/e): 280.1 (M⁺, 5%), 249.1 ([M−MeO]⁺, 100%).

(b) (4-Fluoro-2-hydroxymethyl-5-trifluoromethyl-phenyl)-methanol

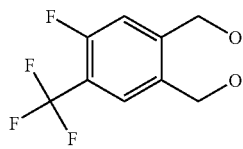

To 23.6 mmol LiAlH₄ in 10 ml THF was added dropwise over 5 min a solution of 3.93 mmol 4-fluoro-5-trifluoromethyl-phthalic acid dimethyl ester in 5 ml THF. The mixture was stirred at room temperature for 2 h, and then heated at 50° C. for 20 min. The reaction mixture was quenched by dropwise addition of 8 ml ethyl acetate, stirred for a further 15 min at 50° C., then cooled to room temperature and acidified to pH 1 by dropwise addition of 5 M aq HCl. The mixture was then partitioned between ethyl acetate and brine and the organic phase was then separated, dried over sodium sulfate, and concentrated in vacuo. The residue was purified by chromatography on silica gel (eluant: methanol/dichloromethane) to afford the title compound as a colourless oil (57% yield). MS (m/e): 283.1 ([M+OAc]⁻, 100%), 223.1 ([M−H]⁻, 20%).

(c) 5-Fluoro-6-trifluoromethyl-2-trityl-2,3-dihydro-1H-isoindole

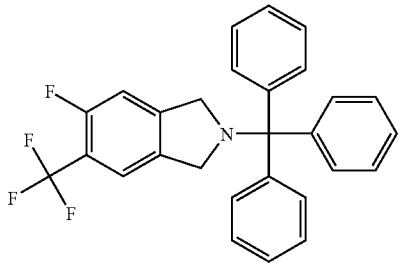

To a mixture of 1.56 mmol (4-fluoro-2-hydroxymethyl-5-trifluoromethyl-phenyl)-methanol and 0.08 mmol DMAP in 5 ml dichloromethane at 0° C. were added dropwise 3.28 mmol methanesulfonyl chloride and 6.25 mmol triethylamine. The mixture was stirred at 0° C. for 1 h, and then heated quenched with water. The mixture was extracted with dichloromethane and the organic phase was dried over sodium sulfate and concentrated in vacuo. The residue was dissolved in DMF and then 4.68 mmol N,N-diisopropylethylamine and 2.03 mmol triphenylmethylamine were added sequentially. The mixture was heated at 60° C. for 1 day and then at 80° C. for a further day. The mixture was then cooled to room temperature and concentrated in vacuo. The residue was purified by chromatography on silica gel (eluant: ethyl acetate/heptane) to afford the title compound as a white amorphous solid (23% yield). EI-MS (m/e): 370.1 ([M−Ph]⁺, 100%).

(d) 5-Fluoro-6-trifluoromethyl-2,3-dihydro-1H-isoindole trifluoroacetate

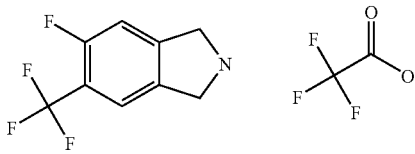

To a mixture of 0.33 mmol 5-fluoro-6-trifluoromethyl-2-trityl-2,3-dihydro-1H-isoindole in 1.5 methanol and 1.5 ml chloroform at 0° C. was added dropwise 1.63 mmol trifluoroacetic acid and the mixture was then stirred at RT for 3 h before being concentrated in vacuo to afford the title compound as a yellow solid (100% yield). EI-MS (m/e): 206.1 ([M+H]⁺, 100%).

EXAMPLE A37

5-Chloro-6-piperidin-1-yl-2,3-dihydro-1H-isoindole hydrochloride (a) 5-Chloro-6-piperidin-1-yl-1,3-dihydro-isoindole-2-carboxylic acid tert-butyl ester

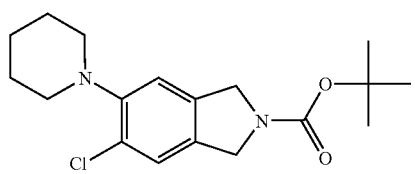

Prepared in analogy to Example A3(d) from 5-chloro-6-iodo-1,3-dihydro-isoindole-2-carboxylic acid tert-butyl ester (Example A3(c)) and piperidine. Yellow solid. MS (m/e): 339.1 ($\{^{37}Cl\}M+H^+$, 29%), 337.1 ($\{^{35}Cl\}M+H^+$, 100%).

(b) 5-Chloro-6-piperidin-1-yl-2,3-dihydro-1H-isoindole hydrochloride

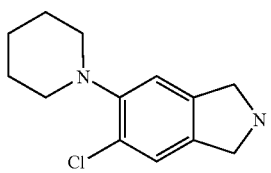

Prepared in analogy to Example A3(e) from 5-chloro-6-piperidin-1-yl-1,3-dihydro-isoindole-2-carboxylic acid tert-butyl ester and hydrochloric acid. Brown solid. MS (m/e): 239.2 ($\{^{37}Cl\}M+H^+$, 35%), 237.1 ($\{^{35}Cl\}M+H^+$, 100%).

EXAMPLE A38

5-(2-Methoxy-ethoxy)-2,3-dihydro-1H-isoindole hydrochloride (a) 5-Iodo-2,3-dihydro-1H-isoindole

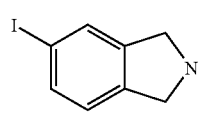

Prepared in analogy to Example A1 from 5-iodo-isoindole-1,3-dione (CAS: 98556-60-6) and borane tetrahydrofuran complex. Brown solid. MS (m/e): 246.1 ([M+H]+, 100%).

(b) 5-Iodo-1,3-dihydro-isoindole-2-carboxylic acid tert-butyl ester

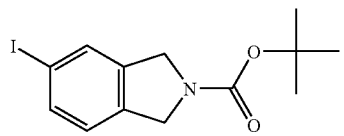

Prepared in analogy to Example A3(c) from 5-iodo-2,3-dihydro-1H-isoindole and di-tert-butyl dicarbonate. White solid. MS (m/e): 290.0 ([M+H−Me$_2$C=CH$_2$]+, 100%).

(c) 5-(2-Methoxy-ethoxy)-1,3-dihydro-isoindole-2-carboxylic acid tert-butyl ester

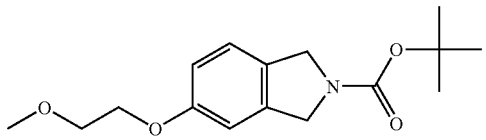

Prepared in analogy to Example A6(a) from 5-iodo-1,3-dihydro-isoindole-2-carboxylic acid tert-butyl ester and 2-methoxyethanol. White solid. MS (m/e): 237.9 ([M+H−Me$_2$C=CH$_2$]+, 100%)

(d) 5-(2-Methoxy-ethoxy)-2,3-dihydro-1H-isoindole hydrochloride

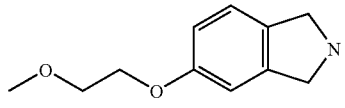

Prepared in analogy to Example A3(e) from 5-(2-methoxy-ethoxy)-1,3-dihydro-isoindole-2-carboxylic acid tert-butyl ester and hydrochloric acid. White solid. MS (m/e): 194.3 ([M+H]+, 100%).

EXAMPLE A39

1-(2,3-Dihydro-1H-isoindol-5-yl)-pyrrolidin-2-one hydrochloride (a) 5-(2-Oxo-pyrrolidin-1-yl)-1,3-dihydro-isoindole-2-carboxylic acid tert-butyl ester

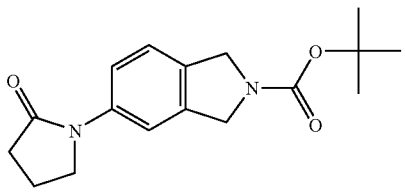

Lit. *J. Am. Chem. Soc.* 2001, 123, 7727-7729. To a stirred suspension of 0.58 mmol 5-iodo-1,3-dihydro-isoindole-2-carboxylic acid tert-butyl ester (Example A38(b)) in 4 ml dioxane were added 0.12 mmol copper(I) iodide, 1.74 mmol potassium carbonate, 0.17 mmol trans-1,2-diaminocyclohexane and 2.90 mmol 2-pyrrolidone and the reaction mixture was stirred at 140° C. for 16 h. The mixture was then cooled to room temperature, filtered, and the filtrate was concentrated in vacuo. The residue was purified by chromatography (SiO$_2$, heptane/ethyl acetate) to yield the title compound as a white solid. MS (m/e): 247.3 ([M+H−Me$_2$C═CH$_2$]$^+$, 100%).

(b) 1-(2,3-Dihydro-1H-isoindol-5-yl)-pyrrolidin-2-one hydrochloride

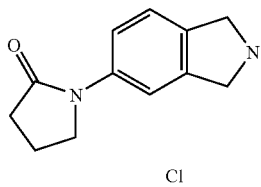

Prepared in analogy to Example A3(e) from 5-(2-oxo-pyrrolidin-1-yl)-1,3-dihydro-isoindole-2-carboxylic acid tert-butyl ester and hydrochloric acid. Off-white solid. MS (m/e): 203.4 ([M+H]$^+$, 100%).

EXAMPLE A40

5-Isopropoxy-2,3-dihydro-1H-isoindole hydrochloride (a) 5-Isopropoxy-1,3-dihydro-isoindole-2-carboxylic acid tert-butyl ester

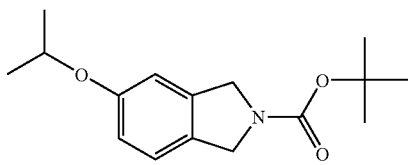

Prepared in analogy to Example A6(a) from 5-iodo-1,3-dihydro-isoindole-2-carboxylic acid tert-butyl ester (Example A38(b)) and 2-propanol. White solid. MS (m/e): 222.1 ([M+H−Me$_2$C═CH$_2$]$^+$, 100%).

(b) 5-Isopropoxy-2,3-Dihydro-1H-isoindole hydrochloride

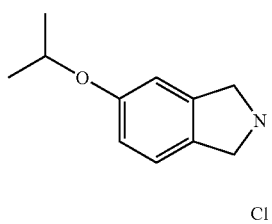

Prepared in analogy to Example A3(e) from 5-isopropoxy-1,3-dihydro-isoindole-2-carboxylic acid tert-butyl ester and hydrochloric acid. Brown solid. MS (m/e): 178.3 ([M+H]$^+$, 100%).

EXAMPLE A41

5-Ethoxy-2,3-dihydro-1H-isoindole hydrochloride (a) 5-Ethoxy-1,3-dihydro-isoindole-2-carboxylic acid tert-butyl ester

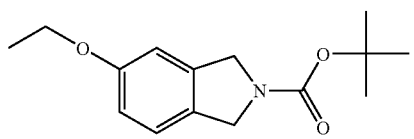

Prepared in analogy to Example A6(a) from 5-iodo-1,3-dihydro-isoindole-2-carboxylic acid tert-butyl ester (Example A38(b)) and ethanol. Light brown solid. MS (m/e): 208.1 ([M+H−Me$_2$C═CH$_2$]$^+$, 100%).

(b) 5-Ethoxy-2,3-dihydro-1H-isoindole hydrochloride

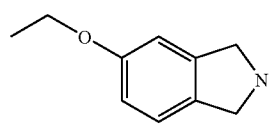

Prepared in analogy to Example A3(e) from 5-ethoxy-1,3-dihydro-isoindole-2-carboxylic acid tert-butyl ester and hydrochloric acid. Brown solid. MS (m/e): 164.4 ([M+H]$^+$, 100%).

EXAMPLE A42

5-(4,4-Difluoro-piperidin-1-yl)-2,3-dihydro-1H-isoindole hydrochloride (a) 5-(4,4-Difluoro-piperidin-1-yl)-1,3-dihydro-isoindole-2-carboxylic acid tert-butyl ester

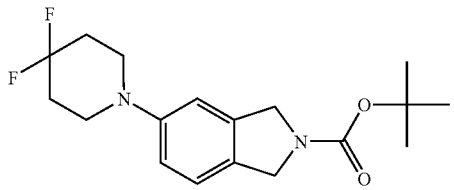

Prepared in analogy to Example A3(d) from 5-iodo-1,3-dihydro-isoindole-2-carboxylic acid tert-butyl ester (Example A38(b)) and 4,4-difluoropiperidine hydrochloride. Yellow solid. MS (m/e): 339.1 ([M+H]$^+$, 100%).

(b) 5-(4,4-Difluoro-piperidin-1-yl)-2,3-Dihydro-1H-isoindole hydrochloride

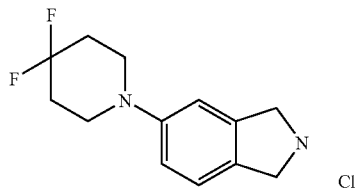

Prepared in analogy to Example A3(e) from 5-(4,4-difluoro-piperidin-1-yl)-1,3-dihydro-isoindole-2-carboxylic acid tert-butyl ester and hydrochloric acid. Light yellow solid. MS (m/e): 239.3 ([M+H]$^+$, 100%).

EXAMPLE A43

5-Ethoxy-6-trifluoromethyl-2,3-dihydro-1H-isoindole hydrochloride (a) 5-Ethoxy-6-trifluoromethyl-1,3-dihydro-isoindole-2-carboxylic acid tert-butyl ester

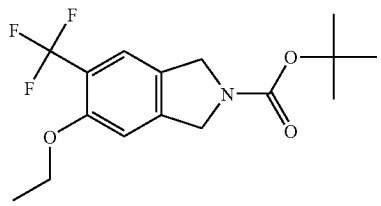

Prepared in analogy to Example A6(a) from 5-iodo-6-trifluoromethyl-1,3-dihydro-isoindole-2-carboxylic acid tert-butyl ester (Example A35(d)) and ethyl mercaptan. White solid. MS (m/e): 276.3 ([M+H−Me$_2$C=CH$_2$]$^+$, 100%).

(b) 5-Ethoxy-6-trifluoromethyl-2,3-dihydro-1H-isoindole hydrochloride

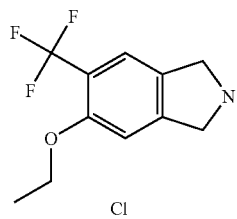

Prepared in analogy to Example A3(e) from 5-ethoxy-6-trifluoromethyl-1,3-dihydro-isoindole-2-carboxylic acid tert-butyl ester and hydrochloric acid. White solid. MS (m/e): 232.1 ([M+H]$^+$, 100%).

EXAMPLE A44

5-Chloro-6-morpholin-4-yl-2,3-dihydro-1H-isoindole hydrochloride (a) 5-Chloro-6-morpholin-4-yl-1,3-dihydro-isoindole-2-carboxylic acid tert-butyl ester

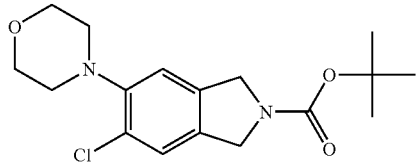

Prepared in analogy to Example A3(d) from 5-chloro-6-iodo-1,3-dihydro-isoindole-2-carboxylic acid tert-butyl ester (Example A3(c)) and morpholine. Yellow solid. MS (m/e): 341.3 ({$^{37}$Cl}M+H$^+$, 20%), 339.1 ({$^{35}$Cl}M+H$^+$, 100%).

(b) 5-Chloro-6-morpholin-4-yl-2,3-dihydro-1H-isoindole hydrochloride

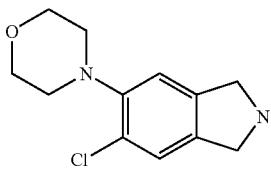

Prepared in analogy to Example A3(e) from 5-chloro-6-morpholin-4-yl-1,3-dihydro-isoindole-2-carboxylic acid tert-butyl ester and hydrochloric acid. Off-white solid. MS (m/e): 241.4 ({$^{37}$Cl}M+H$^+$, 52%), 239.3 ({$^{35}$Cl}M+H$^+$, 100%).

EXAMPLE A45

5-Ethyl-6-trifluoromethyl-2,3-dihydro-1H-isoindole hydrochloride (a) 5-Trifluoromethyl-6-vinyl-1,3-dihydro-isoindole-2-carboxylic acid tert-butyl ester

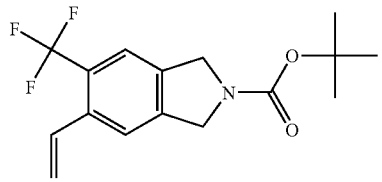

To a stirred solution 0.61 mmol 5-iodo-6-trifluoromethyl-1,3-dihydro-isoindole-2-carboxylic acid tert-butyl ester (Example A35(d)) in 3 ml dioxane were added 0.04 mmol palladium(II) acetate and 0.18 mmol triphenylarsine and the mixture was stirred at RT for 10 min. 0.91 mmol vinyltributylstannane was then added and the mixture was heated at 100° C. for 16 h. The reaction mixture was then cooled to room temperature, filtered, and the filtrate was concentrated in vacuo. The residue was purified by chromatography (SiO$_2$, heptane/ethyl acetate) to yield the title compound as a yellow solid (93% yield). MS (m/e): 258.0 ([M+H−Me$_2$C═CH$_2$]$^+$, 100%).

(b) 5-Ethyl-6-trifluoromethyl-1,3-dihydro-isoindole-2-carboxylic acid tert-butyl ester

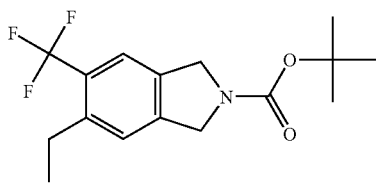

To a stirred solution 0.54 mmol 5-trifluoromethyl-6-vinyl-1,3-dihydro-isoindole-2-carboxylic acid tert-butyl ester in 50 ml methanol was added 50 mg 10% palladium on charcoal and the mixture was stirred under an atmosphere of hydrogen (0.6 bar positive pressure) for 72 h. The reaction mixture was then filtered and the filtrate was concentrated in vacuo. The residue was purified by chromatography (SiO$_2$, heptane/ethyl acetate) to yield the title compound as a white solid (20% yield). MS (m/e): 260.0 ([M+H−Me$_2$C═CH$_2$]$^+$, 100%).

(c) 5-Ethyl-6-trifluoromethyl-2,3-dihydro-1H-isoindole hydrochloride

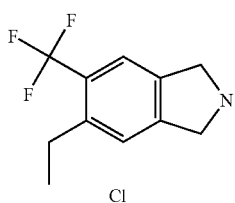

Prepared in analogy to Example A3(e) from 5-ethyl-6-trifluoromethyl-1,3-dihydro-isoindole-2-carboxylic acid tert-butyl ester and hydrochloric acid. White solid. MS (m/e): 216.4 ([M+H]$^+$, 100%).

EXAMPLE A46

5-Morpholin-4-yl-6-trifluoromethyl-2,3-dihydro-1H-isoindole hydrochloride (a) 5-Morpholin-4-yl-6-trifluoromethyl-1,3-dihydro-isoindole-2-carboxylic acid tert-butyl ester

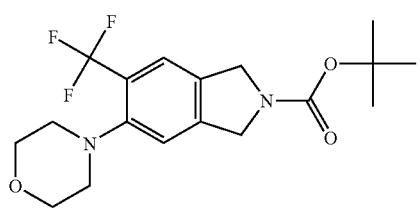

Prepared in analogy to Example A3(d) from 5-iodo-6-trifluoromethyl-1,3-dihydro-isoindole-2-carboxylic acid tert-butyl ester (Example A35(d)) and morpholine. White solid. MS (m/e): 373.0 ([M+H]$^+$, 100%).

(b) 5-Morpholin-4-yl-6-trifluoromethyl-2,3-dihydro-1H-isoindole hydrochloride

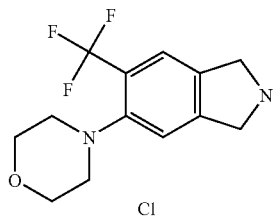

Prepared in analogy to Example A3(e) from 5-morpholin-4-yl-6-trifluoromethyl-1,3-dihydro-isoindole-2-carboxylic acid tert-butyl ester and hydrochloric acid. Off-white solid. MS (m/e): 273.0 ([M+H]$^+$, 100%).

EXAMPLE A47

1-(2,3-Dihydro-1H-isoindol-5-yl)-ethanone

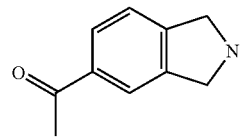

To a stirred solution 0.72 mmol 5-iodo-1,3-dihydro-isoindole-2-carboxylic acid tert-butyl ester (Example A38(b)) in 3 ml dioxane were added 0.05 mmol palladium(II) acetate and 0.22 mmol triphenylarsine and the mixture was stirred at RT for 10 min. 1.01 mmol 1-ethoxyvinyltributylstannane was then added and the mixture was heated at 100° C. for 16 h. The reaction mixture was then cooled to room temperature, filtered, and the filtrate was concentrated in vacuo. The residue was resuspended in THF, 25% aqueous hydrochloric acid was added, and the mixture was stirred at RT for 3 h. The mixture was then partitioned between ethyl acetate and water and the phases were separated. The aqueous phase was made alkaline to pH 14 by addition of 30% aqueous NaOH solution and then extracted with ethyl acetate. The organic phase was then washed with brine, dried over sodium sulfate, and concentrated in vacuo to yield the title compound as a brown solid (95% yield). MS (m/e): 162.6 ([M+H]$^+$, 100%).

EXAMPLE A48

1-(6-Trifluoromethyl-2,3-dihydro-1H-isoindol-5-yl)-ethanone

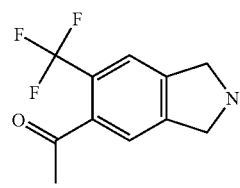

Prepared in analogy to Example A47 from 5-iodo-6-trifluoromethyl-1,3-dihydro-isoindole-2-carboxylic acid tert-butyl ester (Example A35(d)) and I-ethoxyvinyltributylstannane. White solid. MS (m/e): 230.3 ([M+H]⁺, 100%).

EXAMPLE A49

5-(Tetrahydro-pyran-4-yl)-2,3-dihydro-1H-isoindole hydrochloride (a) 5-(3,6-Dihydro-2H-pyran-4-yl)-1,3-dihydro-isoindole-2-carboxylic acid tert-butyl ester

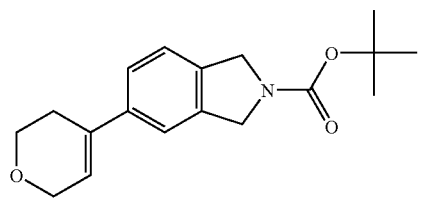

To a stirred solution 6.32 mmol 5-iodo-1,3-dihydro-isoindole-2-carboxylic acid tert-butyl ester (Example A38(b)) in 20 ml DMF were added 12.6 mmol tributyl-(3,6-dihydro-2H-pyran-4-yl)-stannane, 3.79 mmol triphenylarsine, 0.76 mmol bis(triphenylphosphine)palladium(II) chloride, 50.5 mmol lithium chloride and 0.63 mmol 2,6-di-t-butyl-p-cresol and the mixture was heated at 100° C. for 6 h. The reaction mixture was then cooled to room temperature and concentrated in vacuo. The residue was purified by chromatography (SiO₂, heptane/ethyl acetate) to yield the title compound as a yellow solid (74% yield). MS (m/e): 246.1 ([M+H–Me₂C=CH₂]⁺, 100%).

(b) 5-(Tetrahydro-pyran-4-yl)-1,3-dihydro-isoindole-2-carboxylic acid tert-butyl Ester

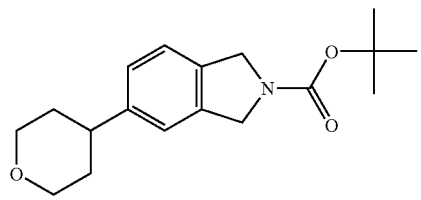

To a stirred solution 7.27 mmol 5-(3,6-dihydro-2H-pyran-4-yl)-1,3-dihydro-isoindole-2-carboxylic acid tert-butyl ester in 60 ml methanol were added 1.60 g 10% palladium on charcoal and 72.7 mmol ammonium formate and the mixture was heated at reflux for 30 min. The reaction mixture was then cooled to room temperature, filtered, and the filtrate concentrated in vacuo. The residue was taken up in THF and washed with brine. The organic phase was then dried over sodium sulfate and concentrated in vacuo. The residue was purified by chromatography (SiO₂, heptane/ethyl acetate) to yield the title compound as a white solid (92% yield). MS (m/e): 248.3 ([M+H–Me₂C=CH₂]⁺, 100%).

(c) 5-(Tetrahydro-pyran-4-yl)-2,3-dihydro-1H-isoindole hydrochloride

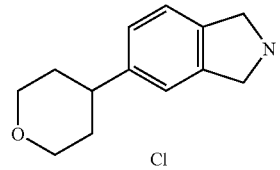

Prepared in analogy to Example A3(e) from 5-(tetrahydro-pyran-4-yl)-1,3-dihydro-isoindole-2-carboxylic acid tert-butyl ester and hydrochloric acid. White solid. MS (m/e): 204.3 ([M+H]⁺, 100%).

EXAMPLE A50

5-(Tetrahydro-pyran-4-yl)-6-trifluoromethyl-2,3-dihydro-1H-isoindole hydrochloride (a) 5-(3,6-Dihydro-2H-pyran-4-yl)-6-trifluoromethyl-1,3-dihydro-isoindole-2-carboxylic acid tert-butyl ester

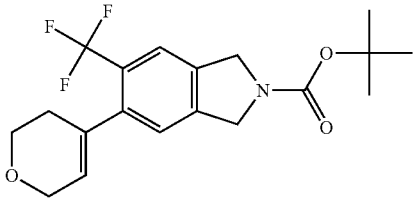

Prepared in analogy to Example A49(a) from 5-iodo-6-trifluoromethyl-1,3-dihydro-isoindole-2-carboxylic acid tert-butyl ester (Example 35(d)) and tributyl-(3,6-dihydro-2H-pyran-4-yl)-stannane. Yellow solid. MS (m/e): 314.0 ([M+H–Me₂C=CH₂]⁺, 100%).

(b) 5-(Tetrahydro-pyran-4-yl)-6-trifluoromethyl-1,3-dihydro-isoindole-2-carboxylic acid tert-butyl ester

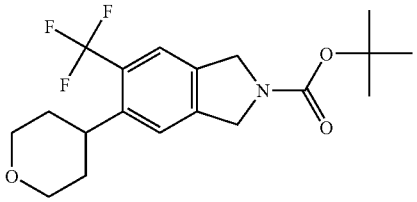

Prepared in analogy to Example A49(b) from 5-(3,6-dihydro-2H-pyran-4-yl)-6-trifluoromethyl-1,3-dihydro-isoindole-2-carboxylic acid tert-butyl ester and ammonium formate. Off-white solid. MS (m/e): 316.1 ([M+H–Me₂C=CH₂]⁺, 100%).

(c) 5-(Tetrahydro-pyran-4-yl)-6-trifluoromethyl-2,3-dihydro-1H-isoindole hydrochloride

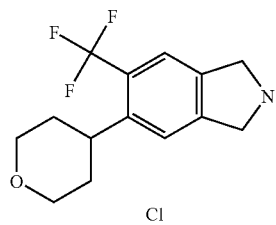

Prepared in analogy to Example A3(e) from 5-(tetrahydro-pyran-4-yl)-6-trifluoromethyl-1,3-dihydro-isoindole-2-carboxylic acid tert-butyl ester and hydrochloric acid. Yellow solid. MS (m/e): 272.3 ([M+H]$^+$, 100%).

EXAMPLE A51

5-(1,1-Dioxo-1-thiomorpholin-4-yl)-2,3-dihydro-1H-isoindole hydrochloride (a) 5-(1,1-Dioxo-1-thiomorpholin-4-yl)-1,3-dihydro-isoindole-2-carboxylic acid tert-butyl ester

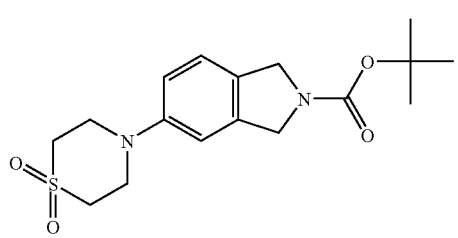

Prepared in analogy to Example A3(d) from 5-iodo-1,3-dihydro-isoindole-2-carboxylic acid tert-butyl ester (Example A38(b)) and tetrahydro-2H-1,4-thiazine 1,1-dioxide. Brown solid. MS (m/e): 353.0 ([M+H]$^+$, 100%).

(b) 5-(1,1-Dioxo-1-thiomorpholin-4-yl)-2,3-dihydro-1H-isoindole hydrochloride

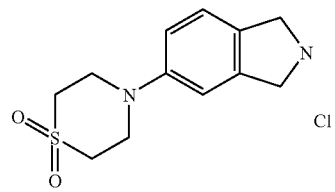

Prepared in analogy to Example A3(e) from 5-(1,1-dioxo-1lambda*6*-thiomorpholin-4-yl)-1,3-dihydro-isoindole-2-carboxylic acid tert-butyl ester and hydrochloric acid. Brown solid. MS (m/e): 253.1 ([M+H]$^+$, 100%).

EXAMPLE A52

5-(3,3-Difluoro-piperidin-1-yl)-2,3-dihydro-1H-isoindole hydrochloride (a) 5-(3,3-Difluoro-piperidin-1-yl)-1,3-dihydro-isoindole-2-carboxylic acid tert-butyl ester

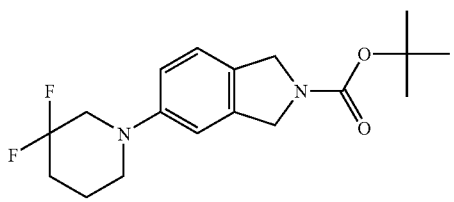

Prepared in analogy to Example A3(d) from 5-iodo-1,3-dihydro-isoindole-2-carboxylic acid tert-butyl ester (Example A38(b)) and 3,3-difluoropiperidine hydrochloride. Pink solid. MS (m/e): 339.1 ([M+H]$^+$, 100%).

(b) 5-(3,3-Difluoro-piperidin-1-yl)-2,3-dihydro-1H-isoindole hydrochloride

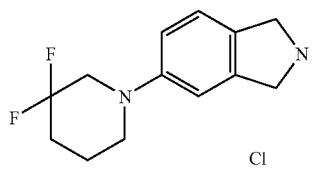

Prepared in analogy to Example A3(e) from 5-(3,3-difluoro-piperidin-1-yl)-1,3-dihydro-isoindole-2-carboxylic acid tert-butyl ester and hydrochloric acid. Brown solid. MS (m/e): 239.3 ([M+H]$^+$, 100%).

EXAMPLE A53

1-(2,3-Dihydro-1H-isoindol-5-yl)-4-phenyl-piperidin-4-ol hydrochloride (a) 5-(4-Hydroxy-4-phenyl-piperidin-1-yl)-1,3-dihydro-isoindole-2-carboxylic acid tert-butyl ester

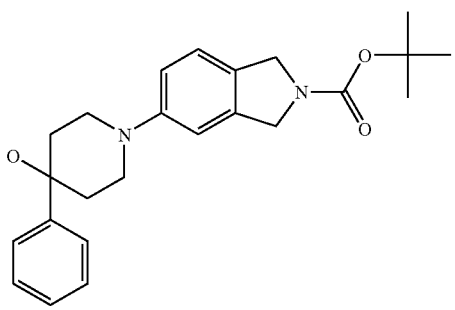

Prepared in analogy to Example A3(d) from 5-iodo-1,3-dihydro-isoindole-2-carboxylic acid tert-butyl ester (Example A38(b)) and 4-hydroxy-4-phenylpiperidine. Yellow solid. MS (m/e): 395.1 ([M+H]$^+$, 100%).

(b) 1-(2,3-Dihydro-1H-isoindol-5-yl)-4-phenyl-piperidin-4-ol hydrochloride

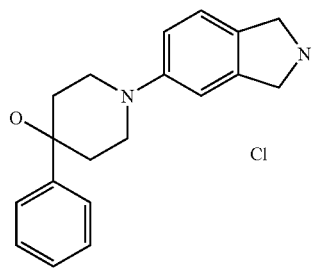

Prepared in analogy to Example A3(e) from 5-(4-hydroxy-4-phenyl-piperidin-1-yl)-1,3-dihydro-isoindole-2-carboxylic acid tert-butyl ester and hydrochloric acid. Off-white solid. MS (m/e): 295.4 ([M+H]$^+$, 100%).

EXAMPLE A54

5-Methyl-6-morpholin-4-yl-2,3-dihydro-1H-isoindole hydrochloride (a) 5-Methyl-6-morpholin-4-yl-1,3-dihydro-isoindole-2-carboxylic acid tert-butyl Ester

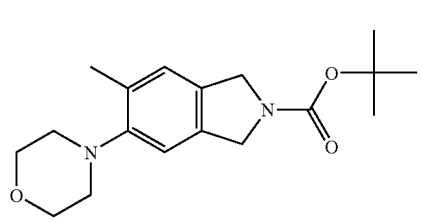

To a stirred solution 0.38 mmol 5-chloro-6-morpholin-4-yl-1,3-dihydro-isoindole-2-carboxylic acid tert-butyl ester (Example A44(a)) in 3 ml dioxane were added 0.02 mmol bis(tri-tert-butylphosphine)palladium(0), 0.84 mmol cesium fluoride and 0.77 mmol tetramethylstannane and the mixture was heated at 80° C. for 5 h. The reaction mixture was then cooled to room temperature and concentrated in vacuo. The residue was purified by chromatography (SiO$_2$, heptane/ethyl acetate) to yield the title compound as a light yellow solid (43% yield). MS (m/e): 219.4 ([M+H−Me$_2$C=CH$_2$]$^+$, 100%).

(b) 5-Methyl-6-morpholin-4-yl-2,3-dihydro-1H-isoindole hydrochloride

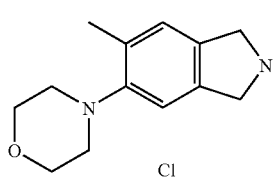

Prepared in analogy to Example A3(e) from 5-methyl-6-morpholin-4-yl-1,3-dihydro-isoindole-2-carboxylic acid tert-butyl ester and hydrochloric acid. Brown solid. MS (m/e): 219.3 ([M+H]$^+$, 100%).

EXAMPLE A55

5-(2,2,2-Trifluoro-ethyl)-2,3-dihydro-1H-isoindole hydrochloride (a) 5-Vinyl-1,3-dihydro-isoindole-2-carboxylic acid tert-butyl Ester

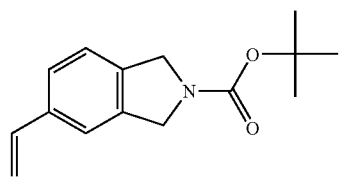

Prepared in analogy to Example A45(a) from 5-iodo-1,3-dihydro-isoindole-2-carboxylic acid tert-butyl ester (Example A38(b)) and vinyltributylstananne. Colourless oil. MS (m/e): 190.4 ([M+H−Me$_2$C=CH$_2$]$^+$, 100%).

(b) 5-Formyl-1,3-dihydro-isoindole-2-carboxylic acid tert-butyl Ester

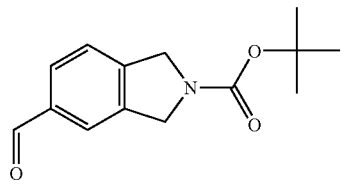

To a stirred solution of 3.79 mmol 5-vinyl-1,3-dihydro-isoindole-2-carboxylic acid tert-butyl ester in 25 ml THF and 5 ml water were added 11.4 mmol sodium metaperiodate and 0.08 mmol osmium tetroxide solution (2.5% in tBuOH) and the mixture was stirred at RT for 2 h before being taken up in ethyl acetate and washed sequentially with water and brine. The organic phase was then dried over sodium sulfate and concentrated in vacuo. The residue was purified by chromatography (SiO$_2$, heptane/ethyl acetate) to yield the title compound as a white solid (62% yield). MS (m/e): 192.1 ([M+H−Me$_2$C=CH$_2$]$^+$, 100%).

(c) 5-(2,2-Difluoro-vinyl)-1,3-dihydro-isoindole-2-carboxylic acid tert-butyl Ester

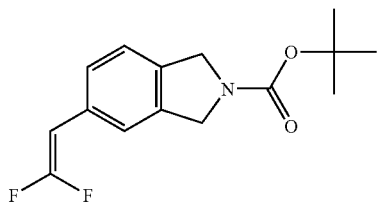

To a stirred solution of 4.69 mmol triphenylphosphine in 5 ml DMF at 0° C. was added dropwise a solution of 4.69 mmol dibromodifluoromethane in 1 ml DMF and the mixture was stirred at RT for 30 min. 2.35 mmol 5-formyl-1,3-dihydro-isoindole-2-carboxylic acid tert-butyl ester was then added at 0° C. and then 4.69 mmol zinc dust was added in small portions. The mixture was stirred at RT for 16 and then concentrated in vacuo. The residue was purified by chromatography (SiO$_2$, heptane/ethyl acetate) to yield the title compound as a white solid (31% yield). MS (m/e): 226.1 ([M+H−Me$_2$C═CH$_2$]$^+$, 100%).

(d) 5-(2,2,2-Trifluoro-ethyl)-1,3-dihydro-isoindole-2-carboxylic acid tert-butyl Ester

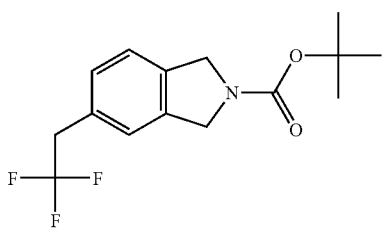

To a stirred solution of 0.71 mmol 5-(2,2-difluoro-vinyl)-1,3-dihydro-isoindole-2-carboxylic acid tert-butyl ester in 5 nml DMSO and 0.25 ml water was added 4.98 mmol potassium fluoride and the mixture was heated at 120° C. for 2 h. The mixture was cooled to room temperature and then taken up in THF and washed sequentially with water and with brine. The organic phase was then dried over sodium sulfate and concentrated in vacuo. The residue was purified by chromatography (SiO$_2$, heptane/ethyl acetate) to yield the title compound as a white solid (48% yield). MS (m/e): 246.3 ([M+H−Me$_2$C═CH$_2$]$^+$, 100%).

(e) 5-(2,2,2-Trifluoro-ethyl)-2,3-dihydro-1H-isoindole hydrochloride

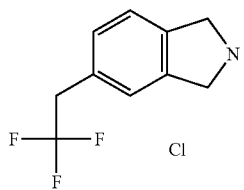

Prepared in analogy to Example A3(e) from 5-(2,2,2-trifluoro-ethyl)-1,3-dihydro-isoindole-2-carboxylic acid tert-butyl Ester and hydrochloric acid. Off-white solid. MS (m/e): 202.4 ([M+H]$^+$, 100%).

EXAMPLE A56

5-(3-Methoxy-azetidin-1-yl)-2,3-Dihydro-1H-isoindole trifluoro-acetate (a) 5-(3-Methoxy-azetidin-1-yl)-1,3-dihydro-isoindole-2-carboxylic acid tert-butyl Ester

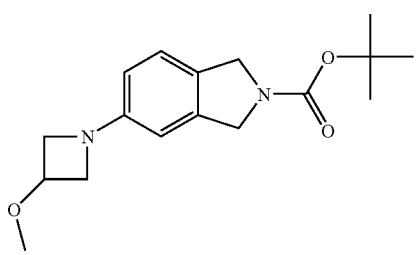

Prepared in analogy to Example A3(d) from 5-iodo-1,3-dihydro-isoindole-2-carboxylic acid tert-butyl ester (Example A38(b)) and 3-methoxy-azetidine hydrochloride. Orange oil. MS (m/e): 305.4 ([M+H]$^+$, 100%).

(b) 5-(3-Methoxy-azetidin-1-yl)-2,3-Dihydro-1H-isoindole trifluoro-acetate

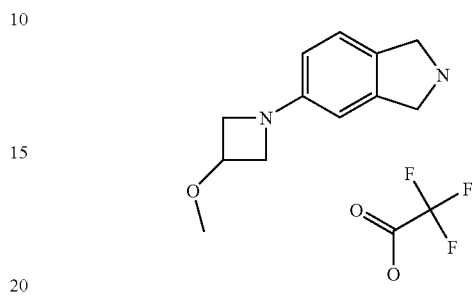

Prepared in analogy to Example A2(c) from 5-(3-methoxy-azetidin-1-yl)-1,3-dihydro-isoindole-2-carboxylic acid tert-butyl Ester and trifluoroacetic acid. Brown foam. MS (m/e): 205.1 ([M+H]$^+$, 100%).

EXAMPLE A57

5-(4-Methoxy-piperidin-1-yl)-2,3-dihydro-1H-isoindole hydrochloride (a) 5-(4-Methoxy-piperidin-1-yl)-1,3-dihydro-isoindole-2-carboxylic acid tert-butyl ester

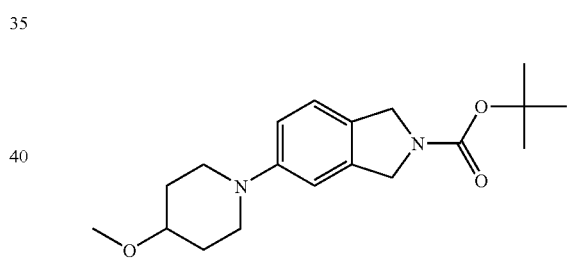

Prepared in analogy to Example A3(d) from 5-iodo-1,3-dihydro-isoindole-2-carboxylic acid tert-butyl ester (Example A38(b)) and 4-methoxy-piperidine trifluoroacetate. Yellow oil. MS (m/e): 333.3 ([M+H]$^+$, 100%).

(b) 5-(4-Methoxy-piperidin-1-yl)-2,3-dihydro-1H-isoindole hydrochloride

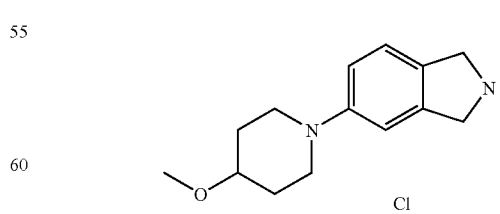

Prepared in analogy to Example A3(e) from 5-(4-methoxy-piperidin-1-yl)-1,3-dihydro-isoindole-2-carboxylic acid tert-butyl ester and hydrochloric acid. Brown solid. MS (m/e): 233.3 ([M+H]$^+$, 100%).

EXAMPLE A58

(1S,4S)-5-(2-Oxa-5-aza-bicyclo[2.2.1]hept-5-yl)-2,3-dihydro-1H-isoindole trifluoroacetate (a) (1S,4S)-5-(2-Oxa-5-aza-bicyclo[2.2.1]hept-5-yl)-1,3-dihydro-isoindole-2-carboxylic acid tert-butyl ester

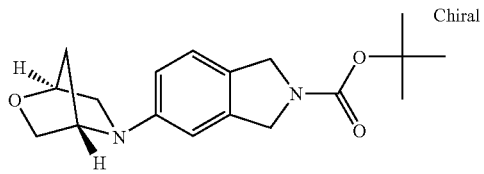

Prepared in analogy to Example A3(d) from 5-iodo-1,3-dihydro-isoindole-2-carboxylic acid tert-butyl ester (Example A38(b)) and (1S,4S)-2-oxa-5-aza-bicyclo[2.2.1]heptane trifluoroacetate. Orange oil. MS (m/e): 317.3 ([M+H]+, 100%).

(b) (1S,4S)-5-(2-Oxa-5-aza-bicyclo[2.2.1]hept-5-yl)-2,3-Dihydro-1H-isoindole trifluoroacetate

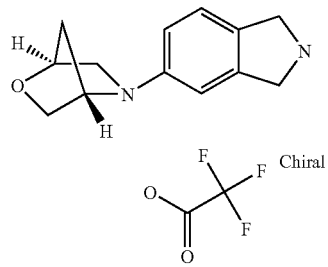

Prepared in analogy to Example A2(c) from (1S,4S)-5-(2-oxa-5-aza-bicyclo[2.2.1]hept-5-yl)-1,3-dihydro-isoindole-2-carboxylic acid tert-butyl ester and trifluoroacetic acid. Orange oil. MS (m/e): 217.4 ([M+H]+, 100%).

EXAMPLE A59

8-(2,3-Dihydro-1H-isoindol-5-yl)-3-oxa-8-aza-bicyclo[3.2.1]octane trifluoro-acetate (a) 5-(3-Oxa-8-aza-bicyclo[3.2.1]oct-8-yl)-1,3-dihydro-isoindole-2-carboxylic acid tert-butyl ester

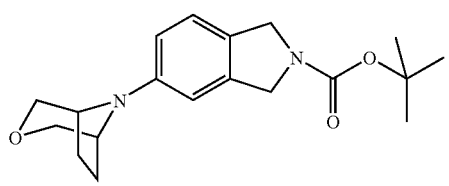

Prepared in analogy to Example A3(d) from 5-iodo-1,3-dihydro-isoindole-2-carboxylic acid tert-butyl ester (Example A38(b)) and 3-oxa-8-azabicyclo[3.2.1]octane hydrochloride. Yellow oil. MS (m/e): 331.4 ([M+H]+, 100%).

(b) 8-(2,3-Dihydro-1H-isoindol-5-yl)-3-oxa-8-azabicylo[3.2.1]octane trifluoro-acetate

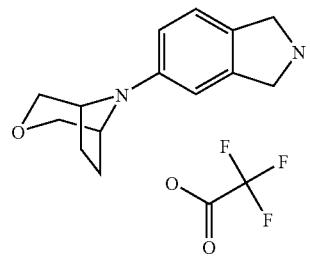

Prepared in analogy to Example A2(c) from 5-(3-oxa-8-aza-bicyclo[3.2.1]oct-8-yl)-1,3-dihydro-isoindole-2-carboxylic acid tert-butyl ester and trifluoroacetic acid. Brown oil. MS (m/e): 231.1 ([M+H]+, 100%).

EXAMPLE A60

5-Cyclopropyl-6-morpholin-4-yl-2,3-dihydro-1H-isoindole trifluoroacetate (a) 5-Cyclopropyl-6-morpholin-4-yl-1,3-dihydro-isoindole-2-carboxylic acid tert-butyl ester

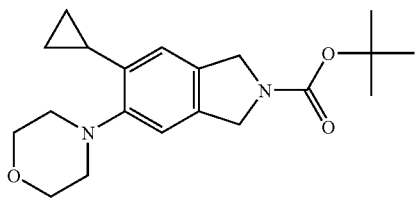

Prepared in analogy to Example A54(a) from 5-chloro-6-morpholin-4-yl-1,3-dihydro-isoindole-2-carboxylic acid tert-butyl ester (Example A44(a)) and tributylcyclopropylstannane. Yellow solid. MS (m/e): 345.4 ([M+H]+, 100%).

(b) 5-Cyclopropyl-6-morpholin-4-yl-2,3-dihydro-1H-isoindole trifluoroacetate

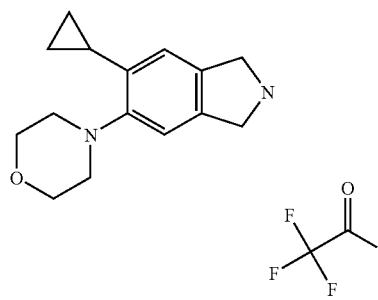

Prepared in analogy to Example A2(c) from 5-cyclopropyl-6-morpholin-4-yl-1,3-dihydro-isoindole-2-carboxylic acid tert-butyl ester and trifluoroacetic acid. Brown solid. MS (m/e): 245.4 ([M+H]⁺, 100%).

EXAMPLE A61

5-Cyclopropyl-6-(tetrahydro-pyran-4-yl)-2,3-dihydro-1H-isoindole trifluoro-acetate (a) 5-Chloro-6-(3,6-dihydro-2H-pyran-4-yl)-1,3-dihydro-isoindole-2-carboxylic acid tert-butyl Ester

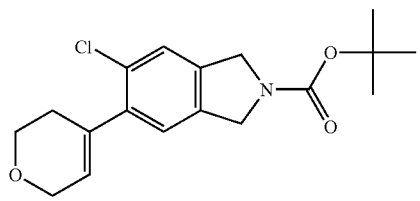

Prepared in analogy to Example A49(a) from 5-chloro-6-iodo-1,3-dihydro-isoindole-2-carboxylic acid tert-butyl ester (Example A3(c)) and tributyl-(3,6-dihydro-2H-pyran-4-yl)-stannane. Yellow solid. MS (m/e): 282.3 ({³⁷Cl}[M+H−Me₂C=CH₂]⁺, 49%), 280.3 ({³⁵Cl}[M+H−Me₂C=CH₂]⁺, 100%).

(b) 5-Cyclopropyl-6-(3,6-dihydro-2H-pyran-4-yl)-1,3-dihydro-isoindole-2-carboxylic acid tert-butyl ester

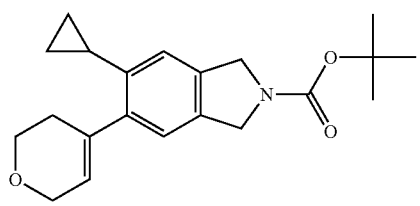

Prepared in analogy to Example A54(a) from 5-chloro-6-(3,6-dihydro-2H-pyran-4-yl)-1,3-dihydro-isoindole-2-carboxylic acid tert-butyl ester and tributylcyclopropylstannane. Yellow oil. MS (m/e): 286.1 ([M+H−Me₂C=CH₂]⁺, 100%).

(c) 5-Cyclopropyl-6-(tetrahydro-pyran-4-yl)-1,3-dihydro-isoindole-2-carboxylic acid tert-butyl Ester

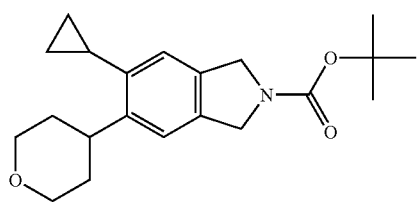

Prepared in analogy to Example A49(b) from 5-cyclopropyl-6-(3,6-dihydro-2H-pyran-4-yl)-1,3-dihydro-isoindole-2-carboxylic acid tert-butyl ester and ammonium formate. Colourless oil. MS (m/e): 288.0 ([M+H−Me₂C=CH₂]⁺, 100%).

(d) 5-Cyclopropyl-6-(tetrahydro-pyran-4-yl)-2,3-dihydro-1H-isoindole trifluoro-acetate

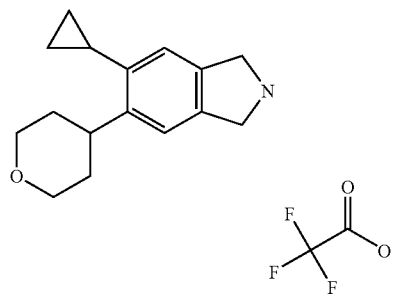

Prepared in analogy to Example A2(c) from 5-cyclopropyl-6-(tetrahydro-pyran-4-yl)-1,3-dihydro-isoindole-2-carboxylic acid tert-butyl ester and trifluoroacetic acid. Brown solid. MS (m/e): 244.4 ([M+H]⁺, 100%).

EXAMPLE A62

4-(2,3-Dihydro-1H-isoindol-5-yl)-tetrahydro-pyran-4-ol (a) 2-Benzyl-5-bromo-2,3-dihydro-1H-isoindole

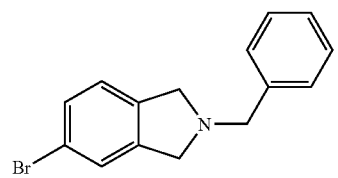

Prepared in analogy to Example A3(b) from 2-benzyl-5-bromo-isoindole-1,3-dione (CAS: 82104-06-1) and borane tetrahydrofuran complex. White solid. MS (m/e): 290.0 ({⁸¹Br}[M+H]⁺, 100%), 288.1 ({⁷⁹Br}[M+H]⁺, 100%).

(b) 4-(2-Benzyl-2,3-dihydro-1H-isoindol-5-yl)-tetrahydro-pyran-4-ol

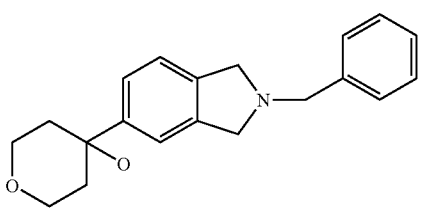

To a stirred suspension of 1.54 mmol 2-benzyl-5-bromo-2,3-dihydro-1H-isoindole in 3 ml THF at −78° C. was added dropwise 3.85 mmol butyllithium solution (1.6 M in hexane) and stirring continued at −78° C. for 1 h. To the resulting yellow solution was added dropwise a solution of 3.08 mmol tetrahydro-4H-pyran-4-one in 0.7 ml THF and the mixture was stirred at −78° C. for 30 min and then allowed to warm to room temperature. The reaction was quenched by addition of 1 M aq HCl, diluted with ethyl acetate, and then made basic by addition of 2 M aq NaOH. The phases were separated and the organic phase was dried over sodium sulfate and concentrated in vacuo. The residue was purified by chromatography (SiO$_2$, heptane/ethyl acetate) to yield the title compound as a yellow solid (25% yield). MS (m/e): 310.3 ([M+H]$^+$, 100%).

(c) 4-(2,3-Dihydro-1H-isoindol-5-yl)-tetrahydro-pyran-4-ol

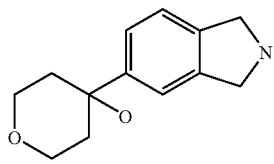

To a stirred solution 0.39 mmol 4-(2-benzyl-2,3-dihydro-1H-isoindol-5-yl)-tetrahydro-pyran-4-ol in 20 ml methanol was added 40 mg 10% palladium on charcoal and the mixture was stirred under an atmosphere of hydrogen for 3 h. The reaction mixture was then filtered and the filtrate was concentrated in vacuo to yield the title compound as a yellow solid (100% yield). MS (m/e): 220.3 ([M+H]$^+$, 100%).

EXAMPLE A63

5-Methyl-6-(tetrahydro-pyran-4-yl)-2,3-dihydro-1H-isoindole trifluoro-acetate (a) 5-(3,6-Dihydro-2H-pyran-4-yl)-6-methyl-1,3-dihydro-isoindole-2-carboxylic acid tert-butyl Ester

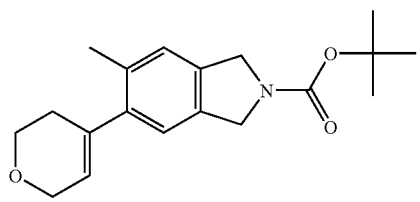

Prepared in analogy to Example A54(a) from 5-chloro-6-(3,6-dihydro-2H-pyran-4-yl)-1,3-dihydro-isoindole-2-carboxylic acid tert-butyl ester (Example A61(a)) and tetramethystannane. White solid. MS (m/e): 260.3 ([M+H–Me$_2$C=CH$_2$]$^+$, 100%).

(b) 5-Methyl-6-(tetrahydro-pyran-4-yl)-1,3-dihydro-isoindole-2-carboxylic acid tert-butyl ester

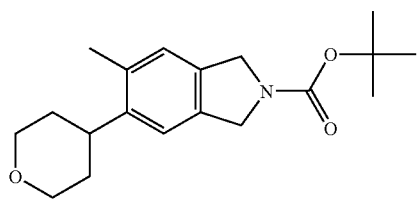

Prepared in analogy to Example A49(b) from 5-(3,6-dihydro-2H-pyran-4-yl)-6-methyl-1,3-dihydro-isoindole-2-car-boxylic acid tert-butyl ester and ammonium formate. Yellow solid. MS (m/e): 262.1 ([M+H–Me$_2$C=CH$_2$]$^+$, 100%).

(c) 5-Methyl-6-(tetrahydro-pyran-4-yl)-2,3-dihydro-1H-isoindole trifluoro-acetate

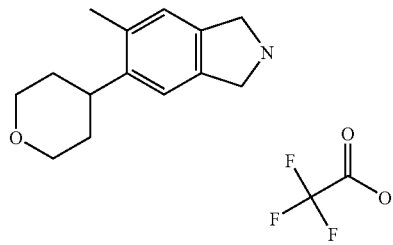

Prepared in analogy to Example A2(c) from 5-methyl-6-(tetrahydro-pyran-4-yl)-1,3-dihydro-isoindole-2-carboxylic acid tert-butyl ester and trifluoroacetic acid. Yellow oil. MS (m/e): 218.4 ([M+H]$^+$, 100%).

EXAMPLE A64

3-(2,3-Dihydro-1H-isoindol-5-yl)-2-methyl-tetrahydro-furan-3-ol (a) 3-(2-Benzyl-2,3-Dihydro-1H-isoindol-5-yl)-2-methyl-tetrahydro-furan-3-ol

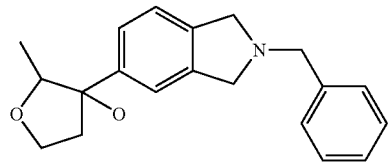

Prepared in analogy to Example A62(b) from 2-benzyl-5-bromo-2,3-dihydro-1H-isoindole (Example A62(a)) and 2-methyltetrahydrofuran-3-one. Brown oil. MS (m/e): 310.4 ([M+H]$^+$, 100%).

(b) 3-(2,3-Dihydro-1H-isoindol-5-yl)-2-methyl-tetrahydro-furan-3-ol

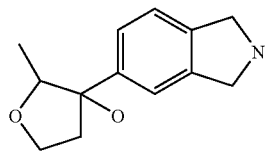

Prepared in analogy to Example A62(c) from 3-(2-benzyl-2,3-dihydro-1H-isoindol-5-yl)-2-methyl-tetrahydro-furan-3-ol and hydrogen. Yellow oil. MS (m/e): 220.3 ([M+H]$^+$, 100%).

EXAMPLE A65

5-(2-Methyl-tetrahydro-furan-3-yl)-2,3-dihydro-1H-isoindole (a) 2-Benzyl-5-(2-methyl-2,5-dihydro-furan-3-yl)-2,3-dihydro-1H-isoindole

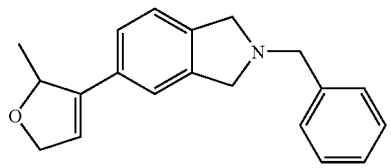

To a solution of 0.65 mmol 3-(2-benzyl-2,3-dihydro-1H-isoindol-5-yl)-2-methyl-tetrahydro-furan-3-ol (Example A64(a)) and 1.81 mmol triethylamine in 2 ml dichloromethane at 0° C. was added dropwise a solution of 0.84 methanesulfonyl chloride in 0.3 ml dichloromethane. The mixture was stirred at room temperature for 2 h and then re-cooled to 0° C. 1.94 mmol DBU was added and the mixture stirred at room temperature overnight. The reaction mixture was then concentrated in vacuo and the residue was purified by chromatography (SiO$_2$, heptane/ethyl acetate) to yield the title compound as a colourless oil (33% yield). MS (m/e): 292.1 ([M+H]$^+$, 100%).

(b) 5-(2-Methyl-tetrahydro-furan-3-yl)-2,3-dihydro-1H-isoindole

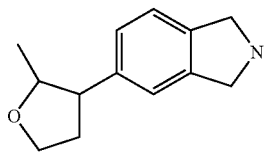

Prepared in analogy to Example A62(c) from 2-benzyl-5-(2-methyl-2,5-dihydro-furan-3-yl)-2,3-dihydro-1H-isoindole and hydrogen. Yellow oil. MS (m/e): 204.1 ([M+H]$^+$, 100%).

EXAMPLE A66

3-(2,3-Dihydro-1H-isoindol-5-yl)-tetrahydro-furan-3-ol (a) 3-(2-Benzyl-2,3-Dihydro-1H-isoindol-5-yl)-tetrahydro-furan-3-ol

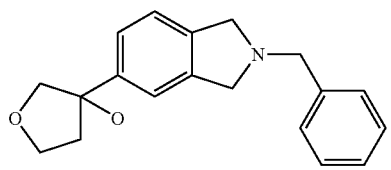

Prepared in analogy to Example A62(b) from 2-benzyl-5-bromo-2,3-dihydro-1H-isoindole (Example A62(a)) and tetrahydrofuran-3-one. Brown oil. MS (m/e): 296.4 ([M+H]$^+$, 100%).

(b) 3-(2,3-Dihydro-1H-isoindol-5-yl)-tetrahydro-furan-3-ol

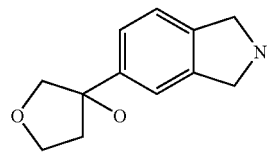

Prepared in analogy to Example A62(c) from 3-(2-benzyl-2,3-dihydro-1H-isoindol-5-yl)-tetrahydro-furan-3-ol and hydrogen. Brown oil. MS (m/e): 206.1 ([M+H]$^+$, 100%).

EXAMPLE A67

5-(Tetrahydro-furan-3-yl)-2,3-dihydro-1H-isoindole (a) 2-Benzyl-5-(2,5-dihydro-furan-3-yl)-2,3-dihydro-1H-isoindole

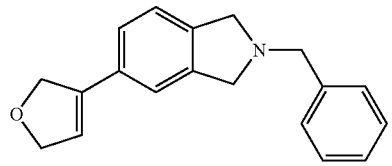

Prepared in analogy to Example A65(a) from 3-(2-benzyl-2,3-dihydro-1H-isoindol-5-yl)-tetrahydro-furan-3-ol (Example A66(a)) and methanesulfonyl chloride, triethylamine, and DBU. Brown solid. MS (m/e): 278.0 ([M+H]$^+$, 100%).

(b) 5-(Tetrahydro-furan-3-yl)-2,3-dihydro-1H-isoindole

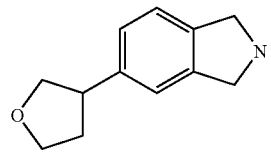

Prepared in analogy to Example A62(c) from 2-benzyl-5-(2,5-dihydro-furan-3-yl)-2,3-dihydro-1H-isoindole and hydrogen. Brown oil. MS (m/e): 190.4 ([M+H]$^+$, 100%).

EXAMPLE A68

5-Chloro-6-(tetrahydro-pyran-4-yl)-2,3-dihydro-1H-isoindole trifluoro-acetate (a) 5-Chloro-6-(tetrahydro-pyran-4-yl)-1,3-dihydro-isoindole-2-carboxylic acid tert-butyl ester

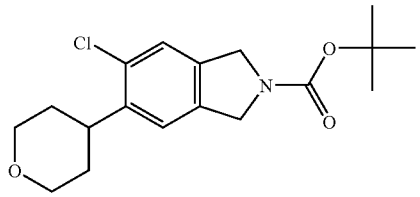

To a stirred solution 0.81 mmol 5-chloro-6-(3,6-dihydro-2H-pyran-4-yl)-1,3-dihydro-isoindole-2-carboxylic acid tert-butyl ester (Example A61(a)) in 40 ml methanol was added 0.41 mmol platinum(IV) oxide and the mixture was stirred under an atmosphere of hydrogen for 16 h. The reaction mixture was then filtered and the filtrate was concentrated in vacuo. The residue was purified by chromatography (SiO$_2$, heptane/ethyl acetate) to yield the title compound as a white solid (38% yield). MS (m/e): 284.3 ({$^{37}$Cl}[M+H–Me$_2$C=CH$_2$]$^+$, 49%), 282.3 ({$^{35}$Cl} [M+H–Me$_2$C=CH$_2$]$^+$, 100%).

(b) 5-Chloro-6-(tetrahydro-pyran-4-yl)-2,3-dihydro-1H-isoindole trifluoro-acetate

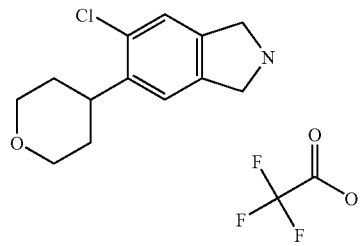

Prepared in analogy to Example A2(c) from 5-chloro-6-(tetrahydro-pyran-4-yl)-1,3-dihydro-isoindole-2-carboxylic acid tert-butyl ester and trifluoroacetic acid. Yellow oil. MS (m/e): 240.2 ({$^{37}$Cl}[M+H]$^+$, 39%), 238.1 ({$^{35}$Cl}[M+H]$^+$, 100%).

EXAMPLE A69

5-Ethyl-6-(tetrahydro-pyran-4-yl)-2,3-dihydro-1H-isoindole trifluoro-acetate (a) 5-(3,6-Dihydro-2H-pyran-4-yl)-6-vinyl-1,3-dihydro-isoindole-2-carboxylic acid tert-butyl ester

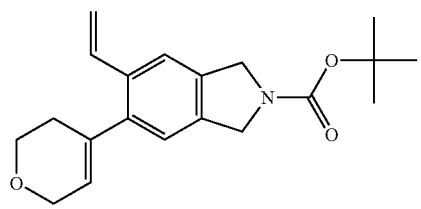

Prepared in analogy to Example A54(a) from 5-chloro-6-(3,6-dihydro-2H-pyran-4-yl)-1,3-dihydro-isoindole-2-carboxylic acid tert-butyl ester (Example A61(a)) and vinyltributylstannane. White solid. MS (m/e): 272.4 ([M+H–Me$_2$C=CH$_2$]$^+$, 100%).

(b) 5-Ethyl-6-(tetrahydro-pyran-4-yl)-1,3-dihydro-isoindole-2-carboxylic acid tert-butyl ester

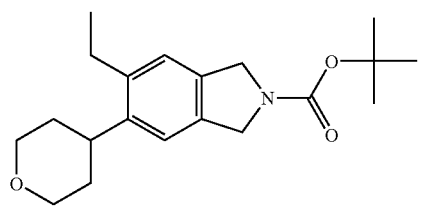

Prepared in analogy to Example A49(b) from 5-(3,6-dihydro-2H-pyran-4-yl)-6-vinyl-1,3-dihydro-isoindole-2-carboxylic acid tert-butyl ester and ammonium formate. Yellow oil. MS (m/e): 276.3 ([M+H–Me$_2$C=CH$_2$]$^+$, 100%).

(c) 5-Ethyl-6-(tetrahydro-pyran-4-yl)-2,3-Dihydro-1H-isoindole trifluoro-acetate

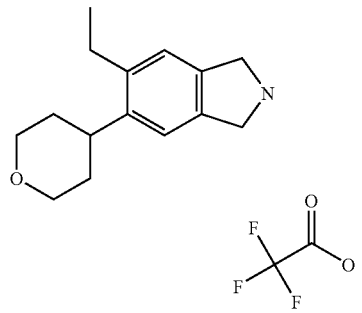

Prepared in analogy to Example A2(c) from 5-ethyl-6-(tetrahydro-pyran-4-yl)-1,3-dihydro-isoindole-2-carboxylic acid tert-butyl ester and trifluoroacetic acid. Yellow oil. MS (m/e): 232.1 ([M+H]$^+$, 100%).

EXAMPLE A70

(2S,6R)-4-(2,3-Dihydro-1H-isoindol-5-yl)-2,6-dimethyl-tetrahydro-pyran-4-ol (a) (2S,6R)-4-(2-Benzyl-2,3-Dihydro-1H-isoindol-5-yl)-2,6-dimethyl-tetrahydro-pyran-4-ol

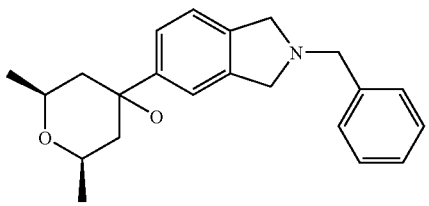

Prepared in analogy to Example A62(b) from 2-benzyl-5-bromo-2,3-dihydro-1H-isoindole (Example A62(a)) and (2R, 6S)-2,6-dimethyl-tetrahydro-pyran-4-one. Brown solid. MS (m/e): 338.4 ([M+H]$^+$, 100%).

(b) (2S,6R)-4-(2,3-Dihydro-1H-isoindol-5-yl)-2,6-dimethyl-tetrahydro-pyran-4-ol

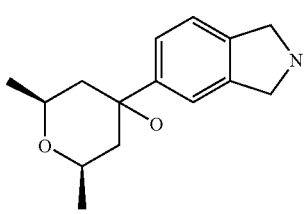

Prepared in analogy to Example A62(c) from (2S,6R)-4-(2-benzyl-2,3-dihydro-1H-isoindol-5-yl)-2,6-dimethyl-tetrahydro-pyran-4-ol and hydrogen. Brown oil. MS (m/e): 248.3 ([M+H]$^+$, 100%).

EXAMPLE A71

5-((2S,6R)-2,6-Dimethyl-tetrahydro-pyran-4-yl)-2,3-dihydro-1H-isoindole (a) 2-Benzyl-5-((2S,6R)-2,6-dimethyl-3,6-dihydro-2H-pyran-4-yl)-2,3-dihydro-1H-isoindole

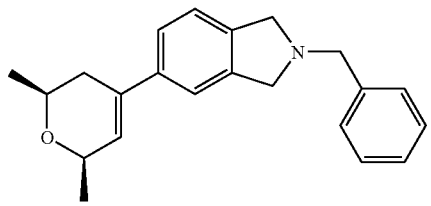

Prepared in analogy to Example A65(a) from (2S,6R)-4-(2-benzyl-2,3-dihydro-1H-isoindol-5-yl)-2,6-dimethyl-tetrahydro-pyran-4-ol (Example A70(a)) and methanesulfonyl chloride, triethylamine, and DBU. Brown oil. MS (m/e): 320.3 ([M+H]$^+$, 100%).

(b) 5-((2S,6R)-2,6-Dimethyl-tetrahydro-pyran-4-yl)-2,3-dihydro-1H-isoindole

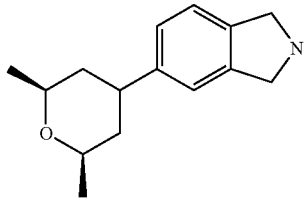

Prepared in analogy to Example A62(c) from 2-benzyl-5-((2S,6R)-2,6-dimethyl-3,6-dihydro-2H-pyran-4-yl)-2,3-dihydro-1H-isoindole and hydrogen. Brown oil. MS (m/e): 232.1 ([M+H]$^+$, 100%).

EXAMPLE A72

5-[1,4]Dioxan-2-yl-2,3-dihydro-1H-isoindole (a) 2-Benzyl-5-(5,6-dihydro-[1,4]dioxin-2-yl)-2,3-Dihydro-1H-isoindole

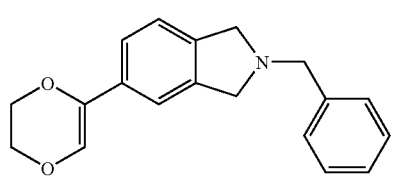

Prepared in analogy to Example A49(a) from 2-benzyl-5-bromo-2,3-dihydro-1H-isoindole (Example A62(a)) and tributyl-(5,6-dihydro-[1,4]dioxin-2-yl)-stannane. Light brown solid. MS (m/e): 294.4 ([M+H]$^+$, 100%).

(b) 5-[1,4]Dioxan-2-yl-2,3-dihydro-1H-isoindole

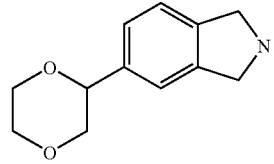

Prepared in analogy to Example A49(b) from 2-benzyl-5-(5,6-dihydro-[1,4]dioxin-2-yl)-2,3-dihydro-1H-isoindole and ammonium formate. Purple solid. MS (m/e): 206.3 ([M+H]$^+$, 100%).

EXAMPLE A73

5-(Tetrahydro-pyran-3-yl)-2,3-dihydro-1H-isoindole (a) 5-(4,4,5,5-Tetramethyl-[1,3,2]dioxaborolan-2-yl)-1,3-dihydro-isoindole-2-carboxylic acid tert-butyl ester

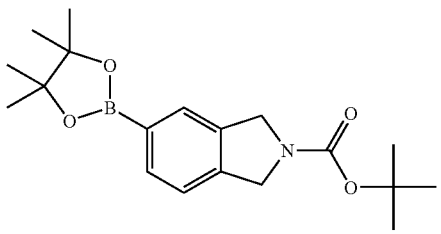

To a solution of 17.1 mmol 5-bromo-1,3-dihydro-isoindole-2-carboxylic acid tert-butyl ester (Example A10(a)) in 50 ml DMF were added 19.3 mmol bis(pinacolato)diboron, 56.0 mmol potassium acetate and 0.57 mmol 1,1-bis(diphenylphosphino)ferrocene dichloro palladium (II) dichloromethane adduct. The mixture was stirred at 70° C. for 17 hours. The solvent was removed in vacuo and the residue was stirred in 50 ml dichloromethane. The mixture was filtered and the filtrate concentrated in vacuo. The residue was purified by chromatography on silica gel (eluant: heptane/ethyl acetate) to yield the title compound as a white solid (yield 76%).

(b) 5-(5,6-Dihydro-4H-pyran-3-yl)-1,3-dihydro-isoindole-2-carboxylic acid tert-butyl ester

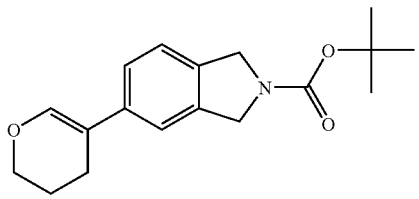

To a stirred solution of 159 mmol 5-(4,4,5,5-tetramethyl-[1,3,2]dioxaborolan-2-yl)-1,3-dihydro-isoindole-2-carboxylic acid tert-butyl ester and 1.44 mmol 5-bromo-3,4-dihydro- 2H-pyran (CAS: 26274-19-1) in 9 ml ethanol and 21 ml toluene was added 0.08 mmol 1,1-bis(diphenylphosphino) ferrocene dichloro palladium (II) dichloromethane adduct. The mixture was heated to 80° C. and then 10 ml of a solution of 2 M aqueous sodium carbonate was added dropwise. After stirring for a further 2 h at 80° C., the reaction mixture was diluted with 50 ml water and extracted with 3×50 ml ethyl acetate. The combined organic phases were dried over sodium sulfate and concentrated in vacuo. The residue was purified by chromatography (SiO$_2$, heptane/ethyl acetate) to yield the title compound as a yellow oil (40% yield). MS (m/e): 246.1 ([M+H−Me$_2$C=CH$_2$]$^+$, 100%).

(c) rac-5-(Tetrahydro-pyran-3-yl)-1,3-dihydro-isoindole-2-carboxylic acid tert-butyl ester

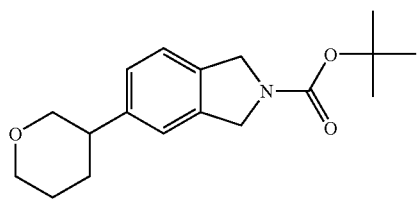

Prepared in analogy to Example A49(b) from 5-(5,6-dihydro-4H-pyran-3-yl)-1,3-dihydro-isoindole-2-carboxylic acid tert-butyl ester and ammonium formate. Light yellow oil. MS (m/e): 248.1 ([M+H−Me$_2$C=CH$_2$]$^+$, 100%).

(d) rac-5-(Tetrahydro-pyran-3-yl)-2,3-dihydro-1H-isoindole

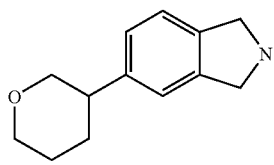

Prepared in analogy to Example A3(e) from rac-5-(tetrahydro-pyran-3-yl)-1,3-dihydro-isoindole-2-carboxylic acid tert-butyl ester and hydrochloric acid. Brown oil. MS (m/e): 204.3 ([M+H]$^+$, 100%).

EXAMPLE A74

5-(2,2,2-Trifluoro-ethoxy)-2,3-Dihydro-1H-isoindole trifluoroacetate (a) 5-(2,2,2-Trifluoro-ethoxy)-1,3-dihydro-isoindole-2-carboxylic acid tert-butyl ester

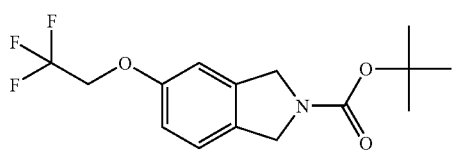

Prepared in analogy to Example A6(a) from 5-iodo-1,3-dihydro-isoindole-2-carboxylic acid tert-butyl ester (Example A38(b)) and 2,2,2-trifluoroethanol. Yellow solid. MS (m/e): 262.0 ([M+H−Me$_2$C=CH$_2$]$^+$, 100%)

(b) 5-(2,2,2-Trifluoro-ethoxy)-2,3-dihydro-1H-isoindole trifluoroacetate

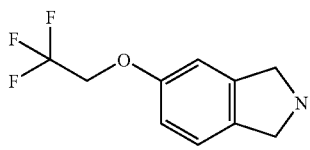

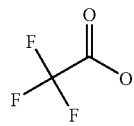

Prepared in analogy to Example A2(c) from 5-(2,2,2-trifluoro-ethoxy)-1,3-dihydro-isoindole-2-carboxylic acid tert-butyl ester and trifluoroacetic acid. Brown oil. MS (m/e): 218.4 ([M+H]$^+$, 100%).

EXAMPLE A75

5-(Tetrahydro-pyran-2-yl)-2,3-Dihydro-1H-isoindole (a) 2-Benzyl-5-(5,6-dihydro-4H-pyran-2-yl)-2,3-dihydro-1H-isoindole

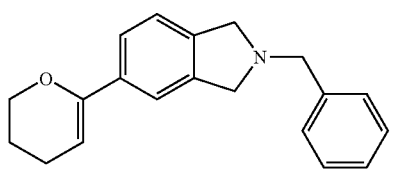

Prepared in analogy to Example A49(a) from 2-benzyl-5-bromo-2,3-dihydro-1H-isoindole (Example A62(a)) and tributyl-(5,6-dihydro-4H-pyran-2-yl)-stannane. Orange oil. MS (m/e): 292.1 ([M+H]$^+$, 100%).

(b) 5-(Tetrahydro-pyran-2-yl)-2,3-dihydro-1H-isoindole

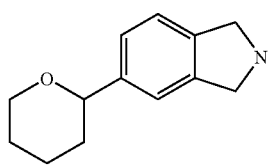

Prepared in analogy to Example A49(b) from 2-benzyl-5-(5,6-dihydro-4H-pyran-2-yl)-2,3-dihydro-1H-isoindole and ammonium formate. Light brown solid. MS (m/e): 204.4 ([M+H]$^+$, 100%).

EXAMPLE A76

5-Chloro-6-(tetrahydro-furan-3-yl)-2,3-dihydro-1H-isoindole trifluoroacetate (a) 5-Chloro-6-(2,5-dihydro-furan-3-yl)-1,3-dihydro-isoindole-2-carboxylic acid tert-butyl ester

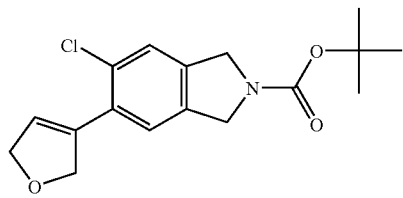

Prepared in analogy to Example A49(a) from 5-chloro-6-iodo-1,3-dihydro-isoindole-2-carboxylic acid tert-butyl ester (Example A3(c)) and tributyl-(2,5-dihydro-furan-3-yl)-stannane. Off-white solid. MS (m/e): 268.3 ([$^{37}$Cl} M+H–Me$_2$C=CH$_2$]$^+$, 32%), 266.1 ([$^{35}$Cl}M+H–Me$_2$C=CH$_2$]$^+$, 100%).

(b) 5-Chloro-6-(tetrahydro-furan-3-yl)-1,3-dihydro-isoindole-2-carboxylic acid tert-butyl ester

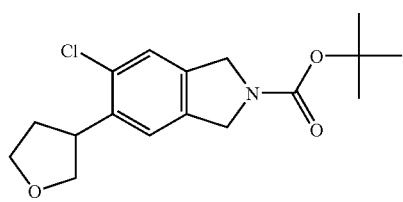

Prepared in analogy to Example A68(a) from 5-chloro-6-(2,5-dihydro-furan-3-yl)-1,3-dihydro-isoindole-2-carboxylic acid tert-butyl ester and platinum(IV) oxide. Off-white solid. MS (m/e): 270.3 ([$^{37}$Cl} M+H-Me$_2$C=CH$_2$]$^+$, 38%), 268.3 ([$^{35}$Cl} M+H-Me$_2$C=CH$_2$]$^+$, 100%).

(c) 5-Chloro-6-(tetrahydro-furan-3-yl)-2,3-Dihydro-1H-isoindole trifluoroacetate

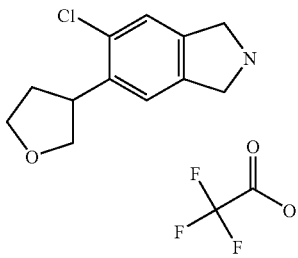

Prepared in analogy to Example A2(c) from 5-chloro-6-(tetrahydro-furan-3-yl)-1,3-dihydro-isoindole-2-carboxylic acid tert-butyl ester and trifluoroacetic acid. Brown oil. MS (m/e): 226.2 ([$^{37}$Cl}M+H]$^+$, 33%), 224.2 ([$^{35}$Cl}M+H]$^+$, 100%).

EXAMPLE A77

8-(6-Chloro-2,3-dihydro-1H-isoindol-5-yl)-3-oxa-8-aza-bicyclo[3.2.1]octane trifluoro-acetate (a) 5-Chloro-6-(3-oxa-8-aza-bicyclo[3.2.1]oct-8-yl)-1,3-dihydro-isoindole-2-carboxylic acid tert-butyl ester

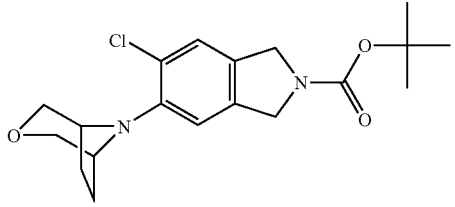

Prepared in analogy to Example A3(d) from 5-chloro-6-iodo-1,3-dihydro-isoindole-2-carboxylic acid tert-butyl ester (Example A3(c)) and 3-oxa-8-azabicyclo[3.2.1]octane hydrochloride. Yellow solid. MS (m/e): 367.1 ([$^{37}$Cl}M+H]$^+$, 35%), 365.1 ([$^{35}$Cl}M+H]$^+$, 100%).

(b) 8-(6-Chloro-2,3-dihydro-1H-isoindol-5-yl)-3-oxa-8-aza-bicyclo[3.2.1]octane trifluoro-acetate

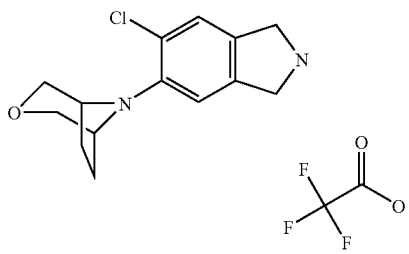

Prepared in analogy to Example A2(c) from 5-chloro-6-(3-oxa-8-aza-bicyclo[3.2.1]oct-8-yl)-1,3-dihydro-isoindole-2-carboxylic acid tert-butyl ester and trifluoroacetic acid. Brown oil. MS (m/e): 267.1 ([$^{37}$Cl}M+H]$^+$, 43%), 265.1 ([$^{35}$Cl}M+H]$^+$, 100%).

EXAMPLE A78

5-Chloro-6-(1S,4S)-2-oxa-5-aza-bicyclo[2.2.1]hept-5-yl-2,3-dihydro-1H-isoindole trifluoroacetate (a) 5-Chloro-6-(1S,4S)-2-oxa-5-aza-bicylo[2.2.1]hept-5-yl-1,3-dihydro-isoindole-2-carboxylic acid tert-butyl ester

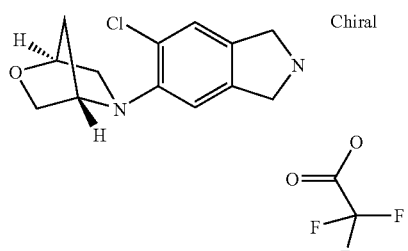

Prepared in analogy to Example A3(d) from 5-chloro-6-iodo-1,3-dihydro-isoindole-2-carboxylic acid tert-butyl ester (Example A3(c)) and (1S,4S)-2-oxa-5-aza-bicyclo[2.2.1]heptane trifluoroacetate. Light yellow solid. MS (m/e): 353.1 ([{$^{37}$Cl}M+H]$^+$, 36%), 351.1 ([{$^{35}$Cl}M+H]$^+$, 100%).

(b) 5-Chloro-6-(1S,4S)-2-oxa-5-aza-bicylo[2.2.1]hept-5-yl-2,3-Dihydro-1H-isoindole trifluoroacetate

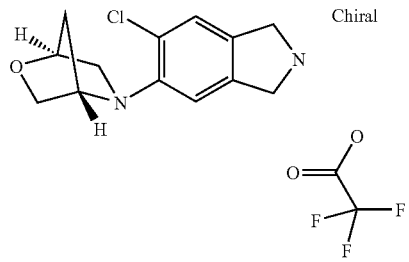

Prepared in analogy to Example A2(c) from 5-chloro-6-(1S,4S)-2-oxa-5-aza-bicyclo[2.2.1]hept-5-yl-1,3-dihydro-isoindole-2-carboxylic acid tert-butyl ester and trifluoroacetic acid. Brown oil. MS (m/e): 253.1 ([{$^{37}$Cl}M+H]$^+$, 26%), 251.1 ([{$^{35}$Cl}M+H]$^+$, 100%).

EXAMPLE A79

5-Fluoro-6-(tetrahydro-pyran-4-yl)-2,3-dihydro-1H-isoindole (a) 1-Fluoro-2-iodo-4,5-dimethyl-benzene

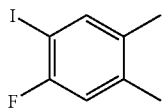

To a stirred suspension of 50.8 mmol 2-fluoro-4,5-dimethyl-phenylamine-(commercial, CAS: 117832-17-4) in 70 ml water was added dropwise at 0° C. a solution of 5 ml concentrated sulfuric acid in 15 ml water. A solution of 66.0 mmol sodium nitrite in 15 ml water was then added dropwise and stirring continued at 0° C. for 60 min. A solution of 173 mmol potassium iodide in 50 ml water was then added dropwise over 30 min while maintaining the reaction temperature between 0 and 5° C. The reaction mixture was then warmed to room temperature and stirred for 3 h before being quenched with aqueous sodium thiosulphite solution and diluted with ethyl acetate. The phases were separated and the organic phase was washed with water and then dried over sodium sulfate and concentrated in vacuo to yield the title compound as a brown solid (69% yield). MS (m/e): 251 ([M+H]$^+$, 100%).

(b) 4-Fluoro-5-iodo-phthalic acid

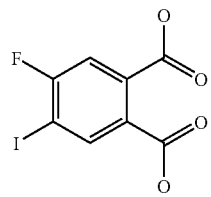

To a stirred solution of 34.7 mmol 1-fluoro-2-iodo-4,5-dimethyl-benzene in 200 ml acetic acid was added dropwise at 0° C. 40 ml concentrated sulfuric acid. 277 mmol chromium(VI) oxide was then added in small portions. The reaction mixture was then cautiously warmed to 40° C., whereupon an exothermic reaction started and the temperature rose to 95° C. Once the initial exotherm was over, the reaction mixture was stirred at 60° C. overnight. The reaction mixture was then diluted with ethyl acetate, tetrahydrofuran and brine. The phases were separated and the organic phase was washed with brine, dried over sodium sulfate, and concentrated in vacuo to afford the title compound as a brown solid which was used in the next step without further purification (60% yield). MS (m/e): 309.0 ([M−H]$^-$, 100%).

(c) 4-Fluoro-5-iodo-phthalic acid dimethyl ester

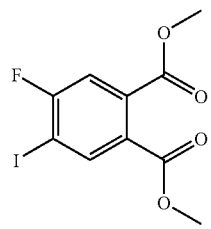

To a stirred solution of 19.4 mmol 4-fluoro-5-iodo-phthalic acid in 60 ml DMF was added 58.1 mmol potassium carbonate. The mixture was then warmed to 35° C. and 38.7 mmol methyl iodide was added dropwise. The mixture was heated at 35° C. for 2 h and then at 60° C. for 4 h before being concentrated in vacuo. The residue was resuspended in ethyl acetate and water and the phases were separated The organic phase was washed sequentially with 0.5 M aq. sodium hydroxide solution and with brine, then dried over sodium sulfate and concentrated in vacuo. The residue was purified by chromatography on silica gel (eluant ethyl acetate/heptane) to afford the title compound as an orange oil (53% yield). EI-MS (m/e): 338.0 (M$^+$, 50%), 307.0 ([M−OMe]$^+$, 100%).

(d) (5-Fluoro-2-hydroxymethyl-4-iodo-phenyl)-methanol

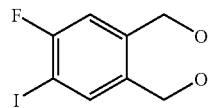

To 9.38 mmol 4-fluoro-5-iodo-phthalic acid dimethyl ester in 25 ml absolute ethanol was added 9.38 mmol calcium chloride. 18.8 mmol sodium borohydride was then added in small portions and the reaction mixture was stirred for 4 h at room temperature, then at reflux for 2 h and then at room temperature overnight. The mixture was quenched by addition of 20 ml 1 M aq. hydrochloric acid and diluted with water and ethyl acetate. The phases were separated and the organic phase was extracted four times with dichloromethane. The combined organic extracts were dried over sodium sulfate and concentrated in vacuo to afford the title compound as a yellow oil (98% yield). MS (m/e): 283.1 ([M+H]$^+$, 100%).

(e) Methanesulfonic acid 4-fluoro-5-iodo-2-methanesulfonyloxymethyl-benzyl ester

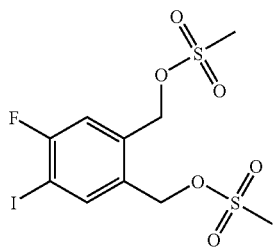

To a suspension of 8.86 mmol (5-fluoro-2-hydroxymethyl-4-iodo-phenyl)-methanol in 30 ml dichloromethane at 0° C. were added dropwise 22.2 mmol triethylamine and 19.5 mmol methanesulfonyl chloride. The mixture was stirred at 0° C. for 1 h, and then at room temperature for 5 h. The reaction mixture was diluted with water and extracted four times with dichloromethane. The combined organic phases were dried over sodium sulfate and concentrated in vacuo to afford the title compound as a yellow oil (67% yield) which was used in the next step without further purification.

(f) 2-Benzhydryl-5-fluoro-6-iodo-2,3-dihydro-1H-isoindole

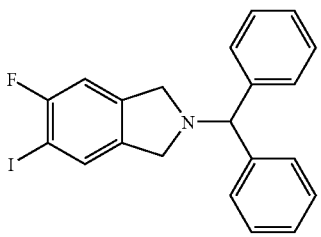

To a mixture of 5.93 mmol methanesulfonic acid 4-fluoro-5-iodo-2-methanesulfonyloxymethyl-benzyl ester and 14.8 mmol N,N-diisopropylethylamine in 7 ml DMF at 0° C. was added dropwise a solution of 6.53 mmol diphenylmethylamine in 5 ml DMF. The mixture was heated at 60° C. for 16 h and was then cooled to room temperature and partitioned between ethyl acetate and water. The organic phase was washed sequentially with water and brine, dried over sodium sulfate, and concentrated in vacuo. The residue was purified by chromatography on silica gel (eluant: ethyl acetate/heptane) to afford the title compound as a light yellow solid (55% yield).

(g) 2-Benzhydryl-5-(3,6-dihydro-2H-pyran-4-yl)-6-fluoro-2,3-dihydro-1H-isoindole

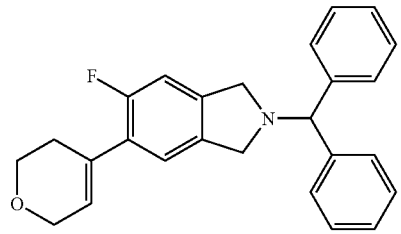

Prepared in analogy to Example A49(a) from 2-benzhydryl-5-fluoro-6-iodo-2,3-dihydro-1H-isoindole and tributyl-(3,6-dihydro-2H-pyran-4-yl)-stannane. Yellow solid. MS (m/e): 386.1 ([M+H]$^+$, 100%).

(h) 2-Benzhydryl-5-fluoro-6-(tetrahydro-pyran-4-yl)-2,3-dihydro-1H-isoindole

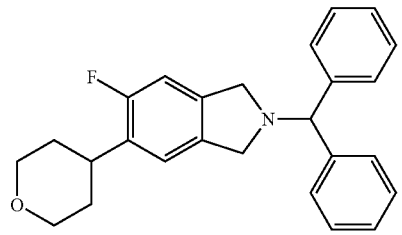

Prepared in analogy to Example A68(a) from 2-benzhydryl-5-(3,6-dihydro-2H-pyran-4-yl)-6-fluoro-2,3-dihydro-1H-isoindole. White solid. MS (m/e): 388.1 ([M+H]$^+$, 100%).

(i) 5-Fluoro-6-(tetrahydro-pyran-4-yl)-2,3-dihydro-1H-isoindole

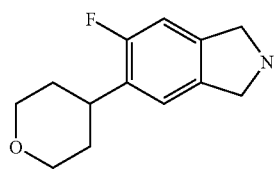

To a stirred solution 0.12 mmol 2-benzhydryl-5-fluoro-6-(tetrahydro-pyran-4-yl)-2,3-dihydro-1H-isoindole in 4 ml methanol was added 4 mg 10% palladium on charcoal and the mixture was stirred under an atmosphere of hydrogen for 16 h. The reaction mixture was then filtered and the filtrate was concentrated in vacuo to yield the title compound as a yellow solid (100% yield). MS (m/e): 222.1 ([M+H]$^+$, 100%).

EXAMPLE A80

5-(Tetrahydro-pyran-4-yloxy)-2,3-dihydro-1H-isoindole trifluoroacetate (a) 5-(Tetrahydro-pyran-4-yloxy)-1,3-dihydro-isoindole-2-carboxylic acid tert-butyl ester

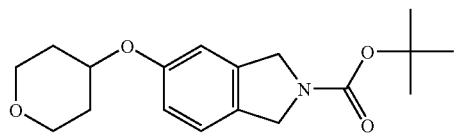

Prepared in analogy to Example A6(a) from 5-iodo-1,3-dihydro-isoindole-2-carboxylic acid tert-butyl ester (Example A38(b)) and tetrahydro-4H-pyran-4-ol. White solid. MS (m/e): 264.1 ([M+H—Me$_2$C=CH$_2$]$^+$, 100%)

(b) 5-(Tetrahydro-pyran-4-yloxy)-2,3-dihydro-1H-isoindole trifluoroacetate

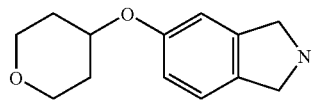

Prepared in analogy to Example A2(c) from 5-(tetrahydro-pyran-4-yloxy)-1,3-dihydro-isoindole-2-carboxylic acid tert-butyl ester and trifluoroacetic acid. Yellow oil. MS (m/e): 220.3 ([M+H]$^+$, 100%).

EXAMPLE A81

5-(3-Fluoro-oxetan-3-yl)-2,3-dihydro-1H-isoindole (a) 3-(2-Benzyl-2,3-dihydro-1H-isoindol-5-yl)-oxetan-3-ol

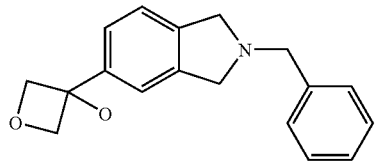

Prepared in analogy to Example A62(b) from 2-benzyl-5-bromo-2,3-dihydro-1H-isoindole (Example A62(a)) and oxetan-3-one (CAS: 6704-31-0). Brown solid. MS (m/e): 282.4 ([M+H]$^+$, 100%).

(b) 3-(2,3-Dihydro-1H-isoindol-5-yl)-oxetan-3-ol

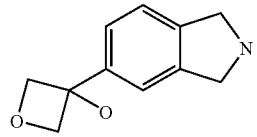

Prepared in analogy to Example A62(c) from 3-(2-benzyl-2,3-dihydro-1H-isoindol-5-yl)-oxetan-3-ol and hydrogen. Brown solid. MS (m/e): 192.3 ([M+H]$^+$, 100%).

(c) 5-(3-Fluoro-oxetan-3-yl)-2,3-dihydro-1H-isoindole

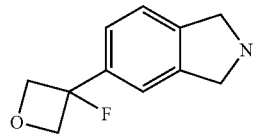

To 0.58 mmol 3-(2,3-dihydro-1H-isoindol-5-yl)-oxetan-3-ol in 2 ml acetonitrile and 2 ml nitromethane at −60° C. was added 1.15 mmol diethylaminosulfur trifluoride and the mixture was allowed to warm to 0° C. over 30 min. The reaction mixture was re-cooled to −60° C. and quenched by addition of 5 ml saturated aq. sodium carbonate solution. The mixture was warmed to RT and diluted with THF and ethyl acetate, then washed sequentially with water and with brine. The organic phase was separated, dried over sodium sulfate, and concentrated in vacuo to afford the title compound as a brown oil (67% yield). MS (m/e): 194.3 ([M+H]$^+$, 100%).

EXAMPLE A82

5-Cyclopropylmethoxy-2,3-dihydro-1H-isoindole trifluoroacetate (a) 5-Cyclopropylmethoxy-1,3-dihydro-isoindole-2-carboxylic acid tert-butyl ester

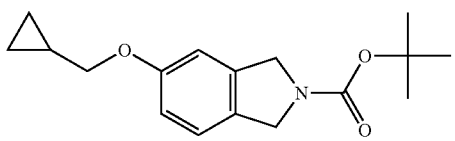

Prepared in analogy to Example A6(a) from 5-iodo-1,3-dihydro-isoindole-2-carboxylic acid tert-butyl ester (Example A38(b)) and cyclopropylmethanol. Off-white solid. MS (m/e): 234.1 ([M+H-Me$_2$C=CH$_2$]$^+$, 100%)

(b) 5-Cyclopropylmethoxy-2,3-dihydro-1H-isoindole trifluoroacetate

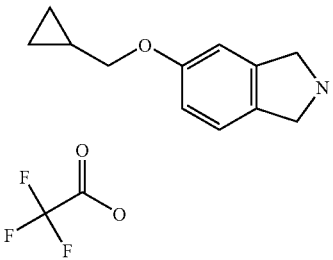

Prepared in analogy to Example A2(c) from 5-cyclopropylmethoxy-1,3-dihydro-isoindole-2-carboxylic acid tert-butyl ester and trifluoroacetic acid. Yellow oil. MS (m/e): 190.4 ([M+H]$^+$, 100%).

EXAMPLE A83

5-(3,3,3-Trifluoro-propoxy)-2,3-Dihydro-1H-isoindole trifluoroacetate (a) 5-(3,3,3-Trifluoro-propoxy)-1,3-dihydro-isoindole-2-carboxylic acid tert-butyl ester

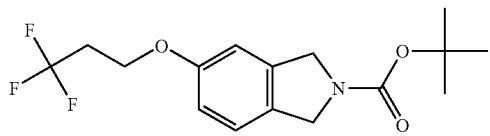

Prepared in analogy to Example A6(a) from 5-iodo-1,3-dihydro-isoindole-2-carboxylic acid tert-butyl ester (Example A38(b)) and 3,3,3-trifluoropropanol. Off-white solid. MS (m/e): 276.3 ([M+H—Me$_2$C=CH$_2$]$^+$, 100%)

(b) 5-(3,3,3-Trifluoro-propoxy)-2,3-dihydro-1H-isoindole trifluoroacetate

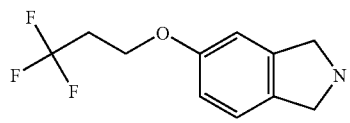

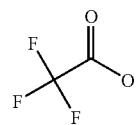

Prepared in analogy to Example A2(c) from 5-(3,3,3-trifluoro-propoxy)-1,3-dihydro-isoindole-2-carboxylic acid tert-butyl ester and trifluoroacetic acid. Brown oil. MS (m/e): 232.1 ([M+H]$^+$, 100%).

EXAMPLE A84

5-Fluoro-6-morpholin-4-yl-2,3-dihydro-1H-isoindole trifluoroacetate (a) 5-Fluoro-isoindole-1,3-dione

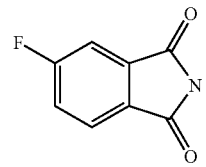

A mixture of 144 mmol 4-fluorophthalic anhydride and 1.16 mol formamide was heated at 200° C. for 2 h. The reaction mixture was poured onto ice-water and the resulting crystals collected by filtration and dried in vacuo to afford the title compound as a yellow solid (100% yield). MS (m/e): 164.4 ([M−H]$^-$, 100%).

(b) 5-Fluoro-6-nitro-isoindole-1,3-dione

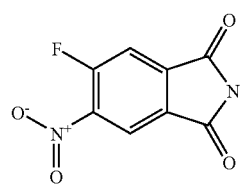

To 753 mmol fuming nitric acid at 0° C. was added dropwise 150 ml 20% oleum. 150.6 mmol 5-fluoro-isoindole-1,3-dione was then added portionwise and the resulting suspension was allowed to warm to room temperature over 4 hours and then stirred for a further 16 h at room temperature and finally was heated at 50° C. for 3 h. The reaction mixture was poured onto ice and the resulting mixture was filtered and the filter cake dried in vacuo to afford the title compound as a yellow solid (68% yield). MS (m/e): 209.1 ([M−H]$^-$, 100%).

(c) 5-Amino-6-fluoro-isoindole-1,3-dione

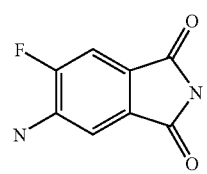

To a suspension of 99.9 mmol 5-fluoro-6-nitro-isoindole-1,3-dione in 400 ml concentrated hydrochloric acid was added 350 mmol tin(II) chloride dehydrate and the resulting mixture was heated at 60° C. for 2 h. The reaction mixture was then poured onto ice-water and then 28% aq sodium hydroxide was added with stirring until a suspension was formed. The crystals were collected by filtration and dried in vacuo to afford the title compound as a yellow solid (80% yield). MS (m/e): 179.1 ([M−H]$^-$, 100%).

113

(d) 5-Fluoro-6-iodo-isoindole-1,3-dione

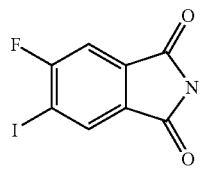

To 99.9 mmol copper(I) iodide in dry acetonitrile was added 112 mmol tert-butyl nitrite and the resulting suspension was heated at 65° C. 66.6 mmol 5-amino-6-fluoro-isoindole-1,3-dione was then added portionwise and the reaction mixture stirred at 65° C. for 2 h and then allowed to cool to room temperature. The mixture was poured onto cold 1 M aq hydrochloric acid and then the acetonitrile was removed in vacuo. The aqueous residue was stirred at 0° C. for 20 min, and the resulting solid was collected by filtration and dried in vacuo to afford the title compound as a brown solid (87% yield). MS (m/e): 290.0 ([M−H]$^-$, 100%).

(e) 5-Fluoro-6-iodo-2,3-Dihydro-1H-isoindole

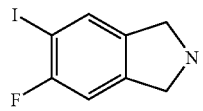

Prepared in analogy to Example A1 from 5-fluoro-6-iodo-isoindole-1,3-dione and borane tetrahydrofuran complex. Yellow oil. MS (m/e): 264.0 ([M+H$^+$, 100%).

(f) 5-Fluoro-6-iodo-1,3-dihydro-isoindole-2-carboxylic acid tert-butyl ester

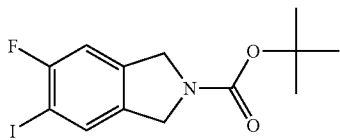

Prepared in analogy to Example A3(c) from 5-fluoro-6-iodo-2,3-dihydro-1H-isoindole and di-tert-butyl dicarbonate. Light yellow solid. MS (m/e): 308.1 ([M+H−Me$_2$C═CH$_2$]$^+$, 100%).

(g) 5-Fluoro-6-morpholin-4-yl-1,3-dihydro-isoindole-2-carboxylic acid tert-butyl ester

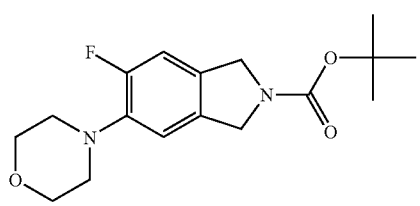

Prepared in analogy to Example A3 (d) from 5-fluoro-6-iodo-1,3-dihydro-isoindole-2-carboxylic acid tert-butyl ester and morpholine. Yellow solid. MS (m/e): 323.4 ([M+H]$^+$, 100%).

114

(h) 5-Fluoro-6-morpholin-4-yl-2,3-dihydro-1H-isoindole trifluoroacetate

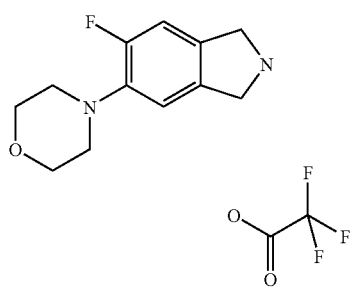

Prepared in analogy to Example A2(c) from 5-fluoro-6-morpholin-4-yl-1,3-dihydro-isoindole-2-carboxylic acid tert-butyl ester and trifluoroacetic acid. Yellow oil. MS (m/e): 223.4 (M+H]$^+$, 100%).

EXAMPLE A85

5-Chloro-6-(tetrahydro-pyran-4-yloxy)-2,3-dihydro-1H-isoindole trifluoroacetate (a) 5-Chloro-6-(tetrahydro-pyran-4-yloxy)-1,3-dihydro-isoindole-2-carboxylic acid tert-butyl ester

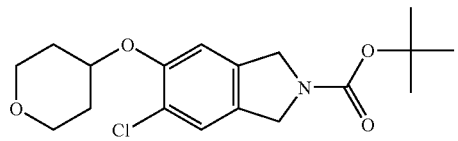

Prepared in analogy to Example A6(a) from 5-chloro-6-iodo-1,3-dihydro-isoindole-2-carboxylic acid tert-butyl ester (Example A3(c)) and tetrahydro-4H-pyran-4-ol. Off-white solid. MS (m/e): 300.1 ([{$^{37}$Cl}M+H—Me$_2$C═CH$_2$]$^+$, 36%), 298.3 ([{$^{35}$Cl}M+H-Me$_2$C═CH$_2$]$^+$, 100%).

(b) 5-Chloro-6-(tetrahydro-pyran-4-yloxy)-2,3-dihydro-1H-isoindole trifluoroacetate

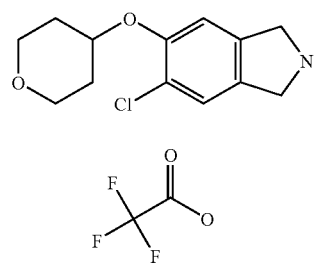

Prepared in analogy to Example A2(c) from 5-chloro-6-(tetrahydro-pyran-4-yloxy)-1,3-dihydro-isoindole-2-carboxylic acid tert-butyl ester and trifluoroacetic acid. Yellow oil. 256.3 ([{$^{37}$Cl}M+H]$^+$, 50%), 254.3 ([{$^{35}$Cl}M+H]$^+$, 100%).

EXAMPLE A86

5-Fluoro-6-(tetrahydro-pyran-4-yloxy)-2,3-dihydro-1H-isoindole trifluoroacetate (a) 5-Fluoro-6-(tetrahydro-pyran-4-yloxy)-1,3-dihydro-isoindole-2-carboxylic acid tert-butyl ester

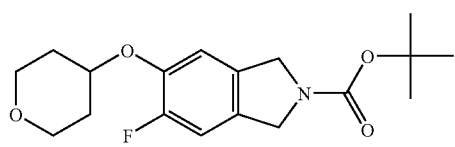

Prepared in analogy to Example A6(a) from 5-fluoro-6-iodo-1,3-dihydro-isoindole-2-carboxylic acid tert-butyl ester (Example A84(f)) and tetrahydro-4H-pyran-4-ol. Yellow solid. MS (m/e): 282.3 ([M+H-Me$_2$C=CH$_2$]$^+$, 100%).

(b) 5-Fluoro-6-(tetrahydro-pyran-4-yloxy)-2,3-dihydro-1H-isoindole trifluoroacetate

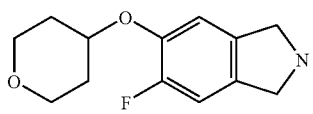

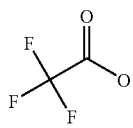

Prepared in analogy to Example A2(c) from 5-fluoro-6-(tetrahydro-pyran-4-yloxy)-1,3-dihydro-isoindole-2-carboxylic acid tert-butyl ester and trifluoroacetic acid. Yellow oil. 238.1 ([M+H]$^+$, 100%).

EXAMPLE B1

2-Isopropoxy-5-methanesulfonyl-benzoic acid (a) 2-Chloro-5-methanesulfonyl-benzoic acid

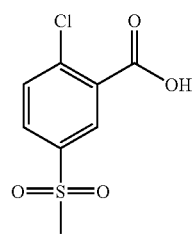

To 99 mmol 2-chloro-5-(methylthio) benzoic acid (purchased from Aldrich) in 400 ml methanol at 0° C. was added 296 mmol oxone® and the mixture was allowed to stir at RT for 3.5 h. The precipitate was filtered off and the filtrate was concentrated under reduced pressure. The residue was extracted 3 times with 400 ml ethyl acetate and the combined organic phases washed twice with 300 ml 1 N HCl and with 300 ml saturated aqueous NaCl solution and dried with MgSO$_4$. Evaporation under reduced pressure yielded the title compound which was used in the next step without further purification.

(b) 2-Isopropoxy-5-methanesulfonyl-benzoic acid

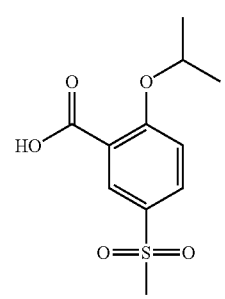

A mixture of 2.13 mmol 2-chloro-5-methanesulfonyl-benzoic acid, 0.64 mmol Cu(I)Br in 5 ml triethylamine and 25 ml isopropanol was heated to 120° C. for 16 h in a sealed tube. The volatiles were removed in vacuo and the residue was taken up in 70 ml 1 N HCl. Extraction with ethyl acetate, drying of the combined organic fractions and evaporation yielded a residue which was purified by reversed phase preparative HPLC eluting with an acetonitrile/water gradient. Evaporation of the product fractions yielded the title compound. MS (m/e): 257.0 ([M−H]$^-$, 100%)

EXAMPLE B2

Rac-5-Methanesulfonyl-2-(2,2,2-trifluoro-1-methyl-ethoxy)-benzoic acid

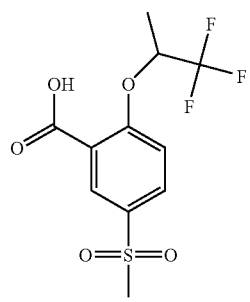

Prepared in analogy to Example B1(b) from 2-chloro-5-methanesulfonyl-benzoic acid (Example B1(a)) and rac-1,1,1-trifluoro-propan-2-ol. The crude material was purified by preparative HPLC to yield the title compound as a white solid. MS (m/e): 311.3 ([M−H]$^-$, 100%).

EXAMPLE B3

5-Methanesulfonyl-2-((S)-2,2,2-trifluoro-1-methylethoxy)-benzoic acid (a) rac-5-Methanesulfonyl-2-(2,2,2-trifluoro-1-methyl-ethoxy)-benzoic acid methyl ester

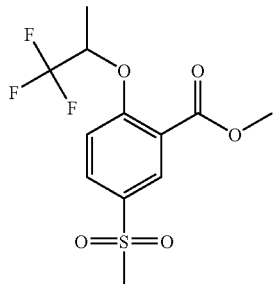

A mixture of 21.7 mmol 2-hydroxy-5-methanesulfonyl-benzoic acid methyl ester (WO 2002074774), 32.5 mmol trifluoro-methanesulfonic acid 2,2,2-trifluoro-1-methyl-ethyl ester [212556-43-9] and 43.4 mmol potassium carbonate in 87 ml DMF was stirred at 80° C. for 48 hours. After cooling to room temperature, the mixture was concentrated in vacuo, resuspended in water and stirred for 1 hour. Filtration yielded the title compound.

(b) 5-Methanesulfonyl-2-((S)-2,2,2-trifluoro-1-methyl-ethoxy)-benzoic acid methyl ester Chircal

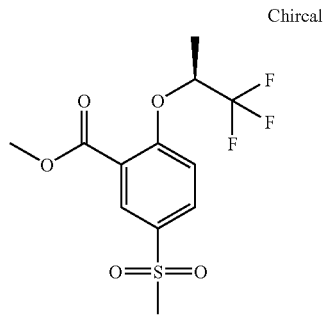

The title compound was obtained by separation of rac-5-methanesulfonyl-2-(2,2,2-trifluoro-1-methyl-ethoxy)-benzoic acid methyl ester by chiral HPLC (Chiralcel OD, 15% ethanol/heptane, flow 35 ml min$^{-1}$, 220 nm, retention time: 86 min.).

(c) 5-Methanesulfonyl-2-((S)-2,2,2-trifluoro-1-methyl-ethoxy)-benzoic acid

Chircal

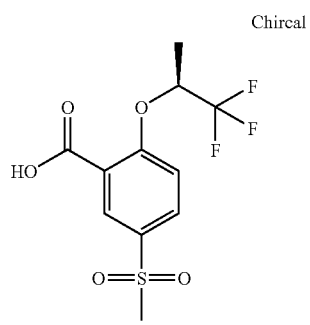

To 0.604 mmol 5-methanesulfonyl-2-((S)-2,2,2-trifluoro-1-methyl-ethoxy)-benzoic acid methyl ester in 1.97 ml ethanol was added 1.21 mmol 2 N aq NaOH solution and the reaction mixture was stirred at 80° C. for 0.5 hour. After such time the solvent was removed in vacuo, the residue was taken in water and acidified by addition of 2N HCl to yield after filtration the title compound as a white solid (88%). MS (m/e): 311.0 ([M–H]$^-$, 100%)

EXAMPLE B4

2-Isopropylsulfanyl-5-methanesulfonyl-benzoic acid a) 2-Fluoro-5-methylsulfanyl-benzoic acid

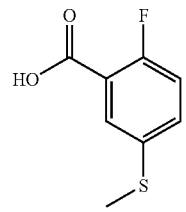

The title compound was prepared by following the procedure described in: Journal of Organometallic Chemistry 1991, 419 (1-2), 1-8.

b) 2-Fluoro-5-methanesulfonyl-benzoic acid

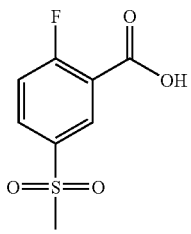

To 2.68 mmol 2-fluoro-5-methanesulfanyl-benzoic acid in 5 ml methanol at 0° C. was added 8.05 mmol oxone® and the mixture was allowed to stir at RT for 72 h. The precipitate was filtered off and the filtrate was concentrated under reduced pressure. The residue was treated with water and extracted 3 times with 400 ml dichloromethane. The combined organic phases were dried over sodium sulfate. Evaporation under reduced pressure yielded the title compound as a white crystalline solid (yield 79%). MS (m/e): 217.2 (M–H$^+$, 100%).

c) 2-Isopropylsulfanyl-5-methanesulfonyl-benzoic acid

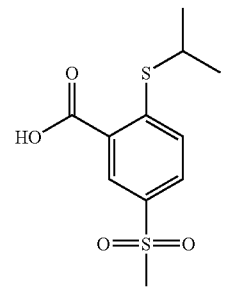

To a solution of 4.58 mmol 2-fluoro-5-methanesulfonyl-benzoic acid in 6 ml N,N-dimethylacetamide were added 15.2 mol cesium carbonate and 10.1 mmol 2-propanethiol and the mixture was stirred at 90° C. for 3 h. The reaction mixture was then cooled to room temperature and acidified to pH1 by addition of hydrochloric acid before being extracted three times with ethyl acetate. The combined organic phases were dried over sodium sulfate and concentrated in vacuo to afford the title compound as a light yellow liquid which was used in the next step without further purification (yield 99%). EI-MS (m/e): 274.1 (M+, 35%), 232.1 ([M–$C_3H_6$]+, 30%, 214.1 (M–$C_3H_6$–$H_2O$)+, 100%).

EXAMPLE B5

5-Methanesulfonyl-2-((R)-2,2,2-trifluoro-1-methyl-ethoxy)-benzoic acid (a) 5-Methanesulfonyl-2-((R)-2,2,2-trifluoro-1-methyl-ethoxy)-benzoic acid methyl ester

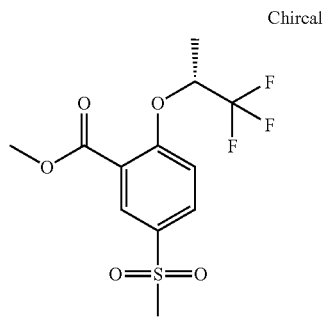

The title compound was obtained by separation of rac-5-methanesulfonyl-2-(2,2,2-trifluoro-1-methyl-ethoxy)-benzoic acid methyl ester (Example B3(a)) by chiral HPLC (Chiralcel OD, 15% ethanol/Heptane, flow 35 ml min$^{-1}$, 220 nm, retention time: 74 min.).

(b) 5-Methanesulfonyl-2-((R)-2,2,2-trifluoro-1-methyl-ethoxy)-benzoic acid

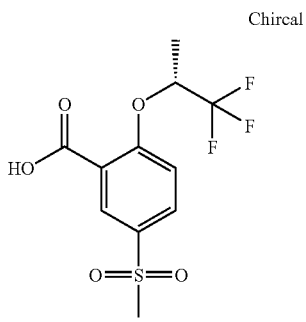

Prepared in analogy to Example B3(c) from 5-methanesulfonyl-2-((R)-2,2,2-trifluoro-1-methyl-ethoxy)-benzoic acid methyl ester. MS (m/e): 311.0 ([M–H]$^-$, 100%)

EXAMPLE B6

2-Ethylsulfanyl-5-methanesulfonyl-benzoic add

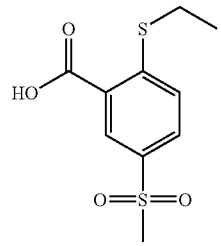

To a solution of 4.58 mmol 2-fluoro-5-methanesulfonyl-benzoic acid (Example B4(b)) in 6 ml N,N-dimethylformamide were added 13.8 mol cesium carbonate and 9.25 mmol ethanethiol and the mixture was stirred at 90° C. for 30 min. The reaction mixture was then cooled to room temperature and acidified to pH1 by addition of hydrochloric acid before being extracted three times with ethyl acetate. The combined organic phases were dried over sodium sulfate and concentrated in vacuo to afford the title compound as a white solid which was used in the next step without further purification (yield 99%). MS (m/e): 259.0 ([M–H]$^-$, 100%).

EXAMPLE B7

5-Methanesulfonyl-2-(2,2,2-trifluoro-ethylsulfanyl)-benzoic acid

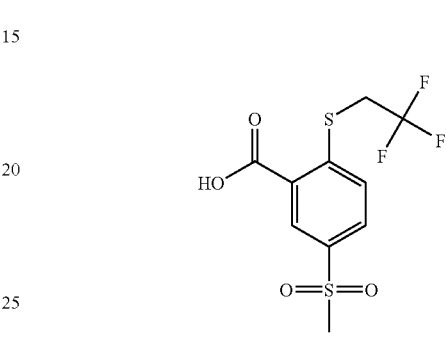

To a solution of 4.58 mmol 2-fluoro-5-methanesulfonyl-benzoic acid (Example B4(b)) in 6 ml N,N-dimethylformamide were added 13.8 mol cesium carbonate and 9.16 mmol 2,2,2-trifluoro-ethanethiol and the mixture was stirred at 90° C. for 30 min. The reaction mixture was then cooled to room temperature and acidified to pH1 by addition of hydrochloric acid before being extracted three times with ethyl acetate. The combined organic phases were dried over sodium sulfate and concentrated in vacuo to afford the title compound as a red-brown solid which was used in the next step without further purification (yield 99%). MS (m/e): 312.9 ([M–H]$^-$, 100%).

EXAMPLE B8

2-Isobutylsulfanyl-5-methanesulfonyl-benzoic acid

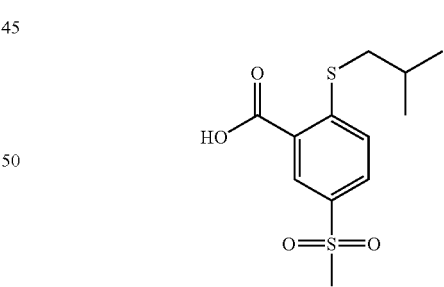

To a solution of 4.58 mmol 2-fluoro-5-methanesulfonyl-benzoic acid (Example B4(b)) in 6 ml N,N-dimethylformamide were added 13.8 mol cesium carbonate and 9.97 mmol 2-methyl-1-propanethiol and the mixture was stirred at 90° C. for 30 min. The reaction mixture was then cooled to room temperature and acidified to pH1 by addition of hydrochloric acid before being extracted three times with ethyl acetate. The combined organic phases were dried over sodium sulfate and concentrated in vacuo to afford the title compound as a white solid which was used in the next step without further purification (yield 99%). MS (m/e): 287.0 ([M–H]$^-$, 100%).

EXAMPLE B9

5-Methanesulfonyl-2-methylsulfanyl-benzoic acid

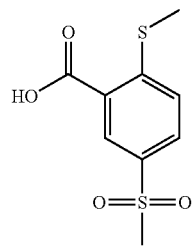

To a solution of 4.58 mmol 2-fluoro-5-methanesulfonyl-benzoic acid (Example B4(b)) in 6 ml N,N-dimethylformamide were added 13.8 mol cesium carbonate and 10.0 mmol sodium methanethiolate and the mixture was stirred at 90° C. for 30 min. The reaction mixture was then cooled to room temperature and acidified to pH1 by addition of hydrochloric acid before being extracted three times with ethyl acetate. The combined organic phases were dried over sodium sulfate and concentrated in vacuo to afford the title compound as a colourless oil which was used in the next step without further purification (yield 99%). MS (m/e): 244.9 ([M–H]$^-$, 100%).

EXAMPLE B10

5-Methanesulfonyl-2-(2,2,2-trifluoro-ethoxy)-benzoic acid

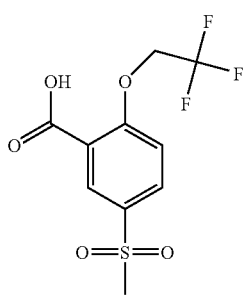

Prepared in analogy to Example B1(b) from 2-chloro-5-methanesulfonyl-benzoic acid (Example B1(a)) and 2,2,2-trifluoro-ethanol. The crude material was purified by preparative HPLC to yield the title compound as a white solid. MS (m/e): 297.0 ([M–H]$^-$, 100%).

EXAMPLE B11

2-Isobutoxy-5-methanesulfonyl-benzoic acid

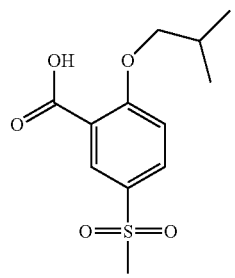

Prepared in analogy to Example B1(b) from 2-chloro-5-methanesulfonyl-benzoic acid (Example B1(a)) and isobutanol. The crude material was purified by flash chromatography to yield the title compound as a white solid. MS (m/e): 271.1 ([M–H]$^-$, 100%).

EXAMPLE B12

5-Methanesulfonyl-2-morpholin-4-yl-benzoic acid

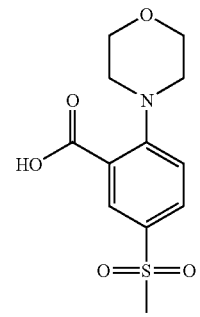

A mixture of 4.26 mmol 2-chloro-5-methanesulfonyl-benzoic acid (Example B1(a)) in 8 ml morpholine was heated at 110° C. for 15 h. After evaporation of all volatiles the residue was acidified by addition of 1 N HCl and extracted three times with ethyl acetate. The combined organic extracts were washed sequentially with 1 N HCl and saturated brine, dried over sodium sulphate, and concentrated in vacuo to afford the title compound as a light yellow amorphous solid (58%). MS (m/e): 284.1 ([M–H]$^-$, 100%).

EXAMPLE B13

2-Methoxy-5-methylsulfamoyl-benzoic acid (a) 5-Chlorosulfonyl-2-hydroxy-benzoic acid

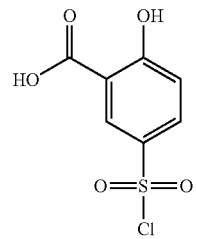

To 3.26 mol chlorosulfonic acid at 0° C. was added 652 mmol salicylic acid in small portions and the mixture was then allowed to stir at RT for 1 h, then at 50° C. for 1 h, and finally at 70° C. for 1 h. The mixture was then added dropwise to 1000 ml ice-water with stirring and stirring continued for an additional 30 min. The ensuing white crystals were collected by filtration, washed three times with water, and then dried in vacuo at 45° C. for 16 h to yield the title compound. MS (m/e): 236.8 ([{$^{37}$Cl}M–H]$^-$, 33%), 235.0 ([{$^{37}$Cl}M–H]$^-$, 100%)

(b) 2-Hydroxy-5-methylsulfamoyl-benzoic acid

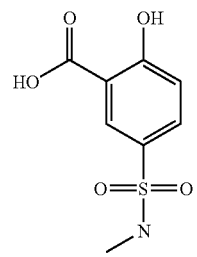

To 63 mmol 5-chlorosulfonyl-2-hydroxy-benzoic acid in 120 ml dichloromethane at RT was added dropwise 317 mmol methylamine (8 M solution in ethanol) and the mixture was allowed to stir at RT for 1 h. The mixture was then concentrated in vacuo. The residue was suspended in 1 M aq NaOH solution and extracted twice with ether. The aqueous phase was acidified with 5 M aq HCl, saturated with NaCl, and extracted 3 times with THF. The combined THF extracts were washed twice with saturated aqueous NaCl solution and dried with $Na_2SO_4$. Evaporation in vacuo yielded the title compound. MS (m/e): 249.0 ($M+NH_4^+$, 100%), 231.9 ($M+H^+$, 63%)

(c) 2-Hydroxy-5-methylsulfamoyl-benzoic acid methyl ester

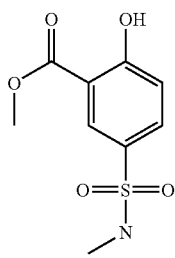

To 77 mmol 2-hydroxy-5-methylsulfamoyl-benzoic acid in 300 ml THF was added 85 mmol CDI and the mixture heated at 70° C. for 1 h. 770 mmol methanol was then added and the mixture was heated at 70° C. for 16 h. The mixture was then cooled to room temperature and concentrated in vacuo. The residue was chromatographed on silica gel (eluant: ethyl acetate/heptane/dichloromethane 45:45:10) to afford the title compound. MS (m/e): 244.1 ($[M-H]^-$, 100%)

d) 2-Methoxy-5-methylsulfamoyl-benzoic acid methyl ester

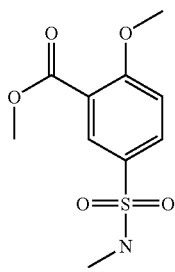

To 2.04 mmol 2-hydroxy-5-methylsulfamoyl-benzoic acid methyl ester, 2.2 mmol methanol and 2.34 mmol triphenylphosphine in 10 ml THF was added 2.24 mmol di-tert-butyl azodicarboxylate and the mixture was stirred at RT for 2 h. The mixture was then concentrated in vacuo. The residue was chromatographed on silica gel (eluant: ethyl acetate/heptane) to afford the title compound.

e) 2-Methoxy-5-methylsulfamoyl-benzoic acid

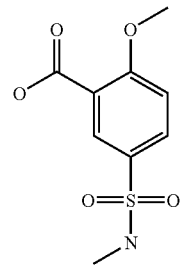

Prepared in analogy to Example B3(c) from 2-Methoxy-5-methylsulfamoyl-benzoic acid methyl ester. MS (m/e): 244.1 ($[M-H]^-$, 100%)

EXAMPLE B14

2-Ethoxy-5-methylsulfamoyl-benzoic acid

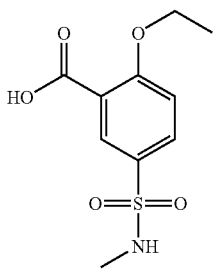

Prepared in analogy to Example B13(d-e) from 2-Hydroxy-5-methylsulfamoyl-benzoic acid methyl ester and ethanol. MS (m/e): 257.9 ($[M-H]^-$, 100%)

EXAMPLE B15

5-Methylsulfamoyl-2-trifluoromethoxy-benzoic acid

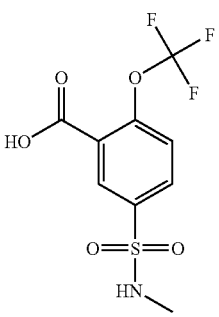

(a) 5-Chlorosulfonyl-2-trifluoromethoxy-benzoic acid

A solution of 2-trifluoromethoxy benzoic acid [1979-29-9](1.0 g) was added in small batches to chlorosulfonic acid (3.2 mL) at 0° C. After completion of the addition, the reaction mixture was stirred at 70° C. for 4 hours then left at room temperature overnight and heated at 75° C. for another 3 hours. After such time the reaction was slowly poured onto ice, and the precipitate was then filtered, washed with water and dried to yield the title compound as a white solid (1.2 g). MS (m/e): 303.3 (M–H, 100%).

(b) 5-Methylsulfamoyl-2-trifluoromethoxy-benzoic acid

To a solution of 5-Chlorosulfonyl-2-trifluoromethoxy-benzoic acid (0.15 g) in dichloromethane (1.5 ml) was added a solution of methylamine in methanol (8M, 0.31 mL) and the reaction mixture was stirred for 2 minutes after precipitation was compete. The reaction mixture was then concentrated in vacuo and the residue was dissolved in 1N NaOH (2 mL) and extracted with diethylether. The aqueous phase was then acidified using 3 N hydrochloric acid solution (2 mL) and the solution was extracted with dichloromethane (2×10 mL). The combined organic phases were dried with sodium sulfate and concentrated in vacuo to yield the title compound as a white solid (0.12 g). MS (m/e): 298.0 (M–H, 100%).

EXAMPLE B16

2-Isopropoxy-5-methylsulfamoyl-benzoic acid

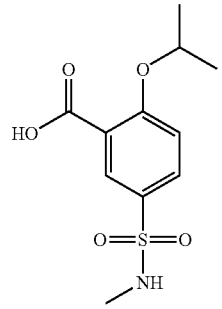

Prepared in analogy to Example B13(d-e) from 2-Hydroxy-5-methylsulfamoyl-benzoic acid methyl ester and 2-Propanol. MS (m/e): 272.2 ([M–H]⁻, 100%)

EXAMPLE B17

5-Methylsulfamoyl-2-(2,2,2-trifluoro-ethoxy)-benzoic acid (a) 5-Methylsulfamoyl-2-(2,2,2-trifluoro-ethoxy)-benzoic acid methyl ester

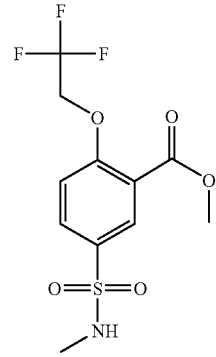

To 3.3 mmol 2-hydroxy-5-methylsulfamoyl-benzoic acid methyl ester (example B13c)) and 3.3 mmol potassium carbonate in 50 ml acetone was added dropwise 4.9 mmol 2,2,2-trifluoro-ethyl trifluoromethanesulfonate and the mixture was heated at 60° C. for 16 h. The mixture was then concentrated in vacuo. The residue was suspended in dichloromethane and filtered. The filtrate was concentrated in vacuo and the residue was chromatographed on silica gel (eluant: ethyl acetate/heptane 3:7) to afford the title compound. MS (m/e): 328.0 (M+H⁺, 100%)

(b) 5-Methylsulfamoyl-2-(2,2,2-trifluoro-ethoxy)-benzoic acid

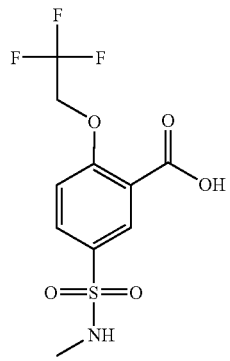

To 2.3 mmol 5-methylsulfamoyl-2-(2,2,2-trifluoro-ethoxy)-benzoic acid methyl ester in 10 ml THF was added 20 mmol 2 M aq NAOH and the mixture was heated at 50° C. for 2 h. The mixture was then cooled to RT and extracted twice with ether. The aqueous phase was acidified with 10% aq citric acid and extracted 3 times with ethyl acetate. The combined organic phases were dried with Na₂SO₄. Evaporation in vacuo followed by trituration in ether afforded the title compound. MS (m/e): 312.0 ([M–H]⁻, 100%)

EXAMPLE B18

Rac-5-methylsulfamoyl-2-(2,2,2-trifluoro-1-methyl-ethoxy)-benzoic acid (a) rac-5-Methylsulfamoyl-2-(2,2,2-trifluoro-1-methyl-ethoxy)-benzoic acid methyl ester

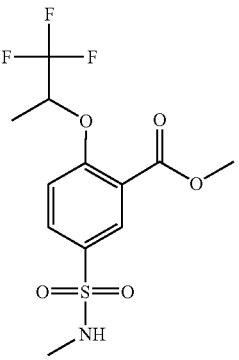

To 4.1 mmol 2-hydroxy-5-methylsulfamoyl-benzoic acid methyl ester and 4.1 mmol potassium carbonate in 5 ml DMF was added dropwise 6.1 mmol trifluoro-methanesulfonic acid 2,2,2-trifluoro-1-methyl-ethyl ester and the mixture was heated at 90° C. for 16 h. The mixture was then cooled to RT, poured onto water and extracted 3 times with ethyl acetate. The combined organic phases were dried with $Na_2SO_4$. Evaporation in vacuo followed by chromatography on silica gel (eluant: dichloromethane) afforded the title compound. MS (m/e): 359.2 ($M+NH_4^+$, 80%), 342.0 ($M+H^+$, 100%)

(b) rac-5-Methylsulfamoyl-2-(2,2,2-trifluoro-1-methyl-ethoxy)-benzoic acid

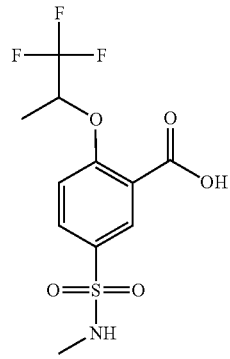

To 1.6 mmol rac-5-methylsulfamoyl-2-(2,2,2-trifluoro-1-methyl-ethoxy)-benzoic acid methyl ester in 10 ml THF was added 20 mmol 2 M aq NaOH and the mixture was heated at 50° C. for 2 h. The mixture was then cooled to RT and extracted twice with ether. The aqueous phase was acidified with 10% aq citric acid and extracted twice with ethyl acetate. The combined organic phases were dried with $Na_2SO_4$. Evaporation in vacuo followed by trituration in ether and hexane afforded the title compound MS (m/e): 326.2 ($[M-H]^-$, 100%)

EXAMPLE B19

4-Methanesulfonyl-biphenyl-2-carboxylic acid (a) 2-Amino-5-methanesulfonyl-benzoic acid

A mixture of 4.26 mmol 2-chloro-5-methanesulfonyl-benzoic acid (example B1a)), step1), 0.39 mmol Copper powder and 10 ml ammonium hydroxide 25% was heated at 125-130° C. with stirring for 18 hours. Mixture was cooled to room temperature and filtered. The solid was washed with methanol. The filtrate was concentrated in vacuo. The residue was acidified with HCl 1 N to pH=2. The obtained solid was washed with water and dried (HV, 50° C., 1 hour) to yield the title compound. MS (m/e): 214.1 (M−H, 100%)

(b) 2-Iodo-5-methanesulfonyl-benzoic acid

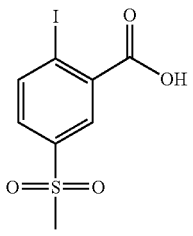

To a suspension of 3.0 mmol 2-amino-5-methanesulfonyl-benzoic acid in a mixture of 1.7 ml sulfuric acid and 1.7 ml water was added dropwise a solution of 3.92 mmol sodium nitrite in 1.7 ml water at such rate that the temperature did not exceed 3° C. The mixture was stirred at 0° C. for 1 hour. A solution of 3.0 mmol KI in 1.7 ml water was added dropwise at 0° C. The brown suspension was allowed to warm to rt and stirred for 30 minutes. Excess iodine was destroyed by addition of a few drops of a sodium hydrogenosulfite solution. The solid was filtered, washed with water and dried (HV, 50° C., 1 hour) to yield the title compound. MS (m/e): 325.0 (M−H, 100%)

(c) 2-Iodo-5-methanesulfonyl-benzoic acid methyl ester

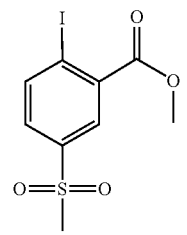

To 30.7 mmol 2-Iodo-5-methanesulfonyl-benzoic acid in 250 ml THF was added 33.7 mmol CDI and the mixture was heated at 70° C. for 1 h. Methanol (12.4 ml) was then added and the mixture was heated at 70° C. for a further 1 h. The mixture was then cooled to room temperature and concentrated in vacuo. The residue was chromatographed over $SiO_2$ (ethyl acetate/dichloromethane 4:1) to afford the title compound (86%) as a white crystalline solid.

(d) 4-Methanesulfonyl-biphenyl-2-carboxylic acid methyl ester

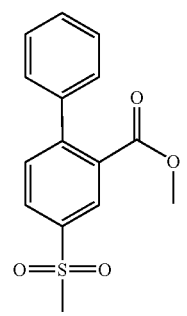

A mixture of 3.53 mmol 2-Iodo-5-methanesulfonyl-benzoic acid methyl ester, 3.88 mmol Phenyltri-n-butyltin, 0.25 mmol Tris(dibenzylideneacetone)dipalladium(0), 0.35 mmol Triphenylarsine and 1.62 mmol Copper iodide in N,N-Dimethylformamide (30 ml) was heated at 90° C. for 16 hours. The mixture was cooled to room temperature and concentrated in vacuo. The residue was chromatographed over $SiO_2$ (ethyl acetate/heptane gradient) to provide the title compound (99%) as an off-white crystalline solid. MS (m/e): 291.0 (MH$^+$, 100%)

(e) 4-Methanesulfonyl-biphenyl-2-carboxylic acid

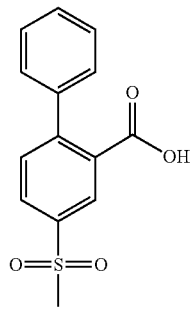

To 3.44 mmol 4-Methanesulfonyl-biphenyl-2-carboxylic acid methyl ester in 5 ml THF was added 37.9 mmol 5 M aq. NaOH solution and the mixture was heated at 60° C. for 16 h. The mixture was then cooled to RT, acidified to pH 1 with conc. hydrochloric acid, and extracted 3 times with ethyl acetate. The combined organic phases were dried with $Na_2SO_4$. Evaporation in vacuo afforded the title compound (95%) as an off-white crystalline solid. MS (m/e): 275.1 (M–H, 100%)

EXAMPLE B20

2-Isopropoxy-5-methanesulfonyl-benzamide

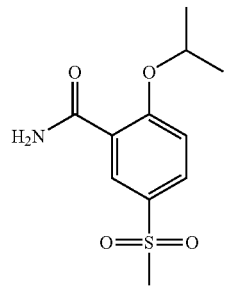

Prepared in analogy to Example A17(a) from 2-Isopropoxy-5-methanesulfonyl-benzoic acid (example B1) and ammonium hydroxyde. MS (m/e): 258.1 ([M+H$^+$, 100%)

EXAMPLE B21

Rac-5-Ethanesulfonyl-2-(2,2,2-trifluoro-1-methylethoxy)-benzoic acid (a) 2-Fluoro-5-sulfino-benzoic acid

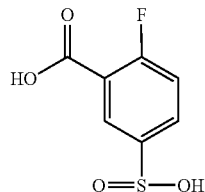

264 mmol 5-Chlorosulfonyl-2-fluoro-benzoic acid (CAS: 37098-75-2) was added portionwise onto a solution of 1.98 mol sodium sulfite in 1 L of water. The reaction mixture was kept under basic conditions by the addition of the proper amount of 20% NaOH and was stirred at room temperature for 45 minutes. After such time the reaction mixture was cooled down with an ice bath and was then acidified by the addition of 20% $H_2SO_4$ solution until reaching pH 2. Water was evaporated and 600 ml methanol was added. The mixture was stirred overnight and filtrated. The filtrate was evaporated and dried to yield the title compound as a white solid (72%). MS (m/e): 203.0 ([M–H, 100%)

(b) 5-Ethanesulfonyl-2-fluoro-benzoic acid ethyl ester

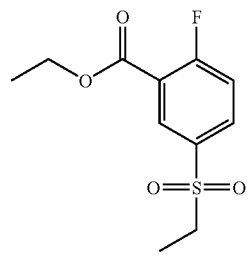

To 24 mmol 2-Fluoro-5-sulfino-benzoic acid in 200 ml of DMF was added 73 mmol potassium carbonate and 86 mmol ethyl iodide. The reaction mixture was then stirred at room temperature for 50 hours. After such time the reaction mixture was concentrated in vacuo and the residue was dissolved in 100 ml water. The aqueous phase was extracted 2×50 ml with ethyl acetate. The combined extracts were dried over sodium sulfate, filtered and the solvent was removed in vacuo. The residue was chromatographed over $SiO_2$ (ethyl acetate/heptane gradient) to provide the title compound (51%) as a colorless oil. MS (m/e): 261.1 ([M+H]$^+$, 100%)

(c) 5-Ethanesulfonyl-2-fluoro-benzoic acid

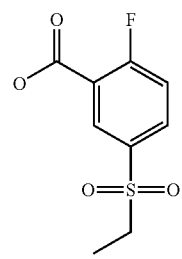

Prepared in analogy to Example B3(c) from 5-Ethanesulfonyl-2-fluoro-benzoic acid ethyl ester using lithium hydroxide instead of sodium hydroxide. White solid. MS (m/e): 232.1 (M$^+$, 100%).

(d) rac-5-Ethanesulfonyl-2-(2,2,2-trifluoro-1-methyl-ethoxy)-benzoic acid

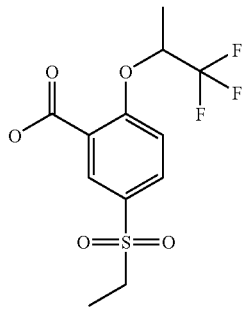

Prepared in analogy to Example B4(c) from 5-Ethanesulfonyl-2-fluoro-benzoic acid and rac-1,1,1-Trifluoro-propan-2-ol (commercial). White solid. MS (m/e): 325.1([M−H], 100%).

EXAMPLE B22 rac-5-Methanesulfonyl-2-(1-trifluoromethyl-propoxy)-benzoic acid

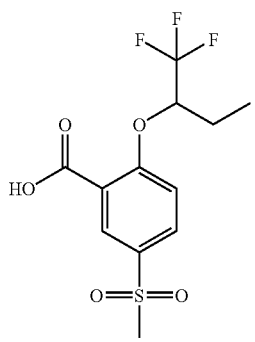

Prepared in analogy to Example B4(c) from 2-Fluoro-5-methanesulfonyl-benzoic acid (example B4(b)) and rac-1,1,1-Trifluoro-butan-2-ol (CAS: 431-36-7). White solid. MS (m/e): 325.0 ([M−H], 100%).

EXAMPLE B23

2-((S)-sec-Butoxy)-5-methanesulfonyl-benzoic acid

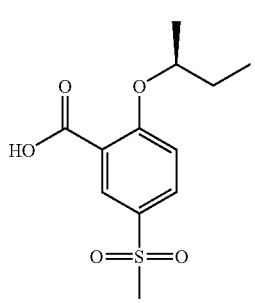

Prepared in analogy to Example B4(c) from 2-Fluoro-5-methanesulfonyl-benzoic acid (example B4(b)) and S-(+)-2-butanol. White solid. MS (m/e): 271.1 ([M−H], 100%).

EXAMPLE B24

2-((R)-sec-Butoxy)-5-methanesulfonyl-benzoic acid

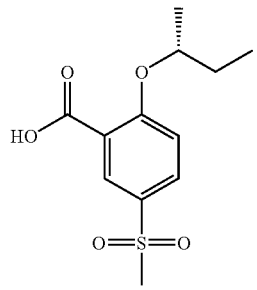

Prepared in analogy to Example B4(c) from 2-Fluoro-5-methanesulfonyl-benzoic acid (example B4(b)) and R-(−)-2-butanol. White solid. MS (m/e): 271.1 ([M−H], 100%).

EXAMPLE B25

4'-Fluoro-4-methanesulfonyl-biphenyl-2-carboxylic acid

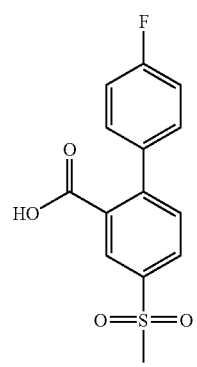

A mixture of 6.1 mmol 2-Iodo-5-methanesulfonyl-benzoic acid (example B19(b)), 12.2 mmol 4-fluorobenzeneboronic acid, 18.4 mmol sodium carbonate and 0.3 mmol palladium (II) acetate in 30 ml water was stirred at room temperature for 48 hours. The mixture was filtered and the filtrate was acidified with HCl 37%. The mixture was stirred at room temperature for 30 minutes. The solid was filtered, washed with water and dried to provide the title compound (92%). Yellow solid. MS (m/e): 293.2 ([M−H], 100%).

EXAMPLE B26

3'-Fluoro-4-methanesulfonyl-biphenyl-2-carboxylic acid

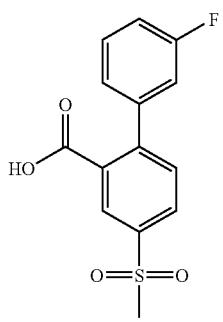

Prepared in analogy to Example B25 from 2-Iodo-5-methanesulfonyl-benzoic acid (example B19(b)) and 3-fluorobenzeneboronic acid. Yellow solid. MS (m/e): 293.2 ([M−H], 100%).

EXAMPLE B27

2'-Fluoro-4-methanesulfonyl-biphenyl-2-carboxylic acid

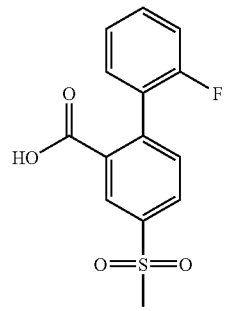

Prepared in analogy to Example B25 from 2-Iodo-5-methanesulfonyl-benzoic acid (example B19(b)) and 2-fluorobenzeneboronic acid. Light brown solid.

EXAMPLE B28

4'-Chloro-4-methanesulfonyl-biphenyl-2-carboxylic acid

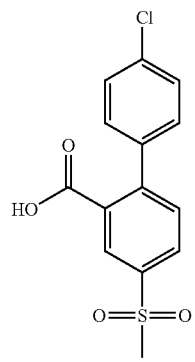

Prepared in analogy to Example B25 from 2-Iodo-5-methanesulfonyl-benzoic acid (example B19(b)) and 4-chlorobenzeneboronic acid. Light brown solid. MS (m/e): 309.1 ([M−H], 100%).

EXAMPLE B29

3',4'-Difluoro-4-methanesulfonyl-biphenyl-2-carboxylic acid

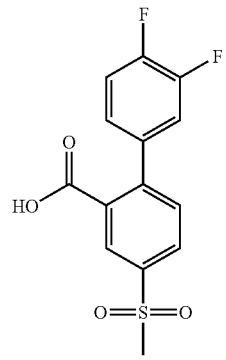

Prepared in analogy to Example B25 from 2-Iodo-5-methanesulfonyl-benzoic acid (example B19(b)) and 3,4-difluorobenzeneboronic acid. Light brown solid. MS (m/e): 311.1 ([M−H], 100%).

EXAMPLE B30

3',5'-Difluoro-4-methanesulfonyl-biphenyl-2-carboxylic acid

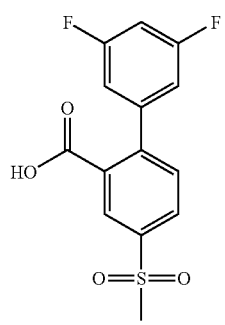

Prepared in analogy to Example B25 from 2-Iodo-5-methanesulfonyl-benzoic acid (example B19(b)) and 3,5-difluorobenzeneboronic acid. Light brown solid. MS (m/e): 311.1 ([M−H], 100%).

EXAMPLE B31

5-Methanesulfonyl-2-pyridin-4-yl-benzoic acid a) 5-Methanesulfonyl-2-pyridin-4-yl-benzoic acid methyl ester

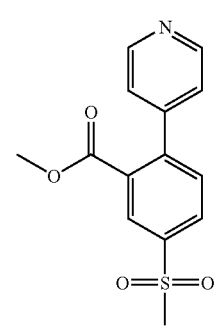

Prepared in analogy to Example B19(d) from 2-Iodo-5-methanesulfonyl-benzoic acid methyl ester (example B19(c)) and 4-tributylstananne-pyridine (commercial). Light yellow solid. MS (m/e): 291.9([M+H]$^+$, 100%).

(b) 5-Methanesulfonyl-2-pyridin-4-yl-benzoic acid

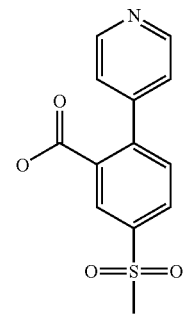

Prepared in analogy to Example B3(c) from 5-Methanesulfonyl-2-pyridin-4-yl-benzoic acid methyl ester. Light yellow solid. MS (m/e): 276.1 ([M−H], 100%).

EXAMPLE B32

5-Methanesulfonyl-2-(4-methyl-pyrazol-1-yl)-benzoic acid a) 5-Methanesulfonyl-2-(4-methyl-pyrazol-1-yl)-benzoic acid methyl ester

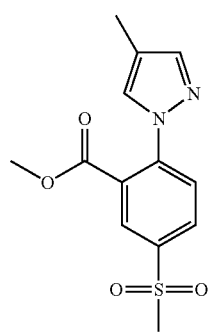

In a glass tube was added successively 0.29 mmol 2-Iodo-5-methanesulfonyl-benzoic acid methyl ester (example B19 (c)), 0.35 mmol 4-methylpyrazole, 0.59 mmol potassium carbonate, 0.06 mmol CuI and a solution of 0.12 mmol trans-1,2-diaminocyclohexane in 0.4 ml dioxane (degassed). The tube was filled with argon and sealed with a cap. The reaction mixture was heated at 120° C. overnight. The reaction mixture was cooled down to room temperature, dichloromethane and water were added. The aqueous phase was extracted 2 times with dichloromethane. The combined organic phases were dried over sodium sulfate and evaporated. The crude compound was purified on a 10g Flashpack cartridge. Eluent: Heptane/ethylacetate to provide the title compound (57%) as a light yellow oil. MS (m/e): 295.0([M+H]$^+$, 100%).

(b) 5-Methanesulfonyl-2-(4-methyl-pyrazol-1-yl)-benzoic acid

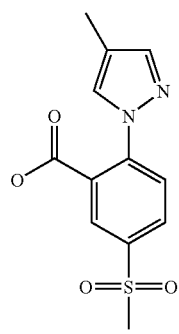

Prepared in analogy to Example B3(c) from 5-Methanesulfonyl-2-(4-methyl-pyrazol-1-yl)-benzoic acid methyl ester. White solid. MS (m/e): 279.1 ([M−H], 100%).

EXAMPLE B33

5-Methanesulfonyl-2-(tetrahydro-pyran-4-yl)-benzoic acid

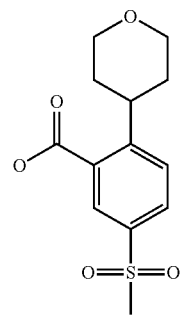

Prepared in analogy to Example B49(b) from 2-(3,6-Dihydro-2H-pyran-4-yl)-5-methanesulfonyl-benzoic acid (CAS: 847547-05-1). Colorless oil. MS (m/e): 283.2([M−H], 100%).

EXAMPLE C1

(4-Iodo-1,3-dihydro-isoindol-2-yl)-[5-methanesulfonyl-2-((S)-2,2,2-trifluoro-1-methyl ethoxy)-phenyl]-methanone (a) 1,2-Bis-bromomethyl-3-iodo-benzene

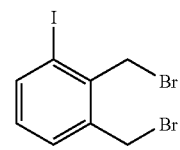

Prepared in analogy to Example A2(a) from 1-Iodo-2,3-dimethyl-benzene (commercial) and NBS. Brown oil.

(b) 4-Iodo-2-trityl-2,3-dihydro-1H-isoindole

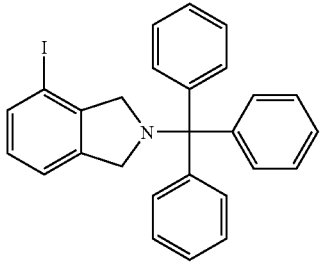

Prepared in analogy to Example A2(b) from 1,2-Bis-bromomethyl-3-iodo-benzene and triphenylmethylamine. White solid.

(c) 4-Iodo-2,3-dihydro-1H-isoindole

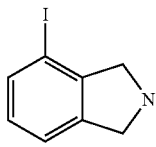

Prepared in analogy to Example A2(c) from 4-Iodo-2-trityl-2,3-dihydro-1H-isoindole and trifluoroacetic acid. Light yellow solid.

(d) (4-Iodo-1,3-dihydro-isoindol-2-yl)-[5-methane-sulfonyl-2-((S)-2,2,2-trifluoro-1-methyl ethoxy)-phenyl]-methanone

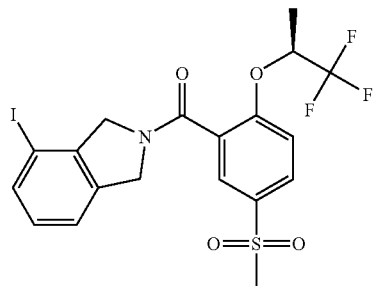

Prepared in analogy to Example 1 from 4-Iodo-2,3-dihydro-1H-isoindole and 5-Methanesulfonyl-2-((S)-2,2,2-trifluoro-1-methyl-ethoxy)-benzoic acid (example B3). Off white solid. MS (m/e): 540.0 (MH+, 100%).

EXAMPLE C2

(5-Iodo-6-trifluoromethyl-1,3-dihydro-isoindol-2-yl)-[5-methanesulfonyl-2-((S)-2,2,2-trifluoro-1-methyl-ethoxy)-phenyl]-methanone (a) 4-Iodo-5-trifluoromethyl-phthalic acid

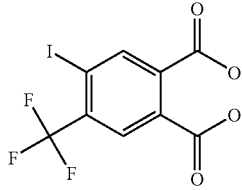

Prepared in analogy to Example A15(a) from 1-Iodo-4,5-dimethyl-2-trifluoromethyl-benzene (CAS: 165323-73-9) and chromium(VI) oxide. Grey solid. MS (m/e): 359.0 ([M−H]−, 100%).

(b) 5-Iodo-6-trifluoromethyl-isoindole-1,3-dione

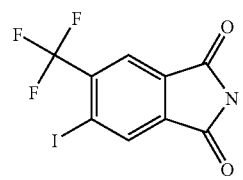

Prepared in analogy to Example A15(b) from 4-Iodo-5-trifluoromethyl-phthalic acid and urea. Light brown solid. MS (m/e): 339.9 ([M−H]−, 100%).

(c) 5-Iodo-6-trifluoromethyl-2,3-dihydro-1H-isoindole

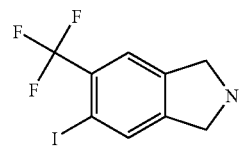

Prepared in analogy to Example A1 from 5-iodo-6-trifluoromethyl-isoindole-1,3-dione and borane tetrahydrofuran complex. Brown solid. MS (m/e): 313.9 ([M+H+, 100%).

(d) (5-Iodo-6-trifluoromethyl-1,3-dihydro-isoindol-2-yl)-[5-methanesulfonyl-2-((S)-2,2,2-trifluoro-1-methyl-ethoxy)-phenyl]-methanone

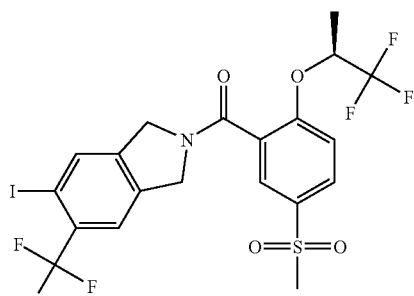

Prepared in analogy to Example 1 from 5-Iodo-6-trifluoromethyl-2,3-dihydro-1H-isoindole and 5-Methanesulfonyl-2-((S)-2,2,2-trifluoro-1-methyl-ethoxy)-benzoic acid (example B3). Yellow foam. MS (m/e): 607.0 (M+, 100%).

EXAMPLE C3

(5-Iodo-1,3-dihydro-isoindol-2-yl)-[5-methanesulfonyl-2-((S)-2,2,2-trifluoro-1-methyl ethoxy)-phenyl]-methanone

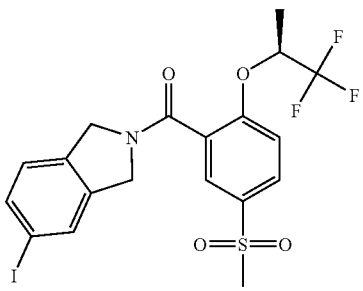

Prepared in analogy to Example 1 from 5-Iodo-2,3-dihydro-1H-isoindole (example A38(a)) and 5-Methanesulfonyl-2-((S)-2,2,2-trifluoro-1-methyl-ethoxy)-benzoic acid (example B3). Off white solid. MS (m/e): 539.1 (M+, 100%).

EXAMPLE C4

(2-Chloro-5,7-dihydro-pyrrolo[3,4-b]pyridin-6-yl)-[5-methanesulfonyl-2-((S)-2,2,2-trifluoro-1-methyl-ethoxy)-phenyl]-methanone R04988168-000

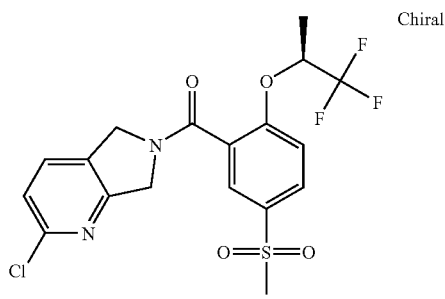

Chiral

Prepared in analogy to Example 1 from 2-chloro-6,7-dihydro-5H-pyrrolo[3,4-b]pyridine (Example A8(b)) and 5-methanesulfonyl-2-((S)-2,2,2-trifluoro-1-methyl-ethoxy)-benzoic acid (example B3). Yellow foam. MS (m/e): 451.0 ({$^{37}$Cl}[M+H]$^+$, 41%), 449.2 ({$^{35}$Cl}[M+H]$^+$, 100%).

EXAMPLE 1

Preparation of (1,3-Dihydro-isoindol-2-yl)-(2-isopropoxy-5-methanesulfonyl-phenyl)-methanone

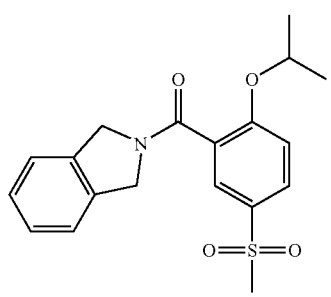

A mixture of 0.387 mmol 2-isopropoxy-5-methanesulfonyl-benzoic acid (example B1), 0.464 mmol 2,3-Dihydro-1H-isoindole (commercial), 0.426 mmol TBTU and 1.935 mmol DIPEA in 1.4 ml DMF was stirred at RT for 2 h. The reaction mixture was evaporated in vacuo. The residue was taken in water and extracted with ethylacetate. The combined organic phases were washed with saturated sodium bicarbonate solution, dried over sodium sulfate, filtered and concentrated in vacuo. The residue was purified by chromatography (SiO$_2$, heptane/ethyl acetate) to yield the title compound as a light brown solid (88% yield). MS (m/e): 360.2 [M+H]$^+$, 100%)

In analogy to Example 1, compounds 2 to 91 of the following table were prepared from the acid derivatives and amine derivatives:

| Expl. No. | Structure | Systematic Name MW found [M + H$^+$] | Starting materials | MW |
|---|---|---|---|---|
| 2 | (structure) | (5-Chloro-1,3-dihydro-isoindol-2-yl)-(2-isopropoxy-5-methanesulfonyl-phenyl)-and methanone 394.1 | 5-Chloro-2,3-dihydro-1H-isoindole (CAS: 127168-76-7) 2-Isopropoxy-5-methanesulfonyl-benzoic acid (example B1) | 393.9 |

-continued

| Expl. No. | Structure | Systematic Name MW found [M + H⁺] | Starting materials | MW |
|---|---|---|---|---|
| 3 | 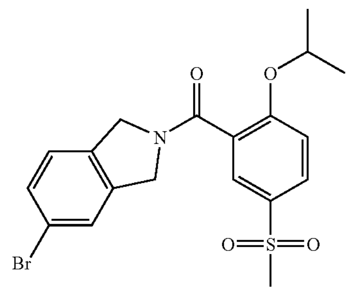 | (5-Bromo-1,3-dihydro-isoindol-2-yl)-(2-isopropoxy-5-methanesulfonyl-phenyl)-methanone<br>440.2 ($^{81}$Br), 438.3 ($^{79}$Br) | 5-Bromo-2,3-dihydro-1H-isoindole (CAS: 127168-84-7) and 2-Isopropoxy-5-methanesulfonyl-benzoic acid (example B1) | 438.3 |
| 4 | 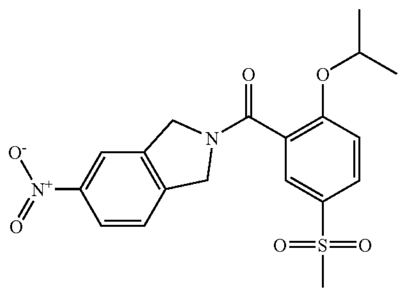 | (2-Isopropoxy-5-methanesulfonyl-phenyl)-(5-nitro-1,3-dihydro-isoindol-2-yl)-methanone<br>405.4 | 5-Nitro-2,3-dihydro-1H-isoindole (CAS: 46053-72-9) and 2-Isopropoxy-5-methanesulfonyl-benzoic acid (example B1) | 404.4 |
| 5 | 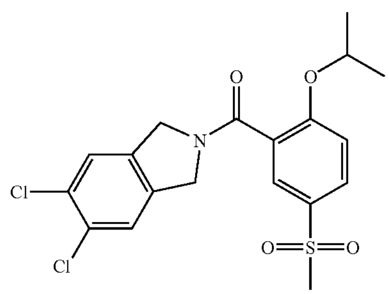 | (5,6-Dichloro-1,3-dihydro-isoindol-2-yl)-(2-isopropoxy-5-methanesulfonyl-phenyl)-methanone<br>432.2 ($^{37}$Cl, $^{37}$Cl), 430.3 ($^{37}$Cl, $^{35}$Cl), 428.3 ($^{35}$Cl, $^{35}$Cl) | 5,6-Dichloro-2,3-dihydro-1H-isoindole (CAS: 15997-90-7) and 2-Isopropoxy-5-methanesulfonyl-benzoic acid (example B1) | 428.3 |
| 6 | 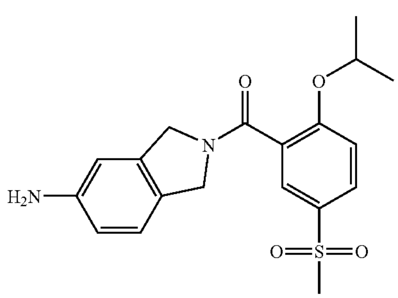 | (5-Amino-1,3-dihydro-isoindol-2-yl)-(2-isopropoxy-5-methanesulfonyl-phenyl)-methanone<br>375.5 | 2,3-Dihydro-1H-isoindol-5-ylamine (CAS: 45766-35-6) and 2-Isopropoxy-5-methanesulfonyl-benzoic acid (example B1) | 374.5 |
| 7 | 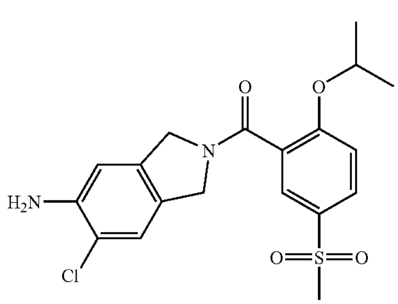 | (5-Amino-6-chloro-1,3-dihydro-isoindol-2-yl)-(2-isopropoxy-5-methanesulfonyl-phenyl)-methanone<br>411.1 ($^{37}$Cl), 409.1 ($^{35}$Cl) | 6-Chloro-2,3-dihydro-1H-isoindol-5-ylamine (example A1) and 2-Isopropoxy-5-methanesulfonyl-benzoic acid (example B1) | 408.9 |

| Expl. No. | Structure | Systematic Name<br>MW found [M + H⁺] | Starting materials | MW |
|---|---|---|---|---|
| 8 | 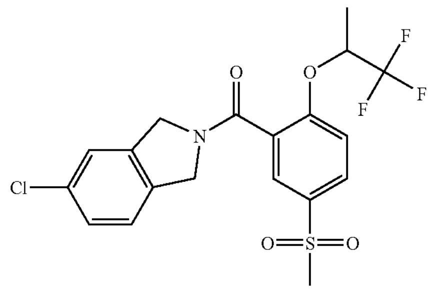 | rac-(5-Chloro-1,3-dihydro-isoindol-2-yl)-[5-methanesulfonyl-2-(2,2,2-trifluoro-1-methyl-ethoxy)-phenyl]-methanone<br>448.3 | 5-Chloro-2,3-dihydro-1H-isoindole (CAS: 127168-76-7) and rac-5-Methanesulfonyl-2-(2,2,2-trifluoro-1-methyl-ethoxy)-benzoic acid (example B2) | 447.9 |
| 9 | 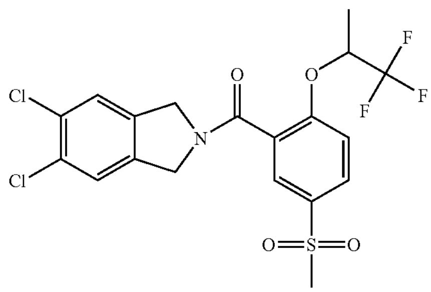 | rac-(5,6-Dichloro-1,3-dihydro-isoindol-2-yl)-[5-methanesulfonyl-2-(2,2,2-trifluoro-1-methyl-ethoxy)-phenyl]-methanone<br>486.2 ($^{37}$Cl, $^{37}$Cl), 484.3 ($^{37}$Cl, $^{35}$Cl), 482.3 ($^{35}$Cl, $^{35}$Cl) | 5,6-Dichloro-2,3-dihydro-1H-isoindole (CAS: 15997-90-7) and rac-5-Methanesulfonyl-2-(2,2,2-trifluoro-1-methyl-ethoxy)-benzoic acid (example B2) | 482.3 |
| 10 | 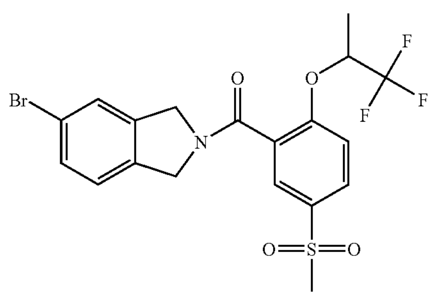 | rac-(5-Bromo-1,3-dihydro-isoindol-2-yl)-[5-methanesulfonyl-2-(2,2,2-trifluoro-1-methyl-ethoxy)-phenyl]-methanone<br>494.2 ($^{81}$Br), 492.1 ($^{79}$Br) | 5-Bromo-2,3-dihydro-1H-isoindole (CAS: 127168-84-7) and rac-5-Methanesulfonyl-2-(2,2,2-trifluoro-1-methyl-ethoxy)-benzoic acid (example B2) | 492.3 |
| 11 | 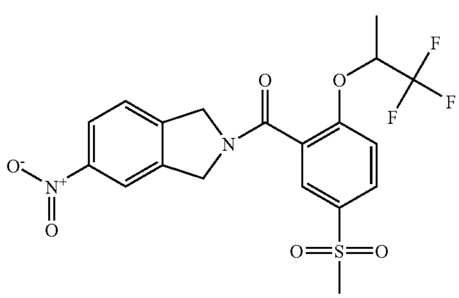 | rac-[5-Methanesulfonyl-2-(2,2,2-trifluoro-1-methyl-ethoxy)-phenyl]-(5-nitro-1,3-dihydro-isoindol-2-yl)-methanone<br>458.1 (M⁺) | 5-Nitro-2,3-dihydro-1H-isoindole (CAS: 46053-72-9) and rac-5-Methanesulfonyl-2-(2,2,2-trifluoro-1-methyl-ethoxy)-benzoic acid (example B2) | 458.4 |
| 12 | 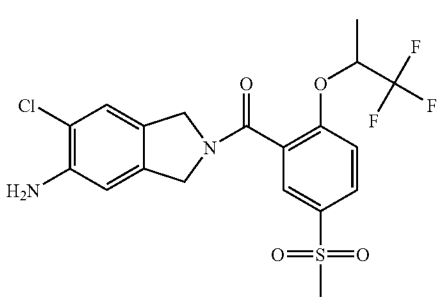 | rac-(5-Amino-6-chloro-1,3-dihydro-isoindol-2-yl)-[5-methanesulfonyl-2-(2,2,2-trifluoro-1-methyl-ethoxy)-2-phenyl]-methanone<br>464.1 ($^{37}$Cl, M⁺), 462.1 ($^{35}$Cl, M⁺) | 6-Chloro-2,3-dihydro-1H-isoindol-5-ylamine (example A1) and rac-5-Methanesulfonyl-(2,2,2-trifluoro-1-methyl-ethoxy)-benzoic acid (example B2) | 462.9 |

-continued

| Expl. No. | Structure | Systematic Name MW found [M + H⁺] | Starting materials | MW |
|---|---|---|---|---|
| 13 | 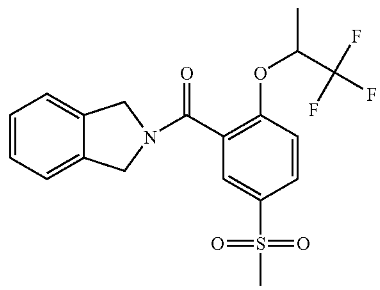 | rac-(1,3-Dihydro-isoindol-2-yl)-[5-methanesulfonyl-2-(2,2,2-trifluoro-1-methyl-ethoxy)-phenyl]-methanone 414.3 | 2,3-Dihydro-1H-isoindole (commercial) and rac-5-Methanesulfonyl-2-(2,2,2-trifluoro-1-methyl-ethoxy)-benzoic acid (example B2) | 413.4 |
| 14 | 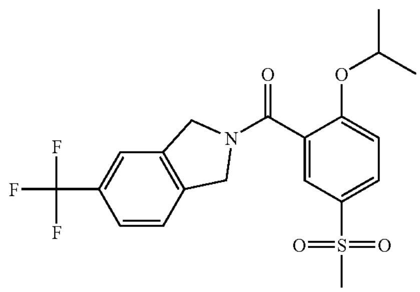 | (2-Isopropoxy-5-methanesulfonyl-phenyl)-(5-trifluoromethyl-1,3-dihydro-isoindol-2-yl)-methanone 428.0 | 5-Trifluoromethyl-2,3-dihydro-1H-isoindole (CAS: 342638-03-3) and 2-Isopropoxy-5-methanesulfonyl-benzoic acid (example B1) | 427.4 |
| 15 | 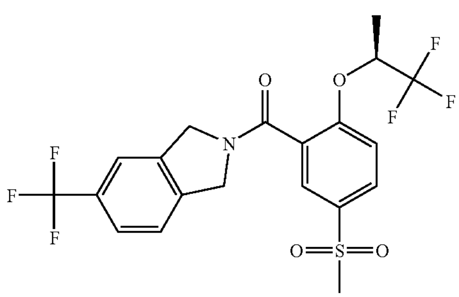 | [5-Methanesulfonyl-2-((S)-2,2,2-trifluoro-1-methyl-ethoxy)-phenyl]-(5-trifluoromethyl-1,3-dihydro-isoindol-2-yl)-methanone 482.0 | 5-Trifluoromethyl-2,3-dihydro-1H-isoindole (CAS: 342638-03-3) and 5-Methanesulfonyl-2-((S)-2,2,2-trifluoro-1-methyl-ethoxy)-benzoic acid (example B3) | 481.4 |
| 16 | 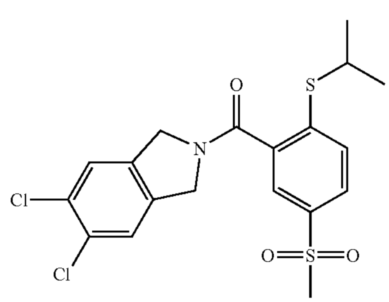 | (5,6-Dichloro-1,3-dihydro-isoindol-2-yl)-(2-isopropylsulfanyl-5-methanesulfonyl-phenyl)-methanone 447.9 ($^{37}Cl$, $^{37}Cl$), 445.9 ($^{37}Cl$, $^{35}Cl$, 444.0 ($^{35}Cl$, $^{35}Cl$) | 5,6-Dichloro-2,3-dihydro-1H-isoindole (CAS: 15997-90-7) and 2-Isopropylsulfanyl-5-methanesulfonyl-benzoic acid example B4) | 444.4 |
| 17 | 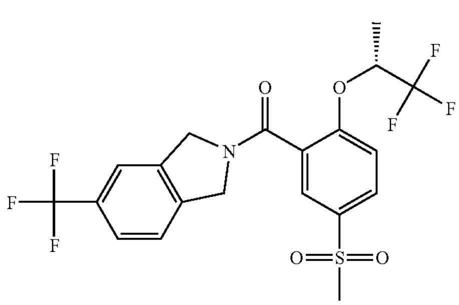 | [5-Methanesulfonyl-2-((R)-2,2,2-trifluoro-1-methyl-ethoxy)-phenyl](5-trifluoromethyl-t,3-dihydro-isoindol-2-yl)-methanone 482.0 | 5-Trifluoromethyl-2,3-dihydro-1H-isoindole (CAS: 342638-03-3) and 5-Methanesulfonyl-2-((R)-2,2,2-trifluoro-1-methyl-ethoxy)-benzoic acid (example B5) | 481.4 |

-continued

| Expl. No. | Structure | Systematic Name MW found [M + H⁺] | Starting materials | MW |
|---|---|---|---|---|
| 18 | 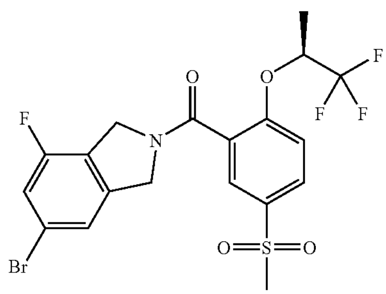 | (6-Bromo-4-fluoro-1,3-dihydro-isoindol-2-yl)-[5-methanesulfonyl-2-((S)-2,2,2-trifluoro-1-methyl-ethoxy)-phenyl]-methanone 510.2 | 6-Bromo-4-fluoro-2,3-dihydro-1H-isoindole (CAS: 689214-92-4) and 5-Methanesulfonyl-2-((S)-2,2,2-trifluoro-1-methyl-ethoxy)-benzoic acid (example B3) | 510.3 |
| 19 | 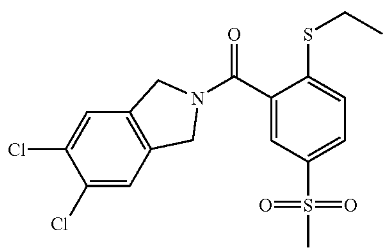 | (5,6-Dichloro-1,3-dihydro-isoindol-2-yl)-(2-ethylsulfanyl-5-methanesulfonyl-phenyl)-methanone 434.0 ($^{37}Cl$, $^{37}Cl$), 432.0 ($^{35}Cl$, $^{37}Cl$), 430.0 ($^{35}Cl$, $^{35}Cl$) | 5,6-Dichloro-2,3-dihydro-1H-isoindole (CAS: 15997-90-7) and 2-Ethylsulfanyl-5-methanesulfonyl-benzoic acid (example B6) | 430.4 |
| 20 | 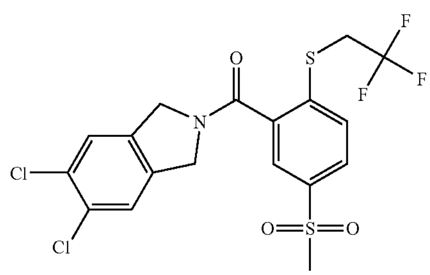 | (5,6-Dichloro-1,3-dihydro-isoindol-2-yl)-[5-methanesulfonyl-2-(2,2,2-trifluoro-ethylsulfanyl)-phenyl]-methanone 487.9 ($^{37}Cl$, $^{37}Cl$), 485.9 ($^{37}Cl$, $^{35}Cl$), 483.9 ($^{35}Cl$, $^{35}Cl$) | 5,6-Dichloro-2,3-dihydro-1H-isoindole (CAS: 15997-90-7) and 5-Methanesulfonyl-2-(2,2,2-trifluoro-ethylsulfanyl)-benzoic acid (example B7) | 484.3 |
| 21 | 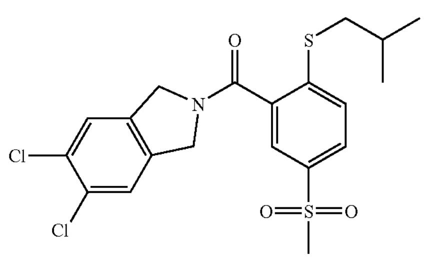 | (5,6-Dichloro-1,3-dihydro-isoindol-2-yl)-(2-isobutylsulfanyl-5-methanesulfonyl-phenyl)-methanone 462.0 $^{37}Cl$, $^{37}Cl$, 460.0 ($^{37}Cl$, $^{35}Cl$), 458.1 ($^{35}Cl$, $^{35}Cl$) | 5,6-Dichloro-2,3-dihydro-1H-isoindole (CAS: 15997-90-7) and 2-Isobutylsulfanyl-5-methanesulfonyl-benzoic acid (example B8) | 458.4 |
| 22 | 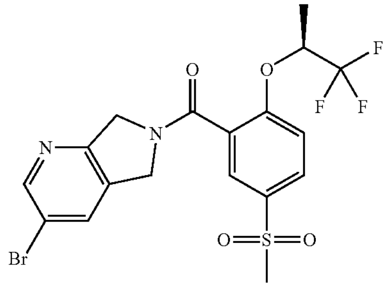 | (3-Bromo-5,7-dihydro-pyrrolo[3,4-b]pyridin-6-yl)-[5-methanesulfonyl-2-((S)-2,2,2-trifluoro-1-methyl-ethoxy)-phenyl]-methanone 493.0 | 3-Bromo-6,7-dihydro-5H-pyrrolo[3,4-b]pyridine (example A2) and 5-Methanesulfonyl-2-((S)-2,2,2-trifluoro-1-methyl-ethoxy)-benzoic acid (example B3) | 493.3 |

-continued

| Expl. No. | Structure | Systematic Name<br>MW found [M + H⁺] | Starting materials | MW |
|---|---|---|---|---|
| 23 | 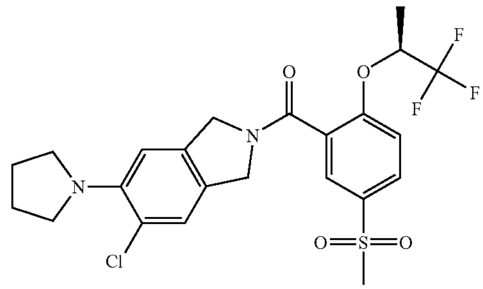 | (5-Chloro-6-pyrrolidin-1-yl-1,3-dihydro-isoindol-2-yl)-[5-methanesulfonyl-2-((S)-2,2,2-trifluoro-1-methyl-ethoxy)-phenyl]-methanone<br>519.3 ($^{37}$Cl), 517.2 ($^{35}$Cl) | 5-Chloro-6-pyrrolidin-1-yl-2,3-dihydro-1H-isoindole-hydrochloride (example A3) and 5-Methanesulfonyl-2-((S)-2,2,2-trifluoro-1-methyl-ethoxy)-benzoic acid (example B3) | 517.0 |
| 24 | 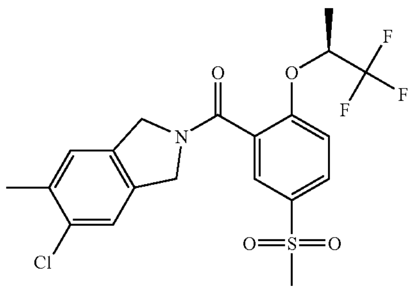 | (5-Chloro-6-methyl-1,3-dihydro-isoindol-2-yl)-[5-methanesulfonyl-2-((S)-2,2,2-trifluoro-1-methyl-ethoxy)-phenyl]-methanone<br>464.0 ($^{37}$Cl), 462.0 ($^{35}$Cl) | 5-Chloro-6-methyl-2,3-dihydro-1H-isoindole hydrochloride (example A4) and 5-Methanesulfonyl-2-((S)-2,2,2-trifluoro-1-methyl ethoxy)-benzoic acid (example B3) | 461.9 |
| 25 | 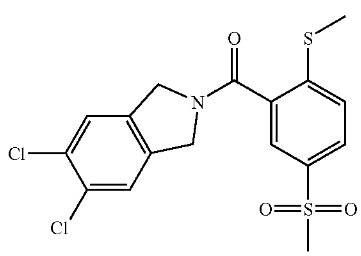 | (5,6-Dichloro-1,3-dihydro-isoindol-2-yl)-(5-methanesulfonyl-2-methylsulfanyl-phenyl)-methanone<br>419.9 $^{37}$Cl, $^{37}$Cl), 418.0 ($^{37}$Cl, $^{35}$Cl), 416.0 ($^{35}$Cl,$^{35}$Cl) | 5,6-Dichloro-2,3-dihydro-1H-isoindole (CAS: 15997-90-7) and 5-Methanesulfonyl-2-methylsulfanyl-benzoic acid (example B9) | 416.3 |
| 26 | 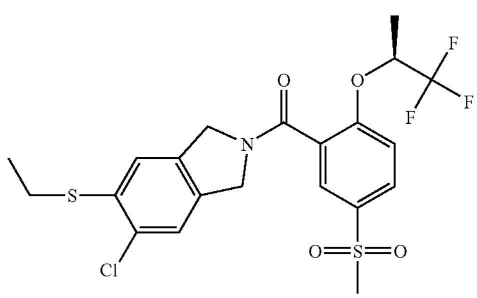 | (5-Chloro-6-ethylsulfanyl-1,3-dihydro-isoindol-2-yl)-[5-methanesulfonyl-2-((S)-2,2,2-trifluoro-1-methyl-ethoxy)-phenyl]-methanone<br>510.0 $^{37}$Cl), 508.0 ($^{35}$Cl) | 5-Chloro-6-ethylsulfanyl-2,3-dihydro-1H-isoindole hydrochloride (example A5) and 5-Methanesulfonyl-2-((S)-2,2,2-trifluoro-1-methyl-ethoxy)-benzoic acid (example B3) | 508.0 |
| 27 | 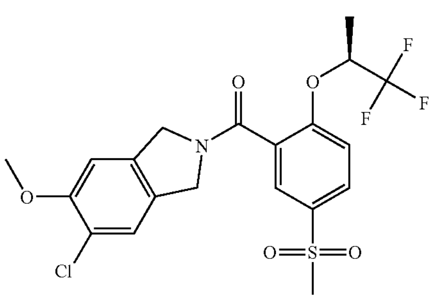 | (5-Chloro-6-methoxy-1,3-dihydro-isoindol-2-yl)-[5-methanesulfonyl-2-((S)-2,2,2-trifluoro-1-methyl-ethoxy)-phenyl]-methanone<br>480.0 $^{37}$Cl), 477.9 ($^{35}$Cl) | 5-Chloro-6-methoxy-2,3-dihydro-1H-isoindole hydrochloride (example A6) and 5-Methanesulfonyl-2-((S)-2,2,2-trifluoro-1-methyl-ethoxy)-benzoic acid (example B3) | 477.9 |

-continued

| Expl. No. | Structure | Systematic Name MW found [M + H+] | Starting materials | MW |
|---|---|---|---|---|
| 28 | 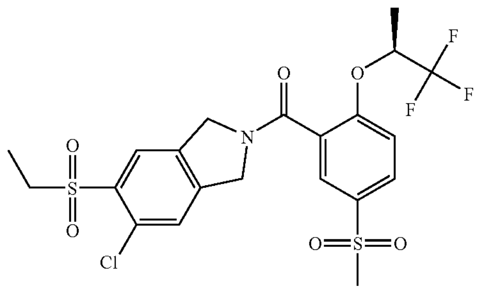 | (5-Chloro-6-ethanesulfonyl-1,3-dihydro-isoindol-2-yl)-[5-methanesulfonyl-2-((S)-2,2,2-trifluoro-1-methyl-ethoxy)-phenyl]-methanone 542.0 $^{37}$Cl), 540.0 ($^{35}$Cl) | 5-Chloro-6-ethanesulfonyl-2,3-dihydro-1H-isoindole hydrochloride (example A7) and 5-Methanesulfonyl-2-((S)-2,2,2-trifluoro-1-methyl-ethoxy)-benzoic acid (example B3) | 540.0 |
| 29 | 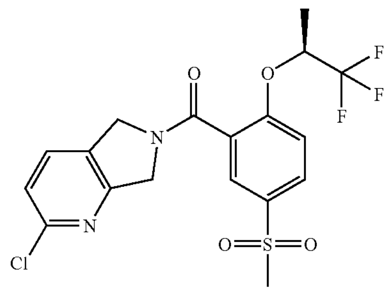 | (2-Chloro-5,7-dihydro-pyrrolo [3,4-b]pyridin-6-yl)-[5-methanesulfonyl-2-((S)-2,2,2-trifluoro-1-methyl-ethoxy)-phenyl]-methanone 448.9 | 2-Chloro-6,7-dihydro-5H-pyrrolo[3,4-b]pyridine (example A8) and 5-Methanesulfonyl-2-((S)-2,2,2-trifluoro-1-methyl-ethoxy) benzoic acid (example B3) | 448.9 |
| 30 | 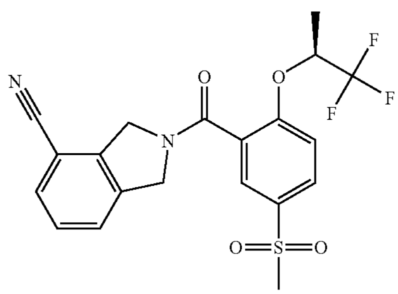 | 2-[5-Methanesulfonyl-2-((S)-2,2,2-trifluoro-1-methyl-ethoxy)-benzoyl]-2,3-dihydro-1H-isoindole-4-carbonitrile 439.4 | 2,3-Dihydro-1H-isoindole-4-carbonitrile (example A9) and 5-Methanesulfonyl-2-((S)-2,2,2-trifluoro-1-methyl-ethoxy)-benzoic acid (example B3) | 438.4 |
| 31 | 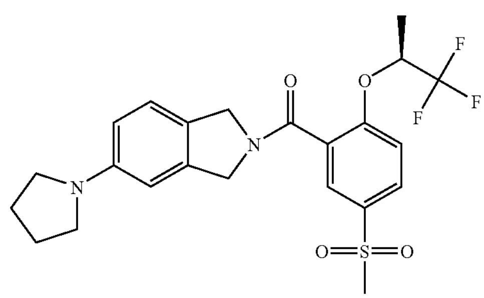 | [5-Methanesulfonyl-2-((S)-2,2,2-trifluoro-1-methyl-ethoxy)-phenyl]-(5-pyrrolidin-1-yl-1,3-dihydro-isoindol-2-yl)-methanone 483.1 | 5-Pyrrolidin-1-yl-2,3-dihydro-1H-isoindole (example A10) and 5-Methanesulfonyl-2-((S)-2,2,2-trifluoro-1-methyl ethoxy)-benzoic acid (example B3) | 482.5 |
| 32 | 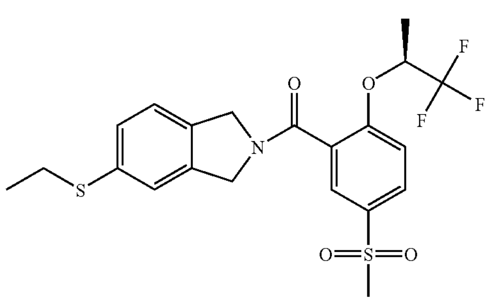 | (5-Ethylsulfanyl-1,3-dihydro-isoindol-2-yl)-[5-methanesulfonyl-2-((S)-2,2,2-trifluoro-1-methyl-ethoxy)-phenyl]-methanone 474.1 | 5-Ethylsulfanyl-2,3-dihydro-1H-isoindole hydrochloride (example A11) and 5-Methanesulfonyl-2-((S)-2,2,2-trifluoro-1-methyl-ethoxy) benzoic acid (example B3) | 473.5 |

| Expl. No. | Structure | Systematic Name MW found [M + H⁺] | Starting materials | MW |
|---|---|---|---|---|
| 33 | 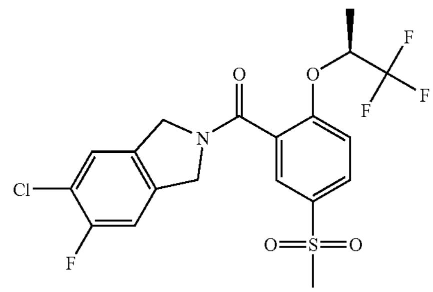 | (5-Chloro-6-fluoro-1,3-dihydro-isoindol-2-yl)-[5-methanesulfonyl-2-((S)-2,2,2-trifluoro-1-methyl-ethoxy)-phenyl]-methanone 466.1 | 5-Chloro-6-fluoro-2,3-dihydro 1H-isoindole (example A12) and 5-Methanesulfonyl-2-((5)-2,2,2-trifluoro-1-methyl-ethoxy)-benzoic acid (example B3) | 465.9 |
| 34 | 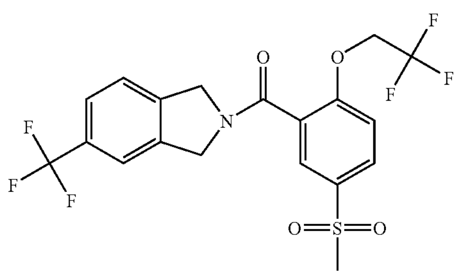 | [5-Methanesulfonyl-2-(2,2,2-trifluoro-ethoxy)-phenyl]-(5-trifluoromethyl-1,3-dihydro-isoindol-2-yl)-methanone 468.0 | 5-Trifluoromethyl-2,3-dihydro-1H-isoindole (CAS: 342638-03-3) and 5-Methanesulfonyl-2-(2,2,2-trifluoro-ethoxy)-benzoic acid (example B10) | 467.4 |
| 35 | 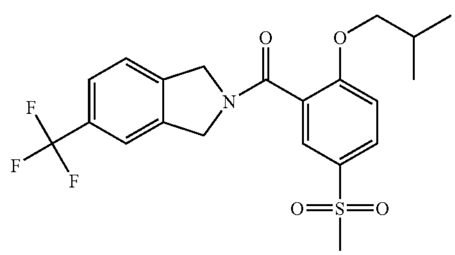 | (2-Isobutoxy-5-methanesulfonyl-phenyl)-(5-trifluoromethyl-1,3-dihydro-isoindol-2-yl)-methanone 442.0 | 5-Trifluoromethyl-2,3-dihydro-1H-isoindole (CAS: 342638-03-3) and 2-Isobutoxy-5-methanesulfonyl-benzoic acid (example B11) | 441.5 |
| 36 | 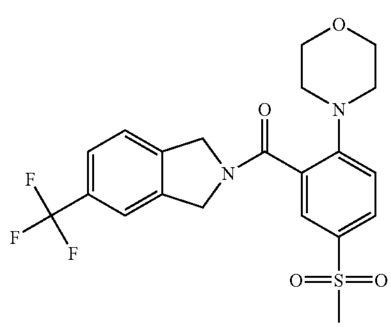 | (5-Methanesulfonyl-2-morpholin-4-yl-phenyl)-(5-trifluoromethyl-1,3-dihydro-isoindol-2-yl)-methanone 455.3 | 5-Trifluoromethyl-2,3-dihydro-1H-isoindole (CAS: 342638-03-3) and 5-Methanesulfonyl-2-morpholin-4-yl-benzoic acid (example B12) | 454.5 |
| 37 | 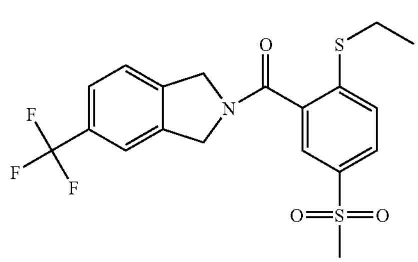 | (2-Ethylsulfanyl-5-methanesulfonyl-phenyl)-(5-trifluoromethyl-1,3-dihydro-2-isoindol-2-yl)-methanone 430.1 | 5-Trifluoromethyl-2,3-dihydro-1H-isoindole (CAS: 342638-03-3) and Ethylsulfanyl-5-methanesulfonyl-benzoic acid (example B6) | 429.5 |

| Expl. No. | Structure | Systematic Name<br>MW found [M + H⁺] | Starting materials | MW |
|---|---|---|---|---|
| 38 | 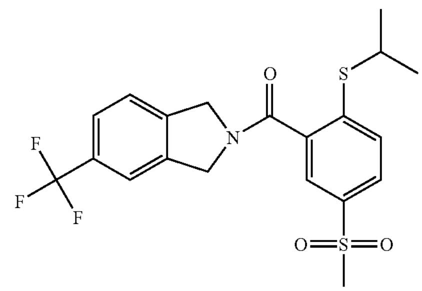 | (2-Isopropylsulfanyl-5-methanesulfonyl-phenyl)-(5-trifluoromethyl-1,3-dihydro-isoindol-2-yl)-methanone<br>444.4 | 5-Trifluoromethyl-2,3-dihydro-1H-isoindole (CAS: 342638-03-3) and 2-Isopropylsulfanyl-5-methanesulfonyl-benzoic acid (example B4) | 443.5 |
| 39 | 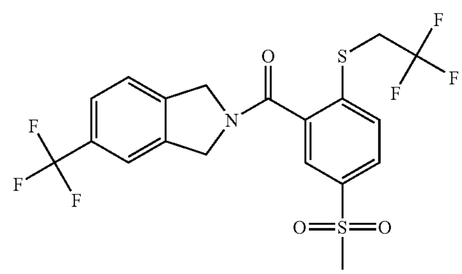 | [5-Methanesulfonyl-2-(2,2,2-trifluoro-ethylsulfanyl)-phenyl]-(5-trifluoromethyl-1,3-dihydro-isoindol-2-yl)-methanone<br>484.5 | 5-Trifluoromethyl-2,3-dihydro-1H-isoindole (CAS: 342638-03-3) and 5-Methanesulfonyl-2-(2,2,2-trifluoro-ethylsulfanyl)-benzoic acid (example B7) | 483.5 |
| 40 | 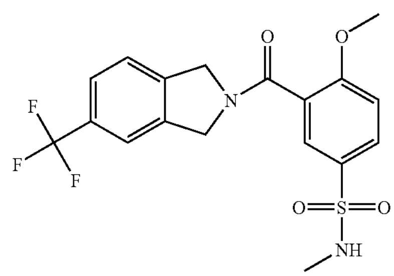 | 4-Methoxy-N-methyl-3-(5-trifluoromethyl-1,3-dihydro-isoindole-2-carbonyl)-benzenesulfonamide<br>415.1 | 5-Trifluoromethyl-2,3-dihydro-1H-isoindole (CAS: 342638-03-3) and 2-Methoxy-5-methylsulfamoyl-benzoic acid (example B13) | 414.4 |
| 41 | 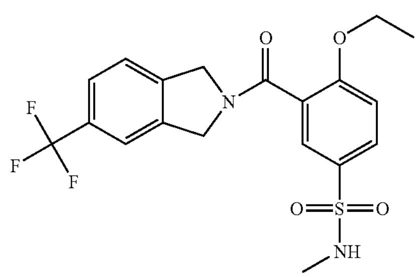 | 4-Ethoxy-N-methyl-3-(5-trifluoromethyl-1,3-dihydro-isoindole-2-carbonyl)-benzenesulfonamide<br>429.0 | 5-Trifluoromethyl-2,3-dihydro-1H-isoindole (CAS: 342638-03-3) and 2-Ethoxy-5-methylsulfamoyl-benzoic acid (example B14) | 428.4 |
| 42 | 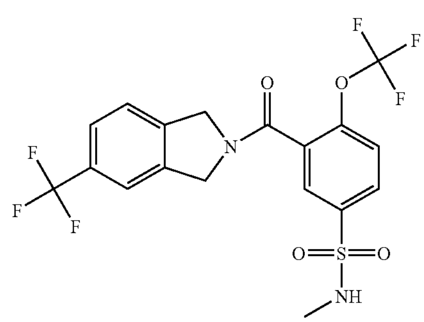 | N-Methyl-4-trifluoromethoxy-3-(5-trifluoromethyl-1,3-dihydro-isoindole-2-carbonyl)-benzenesulfonamide<br>469.0 | 5-Trifluoromethyl-2,3-dihydro-1H-isoindole (CAS: 342638-03-3) and 5-Methylsulfamoyl-2-trifluoromethoxy-benzoic acid (example B15) | 468.4 |

-continued

| Expl. No. | Structure | Systematic Name MW found [M + H⁺] | Starting materials | MW |
|---|---|---|---|---|
| 43 | 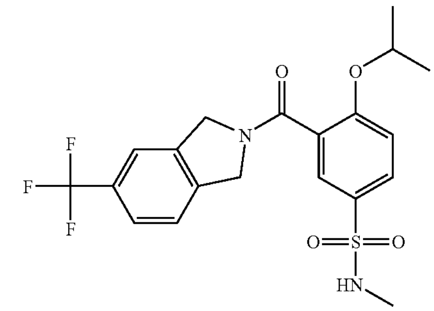 | 4-Isopropoxy-N-methyl-3-(5-trifluoromethyl-1,3-dihydro-isoindole-2-carbonyl)-benzenesulfonamide 443.0 | 5-Trifluoromethyl-2,3-dihydro-1H-isoindole (CAS: 342638-03-3) and 2-Isopropoxy-5-methylsulfamoyl-benzoic acid (example B16) | 442.5 |
| 44 | 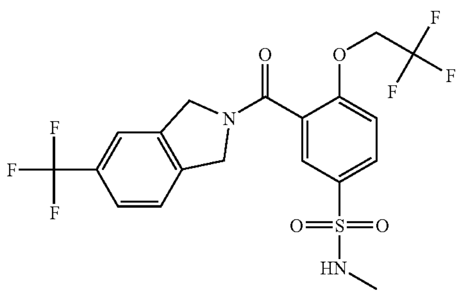 | N-Methyl-4-(2,2,2-trifluoro-ethoxy)-3-(5-trifluoromethyl-1,3-dihydro-isoindole-2-carbonyl)-benzenesulfonamide 483.0 | 5-Trifluoromethyl-2,3-dihydro-1H-isoindole (CAS: 342638-03-3) and 5-Methylsulfamoyl-2-(2,2,2-trifluoro-ethoxy)-benzoic acid (example B17) | 482.4 |
| 45 | 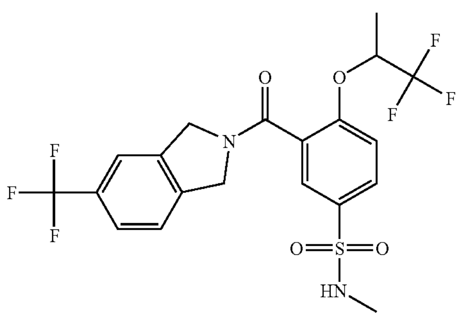 | rac-N-Methyl-3-(5-trifluoromethyl-1,3-dihydro-isoindole-2-carbonyl)-4-(2,2,2-trifluoro-1-methyl-ethoxy)-benzenesulfonamide 497.0 | 5-Trifluoromethyl-2,3-dihydro-1H-isoindole (CAS: 342638-03-3) and rac-5-Methylsulfamoyl-2-(2,2,2-trifluoro-1-methyl-ethoxy)-benzoic acid (example B18) | 496.4 |
| 46 | 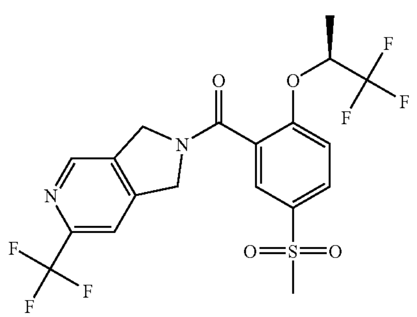 | [5-Methanesulfonyl-2-((S)-2,2,2-trifluoro-1-methyl-ethoxy)-phenyl]-(6-trifluoromethyl-1,3-dihydro-pyrrolo[3,4-c]pyridin-2-yl)-methanone 483.0 | 6-Trifluoromethyl-2,3-dihydro-1H-pyrrolo[3,4-c]pyridine (example A13) and 5-Methanesulfonyl-2-((S)-2,2,2-trifluoro-1-methyl-ethoxy)-benzoic acid (example B3) | 482.4 |
| 47 | 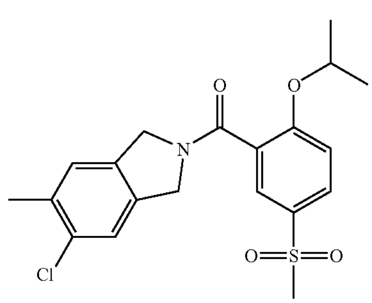 | (5-Chloro-6-methyl-1,3-dihydro-isoindol-2-yl)-(2-isopropoxy-5-methanesulfonyl-phenyl)-methanone 410.1 (³⁷Cl), 408.3 (³⁵Cl) | 5-Chloro-6-methyl-2,3-dihydro-1H-isoindole hydrochloride (example A4) and 2-Isopropoxy-5-methanesulfonyl-benzoic acid (example B1) | 407.9 |

-continued

| Expl. No. | Structure | Systematic Name MW found [M + H+] | Starting materials | MW |
|---|---|---|---|---|
| 48 | 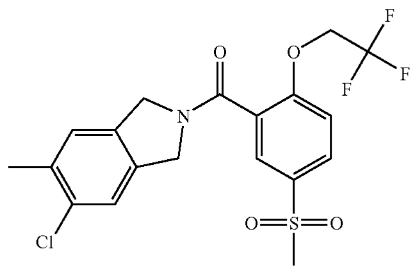 | (5-Chloro-6-methyl-1,3-dihydro-isoindol-2-yl)-[5-methanesulfonyl-2-(2,2,2-trifluoro-ethoxy)-phenyl]-methanone 449.9 37cl), 447.9 ($^{35}$Cl) | 5-Chloro-6-methyl-2,3-dihydro-1H-isoindole hydrochloride (example A4) and 5-Methanesulfonyl-2-(2,2,2-trifluoro-ethoxy)-benzoic acid (example B10) | 447.9 |
| 49 | 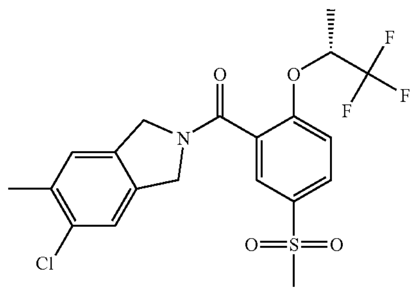 | (5-Chloro-6-methyl-1,3-dihydro-isoindol-2-yl)-[5-methanesulfonyl-2-((R)-2,2,2-trifluoro-1-methyl-ethoxy)-phenyl]-methanone 463.9 $^{37}$Cl), 462.0 ($^{35}$Cl) | 5-Chloro-6-methyl-2,3-dihydro-1H-isoindole hydrochloride (example A4) and 5-Methanesulfonyl-2-((R)-2,2,2-trifluoro-1-methyl-ethoxy)-benzoic acid (example B5) | 461.9 |
| 50 | 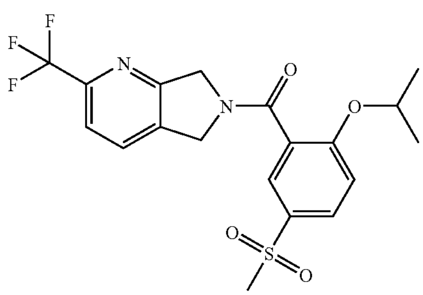 | (2-Isopropoxy-5-methanesulfonyl-phenyl)-(2-trifluoromethyl-5,7-dihydro-pyrrolo[3,4-b]pyridin-6-yl)-methanone 429.5 | 2-Trifluoromethyl-6,7-dihydro-5H-pyrrolo[3,4-b]pyridine (example A14) and 2-Isopropoxy-5-methanesulfonyl-benzoic acid (example B1) | 428.4 |
| 51 | 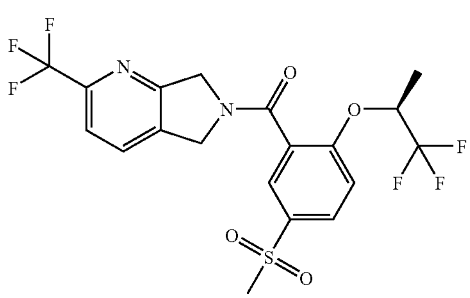 | [5-Methanesulfonyl-2-((S)-2,2,2-trifluoro-1-methyl-ethoxy)-phenyl]-(2-trifluoromethyl-5,7-dihydro-pyrrolo[3,4-b]pyridin-6-yl)-methanone 483.4 | 2-Trifluoromethyl-6,7-dihydro-5H-pyrrolo[3,4-b]pyridine (example A14) and 5-Methanesulfonyl-2-((S)-2,2,2-trifluoro-1-methyl-ethoxy)-benzoic acid (example B3) | 482.4 |
| 52 | 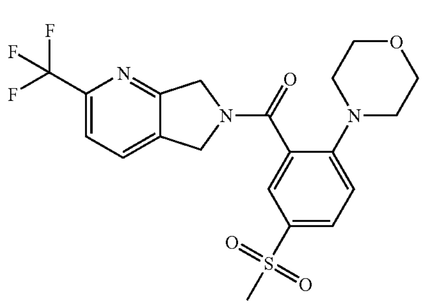 | (5-Methanesulfonyl-2-morpholin-4-yl-phenyl)-(2-trifluoromethyl-5,7-dihydro-pyrrolo[3,4-b]pyridin-6-yl)-methanone 456.4 | 2-Trifluoromethyl-6,7-dihydro-5H-pyrrolo[3,4-b]pyridine (example A14) and 5-Methanesulfonyl-2-morpholin-4-yl-benzoic acid (example B12) | 455.5 |

-continued

| Expl. No. | Structure | Systematic Name MW found [M + H⁺] | Starting materials | MW |
|---|---|---|---|---|
| 53 | 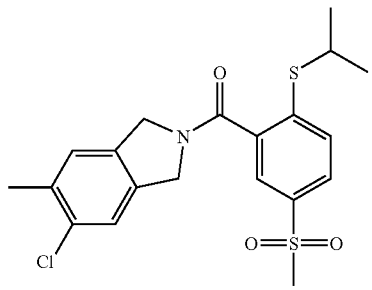 | (5-Chloro-6-methyl-1,3-dihydro-isoindol-2-yl)-(2-isopropylsulfanyl-5-methanesulfonyl-phenyl)-methanone 425.8 ³⁷Cl), 424.0 (³⁵Cl) | 5-Chloro-6-methyl-2,3-dihydro-1H-isoindole A4) hydrochloride (example A4) and 2-Isopropylsulfanyl-5-methanesulfonyl-benzoic acid (example B4) | 424.0 |
| 54 | 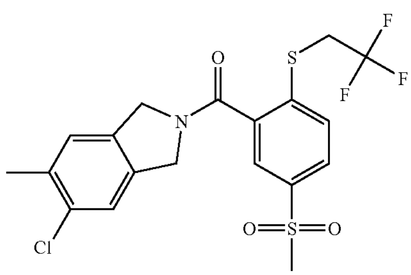 | (5-Chloro-6-methyl-1,3-dihydro-isoindol-2-yl)-[5-methanesulfonyl-2-(2,2,2-trifluoro-ethylsulfanyl)-phenyl]-methanone 465.9 ³⁷Cl), 463.9 (³⁵Cl) | 5-Chloro-6-methyl-2,3-dihydro-1H-isoindole hydrochloride (example A4) and 5-Methanesulfonyl-2-(2,2,2-trifluoro-ethylsulfanyl)-benzoic acid (example B7) | 463.9 |
| 55 | 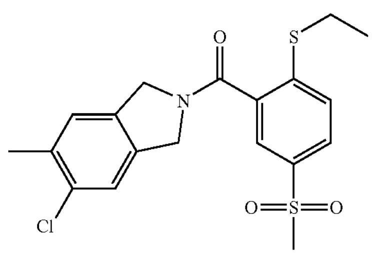 | (5-Chloro-6-methyl-1,3-dihydro-isoindol-2-yl)-(2-ethylsulfanyl-5-methanesulfonyl-phenyl)-methanone 411.9 ³⁷Cl), 410.0 (³⁵Cl) | 5-Chloro-6-methyl-2,3-dihydro-1H-isoindole hydrochloride (example A4) and 2-Ethylsulfanyl-5-methanesulfonyl-benzoic acid (example B6) | 410.0 |
| 56 | 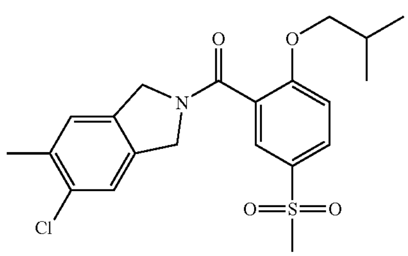 | (5-Chloro-6-methyl-1,3-dihydro-isoindol-2-yl)-(2-isobutoxy-5-methanesulfonyl-phenyl)-methanone 424.2 ³⁷Cl), 422.1 (³⁵Cl) | 5-Chloro-6-methyl-2,3-dihydro-1H-isoindole hydrochloride (example A4) and 2-Isobutoxy-5-methanesulfonyl-benzoic acid (example B11) | 421.9 |
| 57 | 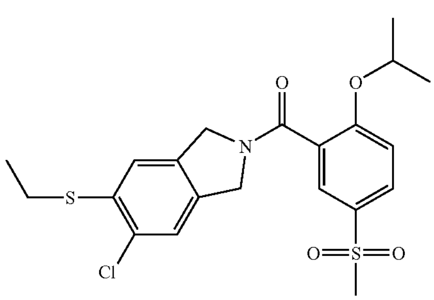 | (5-Chloro-6-ethylsulfanyl-1,3-dihydro-isoindol-2-yl)-(2-isopropoxy-5-methanesulfonyl-phenyl)-methanone 456.3 ³⁷Cl), 454.2 (³⁵Cl) | 5-Chloro-6-ethylsulfanyl-2,3-dihydro-1H-isoindole hydrochloride (example A5) and 2-Isopropoxy-5-methanesulfonyl-benzoic acid (example B1) | 454.0 |

-continued

| Expl. No. | Structure | Systematic Name MW found [M + H⁺] | Starting materials | MW |
|---|---|---|---|---|
| 58 | 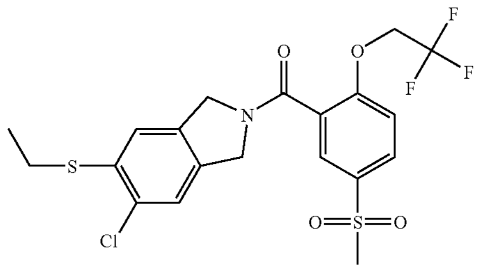 | (5-Chloro-6-ethylsulfanyl-1,3-dihydro-isoindol-2-yl)-[5-methanesulfonyl-2-(2,2,2-trifluoro-ethoxy)-phenyl]-methanone 496.3 $^{37}$Cl), 494.2 ($^{35}$Cl) | 5-Chloro-6-ethylsulfanyl-2,3-dihydro-1H-isoindole hydrochloride (example A5) and 5-Methanesulfonyl-2-(2,2,2-trifluoro-ethoxy)-benzoic acid (example B10) | 494.0 |
| 59 | 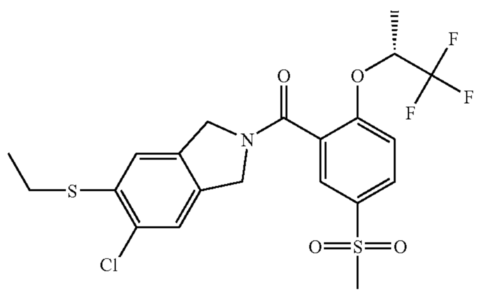 | (5-Chloro-6-ethylsulfanyl-1,3-dihydro-isoindol-2-yl)-[5-methanesulfonyl-2-((R)-2,2,2-trifluoro-1-methyl-ethoxy)-phenyl]-methanone 510.3 $^{37}$Cl), 508.2 ($^{35}$Cl) | 5-Chloro-6-ethylsulfanyl-2,3-dihydro-1H-isoindole hydrochloride (example A5) and 5-Methanesulfonyl-2-((R)-ethoxy)-benzoic acid (example B5) | 508.0 |
| 60 | 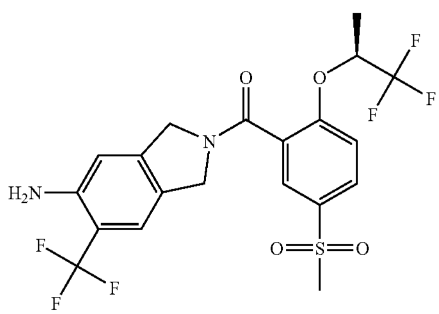 | (5-Amino-6-trifluoromethyl-1,3-dihydro-isoindol-2-yl)-[5-methanesulfonyl-2-((S)-2,2,2-trifluoro-1-methyl-ethoxy)-phenyl]-methanone 497.1 | 6-Trifluoromethyl-2,3-dihydro-1H-isoindol-5-ylamine (example A15) and 5-Methanesulfonyl-2-((S)-2,2,2-trifluoro-1-methyl-ethoxy)-benzoic acid (example B3) | 496.4 |
| 61 | 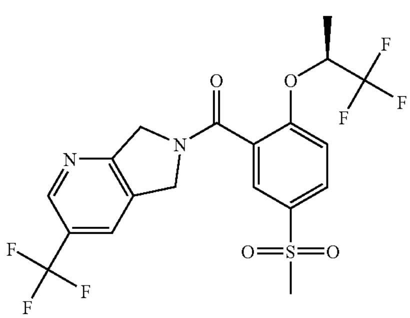 | [5-Methanesulfonyl-2-((S)-2,2,2-trifluoro-1-methyl-ethoxy)-phenyl]-(3-trifluoromethyl-5,7-dihydro-pyrrolo[3,4-b]pyridin-6-yl)-methanone 483.5 | 3-Trifluoromethyl-6,7-dihydro-5H-pyrrolo[3,4-b]pyridine (example A16) and 5-Methanesulfonyl-2-((S)-2,2,2-trifluoro-1-methyl-ethoxy)-benzoic acid (example B3) | 482.4 |
| 62 | 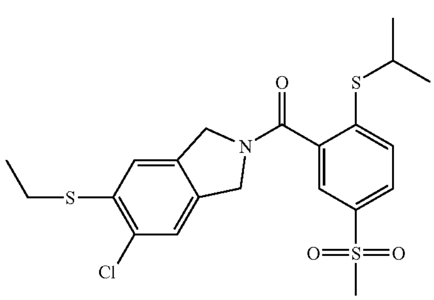 | (5-Chloro-6-ethylsulfanyl-1,3-dihydro-isoindol-2-yl)-(2-isopropylsulfanyl-5-methanesulfonyl-phenyl)-methanone 472.1 $^{37}$Cl), 470.3 ($^{35}$Cl) | 5-Chloro-6-ethylsulfanyl-2,3-dihydro-1H-isoindole hydrochloride (example A5) and 2-Isopropylsulfanyl-5-methanesulfonyl-benzoic acid (example B4) | 470.1 |

-continued

| Expl. No. | Structure | Systematic Name<br>MW found [M + H+] | Starting materials | MW |
|---|---|---|---|---|
| 63 | 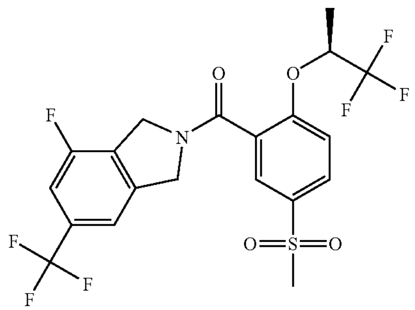 | (4-Fluoro-6-trifluoromethyl-1,3-dihydro-isoindol-2-yl)-[5-methanesulfonyl-2-((S)-2,2,2-trifluoro-1-methyl-ethoxy)-phenyl]-methanone<br>517.1 (M + NH$_4$+) | 4-Fluoro-6-trifluoromethyl-2,3-dihydro-1H-isoindole (example A17) and 5-Methanesulfonyl-2-((S)-2,2,2-trifluoro-1-methyl-ethoxy)-benzoic acid (example B3) | 499.4 |
| 64 | 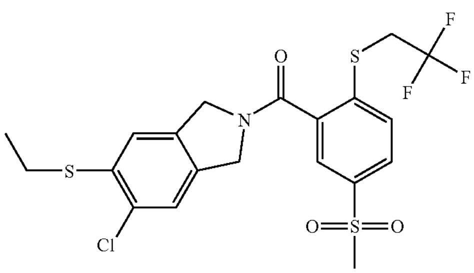 | (5-Chloro-6-ethylsulfanyl-1,3-dihydro-isoindol-2-yl)-[5-methanesulfonyl-2-(2,2,2-trifluoro-ethylsulfanyl)-phenyl]-methanone<br>512.1 $^{37}$Cl), 510.1 ($^{35}$Cl) | 5-Chloro-6-ethylsulfanyl-2,3-dihydro-1H-isoindole hydrochloride (example A5) and 5-Methanesulfonyl-2-(2,2,2-trifluoro-ethylsulfanyl)-benzoic acid (example B7) | 510.0 |
| 65 | 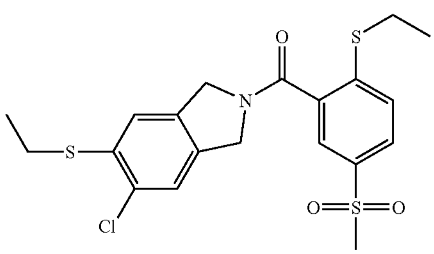 | (5-Chloro-6-ethylsulfanyl-1,3-dihydro-isoindol-2-yl)-(2-ethylsulfanyl-5-methanesulfonyl-phenyl)-methanone<br>458.2 $^{37}$Cl), 456.1 ($^{35}$Cl) | 5-Chloro-6-ethylsulfanyl-2,3-dihydro-1H-isoindole hydrochloride (example A5) and 2-Ethylsulfanyl-5-methanesulfonyl-benzoic acid (example B6) | 456.0 |
| 66 | 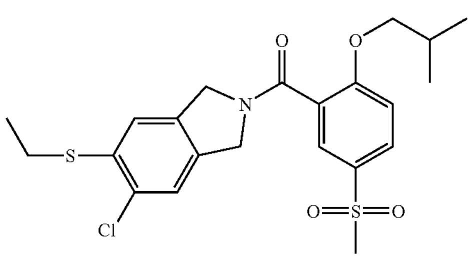 | (5-Chloro-6-ethylsulfanyl-1,3-dihydro-isoindol-2-yl)-(2-isobutoxy-5-methanesulfonyl-phenyl)-methanone<br>470.3 $^{37}$Cl), 468.2 ($^{35}$Cl) | 5-Chloro-6-ethylsulfanyl-2,3-dihydro-1H-isoindole hydrochloride (example A5) and 2-Isobutoxy-5-methanesulfonyl-benzoic acid (example B11) | 468.0 |
| 67 | 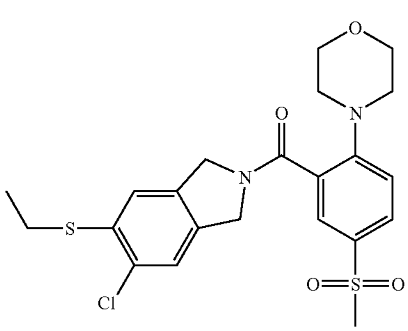 | (5-Chloro-6-ethylsulfanyl-1,3-dihydro-isoindol-2-yl)-(5-methanesulfonyl-2-morpholin-4-yl-phenyl)-methanone<br>483.2 $^{37}$Cl), 481.0 ($^{35}$Cl) | 5-Chloro-6-ethylsulfanyl-2,3-dihydro-1H-isoindole hydrochloride (example A5) and 5-Methanesulfonyl-2-morpholin-4-yl-benzoic acid (example B12) | 481.0 |

-continued

| Expl. No. | Structure | Systematic Name<br>MW found [M + H⁺] | Starting materials | MW |
|---|---|---|---|---|
| 68 | 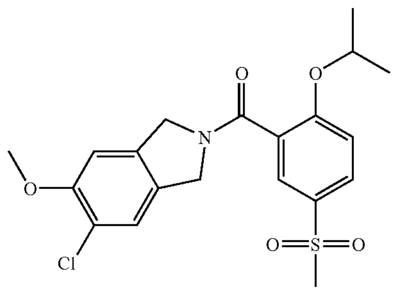 | (5-Chloro-6-methoxy-1,3-dihydro-isoindol-2-yl)-(2-isopropoxy-5-methanesulfonyl-phenyl)-methanone<br>426.1 ³⁷Cl), 424.1 (³⁵Cl) | 5-Chloro-6-methoxy-2,3-dihydro-1H-isoindole hydrochloride (example A6) and 2-Isopropoxy-5-methanesulfonyl-benzoic acid (example B1) | 423.9 |
| 69 | 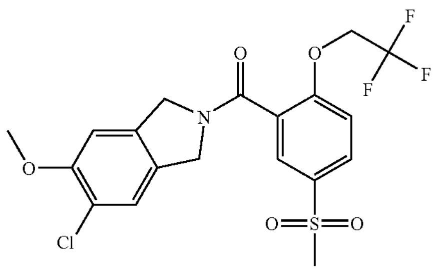 | (5-Chloro-6-methoxy-1,3-dihydro-isoindol-2-yl)-[5-methanesulfonyl-2-(2,2,2-trifluoro-ethoxy)-phenyl]-methanone<br>466.1 ³⁷Cl), 464.0 (³⁵Cl) | 5-Chloro-6-methoxy-2,3-dihydro-1H-isoindole hydrochloride (example A6) and 5-Methanesulfonyl-2-(2,2,2-trifluoro-ethoxy)-benzoic acid (example B10) | 463.9 |
| 70 | 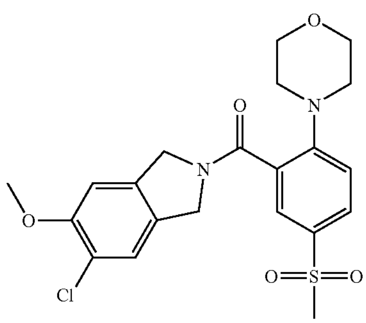 | (5-Chloro-6-methoxy-1,3-dihydro-isoindol-2-yl)-(5-methanesulfonyl-2-morpholin-4-yl-phenyl)-methanone<br>453.2 ³⁷Cl), 451.1 (³⁵Cl) | 5-Chloro-6-methoxy-2,3-dihydro-1H-isoindole hydrochloride (example A6) and 5-Methanesulfonyl-2-morpholin-4-yl-benzoic acid (example B12) | 450.9 |
| 71 | 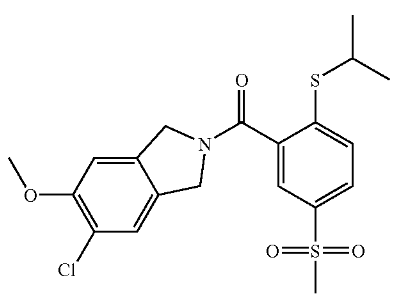 | (5-Chloro-6-methoxy-1,3-dihydro-isoindol-2-yl)-(2-isopropylsulfanyl-5-methanesulfonyl-phenyl)-methanone<br>442.0 ³⁷Cl), 440.1 (³⁵Cl) | 5-Chloro-6-methoxy-2,3-dihydro-1H-isoindole hydrochloride (example A6) and 2-Isopropylsulfanyl-5-methanesulfonyl-benzoic acid (example B4) | 440.0 |
| 72 | 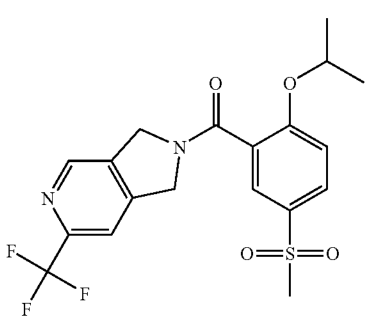 | (2-Isopropoxy-5-methanesulfonyl-phenyl)-(6-trifluoromethyl-1,3-dihydro-pyrrolo[3,4-c]pyridin-2-yl)-methanone<br>429.2 | 6-Trifluoromethyl-2,3-dihydro-1H-pyrrolo [3,4-c]pyridine (example A13) and 2-Isopropoxy-5-methanesulfonyl-benzoic acid (example B1) | 428.4 |

-continued

| Expl. No. | Structure | Systematic Name MW found [M + H⁺] | Starting materials | MW |
|---|---|---|---|---|
| 73 | 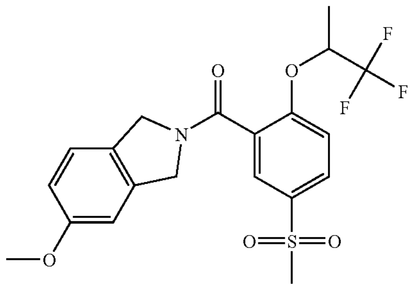 | [5-Methanesulfonyl-2-((S)-2,2,2-trifluoro-1-methyl-ethoxy)-phenyl]-(5-methoxy-1,3-dihydro-isoindol-2-yl)-methanone 444.0 | 5-Methoxy-2,3-dihydro-1H-isoindole (CAS: 127168-88-1) and 5-Methanesulfonyl-2-((S)-2,2,2-trifluoro-1-methyl-ethoxy)-benzoic acid (example B3) | 443.4 |
| 74 | 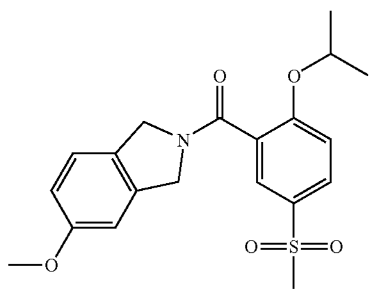 | (2-Isopropoxy-5-methanesulfonyl-phenyl)-(5-methoxy-1,3-dihydro-isoindol-2-yl)-methanone 390.0 | 5-Methoxy-2,3-dihydro-1H-isoindole (CAS: 127168-88-1) and 2-Isopropoxy-5-methanesulfonyl-benzoic acid (example B1) | 389.5 |
| 75 | 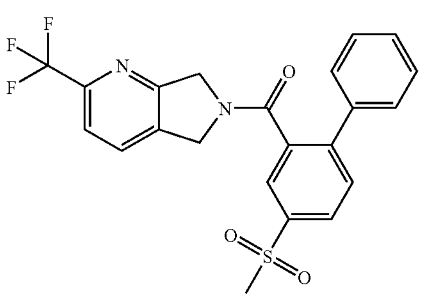 | (4-Methanesulfonyl-biphenyl-2-yl)-(2-trifluoromethyl-5,7-dihydro-pyrrolo[3,4-b]pyridin-6-yl)-methanone 447.0 | 2-Trifluoromethyl-6,7-dihydro-5H-pyrrolo[3,4-b]pyridine (example A14) and 4-Methanesulfonyl-biphenyl-2-carboxylic acid (example B19) | 446.5 |
| 76 | Chiral | (5-Benzyloxy-2,3-dihydro-indol-1-yl)-[5-methanesulfonyl-2-((S)-2,2,2-trifluoro-1-methyl-ethoxy)-phenyl]-methanone 520.3 | 5-Benzyloxy-2,3-dihydro-1H-indole (CAS: 92818-36-5) and 5-Methanesulfonyl-2-((S)-2,2,2-trifluoro-1-methyl-ethoxy) benzoic acid (example B3) | 519.5 |

| Expl. No. | Structure | Systematic Name MW found [M + H⁺] | Starting materials | MW |
|---|---|---|---|---|
| 77 | Chiral | (6-Chloro-5-methyl-2,3-dihydro-indol-1-yl)-[5-methanesulfonyl-2-((S)-2,2,2-trifluoro-1-methyl-ethoxy)-phenyl]-methanone 462.2 | 6-Chloro-5-methyl-2,3-dihydro-1H-indole (CAS: 162100-44-9) and 5-Methanesulfonyl-2-((S)-2,2,2-trifluoro-1-methyl-ethoxy)-benzoic acid (example B3) | 461.9 |
| 78 | Chiral | 1-[5-Methanesulfonyl-2-((S)-2,2,2-trifluoro-1-methyl-ethoxy)-benzoyl]-2,3-dihydro-1H-indole-6-carboxylic acid ethyl ester 486.4 | 2,3-Dihydro-1H-indole-6-carboxylic acid ethyl ester (CAS: 350683-40-8) and 5-Methanesulfonyl-2-((S)-2,2,2-trifluoro-1-methyl-ethoxy)-benzoic acid (example B3) | 485.5 |
| 79 | Chiral | (5-Bromo-6-nitro-2,3-dihydro-indol-1-yl)-[5-methanesulfonyl-2-((S)-2,2,2-trifluoro-1-methyl-ethoxy)-phenyl]-methanone 537.5 | 5-Bromo-6-nitro-2,3-dihydro-1H-indole (CAS: 72159-65-0) and 5-Methanesulfonyl-2-((S)-2,2,2-trifluoro-1-methyl ethoxy)-benzoic acid (example B3) | 537.3 |
| 80 | Chiral | [5-Methanesulfonyl-2-((S)-2,2,2-trifluoro-1-methyl-ethoxy)-phenyl]-(5-nitro-2,3-dihydro-indol-1-yl)-methanone 459.4 | 5-Nitro-2,3-dihydro-1H-indole (CAS: 32692-19-6) and 5-Methanesulfonyl-2-((S)-2,2,2-trifluoro-1-methyl-ethoxy) benzoic acid (example B3) | 458.4 |

| Expl. No. | Structure | Systematic Name MW found [M + H⁺] | Starting materials | MW |
|---|---|---|---|---|
| 81 | Chiral 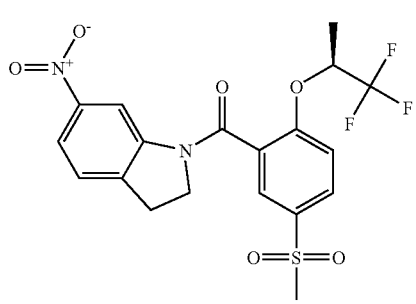 | [5-Methanesulfonyl-2-((S)-2,2,2-trifluoro-1-methyl-ethoxy)-phenyl]-(6-nitro-2,3-dihydro-indol-1-yl)-methanone 459.4 | 6-Nitro-2,3-dihydro-1H-indole (CAS: 19727-83-4) and 5-Methanesulfonyl-2-((S)-2,2,2-trifluoro-1-methyl-ethoxy)-benzoic acid (example B3) | 458.4 |
| 82 | Chiral 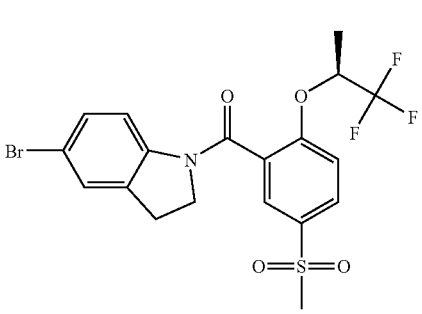 | (5-Bromo-2,3-dihydro-indol-1-yl)-[5-methanesulfonyl-2-((S)-2,2,2-trifluoro-1-methyl-ethoxy)-phenyl]-methanone 492.2 | 5-Bromo-2,3-dihydro-1H-indole (CAS: 22 190-33-6) and 5-Methanesulfonyl-2-((S)-2,2,2-trifluoro-1-methyl-ethoxy)-benzoic acid (example B3) | 492.3 |
| 83 | Chiral 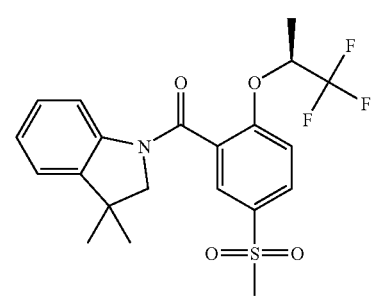 | (3,3-Dimethyl-2,3-dihydro-indol-1-yl)-[5-methanesulfonyl-2-((S)-2,2,2-trifluoro-1-methyl-ethoxy)-phenyl]-methanone 442.1 | 3,3-Dimethyl-2,3-dihydro-1H-indole (CAS: 1914-02-9) and 5-Methanesulfonyl-2-((S)-2,2,2-trifluoro-1-methyl-ethoxy) benzoic acid (example B3) | 441.5 |
| 84 | Chiral 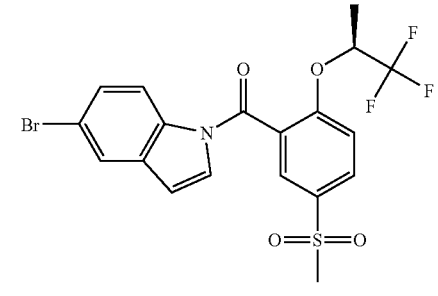 | (5-Bromo-indol-1-yl)-[5-methanesulfonyl-2-((S)-2,2,2-trifluoro-1-methyl-ethoxy)-phenyl]-methanone 492.1 | 5-bromoindole (commercial) and 5-Methanesulfonyl-2-((S)-2,2,2-trifluoro-1-methyl-ethoxy)-benzoic acid (example B3) | 490.3 |

-continued

| Expl. No. | Structure | Systematic Name MW found [M + H⁺] | Starting materials | MW |
|---|---|---|---|---|
| 85 | Chiral | 1-[5-Methanesulfonyl-2-((S)-2,2,2-trifluoro-1-methyl-ethoxy)-benzoyl]-1H-indole-6-carbonitrile 454.4 (M + NH₄⁺) | 1H-Indole-6-carbonitrile (CAS: 15861-36-6) and 5-Methanesulfonyl-2-((S)-2,2,2-trifluoro-1-methyl-ethoxy)-benzoic acid (example B3) | 436.4 |
| 86 | Chiral | (6-Chloro-indol-1-yl)-[5-methanesulfonyl-2-((S)-2,2,2-trifluoro-1-methyl-ethoxy)-phenyl]-methanone 446.1 | 6-Chloro-1H-indole (commercial) and 5-Methanesulfonyl-2-((S)-2,2,2-trifluoro-1-methyl-ethoxy)-benzoic acid (example B3) | 445.9 |
| 87 | Chiral | (4-Bromo-indol-1-yl)-[5-methanesulfonyl-2-(2,2,2-trifluoro-1-methyl-ethoxy)-phenyl]-methanone 490.1 | 4-Bromo-1H-indole (commercial) and 5-Methanesulfonyl-2-((S)-2,2,2-trifluoro-1-methyl-ethoxy)-benzoic acid (example B3) | 490.3 |
| 88 | Chiral | [5-Methanesulfonyl-2-((S)-2,2,2-trifluoro-1-methyl-ethoxy)-phenyl]-(5-nitro-indazol-1-yl)-methanone 475.2 (M + NH₄⁺) | 5-Nitro-1H-indazole (CAS:161287-82-7) and 5-Methanesulfonyl-2-((S)-2,2,2-trifluoro-1-methyl-ethoxy)-benzoic acid (example B3) | 457.4 |

| Expl. No. | Structure | Systematic Name MW found [M + H⁺] | Starting materials | MW |
|---|---|---|---|---|
| 89 | Chiral | (5-Chloro-indazol-1-yl)-[5-methanesulfonyl-2-((S)-2,2,2-trifluoro-1-methyl-ethoxy)-phenyl]-methanone 447.1 | 5-Chloro-1H-indazole (CAS:698-26-0) and 5-Methanesulfonyl-2-((S)-2,2,2-trifluoro-1-methyl-ethoxy)-benzoic acid (example B3) | 446.8 |
| 90 | Chiral | (5,7-Dichloro-indazol-1-yl)-[5-methanesulfonyl-2-((S)-2,2,2-trifluoro-1-methyl-ethoxy)-phenyl]-methanone 481.2 | 5,7-Dichloro-1H-indazole (CAS: 50477-27-5) and 5-Methanesulfonyl-2-((S)-2,2,2-trifluoro-1-methyl-ethoxy)-benzoic acid (example B3) | 481.3 |
| 91 | Chiral | (5,6-Dimethyl-benzoimidazol-yl)-[5-methanesulfonyl-2-((S)-2,2,2-trifluoro-1-methyl-ethoxy)-phenyl]-methanone 441.4 | 5,6-Dimethyl-1H-benzoimidazole (CAS: 117140-27-9) and 5-Methanesulfonyl-2-((S)-2,2,2-trifluoro-1-methyl-ethoxy)-benzoic acid (example B3) | 440.4 |

EXAMPLE 92

Preparation of (4-Fluoro-1,3-dihydro-isoindol-2-yl)-(2-isopropoxy-5-methanesulfonyl-phenyl)-methanone

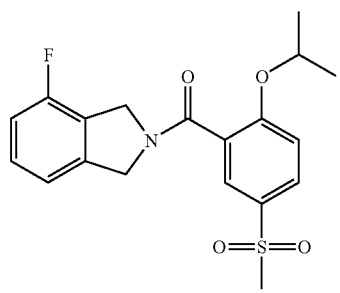

To a RT suspension of 0.61 mmol sodium hydride (50% in mineral oil) in 0.5 ml dry DMF, a solution of 0.29 mmol 2-Isopropoxy-5-methanesulfonyl-benzamide (example B20) in 1 ml dry DMF was added dropwise. After 15 minutes at RT and 15 minutes at 50° C., the reaction mixture was cooled to 0° C., and treated by a solution of 0.29 mmol 1,2-Bis-bromomethyl-3-fluoro-benzene (CAS: 62590-16-3) in 1 ml dry DMF. The reaction mixture was allowed to warm to RT and stirred for 15 minutes then cooled to 0° C., quenched with water and extracted with ethylacetate. The combined organic phases were washed with water, dried over sodium sulfate, filtered and concentrated in vacuo. The residue was purified by chromatography (SiO₂, heptane/ethyl acetate) to yield the title compound as a white solid (27% yield). MS (m/e): 378.3 [M+H⁺], 100%)

In analogy to Example 92, compounds 93 to 96 of the following table were prepared from 2-Isopropoxy-5-methanesulfonyl-benzamide (example B20) and the corresponding 1,2-Bis-bromomethyl-aryl derivatives.

| Expl. No. | Structure | Systematic Name MW found (MH+) | Starting materials | MW |
|---|---|---|---|---|
| 93 | 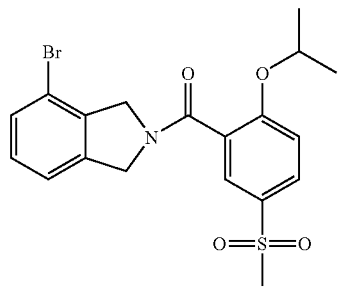 | (4-Bromo-1,3-dihydro-isoindol-2-yl)-(2-isopropoxy-5-methanesulfonyl-phenyl)-methanone 440.2 | 1-Bromo-2,3-bis-bromomethyl-benzene (CAS: 127168-82-5) and 2-Isopropoxy-5-methanesulfonyl-benzamide (example B20) | 438.3 |
| 94 | 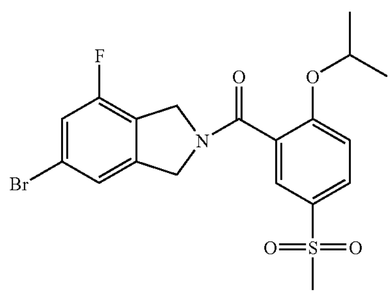 | (6-Bromo-4-fluoro-1,3-dihydro-isoindol-2-yl)-(2-isopropoxy-5-methanesulfonyl-phenyl)-methanone 458.3 | 5-Bromo-1,2-bis-bromomethyl-3-fluoro-benzene (CAS: 194805-17-9) and 2-Isopropoxy-5-methanesulfonyl-benzamide (example B20) | 456.3 |
| 95 | 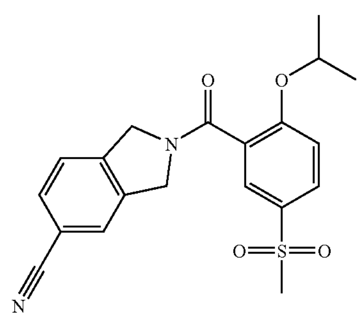 | 2-(2-Isopropoxy-5-methanesulfonyl-benzoyl)-2,3-dihydro-1H-isoindole-5-carbonitrile 385.1 | 3,4-Bis-bromomethyl-benzonitrile (CAS: 66126-17-8) and 2-Isopropoxy-5-methanesulfonyl-benzamide (example B20) | 384.5 |
| 96 | 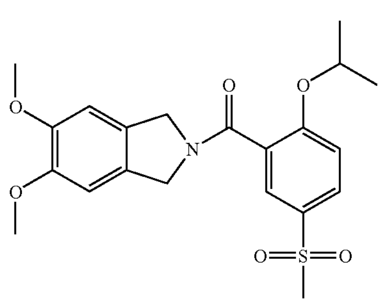 | (5,6-Dimethoxy-1,3-dihydro-isoindol-2-yl)-(2-isopropoxy-5-methanesulfonyl-phenyl)-methanone 420.3 | 1,2-Bis-bromomethyl-4,5-dimethoxy-benzene (CAS:26726-81-8) and 2-Isopropoxy-5-methanesulfonyl-benzamide (example B20) | 419.5 |

EXAMPLE 97

[5-Methanesulfonyl-2-((S)-2,2,2-trifluoro-1-methyl-ethoxy)-phenyl]-(4-methyl-1,3-dihydro-isoindol-2-yl)-methanone

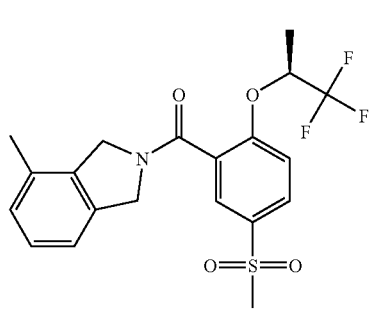

Prepared in analogy to Example A4(a) from (4-Iodo-1,3-dihydro-isoindol-2-yl)-[5-methanesulfonyl-2-((S)-2,2,2-trifluoro-1-methyl-ethoxy)-phenyl]-methanone (Example C1). Light brown solid. MS (m/e): 428.3 [M+H]$^+$, 100%).

EXAMPLE 98

[5-Methanesulfonyl-2-((S)-2,2,2-trifluoro-1-methyl-ethoxy)-phenyl]-(4-methoxy-1,3-dihydro-isoindol-2-yl)-methanone

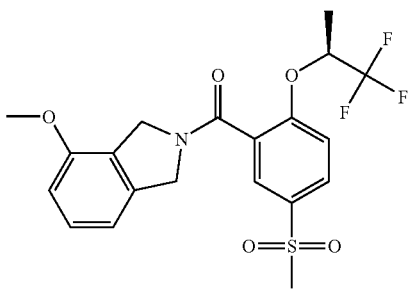

Prepared in analogy to Example A6(a) from (4-Iodo-1,3-dihydro-isoindol-2-yl)-[5-methanesulfonyl-2-((S)-2,2,2-trifluoro-1-methyl-ethoxy)-phenyl]-methanone (Example C1). Light brown solid. MS (m/e): 444.4 [M+H$^+$], 100%).

EXAMPLE 99

[[5-Methanesulfonyl-2-((S)-2,2,2-trifluoro-1-methyl-ethoxy)-phenyl]-(5-methyl-6-trifluoromethyl-1,3-dihydro-isoindol-2-yl)-methanone

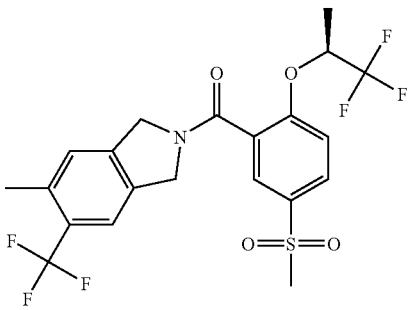

Prepared in analogy to Example A4(a) from (5-iodo-6-trifluoromethyl-1,3-dihydro-isoindol-2-yl)-[5-methanesulfonyl-2-((S)-2,2,2-trifluoro-1-methyl-ethoxy)-phenyl]-methanone (Example C2). White solid. MS (m/e): 496.0 [M+H]$^+$, 100%).

EXAMPLE 100

[[5-Methanesulfonyl-2-((S)-2,2,2-trifluoro-1-methyl-ethoxy)-phenyl]-(5-methoxy-6-trifluoromethyl-1,3-dihydro-isoindol-2-yl)-methanone

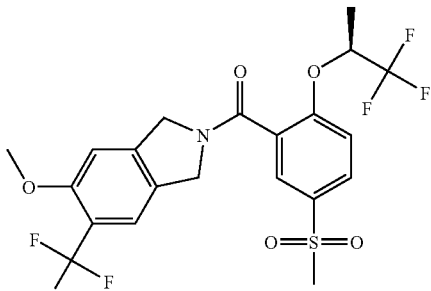

Prepared in analogy to Example A6(a) from (5-Iodo-6-trifluoromethyl-1,3-dihydro-isoindol-2-yl)-[5-methanesulfonyl-2-((S)-2,2,2-trifluoro-1-methyl-ethoxy)-phenyl]-methanone (Example C2). White solid. MS (m/e): 512.0 [M+H]$^+$, 100%).

In analogy to Example 1, compounds 101 to 312 of the following table were prepared from the acid derivatives and amine derivatives:

| Expl. No. | Structure | Systematic Name | Starting materials | MW Calc. | MW Found [M + H]+ |
|---|---|---|---|---|---|
| 101 | 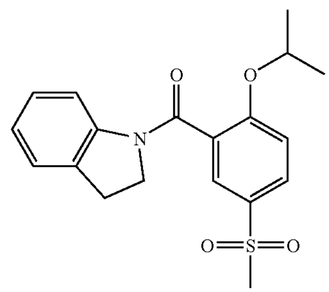 | (2,3-Dihydro-indol-1-yl)-(2-isopropoxy-5-methanesulfonyl-phenyl)-methanone | 2,3-Dihydro-1H-indole (commercial) and 2-Isopropoxy-5-methanesulfonyl-benzoic acid (example B1) | 359.4 | 359.1 |
| 102 | 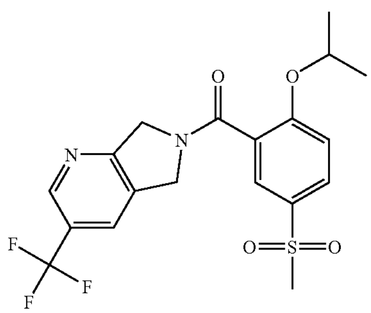 | (2-Isopropoxy-5-methanesulfonyl-phenyl)-(3-trifluoromethyl-5,7-dihydro-pyrrolo[3,4-b]pyridin-6-yl)-methanone | 3-Trifluoromethyl-6,7-dihydro-5H-pyrrolo[3,4-b]bipyridine (example A16) and 2-Isopropo-5-methanesulfonyl-benzoic acid (example B1) | 428.4 | 429.2 |
| 103 | Chiral | [5-Methanesulfonyl-2-((S)-2,2,2-trifluoro-1-methyl-ethoxy)-phenyl]-(5-trifluoromethoxy-1,3-dihydro-isoindol-2-yl)-methanone | 5-Trifluoromethoxy-2,3-dihydro-1H-isoindole (example A18) and 5-Methanesulfonyl-2-((S)-2,2,2-trifluoro-1-methyl-ethoxy)-benzoic acid (example B3) | 497.4 | 498.0 |
| 104 | Chiral | rac-[5-Ethanesulfonyl-2-(2,2,2-trifluoro-1-methyl-ethoxy)-phenyl]-(6-trifluoromethyl-1,3-dihydro-pyrrolo[3,4-c]pyridin-2-yl)-methanone | 6-Trifluoromethyl-2,3-dihydro-1H-pyrrolo [3,4-c]pyridine (example A13) and rac-5-Ethanesulfonyl-2-(2,2,2-trifluoro-1-methyl ethoxy)-benzoic acid (example B21) | 496.4 | 496.9 |

| Expl. No. | Structure | Systematic Name | Starting materials | MW Calc. | MW Found [M + H]+ |
|---|---|---|---|---|---|
| 105 | 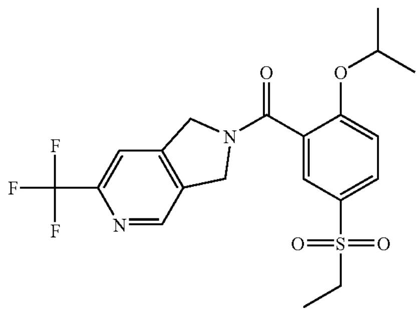 | (5-Ethanesulfonyl-2-isopropoxy-phenyl)-(6-trifluoromethyl-1,3-dihydro-pyrrolo[3,4-c]pyridin-2-yl)-methanone | 6-Trifluoromethyl-2,3-dihydro-1H-pyrrolo[3,4-c]pyridine (example A13) and 5-Ethanesulfonyl-2-isopropoxy-benzoic acid (CAS: 8456 17-27-8) | 442.4 | 443.0 |
| 106 | 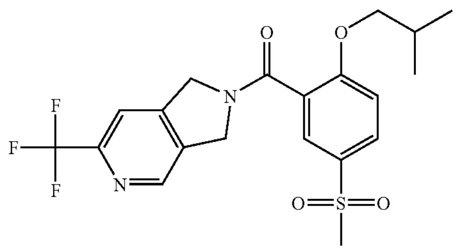 | (2-Isobutoxy-5-methanesulfonyl-phenyl)-(6-trifluoromethyl-1,3-dihydro-pyrrolo[3,4-c]pyridin-2-yl)-methanone | 6-Trifluoromethyl-2,3-dihydro-1H-pyrrolo[3,4-c]pyridine (example A13) and 2-Isobutoxy-5-methanesulfonyl-benzoic acid (example B11) | 442.5 | 442.1 |
| 107 | 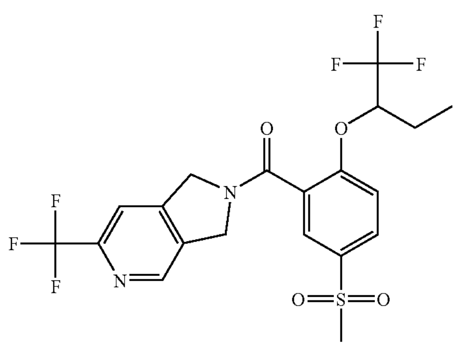 | rac-[5-Methanesulfonyl-2-(1-trifluoromethyl-propoxy)-phenyl]-(6-trifluoromethyl-1,3-dihydro-pyrrolo[3,4-c]pyridin-2-yl)-methanone | 6-Trifluoromethyl-2,3-dihydro-1H-pyrrolo[3,4-c]pyridine (example A13) and rac-5-Methanesulfonyl-2-(1-trifluoromethyl-propoxy)-benzoic acid (example B22) | 496.4 | 496.1 |
| 108 | 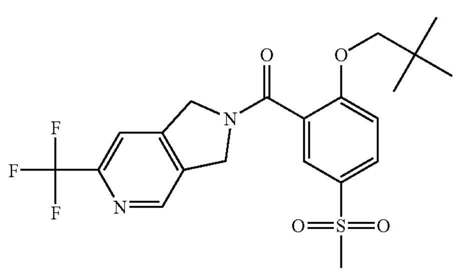 | [2-(2,2-Dimethyl-propoxy)-5-methanesulfonyl-phenyl]-(6-trifluoromethyl-1,3-dihydro-pyrrolo[3,4-c]pyridin-2-yl)-methanone | 6-Trifluoromethyl-2,3-dihydro-1H-pyrrolo[3,4-c]pyridine (example A13) and 2-(2,2-Dimethyl-propoxy)-5-methanesulfonyl-benzoic acid (CAS: 845616-85-5) | 456.5 | 456.2 |
| 109 | 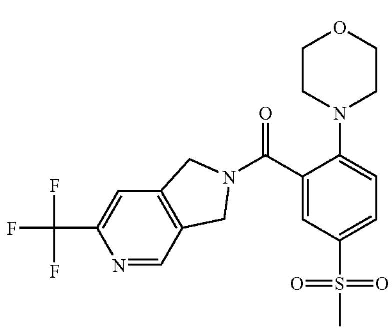 | (5-Methanesulfonyl-2-morpholin-4-yl-phenyl)-(6-trifluoromethyl-1,3-dihydro-pyrrolo[3,4-c]pyridin-2-yl)-methanone | 6-Trifluoromethyl-2,3-dihydro-1H-pyrrolo[3,4-c]pyridine (example A13) and 5-Methanesulfonyl-2-morpholin-4-yl-benzoic acid (example B12) | 455.5 | 456.3 |

| Expl. No. | Structure | Systematic Name | Starting materials | MW Calc. | MW Found [M + H]+ |
|---|---|---|---|---|---|
| 110 | 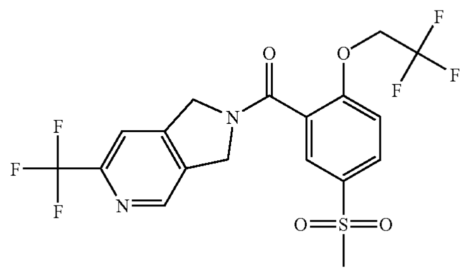 | [5-Methanesulfonyl-2-(2,2,2-trifluoro-ethoxy)-phenyl]-(6-trifluoromethyl-1,3-dihydro-pyrrolo[3,4-c]pyridin-2-yl)-methanone | 6-Trifluoromethyl-2,3-dihydro-1H-pyrrolo[3,4-c]pyridine (example A13) and 5-Methanesulfonyl-2-(2,2,2-trifluoro-ethoxy)-benzoic acid (example B10) | 468.4 | 468.0 |
| 111 | 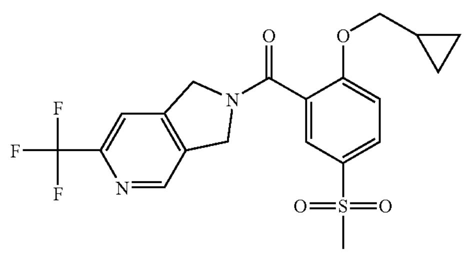 | (2-Cyclopropylmethoxy-5-methanesulfonyl-phenyl)-(6-trifluoromethyl-1,3-dihydro-pyrrolo[3,4-c]pyridin-2-yl)-methanone | 6-Trifluoromethyl-2,3-dihydro-1H-pyrrolo[3,4-c]pyridine (example A13) and 2-Cyclopropylmethoxy-5-methanesulfonyl-benzoic acid (CAS: 845616-03-7) | 440.4 | 441.1 |
| 112 | 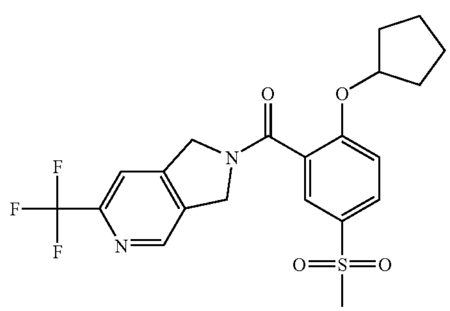 | (2-Cyclopentyloxy-5-methanesulfonyl-phenyl)-(6-trifluoromethyl-1,3-dihydro-pyrrolo[3,4-c]pyridin-2-yl)-methanone | 6-Trifluoromethyl-2,3-dihydro-1H-pyrrolo[3,4-c]pyridine (example A13) and 2-Cyclopentyloxy-5-methanesulfonyl-benzoic acid (CAS: 845616-05-9) | 454.5 | 454.1 |
| 113 | 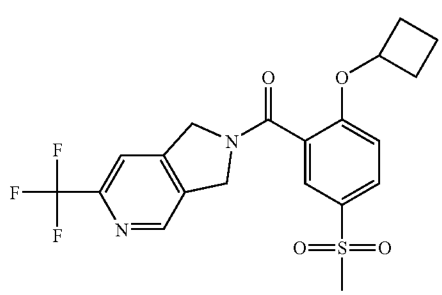 | (2-Cyclobutoxy-5-methanesulfonyl-phenyl)-(6-trifluoromethyl-1,3-dihydro-pyrrolo[3,4-c]pyridin-2-yl)-methanone | 6-Trifluoromethyl-2,3-dihydro-1H-pyrrolo[3,4-c]pyridine (example A13) and 2-Cyclobutoxy-5-methanesulfonyl-benzoic acid (CAS: 845616-86-6) | 440.4 | 440.1 |
| 114 | 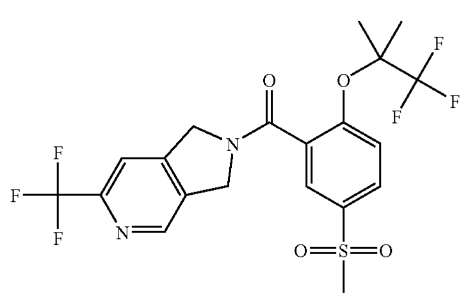 | [5-Methanesulfonyl-2-(2,2,2-trifluoro-1,1-dimethyl-ethoxy)-phenyl]-(6-trifluoromethyl-1,3-dihydro-pyrrolo[3,4-c]pyridin-2-yl)-methanone | 6-Trifluoromethyl-2,3-dihydro-1H-pyrrolo[3,4-c]pyridine (example A13) and 5-Methanesulfonyl-2-(2,2,2-trifluoro-1,1-dimethyl-ethoxy)-benzoic acid (CAS: 845618-01-1) | 496.4 | 496.1 |

-continued

| Expl. No. | Structure | Systematic Name | Starting materials | MW Calc. | MW Found [M + H]+ |
|---|---|---|---|---|---|
| 115 | 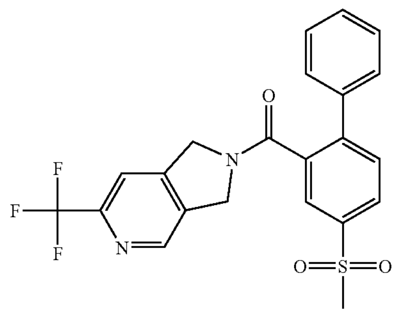 | (4-Methanesulfonyl-biphenyl-2-yl)-(6-trifluoromethyl-1,3-dihydro-pyrrolo[3,4-c]pyridin-2-yl)-methanone | 6-Trifluoromethyl-2,3-dihydro-1H-pyrrolo[3,4-c]pyridine (example A13) and 4-Methanesulfonyl-biphenyl-2-carboxylic acid (example B19) | 446.4 | 464.0 (M + NH4+) |
| 116 | Chiral | [2-((S)-sec-Butoxy)-5-methanesulfonyl-phenyl]-(6-trifluoromethyl-1,3-dihydro-pyrrolo[3,4-c]pyridin-2-yl)-methanone | 6-Trifluoromethyl-2,3-dihydro-1H-pyrrolo[3,4-c]pyridine (example A13) and 2-((S)-sec-Butoxy)-5-methanesulfonyl-benzoic acid (example B23) | 442.5 | 442.2 |
| 117 | Chiral | [2-((R)-sec-Butoxy)-5-methanesulfonyl-phenyl]-(6-trifluoromethyl-1,3-dihydro-pyrrolo[3,4-c]pyridin-2-yl)-methanone | 6-Trifluoromethyl-2,3-dihydro-1H-pyrrolo[3,4-c]pyridine (example A13) and 2-((R)-sec-Butoxy)-5-methanesulfonyl-benzoic acid (example B24) | 442.5 | 442.1 |
| 118 | 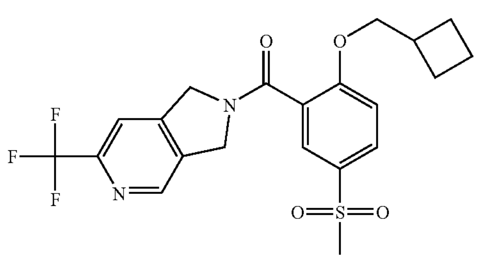 | (2-Cyclobutylmethoxy-5-methanesulfonyl-phenyl)-(6-trifluoromethyl-1,3-dihydro-pyrrolo[3,4-c]pyridin-2-yl)-methanone | 6-Trifluoromethyl-2,3-dihydro-1H-pyrrolo[3,4-c]pyridine (example A13) and 2-Cyclobutylmethoxy-5-methanesulfonyl-benzoic acid (CAS: 845616-33-3) | 454.5 | 471.9 (M + NH4+) |

| Expl. No. | Structure | Systematic Name | Starting materials | MW Calc. | MW Found [M + H]+ |
|---|---|---|---|---|---|
| 119 | 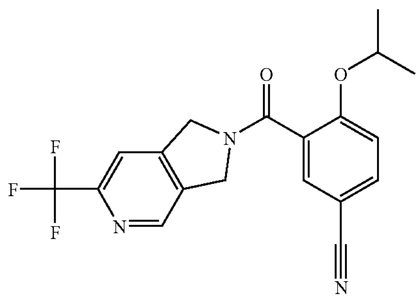 | 4-Isopropoxy-3-(6-trifluoromethyl-1,3-dihydro-pyrrolo[3,4-c]pyridine-2-carbonyl)-benzonitrile | 6-Trifluoromethyl-2,3-dihydro-1H-pyrrolo[3,4-c]pyridine (example A13) and 5-Cyano-2-isopropoxy-benzoic acid (CAS: 845616-14-0) | 375.3 | 375.3 |
| 120 | 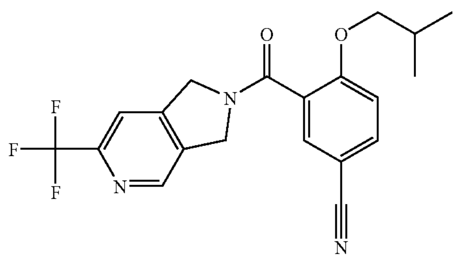 | 4-Isobutoxy-3-(6-trifluoromethyl-1,3-dihydro-pyrrolo[3,4-c]pyridine-2-carbonyl)-benzonitrile | 6-Trifluoromethyl-2,3-dihydro-1H-pyrrolo[3,4-c]pyridine (example A13) and 5-Cyano-2-isobutoxy-benzoic acid (CAS: 845616-16-2) | 389.4 | 390.0 |
| 121 | 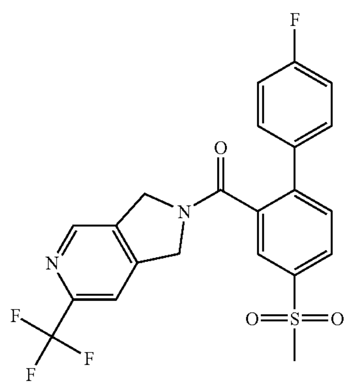 | (4-Fluoro-4-methanesulfonyl-biphenyl-2-yl)-(6-trifluoromethyl-1,3-dihydro-pyrrolo[3,4-c]pyridin-2-yl)-methanone | 6-Trifluoromethyl-2,3-dihydro-1H-pyrrolo[3,4-c]pyridine (example A13) and 4'-Fluoro-4-methanesulfonyl-biphenyl-2-carboxylic acid (example B25) | 464.0 | 465.0 |
| 122 | 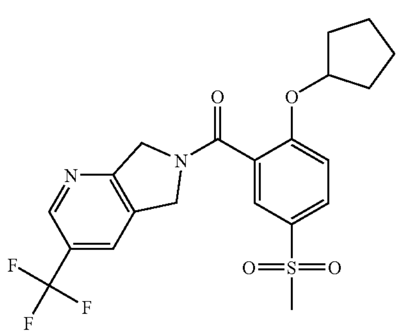 | (2-Cyclopentyloxy-5-methanesulfonyl-phenyl)-(3-trifluoromethyl-5,7-dihydro-pyrrolo[3,4-b]pyridin-6-yl)-methanone | 3-Trifluoromethyl-6,7-dihydro-5H-pyrrolo[3,4-b]pyridine (example A16) and 2-Cyclopentyloxy-5-methanesulfonyl-benzoic acid (CAS: 845616-05-9) | 454.5 | 455.2 |

| Expl. No. | Structure | Systematic Name | Starting materials | MW Calc. | MW Found [M + H]+ |
|---|---|---|---|---|---|
| 123 | 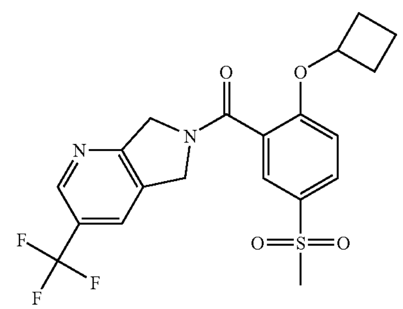 | (2-Cyclobutoxy-5-methanesulfonyl-phenyl)-(3-trifluoromethyl-5,7-dihydro-pyrrolo[3,4-b]pyridin-6-yl)-methanone | 3-Trifluoromethyl-6,7-dihydro-5H-pyrrolo[3,4-b]pyridine (example A16) and 2-Cyclobutoxy-5-methanesulfonyl-benzoic acid (CAS: 845616-86-6) | 440.4 | 441.1 |
| 124 | 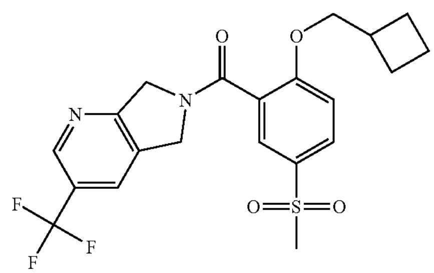 | (2-Cyclobutylmethoxy-5-methanesulfonyl-phenyl)-(3-trifluoromethyl-5,7-dihydro-pyrrolo[3,4-b]pyridin-6-yl)-methanone | 3-Trifluoromethyl-6,7-dihydro-5H-pyrrolo[3,4-b]pyridine (example A16) and 2-Cyclobutylmethoxy-5-methanesulfonyl-benzoic acid (CAS: 845616-33-3) | 454.5 | 471.9 (M + NH4+) |
| 125 | 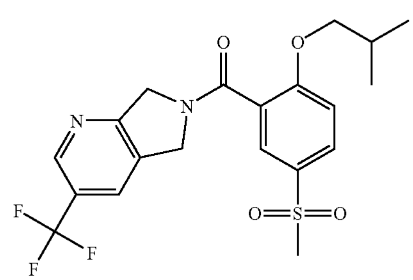 | (2-Isobutoxy-5-methanesulfonyl-(phenyl)-(3-trifluoromethyl-5,7-dihydro-pyrrolo[3,4-b]pyridin-6-yl)-methanone | 3-Trifluoromethyl-6,7-dihydro-5H-pyrrolo[3,4-b]pyridine (example A16) and 2-Isobutoxy-5-methanesulfonyl-benzoic acid (example B11) | 442.5 | 443.0 |
| 126 | 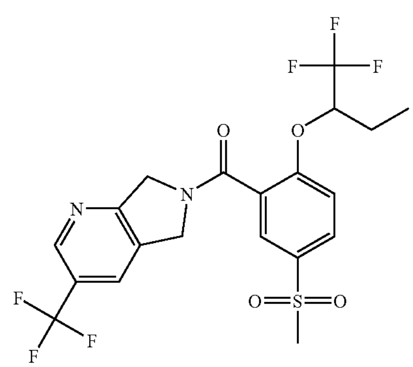 | rac-[5-Methanesulfonyl-2-(1-trifluoromethyl-opropoxy)-phenyl]-(3-trifluoromethyl-5,7-dihydro-pyrrolo[3,4-b]pyridin-6-yl)-methanone | 3-Trifluoromethyl-6,7-dihydro-5H-pyrrolo[3,4-b]pyridine (example A16) and rac-5-Methanesulfonyl-2-(1-trifluoromethyl-propoxy)-benzoic acid (example B22) | 496.4 | 497.0 |
| 127 | 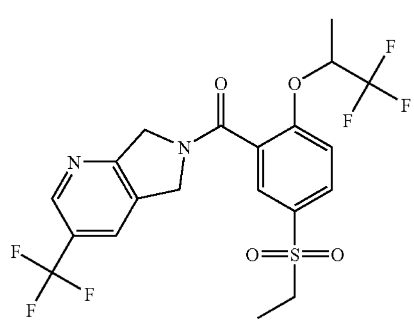 | rac-[5-Ethanesulfonyl-2-(2,2,2-trifluoro-1-(3-trifluoromethyl-5,7-dihydroppyrrolo[3,4-b]pyridin-6-yl)-methanone | 3-Trifluoromethyl-6,7-dihydro-5H-pyrrolo[3,4-b]pyridine (example A16) and rac-5-Ethanesulfonyl-2-(2,2,2-trifluoro-1-methyl-ethoxy)-benzoic acid (example B21) | 496.4 | 497.1 |

-continued

| Expl. No. | Structure | Systematic Name | Starting materials | MW Calc. | MW Found [M + H]+ |
|---|---|---|---|---|---|
| 128 | 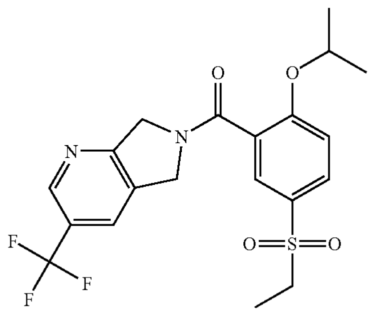 | (5-Ethanesulfonyl-2-isopropoxy-phenyl)-(3-trifluoromethyl-5,7-dihydro-pyrrolo[3,4-b]pyridin-6-yl)-methanone | 3-Trifluoromethyl-6,7-dihydro-5H-pyrrolo[3,4-b]pyridine (example A16) and 5-Ethanesulfonyl-2-isopropoxy-benzoic acid (CAS: 845617-27-8) | 442.5 | 443.0 |
| 129 | 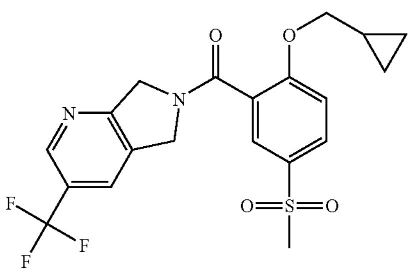 | (2-Cyclopropylmethoxy-5-methanesulfonyl-phenyl)-(3-trifluoromethyl-5,7-dihydro-pyrrolo[3,4-b]pyridin-6-yl)-methanone | 3-Trifluoromethyl-6,7-dihydro-5H-pyrrolo[3,4-b]pyridine (example A16) and 2-Cyclopropylmethoxy-5-methanesulfonyl-benzoic acid (CAS: 845616-03-7) | 440.4 | 441.0 |
| 130 | 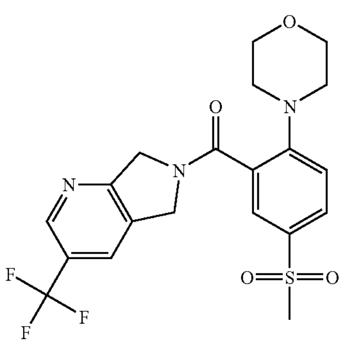 | (5-Methanesulfonyl-2-morpholin-4-yl-phenyl)-(3-trifluoromethyl-5,7-dihydro-pyrrolo[3,4-b]pyridin-6-yl)-methanone | 3-Trifluoromethyl-6,7-dihydro-5H-pyrrolo[3,4-b]pyridine (example A16) and 5-Methanesulfonyl-2-morpholin-4-yl-benzoic acid (example B12) | 455.5 | 456.0 |
| 131 | 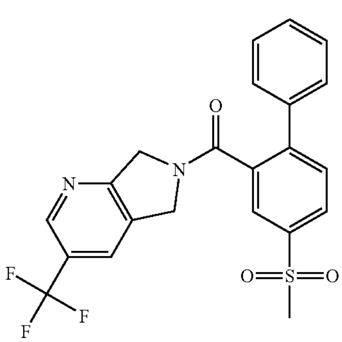 | (4-Methanesulfonyl-biphenyl-2-yl)-(3-trifluoromethyl-5,7-dihydro-pyrrolo[3,4-b]pyridin-6-yl)-methanone | 3-Trifluoromethyl-6,7-dihydro-5H-pyrrolo[3,4-b]pyridine (example A16) and 4-Methanesulfonyl-biphenyl-2-carboxylic acid (example B19) | 446.4 | 446.9 |

-continued

| Expl. No. | Structure | Systematic Name | Starting materials | MW Calc. | MW Found [M + H]+ |
|---|---|---|---|---|---|
| 132 | 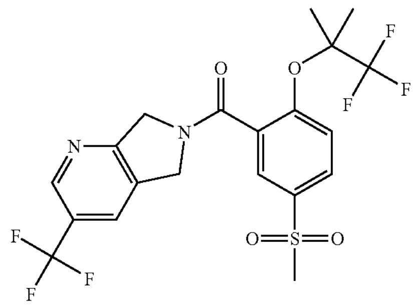 | [5-Methanesulfonyl-2-(2,2,2-trifluoro-1,1-dimethyl-ethoxy)-phenyl]-(3-trifluoromethyl-5,7-dihydro-pyrrolo[3,4-b]pyridin-6-yl)-methanone | 3-Trifluoromethyl-6,7-dihydro-5H-pyrrolo[3,4-b]pyridine (example A16) and 5-Methanesulfonyl-2-(2,2,2-trifluoro-1,1-dimethyl-ethoxy)-benzoic acid (CAS: 845618-01-1) | 496.4 | 497.3 |
| 133 | 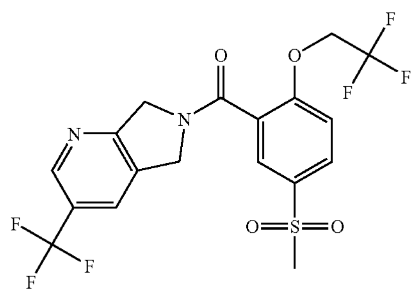 | [5-Methanesulfonyl-2-(2,2,2-trifluoro-ethoxy)-phenyl]-(3-trifluoromethyl-5,7-dihydro-pyrrolo[3,4-b]pyridin-6-yl)-methanone | 3-Trifluoromethyl-6,7-dihydro-5H-pyrrolo[3,4-b]pyridine (example A16) and 5-Methanesulfonyl-2-(2,2,2-trifluoro-ethoxy)-benzoic acid (example B10) | 468.4 | 468.9 |
| 134 | 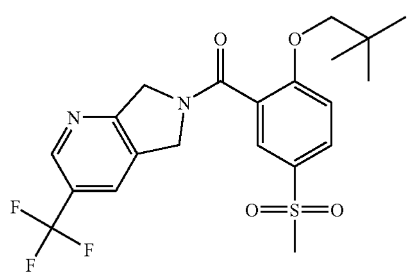 | [2-(2,2-Dimethyl-propoxy)-5-methanesulfonyl-phenyl]-(3-trifluoromethyl-5,7-dihydro-pyrrolo[3,4-#b!]pyridin-6-yl)-methanone | 3-Trifluoromethyl-6,7-dihydro-5H-pyrrolo[3,4-b]pyridine (example A16) and 2-(2,2-Dimethyl-propoxy)-5-methanesulfonyl-benzoic acid (CAS: 845616-85-5) | 456.5 | 473.9 (M + NH4+) |
| 135 | Chiral | [2-((S)-sec-Butoxy)-5-methanesulfonyl-phenyl]-(3-trifluoromethyl-5,7-dihydro-pyrrolo[3,4-b]pyridin-6-yl)-methanone | 3-Trifluoromethyl-6,7-dihydro-5H-pyrrolo[3,4-b]pyridine (example A16) and 2-((S)-sec-Butoxy)-5-methanesulfonyl-benzoic acid (example B23) | 442.4 | 443.3 |

-continued

| Expl. No. | Structure | Systematic Name | Starting materials | MW Calc. | MW Found [M + H]+ |
|---|---|---|---|---|---|
| 136 | Chiral 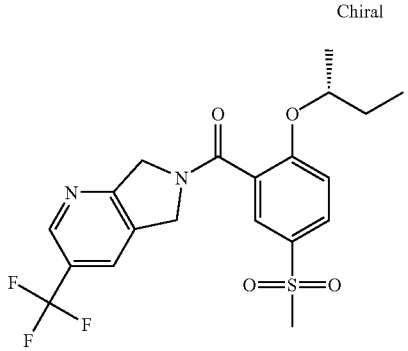 | [2-((R)-sec-Butoxy)-5-methanesulfonyl-phenyl]-(3-trifluoromethyl-5,7-dihydro-pyrrolo[3,4-b]pyridin-6-yl)-methanone | 3-Trifluoromethyl-6,7-dihydro-5H-pyrrolo[3,4-b]pyridine (example A16) and 2-((R)-sec-Butoxy)-5-methanesulfonyl-benzoic acid (example B24) | 442.5 | 443.3 |
| 137 | 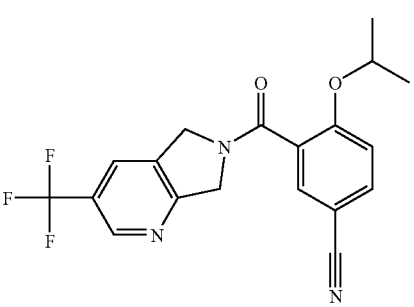 | 4-Isopropoxy-3-(3-trifluoromethyl-5,7-dihydro-pyrrolo[3,4-b]pyridine-6-carbonyl)-benzonitrile | 3-Trifluoromethyl-6,7-dihydro-5H-pyrrolo[3,4-b]pyridine (example A16) and 5-Cyano-2-isopropoxy-benzoic acid (CAS: 845616-14-0) | 375.3 | 375.1 |
| 138 | 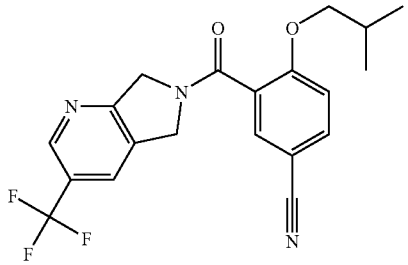 | 4-Isobutoxy-3-(3-trifluoromethyl-5,7-dihydro-pyrrolo[3,4-b]pyridine-6-carbonyl)-benzonitrile | 3-Trifluoromethyl-6,7-dihydro-5H-pyrrolo[3,4-b]pyridine (example A16) and 5-Cyano-2-isobutoxy-benzoic acid (CAS: 845616-16-2) | 389.4 | 390.0 |
| 139 | Chiral 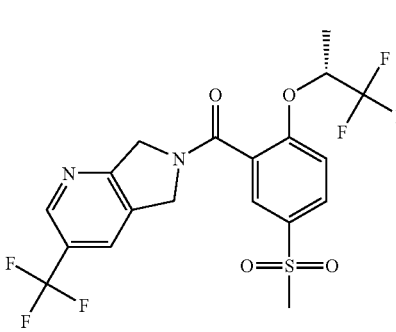 | [5-Methanesulfonyl-2-((R)-2,2,2-trifluoro-1-methyl-ethoxy)-phenyl]-(3-trifluoromethyl-5,7-dihydro-pyrrolo[3,4-b]pyridin-6-yl)-methanone | 3-Trifluoromethyl-6,7-dihydro-5H-pyrrolo[3,4-b]pyridine (example A16) and 5-Methanesulfonyl-2-((R)-2,2,2-trifluoro-1-methyl-ethoxy)-benzoic acid (example B5) | 482.4 | 483.1 |

-continued

| Expl. No. | Structure | Systematic Name | Starting materials | MW Calc. | MW Found [M + H]+ |
|---|---|---|---|---|---|
| 140 | 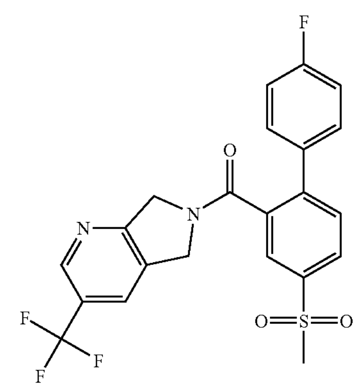 | (4'-Fluoro-4-methanesulfonyl-biphenyl-2-yl)-(3-trifluoromethyl-5,7-dihydro-pyrrolo[3,4-b]pyridin-6-yl)-methanone | 3-Trifluoromethyl-6,7-dihydro-5H-pyrrolo[3,4-b]pyridine (example A16) and 4-Fluoro-4-methanesulfonyl-biphenyl-2-carboxylic acid (example B25) | 464.4 | 482.2 (M + NH4+) |
| 141 | 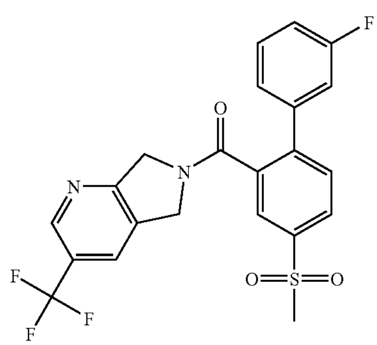 | (3'-Fluoro-4-methanesulfonyl-biphenyl-2-yl)-(3-trifluoromethyl-5,7-dihydro-pyrrolo[3,4-b]pyridin-6-yl)-methanone | 3-Trifluoromethyl-6,7-dihydro-5H-pyrrolo[3,4-b]pyridine (example A16) and 3'-Fluoro-4-methanesulfonyl-biphenyl-2-carboxylic acid (example B26) | 465.4 | 482.2 (M + NH4+) |
| 142 | 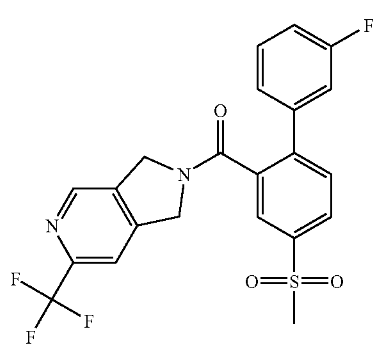 | (3'-Fluoro-4-methanesulfonyl-biphenyl-2-yl)-(6-trifluoromethyl-1,3-dihydro-pyrrolo[3,4-c]pyridin-2-yl)-methanone | 6-Trifluoromethyl-2,3-dihydro-1H-pyrrolo[3,4-c]pyridine (example A13) and 3'-Fluoro-4-methanesulfonyl-biphenyl-2-carboxylic acid (example B26) | 464.4 | 465.0 |
| 143 | 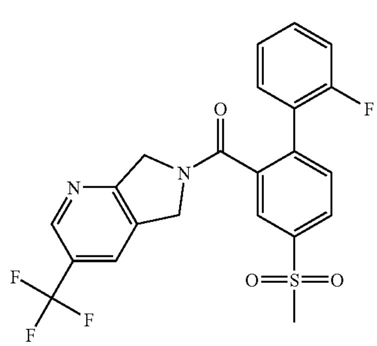 | (2'-Fluoro-4-methanesulfonyl-biphenyl-2-yl)-(3-trifluoromethyl-5,7-dihydro-pyrrolo[3,4-b]pyridin-6-yl)-methanone | 3-Trifluoromethyl-6,7-dihydro-5H-pyrrolo[3,4-b]pyridine (example A16) and 2-Fluoro-4-methanesulfonyl-biphenyl-2-carboxylic acid (example B27) | 464.4 | 465.0 |

-continued

| Expl. No. | Structure | Systematic Name | Starting materials | MW Calc. | MW Found [M + H]+ |
|---|---|---|---|---|---|
| 144 | 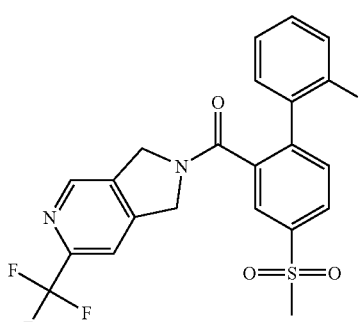 | (2'-Fluoro-4-methanesulfonyl-biphenyl-2-yl)-(6-trifluoromethyl-1,3-dihydro-pyrrolo[3,4-c]pyridin-2-yl)-methanone | 6-Trifluoromethyl-2,3-dihydro-1H-pyrrolo[3,4-c]pyridine (example A13) and 2-Fluoro-4-methanesulfonyl-biphenyl-2-carboxylic acid (example B27) | 464.4 | 465.0 |
| 145 | 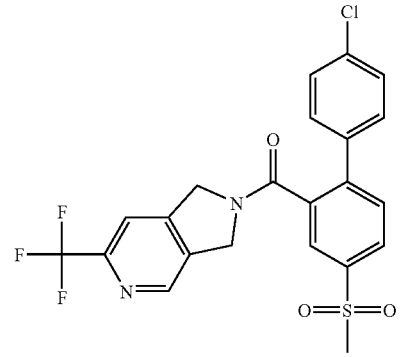 | (4'-Chloro-4-methanesulfonyl-biphenyl-2-yl)-(6-trifluoromethyl-1,3-dihydro-pyrrolo[3,4-c]pyridin-2-yl)-methanone | 6-Trifluoromethyl-2,3-dihydro-1H-pyrrolo[3,4-c]pyridine (example A13) and 4'-Chloro-4-methanesulfonyl-biphenyl-2-carboxylic acid (example B28) | 480.9 | 481.2 |
| 146 | 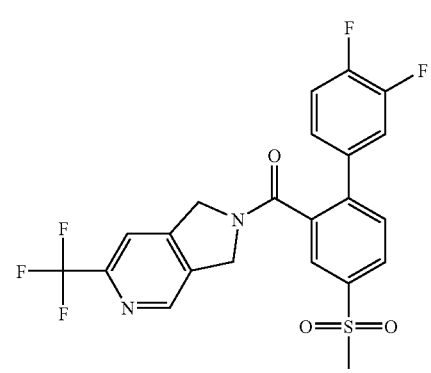 | (3,4'-Difluoro-4-methanesulfonyl-biphenyl-2-yl)-(6-trifluoromethyl-1,3-dihydro-pyrrolo[3,4-c]pyridin-2-yl)-methanone | 6-Trifluoromethyl-2,3-dihydro-1H-pyrrolo[3,4-c]pyridine (example A13) and 3',4'-Difluoro-4-methanesulfonyl-biphenyl-2-carboxylic acid (example B29) | 482.4 | 483.4 |
| 147 | 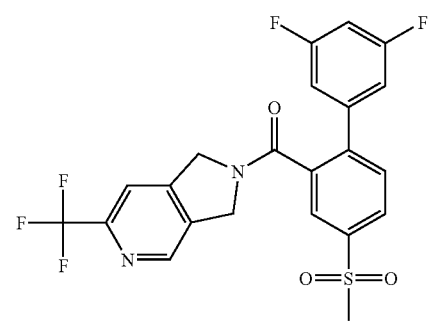 | (3',5'-Difluoro-4-methanesulfonyl-biphenyl-2-yl)-(6-trifluoromethyl-1,3-dihydro-pyrrolo[3,4-c]pyridin-2-yl)-methanone | 6-Trifluoromethyl-2,3-dihydro-1H-pyrrolo[3,4-c]pyridine (example A13) and 3',5'-Difluoro-4-methanesulfonyl-biphenyl-2-carboxylic acid (example B30) | 482.4 | 483.4 |

-continued

| Expl. No. | Structure | Systematic Name | Starting materials | MW Calc. | MW Found [M + H]+ |
|---|---|---|---|---|---|
| 148 | 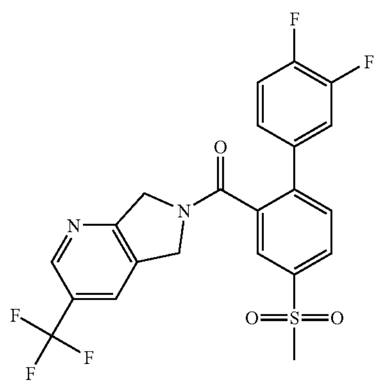 | (3',4'-Difluoro-4-methanesulfonyl-biphenyl-2-yl)-(3-trifluoromethyl-5,7-dihydro-pyrrolo[3,4-b]pyridin-6-yl)-methanone | 3-Trifluoromethyl-6,7-dihydro-5H-pyrrolo[3,4-b]pyridine (example A16) and 3',4'-Difluoro-4-methanesulfonyl-biphenyl-2-carboxylic acid (example B29) | 482.4 | 483.0 |
| 149 | 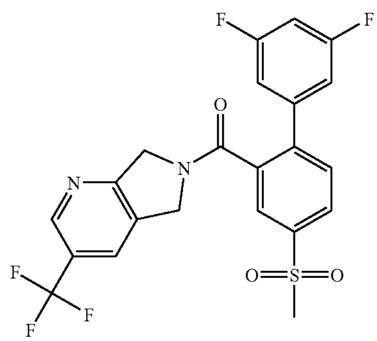 | (3',5'-Difluoro-4-methanesulfonyl-biphenyl-2-yl)-(3-trifluoromethyl-5,7-dihydro-pyrrolo[3,4-#b!]pyridin-6-yl)-methanone | 3-Trifluoromethyl-6,7-dihydro-5H-pyrrolo[3,4-b]pyridine (example A16) and 3',5'-Difluoro-4-methanesulfonyl-biphenyl-2-carboxylic acid (example B30) | 482.4 | 483.0 |
| 150 | 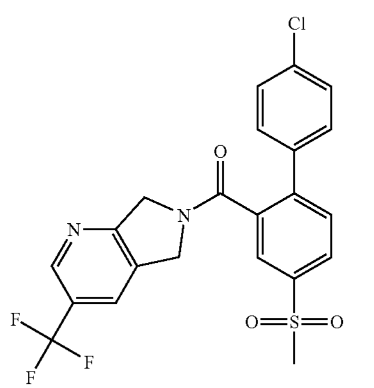 | (4'-Chloro-4-methanesulfonyl-biphenyl-2-yl)-(3-trifluoromethyl-5,7-dihydro-pyrrolo[3,4-#b!]pyridin-6-yl)-methanone | 3-Trifluoromethyl-6,7-dihydro-5H-pyrrolo[3,4-b]pyridine (example A16) and 4'-Chloro-4-methanesulfonyl-biphenyl-2-carboxylic acid (example B28) | 480.9 | 480.9 |
| 151 | 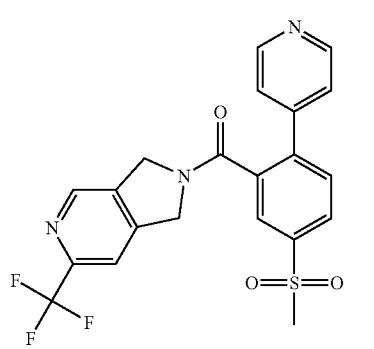 | (5-Methanesulfonyl-2-pyridin-4-yl-phenyl)-(6-trifluoromethyl-1,3-dihydro-pyrrolo[3,4-#c!]pyridin-2-yl)-methanone | 6-Trifluoromethyl-2,3-dihydro-1H-pyrrolo[3,4-b]pyridine (example A13) and 5-Methanesulfonyl-2-pyridin-4-yl-benzoic acid (example B31) | 447.4 | 448.0 |

| Expl. No. | Structure | Systematic Name | Starting materials | MW Calc. | MW Found [M + H]+ |
|---|---|---|---|---|---|
| 152 | 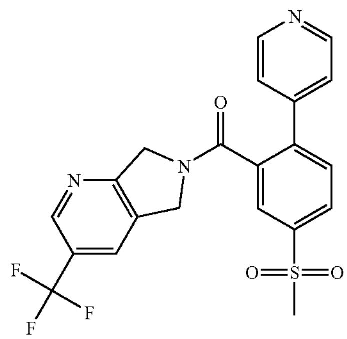 | (5-Methanesulfonyl-2-pyridin-4-yl-phenyl)-(3-trifluoromethyl-5,7-dihydro-pyrrolo[3,4-#b!]pyridin-6-yl)-methanone | 3-Trifluoromethyl-6,7-dihydro-5H-pyrrolo[3,4-b]pyridine (example A16) and 5-Methanesulfonyl-2-pyridin-4-yl-benzoic acid (example B31) | 447.4 | 448.0 |
| 153 | 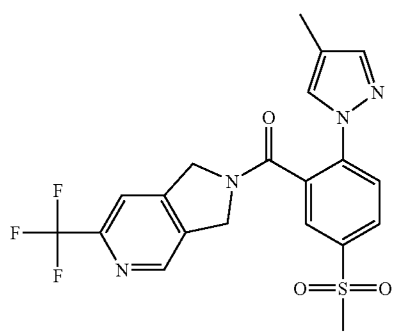 | [5-Methanesulfonyl-2-(4-methyl-pyrazol-1-yl)-phenyl]-(6-trifluoromethyl-1,3-dihydro-pyrrolo[3,4-c]pyridin-2-yl)-methanone | 6-Trifluoromethyl-2,3-dihydro-1H-pyrrolo[3,4-c]pyridine (example A13) and 5-Methanesulfonyl-2-(4-methyl-pyrazol-1-yl)-benzoic acid (example B32) | 450.4 | 451.0 |
| 154 | 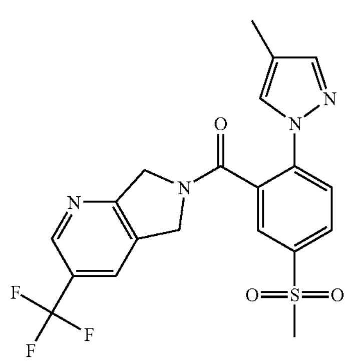 | [5-Methanesulfonyl-2-(4-methyl-pyrazol-1-yl)-phenyl]-(3-trifluoromethyl-5,7-dihydro-pyrrolo[3,4-b]pyridin-6-yl)-methanone | 3-Trifluoromethyl-6,7-dihydro-5H-pyrrolo[3,4-b]pyridine (example A16) and 5-Methanesulfonyl-2-(4-methyl-pyrazol-1-yl)-benzoic acid (example B32) | 450.4 | 451.0 |
| 155 | 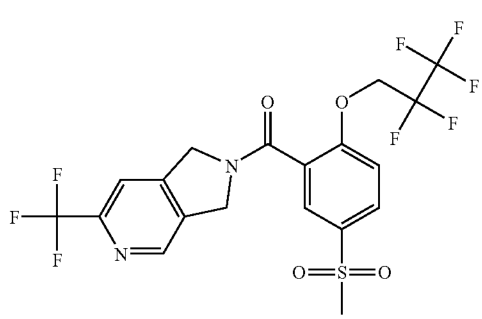 | [5-Methanesulfonyl-2-(2,2,3,3,3-pentafluoro-propoxy)-phenyl]-(6-trifluoromethyl-1,3-dihydro-pyrrolo[3,4-c]pyridin-2-yl)-methanone | 6-Trifluoromethyl-2,3-dihydro-1H-pyrrolo[3,4-c]pyridine (example A13) and 5-Methanesulfonyl-2-(2,2,3,3,3-pentafluoro-propoxy)-benzoic acid (CAS: 845616-42-4) | 518.4 | 519.2 |

-continued

| Expl. No. | Structure | Systematic Name | Starting materials | MW Calc. | MW Found [M + H]+ |
|---|---|---|---|---|---|
| 156 | 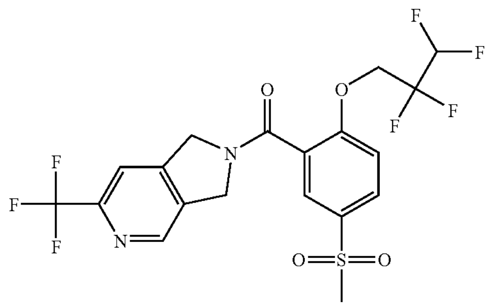 | [5-Methanesulfonyl-2-(2,2,3,3-tetrafluoro-propoxy)-phenyl]-(6-trifluoromethyl-1,3-dihydro-pyrrolo[3,4-c]pyridin-2-yl)-methanone | 6-Trifluoromethyl-2,3-dihydro-1H-pyrrolo[3,4-c]pyridine (example A13) and 5-Methanesulfonyl-2-(2,2,3,3-tetrafluoro-propoxy)-benzoic acid (CAS: 845616-52-6) | 500.4 | 501.2 |
| 157 | 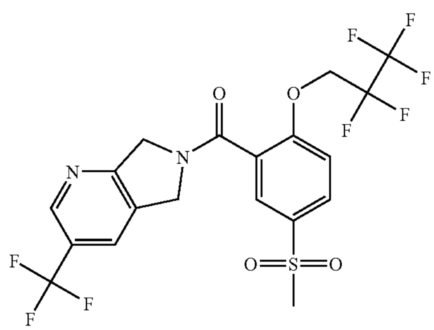 | [5-Methanesulfonyl-2-(2,2,3,3,3-pentafluoro-propoxy)-phenyl]-(3-trifluoromethyl-5,7-dihydro-pyrrolo[3,4-b]pyridin-6-yl)-methanone | 3-Trifluoromethyl-6,7-dihydro-5H-pyrrolo[3,4-b]pyridine (example A16) and 5-Methanesulfonyl-2-(2,2,3,3,3-pentafluoro-propoxy)-benzoic acid (CAS: 845616-42-4) | 518.4 | 519.0 |
| 158 | 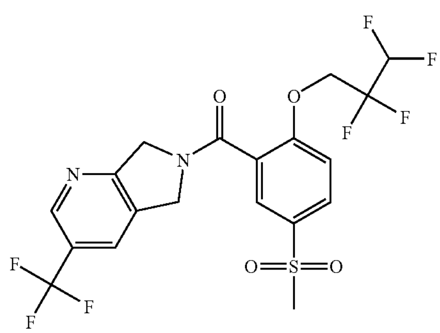 | [5-Methanesulfonyl-2-(2,2,3,3-tetrafluoro-propoxy)-phenyl]-(3-trifluoromethyl-5,7-dihydro-pyrrolo[3,4-b]pyridin-6-yl)-methanone | 3-Trifluoromethyl-6,7-dihydro-5H-pyrrolo[3,4-b]pyridine (example A16) and 5-Methanesulfonyl-2-(2,2,3,3-tetrafluoro-propoxy)-benzoic acid (CAS: 845616-52-6) | 500.4 | 501.0 |
| 159 | 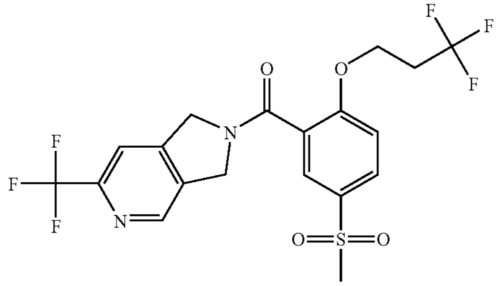 | [5-Methanesulfonyl-2-(3,3,3-trifluoro-propoxy)-phenyl]-(6-trifluoromethyl-1,3-dihydro-pyrrolo[3,4-#c!]pyridin-2-yl)-methanone | 6-Trifluoromethyl-2,3-dihydro-1H-pyrrolo[3,4-c]pyridine (example A13) and 5-Methanesulfonyl-2-(3,3,3-trifluoro-propoxy)-benzoic acid (CAS: 845616-30-0) | 482.4 | 483.0 |

-continued

| Expl. No. | Structure | Systematic Name | Starting materials | MW Calc. | MW Found [M + H]+ |
|---|---|---|---|---|---|
| 160 | 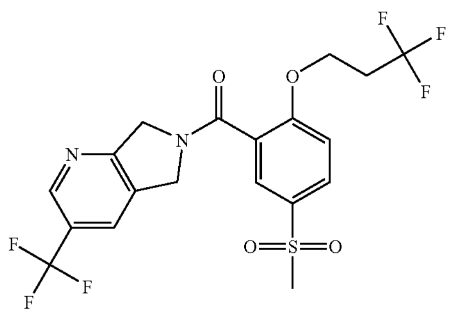 | [5-Methanesulfonyl-2-(3,3,3-trifluoro-propoxy)-phenyl]-(3-trifluoromethyl-5,7-dihydro-pyrrolo[3,4-#b!]pyridin-6-yl)-methanone | 3-Trifluoromethyl-6,7-dihydro-5H-pyrrolo[3,4-b]pyridine (example A16) and 5-Methanesulfonyl-2-(3,3,3-trifluoro-propoxy)-benzoic acid (CAS: 845616-30-0) | 482.4 | 483.0 |
| 161 | 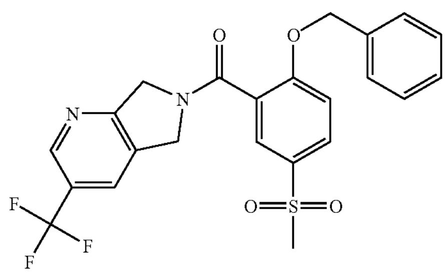 | (2-Benzyloxy-5-methanesulfonyl-phenyl)-(3-trifluoromethyl-5,7-dihydro-pyrrolo[3,4-b]pyridin-6-yl)-methanone | 3-Trifluoromethyl-6,7-dihydro-5H-pyrrolo[3,4-b]pyridine (example A16) and 2-Benzyloxy-5-methanesulfonyl-benzoic acid (CAS: 845618-06-6) | 476.5 | 477.0 |
| 162 | Chiral | (5-Difluoromethoxy-1,3-dihydro-isoindol-2-yl)-[5-methanesulfonyl-2-((S)-2,2,2-trifluoro-1-methyl-ethoxy)-phenyl]-methanone | 5-difluoromethoxy-2,3-dihydro-1H-isoindoline Trifluoro-acetic acid (example A19) and 5-Methanesulfonyl-2-((S)-2,2,2-trifluoro-1-methyl-ethoxy)-benzoic acid (example B3) | 479.4 | 479.9 |
| 163 | Chiral | [5-Methanesulfonyl-2-((S)-2,2,2-trifluoro-1-methyl-ethoxy)-phenyl]-trifluoromethyl-5,7-dihydro-pyrrolo[3,4-b]pyridin-6-yl)-methanone | 2-Methyl-3-trifluoromethyl-6,7-dihydro-5H-pyrrolo[3,4-b]pyridine (example A20) and 5-Methanesulfonyl-2-((S)-2,2,2-trifluoro-1-methyl-ethoxy)-benzoic acid (example B3) | 496.4 | 497.0 |

-continued

| Ex-pl. No. | Structure | Systematic Name | Starting materials | MW Calc. | MW Found [M + H]+ |
|---|---|---|---|---|---|
| 164 | 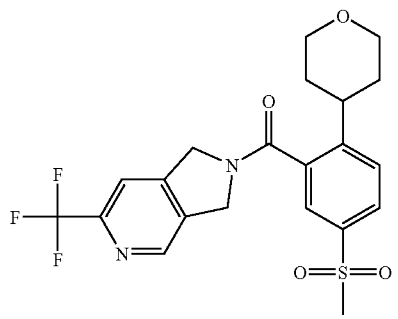 | [5-Methanesulfonyl-2-(tetrahydro-pyran-4-yl)-phenyl]-(6-trifluoromethyl-1,3-dihydro-pyrrolo[3,4-c]pyridin-2-yl)-methanone | 6-Trifluoromethyl-2,3-dihydro-1H-pyrrolo[3,4-c]pyridine (example A13) and 5-Methanesulfonyl-2-(tetrahydro-pyran-4-yl)-benzoic acid (example B33) | 454.5 | 455.1 |
| 165 | 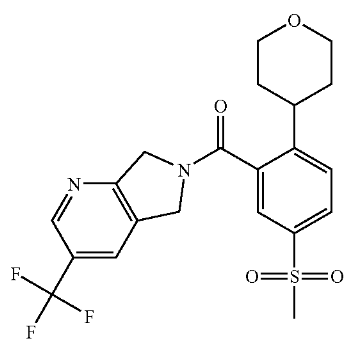 | [5-Methanesulfonyl-2-(tetrahydro-pyran-4-yl)-phenyl]-(3-trifluoromethyl-5,7-dihydro-pyrrolo[3,4-b]pyridin-6-yl)-methanone | 3-Trifluoromethyl-6,7-dihydro-5H-pyrrolo[3,4-b]pyridine (example A16) and 5-Methanesulfonyl-2-(tetrahydro-pyran-4-yl)-benzoic acid (example B33) | 454.5 | 455.0 |
| 166 | 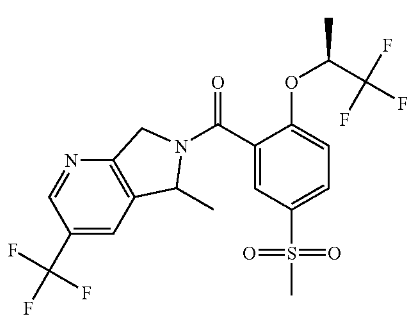 | [5-Methanesulfonyl-2-((S)-2,2,2-trifluoro-1-methyl-ethoxy)-phenyl]-(5-methyl-3-trifluoromethyl-5,7-dihydro-pyrrolo[3,4-b]pyridin-6-yl)-methanone | rac-5-Methyl-3-trifluoromethyl-6,7-dihydro-5H-pyrrolo[3,4-b]pyridine (example A21) and 5-Methanesulfonyl-2-((S)-2,2,2-trifluoro-1-methyl-ethoxy)-benzoic acid (example B3) | 496.4 | 497.1 |
| 167 | Chiral | (6-Chloro-1,3-dihydro-pyrrolo[3,4-c]pyridin-2-yl)-[5-methanesulfonyl-2-((S)-2,2,2-trifluoro-1-methyl-ethoxy)-phenyl]-methanone | 6-Chloro-2,3-dihydro-1H-pyrrolo[3,4-c]pyridine (example A22) and 5-Methanesulfonyl-2-((S)-2,2,2-trifluoro-1-methyl-ethoxy)-benzoic acid (example B3) | 448.8 | 449.2 |

-continued

| Expl. No. | Structure | Systematic Name | Starting materials | MW Calc. | MW Found [M + H]+ |
|---|---|---|---|---|---|
| 168 | Chiral | [5-Methanesulfonyl-2-((S)-2,2,2-trifluoro-1-methyl-ethoxy)-phenyl]-[5-(4-methyl-thiazol-2-yl)-1,3-dihydro-isoindol-2-yl]-methanone | 5-(4-Methyl-thiazol-2-yl)-2,3-dihydro-1H-isoindole (example A23) and 5-Methanesulfonyl-2-((S)-2,2,2-trifluoro-1-methyl-ethoxy)-benzoic acid (example B3) | 510.5 | 511.1 |
| 169 | Chiral | [5-Methanesulfonyl-2-((S)-2,2,2-trifluoro-1-methyl-ethoxy)-phenyl]-[5-(2-methyl-pyridin-4-yl)-1,3-dihydro-isoindol-2-yl]-methanone | 5-(2-Methyl-pyridin-4-yl)-2,3-dihydro-1H-isoindole (example A24) and 5-Methanesulfonyl-2-((S)-2,2,2-trifluoro-1-methyl-ethoxy)-benzoic acid (example B3) | 504.5 | 501.1 |
| 170 | Chiral | [5-Methanesulfonyl-2-((S)-2,2,2-trifluoro-1-methyl-ethoxy)-phenyl]-[5-(5-methyl-thiophen-3-yl)-1,3-dihydro-isoindol-2-yl]-methanone | 5-(5-Methyl-thiophen-3-yl)-2,3-dihydro-1H-isoindole (example A25) and 5-Methanesulfonyl-2-((S)-2,2,2-trifluoro-1-methyl-ethoxy)-benzoic acid (example B3) | 509.6 | 510.4 |
| 171 | Chiral | [5-Methanesulfonyl-2-((S)-2,2,2-trifluoro-1-methyl-ethoxy)-phenyl]-[5-(5-methyl-thiazol-2-yl)-1,3-dihydro-isoindol-2-yl]-methanone | 5-(5-Methyl-thiazol-2-yl)-2,3-dihydro-1H-isoindole (example A26) and 5-Methanesulfonyl-2-((S)-2,2,2-trifluoro-1-methyl-ethoxy)-benzoic acid (example B3) | 510.6 | 511.2 |

-continued

| Expl. No. | Structure | Systematic Name | Starting materials | MW Calc. | MW Found [M + H]+ |
|---|---|---|---|---|---|
| 172 | Chiral | [5-Methanesulfonyl-2-((S)-2,2,2-trifluoro-1-methyl-ethoxy)-phenyl]-(5-thiazol-2-yl-1,3-dihydro-isoindol-2-yl)-methanone | 5-Thiazol-2-yl-2,3-dihydro-1H-isoindole (example A27) and 5-Methanesulfonyl-2-((S)-2,2,2-trifluoro-1-methyl-ethoxy)-benzoic acid (example B3) | 496.5 | 496.9 |
| 173 | Chiral | [5-Methanesulfonyl-2-((S)-2,2,2-trifluoro-1-methyl-ethoxy)-phenyl]-(2-trifluoromethyl-5,7-dihydro-pyrrolo[3,4-d]pyrimidin-6-yl)-methanone | 2-Trifluoromethyl-6,7-dihydro-5H-pyrrolo[3,4-d]pyrimidine (example A28) and 5-Methanesulfonyl-2-((S)-2,2,2-trifluoro-1-methyl-ethoxy)-benzoic acid (example B3) | 483.4 | 484.5 |
| 174 | 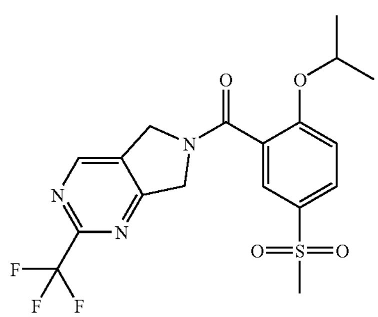 | (2-Isopropoxy-5-methanesulfonyl-phenyl)-(2-trifluoromethyl-5,7-dihydro-pyrrolo[3,4-d]pyrimidin-6-yl)-methanone | 2-Trifluoromethyl-6,7-dihydro-5H-pyrrolo[3,4-d]pyrimidine (example A28) and 2-Isopropoxy-5-methanesulfonyl-benzoic acid (example B1) | 429.4 | 428.1 |
| 175 | 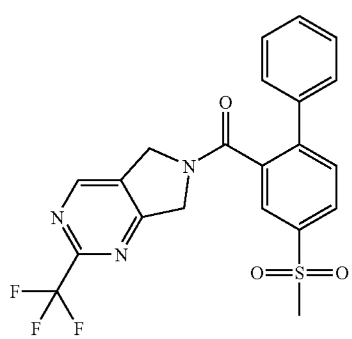 | (4-Methanesulfonyl-biphenyl-2-yl)-(2-trifluoromethyl-5,7-dihydro-pyrrolo[3,4-d]pyrimidin-6-yl)-methanone | 2-Trifluoromethyl-6,7-dihydro-5H-pyrrolo[3,4-d]pyrimidine (example A28) and 4-Methanesulfonyl-biphenyl-2-carboxylic acid (example B19) | 447.4 | 448.3 |

| Expl. No. | Structure | Systematic Name | Starting materials | MW Calc. | MW Found [M + H]+ |
|---|---|---|---|---|---|
| 176 | 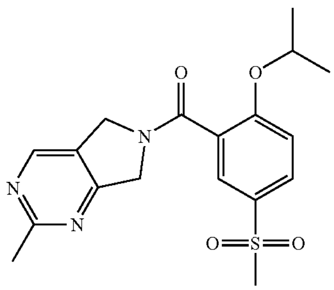 | (2-Isopropoxy-5-methanesulfonyl-phenyl)-(2-methyl-5,7-dihydro-pyrrolo[3,4-d]pyrimidin-6-yl)-methanone | 2-Methyl-6,7-dihydro-5H-pyrrolo[3,4-d]pyrimidine (CAS: 424819-90-9) and 2-Isopropoxy-5-methanesulfonyl-benzoic acid (example B1) | 375.4 | 376.0 |
| 177 | Chiral | [5-Methanesulfonyl-2-((S)-2,2,2-trifluoro-1-methyl-ethoxy)-phenyl]-(2-methyl-5,7-dihydro-pyrrolo[3,4-d]pyrimidin-6-yl)-methanone | 2-Methyl-6,7-dihydro-5H-pyrrolo[3,4-d]pyrimidine (CAS: 424819-90-9) and 5-Methanesulfonyl-2-((S)-2,2,2-trifluoro-1-methyl-ethoxy)-benzoic acid (example B3) | 429.4 | 430.5 |
| 178 | Chiral | [5-Methanesulfonyl-2-((S)-2,2,2-trifluoro-1-methyl-ethoxy)-phenyl]-(6-trifluoromethyl-2,3-dihydro-indol-1-yl)-methanone | 6-Trifluoromethyl-2,3-dihydro-1H-indole (CAS: 181513-29-1) and 5-Methanesulfonyl-2-((S)-2,2,2-trifluoro-1-methyl-ethoxy)-benzoic acid (example B3) | 481.4 | 482.5 |
| 179 | 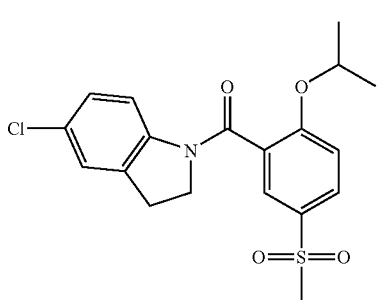 | (5-Chloro-2,3-dihydro-indol-1-yl)-(2-isopropoxy-5-methanesulfonyl-phenyl)-methanone | 5-Chloro-2,3-dihydro-1H-indole (CAS: 25658-80-4) and 2-Isopropoxy-5-methanesulfonyl-benzoic acid (example B1) | 393.9 | 394.0 |

-continued

| Expl. No. | Structure | Systematic Name | Starting materials | MW Calc. | MW Found [M + H]+ |
|---|---|---|---|---|---|
| 180 | Chiral | (5-Chloro-2,3-dihydro-indol-1-yl)-[5-methanesulfonyl-2-((S)-2,2,2-trifluoro-1-methyl-ethoxy)-phenyl]-methanone | 5-Chloro-2,3-dihydro-1H-indole (CAS: 25658-80-4) and 5-Methanesulfonyl-2-((S)-2,2,2-trifluoro-1-methyl-ethoxy)-benzoic acid (example B3) | 447.9 | 448.1 |
| 181 | 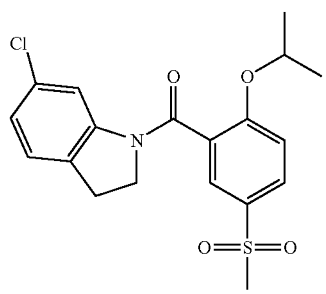 | (6-Chloro-2,3-dihydro-indol-1-yl)-(2-isopropoxy-5-methanesulfonyl-phenyl)-methanone | 6-Chloro-2,3-dihydro-1H-indole (CAS: 52537-00-5) and 2-Isopropoxy-5-methanesulfonyl-benzoic acid (example B1) | 393.9 | 394.1 |
| 182 | Chiral | (6-Chloro-2,3-dihydro-indol-1-yl)-[5-2,2,2-trifluoro-1-methyl-ethoxy)-phenyl]-methanone | 6-Chloro-2,3-dihydro-1H-indole (CAS: 52537-00-5) and 5-Methanesulfonyl-2-((S)-2,2,2-trifluoro-1-methyl-ethoxy)-benzoic acid (example B3) | 447.9 | 448.1 |
| 183 | 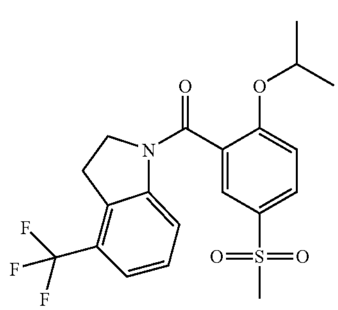 | (2-Isopropoxy-5-methanesulfonyl-phenyl)-(4-trifluoromethyl-2,3-dihydro-indol-1-yl)-methanone | 4-Trifluoromethyl-2,3-dihydro-1H-indole (example A29) and 2-Isopropoxy-5-methanesulfonyl-benzoic acid (example B1) | 427.4 | 428.1 |

-continued

| Expl. No. | Structure | Systematic Name | Starting materials | MW Calc. | MW Found [M + H]+ |
|---|---|---|---|---|---|
| 184 | Chiral 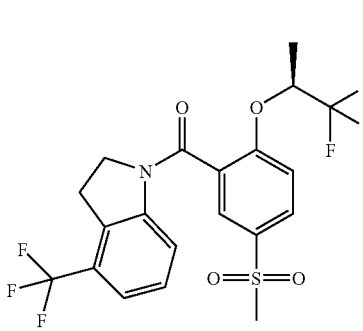 | [5-Methanesulfonyl-2-((S)-2,2,2-trifluoro-1-methyl-ethoxy)-phenyl]-(4-trifluoromethyl-2,3-dihydro-indol-1-yl)-methanone | 4-Trifluoromethyl-2,3-dihydro-1H-indole (example A29) and 5-Methanesulfonyl-2-((S)-2,2,2-trifluoro-1-methyl-ethoxy)-benzoic acid (example B3) | 481.4 | 482.0 |
| 185 | 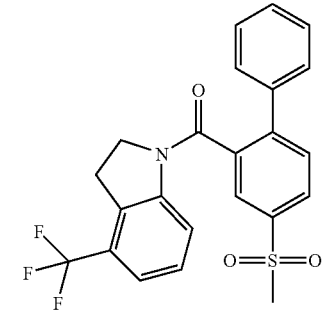 | (4-Methanesulfonyl-biphenyl-2-yl)-(4-trifluoromethyl-2,3-dihydro-indol-1-yl)-methanone | 4-Trifluoromethyl-2,3-dihydro-1H-indole (example A29) and 4-Methanesulfonyl-biphenyl-2-carboxylic acid (example B19) | 445.4 | 446.0 |
| 186 | Chiral 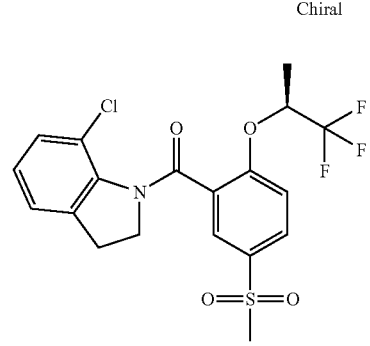 | (7-Chloro-2,3-dihydro-indol-1-yl)-[5-methanesulfonyl-2-((S)-2,2,2-trifluoro-1-methyl-ethoxy)-phenyl]-methanone | 7-Chloro-2,3-dihydro-1H-indole (CAS: 114144-22-8) and 5-Methanesulfonyl-2-((S)-2,2,2-trifluoro-1-methyl-ethoxy)-benzoic acid (example B3) | 447.9 | 448.3 |
| 187 | 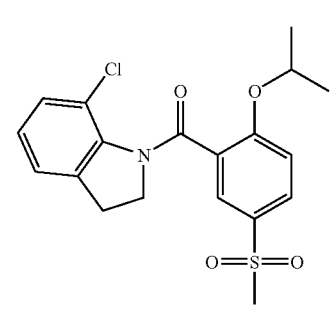 | (7-Chloro-2,3-dihydro-indol-1-yl)-(2-isopropoxy-5-methanesulfonyl-phenyl)-methanone | 7-Chloro-2,3-dihydro-1H-indole (CAS: 114144-22-8) and 2-Isopropoxy-5-methanesulfonyl-benzoic acid (example B1) | 393.9 | 393.9 |

-continued

| Expl. No. | Structure | Systematic Name | Starting materials | MW Calc. | MW Found [M + H]+ |
|---|---|---|---|---|---|
| 188 | 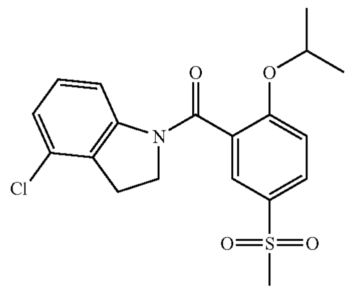 | (4-Chloro-2,3-dihydro-indol-1-yl)-(2-isopropoxy-5-methanesulfonyl-phenyl)-methanone | 4-Chloro-2,3-dihydro-1H-indole (CAS: 41910-64-9) and 2-Isopropoxy-5-methanesulfonyl-benzoic acid (example B1) | 393.9 | 394.9 |
| 189 | Chiral | (4-Chloro-2,3-dihydro-indol-1-yl)-[5-methanesulfonyl-2-((S)-2,2,2-trifluoro-1-methyl-ethoxy)-phenyl]-methanone | 4-Chloro-2,3-dihydro-1H-indole (CAS: 41910-64-9) and 5-Methanesulfonyl-2-((S)-2,2,2-trifluoro-1-methyl-ethoxy)-benzoic acid (example B3) | 447.9 | 448.9 |
| 190 | Chiral | [5-Methanesulfonyl-2-((S)-2,2,2-trifluoro-1-methyl-ethoxy)-phenyl]-(4-methoxy-2,3-dihydro-indol-1-yl)-methanone | 4-Methoxy-2,3-dihydro-1H-indole (CAS: 7555-94-4) and 5-Methanesulfonyl-2-((S)-2,2,2-trifluoro-1-methyl-ethoxy)-benzoic acid (example B3) | 443.4 | 444.1 |
| 191 | 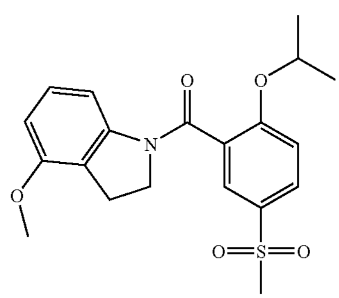 | (2-Isopropoxy-5-methanesulfonyl-phenyl)-(4-methoxy-2,3-dihydro-indol-1-yl)-methanone | 4-Methoxy-2,3-dihydro-1H-indole (CAS: 7555-94-4) and 2-Isopropoxy-5-methanesulfonyl-benzoic acid (example B1) | 389.5 | 390.2 |

-continued

| Expl. No. | Structure | Systematic Name | Starting materials | MW Calc. | MW Found [M + H]+ |
|---|---|---|---|---|---|
| 192 | Chiral | [5-Methanesulfonyl-2-((S)-2,2,2-trifluoro-1-methyl-ethoxy)-phenyl]-(5-methoxy-2,3-dihydro-indol-1-yl)-methanone | 5-Methoxy-2,3-dihydro-1H-indole (CAS: 21857-45-4) and 5-Methanesulfonyl-2-((S)-2,2,2-trifluoro-1-methyl-ethoxy)-benzoic acid (example B3) | 443.4 | 444.1 |
| 193 | 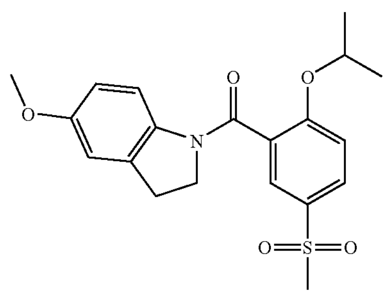 | (2-Isopropoxy-5-methanesulfonyl-phenyl)-(5-methoxy-2,3-dihydro-indol-1-yl)-methanone | 5-Methoxy-2,3-dihydro-1H-indole (CAS: 21857-45-4) and 2-Isopropoxy-5-methanesulfonyl-benzoic acid (example B1) | 389.5 | 390.1 |
| 194 | Chiral | (6-Chloro-1,2,3,4,4a,9a-hexahydro-carbazol-9-yl)-[5-methanesulfonyl-2-((S)-2,2,2-trifluoro-1-methyl-ethoxy)-phenyl]-methanone | rac-6-Chloro-2,3,4,4a,9,9a-hexahydro-1H-carbazole (CAS: 216856-80-3) and 5-Methanesulfonyl-2-((S)-2,2,2-trifluoro-1-methyl-ethoxy)-benzoic acid (example B3) | 502.0 | 502.1 |
| 195 | 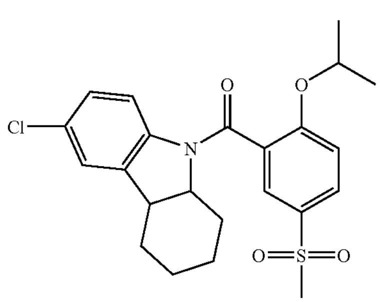 | (6-Chloro-1,2,3,4,4a,9a-hexahydro-carbazol-9-yl)-(2-isopropoxy-5-methanesulfonyl-phenyl)-methanone | rac-6-Chloro-2,3,4,4a,9,9a-hexahydro-1H-carbazole (CAS: 216856-80-3) and 2-Isopropoxy-5-methanesulfonyl-benzoic acid (example B1) | 448.0 | 448.3 |

| Expl. No. | Structure | Systematic Name | Starting materials | MW Calc. | MW Found [M + H]+ |
|---|---|---|---|---|---|
| 196 | 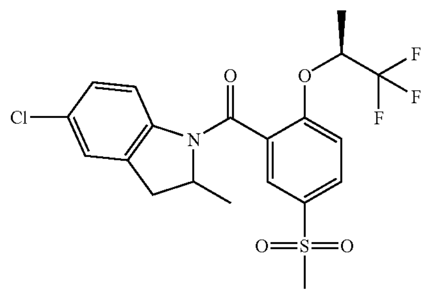 | (5-Chloro-2-methyl-2,3-dihydro-indol-1-yl)-[5-methanesulfonyl-2-((S)-2,2,2-trifluoro-1-methyl-ethoxy)-phenyl]-methanone | rac-5-Chloro-2-methyl-2,3-dihydro-1H-indole (CAS:68579-13-5) and 5-Methanesulfonyl-2-((S)-2,2,2-trifluoro-1-methyl-ethoxy)-benzoic acid (example B3) | 461.9 | 462.0 |
| 197 | 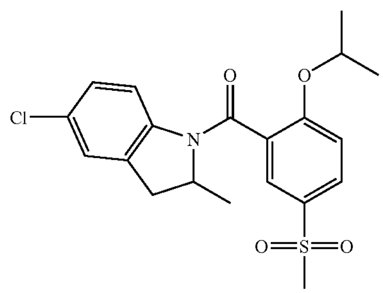 | (5-Chloro-2-methyl-2,3-dihydro-indol-1-yl)-(2-isopropoxy-5-methanesulfonyl-phenyl)-methanone | rac-5-Chloro-2-methyl-2,3-dihydro-1H-indole (CAS:68579-13-5) and 2-Isopropoxy-5-methanesulfonyl-benzoic acid (example B1) | 407.9 | 465.8 M + CH3CO |
| 198 | 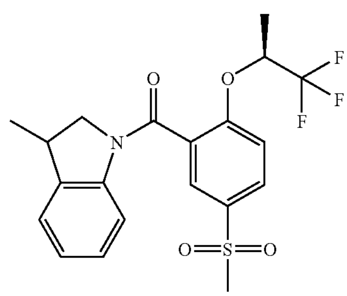 | [5-Methanesulfonyl-2-((S)-2,2,2-trifluoro-1-methyl-ethoxy)-phenyl]-(3-methyl-2,3-dihydro-indol-1-yl)-methanone | rac-3-Methyl-2,3-dihydro-1H-indole (CAS: 4375-15-9) and 5-Methanesulfonyl-2-((S)-2,2,2-trifluoro-1-methyl-ethoxy)-benzoic acid (example B3) | 427.4 | 428.0 |
| 199 | 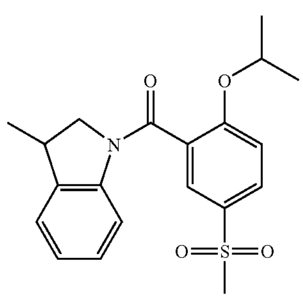 | (2-Isopropoxy-5-methanesulfonyl-phenyl)-(3-methyl-2,3-dihydro-indol-1-yl)-methanone | rac-3-Methyl-2,3-dihydro-1H-indole (CAS: 4375-15-9) and 2-Isopropoxy-5-methanesulfonyl-benzoic acid (example B1) | 373.5 | 374.4 |
| 200 | 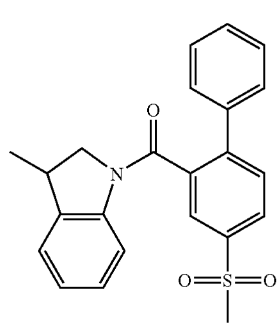 | (4-Methanesulfonyl-biphenyl-2-yl)-(3-methyl-2,3-dihydro-indol-1-yl)-methanone | rac-3-Methyl-2,3-dihydro-1H-indole (CAS: 4375-15-9) and 4-Methanesulfonyl-biphenyl-2-carboxylic acid (example B19) | 391.5 | 392.3 |

-continued

| Expl. No. | Structure | Systematic Name | Starting materials | MW Calc. | MW Found [M + H]+ |
|---|---|---|---|---|---|
| 201 | 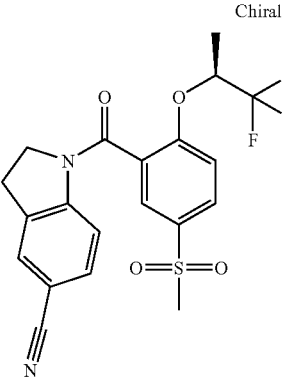 Chiral | [5-Methanesulfonyl-2-((S)-2,2,2-trifluoro-1-methyl-ethoxy)-benzoyl]-2,3-dihydro-1H-indole-5-carbonitrile | 2,3-Dihydro-1H-indole-5-carbonitrile (CAS: 15861-23-1) and 5-Methanesulfonyl-2-((S)-2,2,2-trifluoro-1-methyl-ethoxy)-benzoic acid (example B3) | 438.4 | 497.3 |
| 202 | 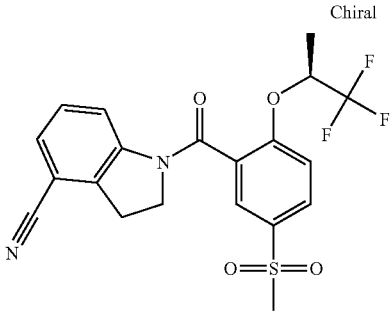 Chiral | 1-[5-Methanesulfonyl-2-((S)-2,2,2-trifluoro-1-methyl-ethoxy)-benzoyl]-2,3-dihydro-1H-indole-4-carbonitrile | 2,3-Dihydro-1H-indole-4-carbonitrile (example A30) and 5-Methanesulfonyl-2-((S)-2,2,2-trifluoro-1-methyl-ethoxy)-benzoic acid (example B3) | 438.4 | 439.1 |
| 203 | 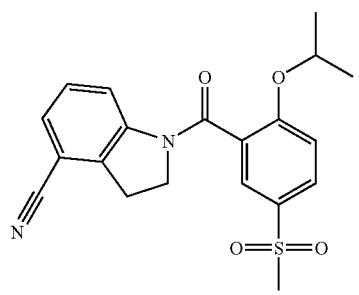 | 1-(2-Isopropoxy-5-methanesulfonyl-benzoyl)-2,3-dihydro-1H-indole-4-carbonitrile | 2,3-Dihydro-1H-indole 4-carbonitrile (example A30) and 2-Isopropoxy-5-methanesulfonyl-benzoic acid (example B1) | 384.5 | 385.3 |
| 204 | 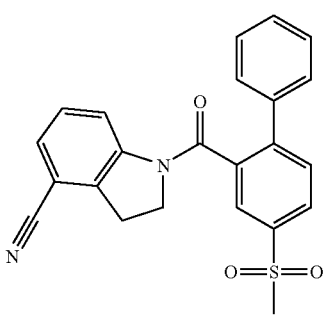 | 1-(4-Methanesulfonyl-biphenyl-2-carbonyl)-2,3-dihydro-1H-indole-4-carbonitnie | 2,3-Dihydro-1H-indole-4-carbonitrile (example A30) and 4-Methanesulfonyl-biphenyl-2-carboxyhc acid (example B19) | 402.5 | 403.3 |

-continued

| Expl. No. | Structure | Systematic Name | Starting materials | MW Calc. | MW Found [M + H]+ |
|---|---|---|---|---|---|
| 205 | Chiral | 1-[5-Methanesulfonyl-2-((S)-2,2,2-trifluoro-1-methyl-ethoxy)-benzoyl]-2,3-dihydro-1H-indole-4-carboxylic acid methyl ester | 2,3-Dihydro-1H-indole-4-carboxylic acid methyl ester (CAS: 155135-61-8) and 5-Methanesulfonyl-2-((S)-2,2,2-trifluoro-1-methyl-ethoxy)-benzoic acid (example B3) | 471.5 | 472.1 |
| 206 | 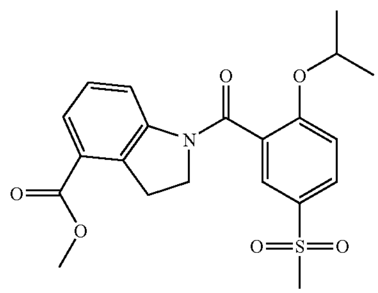 | 1-(2-Isopropoxy-5-methanesulfonyl-benzoyl)-2,3-dihydro-1#H!-indole-4-carboxylic acid methyl ester | 2,3-Dihydro-1H-indole-4-carboxylic acid methyl ester (CAS: 155135-61-8) and 2-Isopropoxy-5-methanesulfonyl-benzoic acid (example B1) | 417.5 | 418.2 |
| 207 | 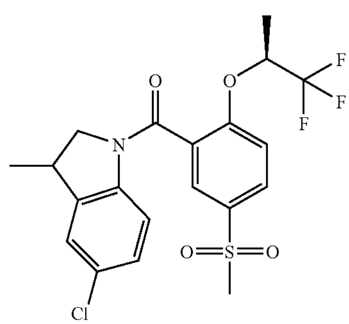 | (5-Chloro-3-methyl-2,3-dihydro-indol-1-yl)-[5-methanesulfonyl-2-((S)-2,2,2-trifluoro-1-methyl-ethoxy)-phenyl]-methanone | rac-5-Chloro-3-methyl-2,3-dihydro-1H-indole (example A31) and 5-Methanesulfonyl-2-((S)-2,2,2-trifluoro-1-methyl-ethoxy)-benzoic acid (example B3) | 461.9 | 462.2 |
| 208 | Chiral | [5-Methanesulfonyl-2-((S)-2,2,2-trifluoro-1-methyl-ethoxy)-phenyl]-(4-methyl-2,3-dihydro-indol-1-yl)-methanone | 4-Methyl-2,3-dihydro-1H-indole (CAS:62108-16-1) and 5-Methanesulfonyl-2-((S)-2,2,2-trifluoro-1-methyl-ethoxy)-benzoic acid (example B3) | 427.4 | 428.0 |

| Expl. No. | Structure | Systematic Name | Starting materials | MW Calc. | MW Found [M + H]+ |
|---|---|---|---|---|---|
| 209 | Chiral 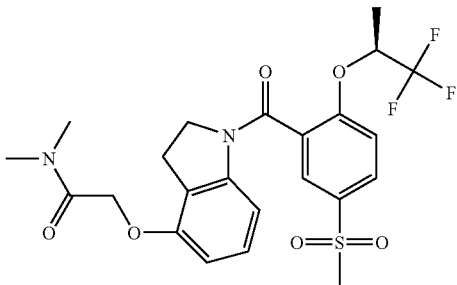 | 2-{1-[5-Methanesulfonyl-2-((S)-2,2,2-trifluoro-1-methyl-ethoxy)-benzoyl]-2,3-dihydro-1H-indol-4-yloxy}-N,N-dimethyl-acetamide | 2-(2,3-Dihydro-1H-indol-4-yloxy)-N,N-dimethyl-acetamide (example A32) and 5-Methanesulfonyl-2-((S)-2,2,2-trifluoro-1-methyl-ethoxy)-benzoic acid (example B3) | 514.5 | 515.3 |
| 210 | 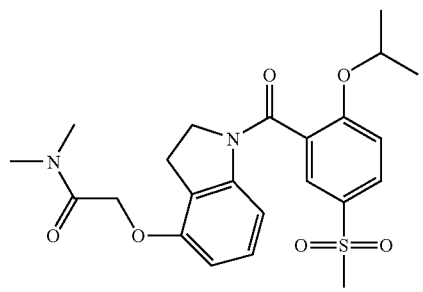 | 2-[1-(2-Isopropoxy-5-methanesulfonyl-benzoyl)-2,3-dihydro-1H-indol-4-yloxy]-N,N-dimethyl-acetamide acid | 2-(2,3-Dihydro-1H-indol-4-yloxy)-N,N-dimethyl-acetamide (example A32) and 2-Isopropoxy-5-methanesulfonyl-benzoic (example B1) | 460.5 | 461.4 |
| 211 | Chiral 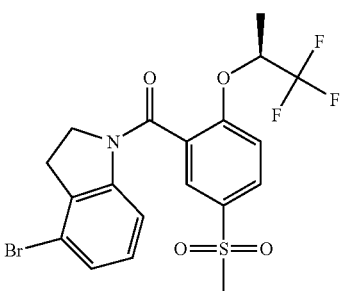 | (4-Bromo-2,3-dihydro-indol-1-yl)-[5-methanesulfonyl-2-((S)-2,2,2-trifluoro-1-methyl-ethoxy)-phenyl]-methanone | 4-Bromo-2,3-dihydro-1H-indole (CAS: 86626-38-2) and 5-Methanesulfonyl-2-((S)-2,2,2-trifluoro-1-methyl-ethoxy)-benzoic acid (example B3) | 492.3 | 494.0 |
| 212 | 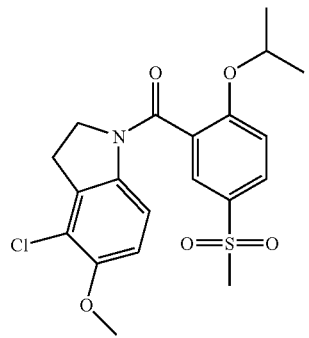 | (4-Chloro-5-methoxy-2,3-dihydro-indol-1-yl)-(2-isopropoxy-5-methanesulfonyl-phenyl)-methanone | 4-Chloro-5-methoxy-2,3-dihydro-1H-indole (example A33) and 2-Isopropoxy-5-methanesulfonyl-benzoic acid (example B1) | 423.9 | 424.1 |

-continued

| Expl. No. | Structure | Systematic Name | Starting materials | MW Calc. | MW Found [M + H]+ |
|---|---|---|---|---|---|
| 213 | Chiral | (4-Chloro-5-methoxy-2,3-dihydro-indol-1-yl)-[5-methanesulfonyl-2-((S)-2,2,2-trifluoro-1-methyl-ethoxy)-phenyl]-methanone | 4-Chloro-5-methoxy-2,3-dihydro-1H-indole (example A33) and 5-Methanesulfonyl-2-((S)-2,2,2-trifluoro-1-methyl-ethoxy)-benzoic acid (example B3) | 477.9 | 478.0 |
| 214 | Chiral | (4-Hydroxymethyl-2,3-dihydro-indol-1-yl)-[5-methanesulfonyl-2-((S)-2,2,2-trifluoro-1-methyl-ethoxy)-phenyl]-methanone | (2,3-Dihydro-1H-indol-4-yl)-methanol (example A34) and 5-Methanesulfonyl-2-((S)-2,2,2-trifluoro-1-methyl-ethoxy)-benzoic acid (example B3) | 443.4 | 444.1 |
| 215 | 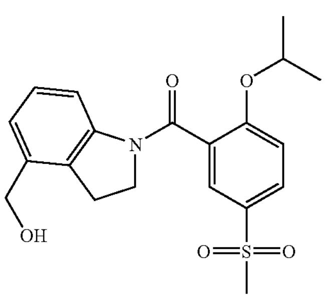 | (4-Hydroxymethyl-2,3-dihydro-indol-1-yl)-(2-isopropoxy-5-methanesulfonyl-phenyl)-methanone | (2,3-Dihydro-1H-indol-4-yl)-methanol (example A34) and 2-Isopropoxy-5-methanesulfonyl-benzoic acid (example B1) | 389.5 | 390.2 |
| 216 | 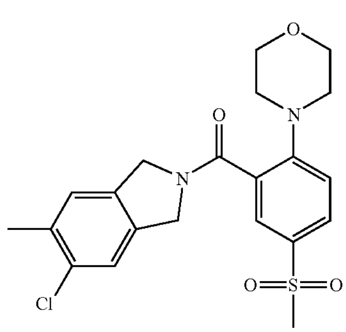 | (5-Chloro-6-methyl-1,3-dihydro-isoindol-2-yl)-(5-methanesulfonyl-2-morpholin-4-yl-phenyl)-methanone | 5-Chloro-6-methyl-2,3-dihydro-1H-isoindole hydrochloride (example A4) and 5-Methanesulfonyl-2-morpholin-4-yl-benzoic acid (example B12) | 434.9 | 437.1 ($^{37}$Cl) 435.2 ($^{35}$Cl) |

-continued

| Expl. No. | Structure | Systematic Name | Starting materials | MW Calc. | MW Found [M + H]+ |
|---|---|---|---|---|---|
| 217 | Chiral | (5-Ethylsulfanyl-6-trifluoromethyl-1,3-dihydro-isoindol-2-yl)-[5-methanesulfonyl-2-((S)-2,2,2-trifluoro-1-methyl-ethoxy)-phenyl]-methanone | 5-Ethylsulfanyl-6-trifluoromethyl-2,3-dihydro-1H-isoindole hydrochloride (example A35) and 5-Methanesulfonyl-2-((S)-2,2,2-trifluoro-1-methyl-ethoxy)-benzoic acid (example B3) | 541.5 | 542.2 |
| 218 | Chiral | (5-Chloro-6-methoxy-1,3-dihydro-isoindol-2-yl)-[5-methanesulfonyl-2-((R)-2,2,2-trifluoro-1-methyl-ethoxy)-phenyl]-methanone | 5-Chloro-6-methoxy-2,3-dihydro-1H-isoindole hydrochloride (example A6) and 5-Methanesulfonyl-2-((R)-2,2,2-trifluoro-1-methyl-ethoxy)-benzoic acid (example B5) | 477.9 | 479.9 ($^{37}$Cl) 477.9 ($^{35}$Cl) |
| 219 | 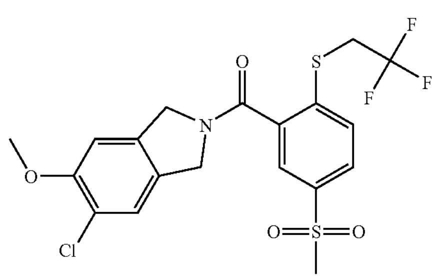 | (5-Chloro-6-methoxy-1,3-dihydro-isoindol-2-yl)-[5-methanesulfonyl-2-(2,2,2-trifluoro-ethylsulfanyl)-phenyl]-methanone | 5-Chloro-6-methoxy-2,3-dihydro-1H-isoindole hydrochloride (example A6) and 5-Methanesulfonyl-2-(2,2,2-trifluoro-ethylsulfanyl)-benzoic acid (example B7) | 480.0 | 481.9 ($^{37}$Cl) 479.8 ($^{35}$Cl) |
| 220 | 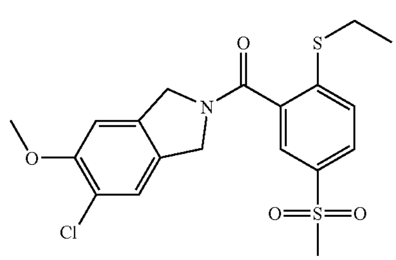 | (5-Chloro-6-methoxy-1,3-dihydro-isoindol-2-yl)-(2-ethylsulfanyl-5-methanesulfonyl-phenyl)-methanone | 5-Chloro-6-methoxy-2,3-dihydro-1H-isoindole hydrochloride (example A6) and 2-Ethylsulfanyl-5-methanesulfonyl-benzoic acid (example B6) | 426.0 | 427.9 ($^{37}$Cl) 425.8 ($^{35}$Cl) |
| 221 | 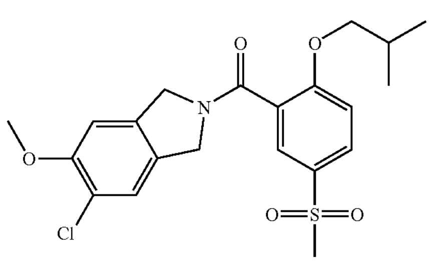 | (5-Chloro-6-methoxy-1,3-dihydro-isoindol-2-yl)-(2-isobutoxy-5-methanesulfonyl-phenyl)-methanone | 5-Chloro-6-methoxy-2,3-dihydro-1H-isoindole hydrochloride (example A6) and 2-Isobutoxy-5-methanesulfonyl-benzoic acid (example B11) | 437.9 | 440.1 ($^{37}$Cl) 438.0 ($^{35}$Cl) |

| Expl. No. | Structure | Systematic Name | Starting materials | MW Calc. | MW Found [M + H]+ |
|---|---|---|---|---|---|
| 222 | 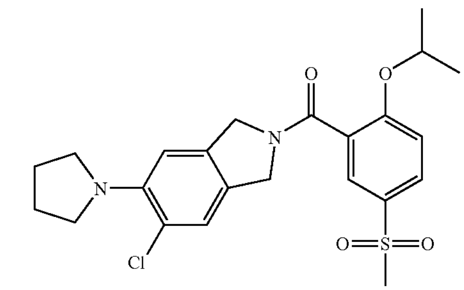 | (5-Chloro-6-pyrrolidin-1-yl-1,3-dihydro-isoindol-2-yl)-(2-isopropoxy-5-methanesulfonyl-phenyl)-methanone | 5-Chloro-6-pyrrolidin-1-yl-2,3-dihydro-1H-isoindole-hydrochloride (example A3) and 2-Isopropoxy-5-methanesulfonyl-benzoic acid (example B1) | 463.0 | 465.1 ($^{37}$Cl) 463.1 ($^{35}$Cl) |
| 223 | 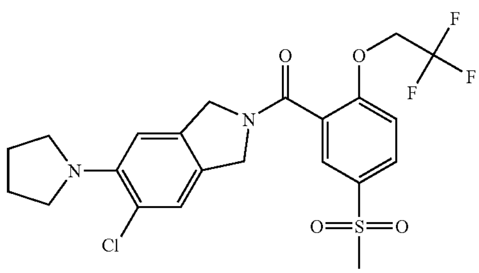 | (5-Chloro-6-pyrrolidin-1-yl-1,3-dihydro-isoindol-2-yl)-[5-methanesulfonyl-2-(2,2,2-trifluoro-ethoxy)-phenyl]-methanone | 5-Chloro-6-pyrrolidin-1-yl-2,3-dihydro-1H-isoindole-hydrochloride (example A3) and 5-Methanesulfonyl-2-(2,2,2-trifluoro-ethoxy)-benzoic acid (example B10) | 502.9 | 505.2 ($^{37}$Cl) 503.2 ($^{35}$Cl) |
| 224 | Chiral | (5-Fluoro-6-trifluoromethyl-1,3-dihydro-isoindol-2-yl)-[5-methanesulfonyl-2-((S)-2,2,2-trifluoro-1-methyl-ethoxy)-phenyl]-methanone | 5-Fluoro-6-trifluoromethyl-2,3-dihydro-1H-isoindole trifluoroacetate (example A36) and 5-Methanesulfonyl-2-((S)-2,2,2-trifluoro-1-methyl-ethoxy)-benzoic acid (example B3) | 499.4 | 500.0 |
| 225 | Chiral | (5-Chloro-6-piperidin-1-yl-1,3-dihydro-isoindol-2-yl)-[5-methanesulfonyl-2-((S)-2,2,2-trifluoro-1-methyl-ethoxy)-phenyl]-methanone | 5-Chloro-6-piperidin-1-yl-2,3-dihydro-1H-isoindole hydrochloride (example A37) and 5-Methanesulfonyl-2-((S)-2,2,2-trifluoro-1-methyl-ethoxy)-benzoic acid (example B3) | 531.0 | 533.2 ($^{37}$Cl) 531.2 ($^{35}$Cl) |

| Expl. No. | Structure | Systematic Name | Starting materials | MW Calc. | MW Found [M + H]+ |
|---|---|---|---|---|---|
| 226 | 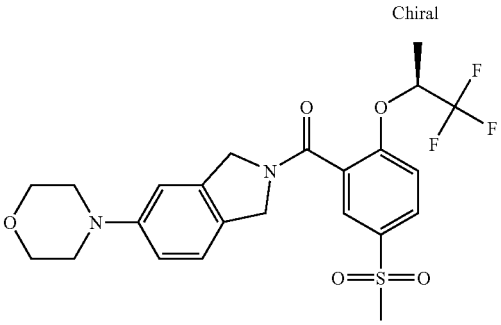 Chiral | [5-Methanesulfonyl-2-((S)-2,2,2-trifluoro-1-methyl-ethoxy)-phenyl]-(5-morpholin-4-yl-1,3-dihydro-isoindol-2-yl)-methanone | 5-Morpholin-4-yl-2,3-dihydro-1H-isoindole hydrochloride (CAS: 850876-30-1) and 5-Methanesulfonyl-2-((S)-2,2,2-trifluoro-1-methyl-ethoxy)-benzoic acid (example B3) | 498.5 | 499.3 |
| 227 | 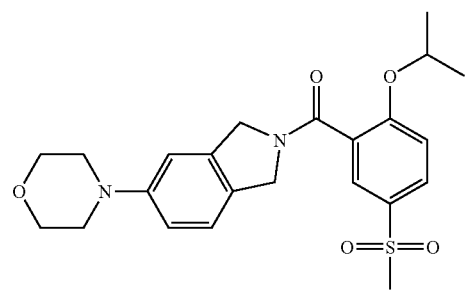 | (2-Isopropoxy-5-methanesulfonyl-phenyl)-(5-morpholin-4-yl-1,3-dihydro-isoindol-2-yl)-methanone | 5-Morpholin-4-yl-2,3-dihydro-1H-isoindole hydrochloride (CAS: 850876-30-1) and 2-Isopropoxy-5-methanesulfonyl-benzoic acid (example B1) | 444.5 | 445.2 |
| 228 | 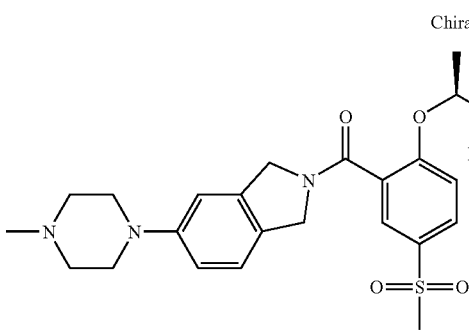 Chiral | [5-Methanesulfonyl-2-((S)-2,2,2-trifluoro-1-methyl-ethoxy)-phenyl]-[5-(4-methyl-piperazin-1-yl)-1,3-dihydro-isoindol-2-yl]-methanone | 5-(4-Methyl-piperazin-1-yl)-2,3-dihydro-1H-isoindole dihydrochloride (CAS: 850877-57-5) and 5-Methanesulfonyl-2-((S)-2,2,2-trifluoro-1-methyl-ethoxy)-benzoic acid (example B3) | 511.6 | 512.5 |
| 229 | 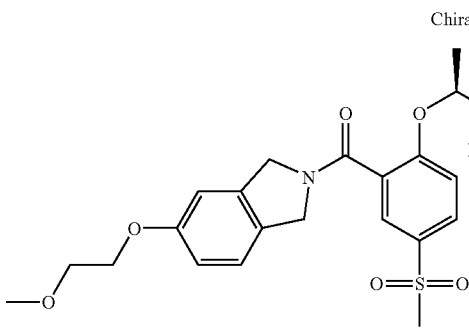 Chiral | [5-Methanesulfonyl-2-((S)-2,2,2-trifluoro-1-methyl-ethoxy)-phenyl]-[5-(2-methoxy-ethoxy)-1,3-dihydro-isoindol-2-yl]-methanone | 5-(2-Methoxy-ethoxy)-2,3-dihydro-1H-isoindole hydrochloride (example A38) and 5-Methanesulfonyl-2-((S)-2,2,2-trifluoro-1-methyl-ethoxy)-benzoic acid (example B3) | 487.5 | 488.3 |

-continued

| Expl. No. | Structure | Systematic Name | Starting materials | MW Calc. | MW Found [M + H]+ |
|---|---|---|---|---|---|
| 230 | 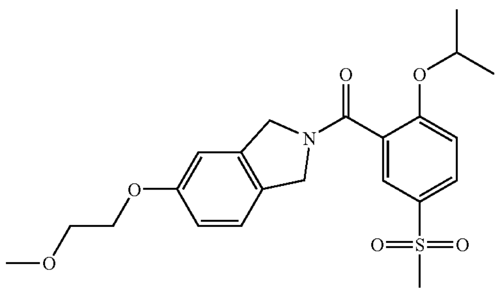 | (2-Isopropoxy-5-methanesulfonyl-phenyl)-[5-(2-methoxy-ethoxy)-1,3-dihydro-isoindol-2-yl]-methanone | 5-(2-Methoxy-ethoxy)-2,3-dihydro-1H-isoindole hydrochloride (example A38) and 2-Isopropoxy-5-methanesulfonyl-benzoic acid (example methanone B1) | 433.5 | 434.2 |
| 231 | 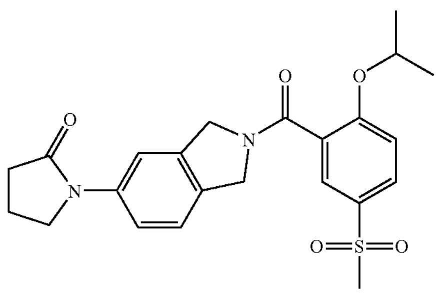 | 1-[2-(2-Isopropoxy-5-methanesulfonyl-benzoyl)-2,3-dihydro-1#H!-isoindol-5-yl]-pyrrolidin-2-one | 1-(2,3-Dihydro-1H-isoindol-5-yl)-pyrrolidin-2-one hydrochloride (example A39) and 2-Isopropoxy-5-methanesulfonyl-benzoic acid (example B1) | 442.5 | 443.3 |
| 232 | Chiral | 1-{2-[5-Methanesulfonyl-2-((S)-2,2,2-trifluoro-1-methyl-ethoxy)-benzoyl]-2,3-dihydro-1#H!-isoindol-5-yl}-pyrrolidin-2-one | 1-(2,3-Dihydro-1H-isoindol-5-yl)-pyrrolidin-2-one hydrochloride (example A39) and 5-Methanesulfonyl-2-((S)-2,2,2-trifluoro-1-methyl-ethoxy)-benzoic acid (example B3) | 496.5 | 497.3 |
| 233 | Chiral | (5-Isopropoxy-1,3-dihydro-isoindol-2-yl)-[5-methanesulfonyl-2-((S)-2,2,2-trifluoro-1-methyl-ethoxy)-phenyl]-methanone | 5-Isopropoxy-2,3-dihydro-1H-isoindole hydrochloride (example A40) and 5-Methanesulfonyl-2-((S)-2,2,2-trifluoro-1-methyl-ethoxy)-benzoic acid (example B3) | 471.5 | 472.2 |

-continued

| Expl. No. | Structure | Systematic Name | Starting materials | MW Calc. | MW Found [M + H]+ |
|---|---|---|---|---|---|
| 234 | 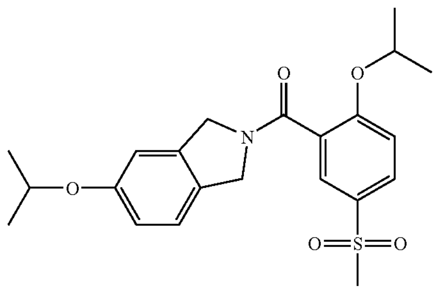 | (5-Isopropoxy-1,3-dihydro-isoindol-2-yl)-(2-isopropoxy-5-methanesulfonyl-phenyl)-methanone | 5-Isopropoxy-2,3-dihydro-1H-isoindole hydrochloride (example A40) and 2-Isopropoxy-5-methanesulfonyl-benzoic acid (example B1) | 417.5 | 418.3 |
| 235 | 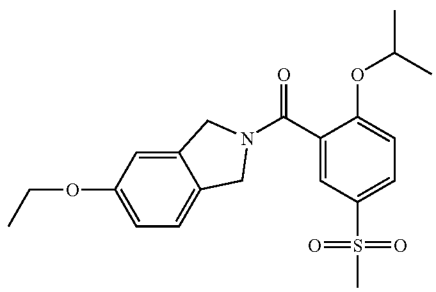 | (5-Ethoxy-1,3-dihydro-isoindol-2-yl)-(2-isopropoxy-5-methanesulfonyl-phenyl)-methanone | 5-Ethoxy-2,3-dihydro-1H-isoindole hydrochloride (example A41) and 2-Isopropoxy-5-methanesulfonyl-benzoic acid (example B1) | 403.5 | 404.3 |
| 236 | Chiral | (5-Ethoxy-1,3-dihydro-isoindol-2-yl)-[5-methanesulfonyl-2-((S)-2,2,2-trifluoro-1-methyl-ethoxy)-phenyl]-methanone | 5-Ethoxy-2,3-dihydro-1H-isoindole hydrochloride (example A41) and 5-Methanesulfonyl-2-((S)-2,2,2-trifluoro-1-methyl-ethoxy)-benzoic acid (example B3) | 457.5 | 458.3 |
| 237 | Chiral | [5-(4,4-Difluoro-piperidin-1-yl)-1,3-dihydro-isoindol-2-yl]-[5-methanesulfonyl-2-((S)-2,2,2-trifluoro-1-methyl-ethoxy)-phenyl]-methanone | 5-(4,4-Difluoro-piperidin-1-yl)-2,3-dihydro-1H-isoindole hydrochloride (example A42) and 5-Methanesulfonyl-2-((S)-2,2,2-trifluoro-1-methyl-ethoxy)-benzoic acid (example B3) | 532.5 | 533.2 |

| Expl. No. | Structure | Systematic Name | Starting materials | MW Calc. | MW Found [M + H]+ |
|---|---|---|---|---|---|
| 238 | 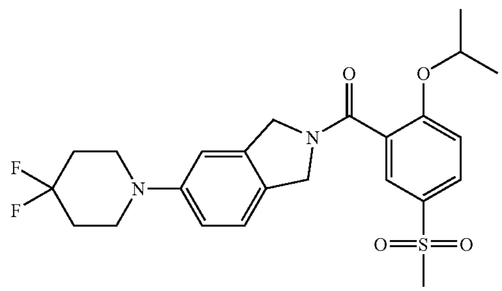 | [5-(4,4-Difluoro-piperidin-1-yl)-1,3-dihydro-isoindol-2-yl]-(2-isopropoxy-5-methanesulfonyl-phenyl)-methanone | 5-(4,4-Difluoro-piperidin-1-yl)-2,3-dihydro-1H-isoindole hydrochloride (example A42) and 2-Isopropoxy-5-methanesulfonyl-benzoic acid (example B1) | 478.6 | 479.3 |
| 239 | Chiral | (5-Ethoxy-6-trifluoromethyl-1,3-dihydro-isoindol-2-yl)-[5-methanesulfonyl-2-((S)-2,2,2-trifluoro-1-methyl-ethoxy)-phenyl]-methanone | 5-Ethoxy-6-trifluoromethyl-2,3-dihydro-1H-isoindole hydrochloride (example A43) and 5-Methanesulfonyl-2-((S)-2,2,2-trifluoro-1-methyl-ethoxy)-benzoic acid (example B3) | 525.5 | 526.3 |
| 240 | 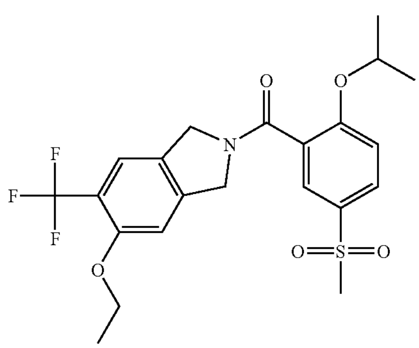 | (5-Ethoxy-6-trifluoromethyl-1,3-dihydro-isoindol-2-yl)-(2-isopropoxy-5-methanesulfonyl-phenyl)-methanone | 5-Ethoxy-6-trifluoromethyl-2,3-dihydro-1H-isoindole hydrochloride (example A43) and 2-Isopropoxy-5-methanesulfonyl-benzoic acid (example B1) | 471.5 | 472.2 |
| 241 | Chiral | (5-Chloro-6-morpholin-4-yl-1,3-dihydro-isoindol-2-yl)-[5-methanesulfonyl-2-((S)-2,2,2-trifluoro-1-methyl-ethoxy)-phenyl]-methanone | 5-Chloro-6-morpholin-4-yl-2,3-dihydro-1H-isoindole hydrochloride (example A44) and 5-Methanesulfonyl-2-((S)-2,2,2-trifluoro-1-methyl-ethoxy)-benzoic acid (example B3) | 533.0 | 535.0 ($^{37}$Cl) 532.8 ($^{35}$Cl) |

| Expl. No. | Structure | Systematic Name | Starting materials | MW Calc. | MW Found [M + H]+ |
|---|---|---|---|---|---|
| 242 | 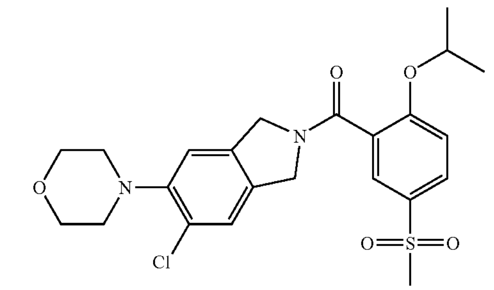 | (5-Chloro-6-morpholin-4-yl-1,3-dihydro-isoindol-2-yl)-(2-isopropoxy-5-methanesulfonyl-phenyl)-methanone | 5-Chloro-6-morpholin-4-yl-2,3-dihydro-1H-isoindole hydrochloride (example A44) and 2-Isopropoxy-5-methanesulfonyl-benzoic acid (example B1) | 479.0 | 481.2 ($^{37}$Cl) 479.3 ($^{35}$Cl) |
| 243 | 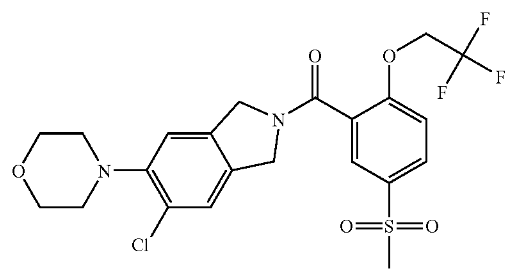 | (5-Chloro-6-morpholin-4-yl-1,3-dihydro-isoindol-2-yl)-(5-methanesulfonyl-2-(2,2,2-trifluoro-ethoxy)-phenyl]-methanone | 5-Chloro-6-morpholin-4-yl-2,3-dihydro-1H-isoindole hydrochloride (example A44) and 5-Methanesulfonyl-2-(2,2,2-trifluoro-ethoxy)-benzoic acid (example B10) | 518.9 | 521.3 ($^{37}$Cl) 519.2 ($^{35}$Cl) |
| 244 | Chiral | (5-Chloro-6-morpholin-4-yl-1,3-dihydro-isoindol-2-yl)-[5-methanesulfonyl-2-((R)-2,2,2-trifluoro-1-methyl-ethoxy)-phenyl]-methanone | 5-Chloro-6-morpholin-4-yl-2,3-dihydro-1H-isoindole hydrochloride (example A44) and 5-Methanesulfonyl-2-((R)-2,2,2-trifluoro-1-methyl-ethoxy)-benzoic acid (example B5) | 533.0 | 535.3 ($^{37}$Cl) 533.2 ($^{35}$Cl) |
| 245 | 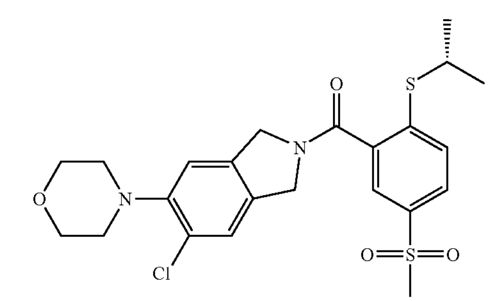 | (5-Chloro-6-morpholin-4-yl-1,3-dihydro-isoindol-2-yl)-(2-isopropylsulfanyl-5-methanesulfonyl-phenyl)-methanone | 5-Chloro-6-morpholin-4-yl-2,3-dihydro-1H-isoindole hydrochloride (example A44) and 2-Isopropylsulfanyl-5-methanesulfonyl-benzoic acid (example B4) | 495.1 | 497.3 ($^{37}$Cl) 495.3 ($^{35}$Cl) |
| 246 | 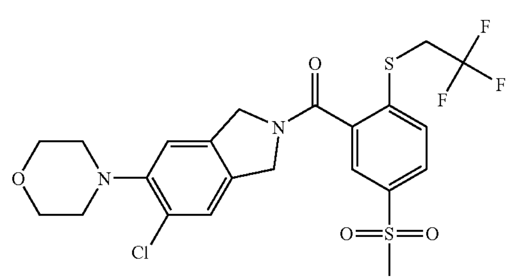 | (5-Chloro-6-morpholin-4-yl-1,3-dihydro-isoindol-2-yl)-[5-methanesulfonyl-2-(2,2,2-trifluoro-ethylsulfanyl)-phenyl]-methanone | 5-Chloro-6-morpholin-4-yl-2,3-dihydro-1H-isoindole hydrochloride (example A44) and 5-Methanesulfonyl-2-(2,2,2-trifluoro-ethylsulfanyl)-benzoic acid (example B7) | 535.0 | 537.3 ($^{37}$Cl) 535.3 ($^{35}$Cl) |

-continued

| Expl. No. | Structure | Systematic Name | Starting materials | MW Calc. | MW Found [M + H]+ |
|---|---|---|---|---|---|
| 247 | 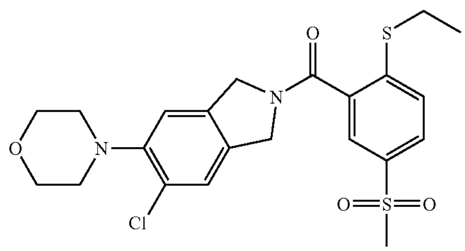 | (5-Chloro-6-morpholin-4-yl-1,3-dihydro-isoindol-2-yl)-(2-ethylsulfanyl-5-methanesulfonyl-phenyl)-methanone | 5-Chloro-6-morpholin-4-yl-2,3-dihydro-1H-isoindole hydrochloride (example A44) and 2-Ethylsulfanyl-5-methanesulfonyl-benzoic acid (example B6) | 481.0 | 483.4 ($^{37}$Cl) 481.2 ($^{35}$Cl) |
| 248 | 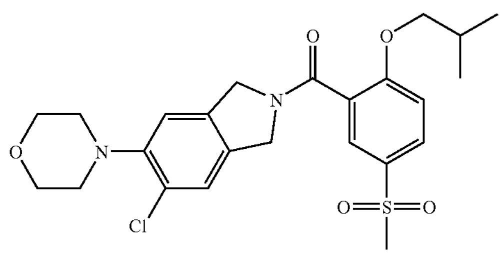 | (5-Chloro-6-morpholin-4-yl-1,3-dihydro-isoindol-2-yl)-(2-isobutoxy-5-methanesulfonyl-phenyl)-methanone | 5-Chloro-6-morpholin-4-yl-2,3-dihydro-1H-isoindole hydrochloride (example A44) and 2-Isobutoxy-5-methanesulfonyl-benzoic acid (example B11) | 493.0 | 495.4 ($^{37}$Cl) 493.3 ($^{35}$Cl) |
| 249 | 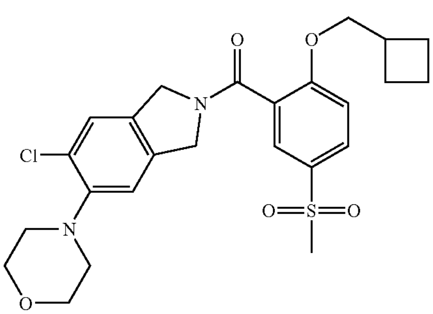 | (5-Chloro-6-morpholin-4-yl-1,3-dihydro-isoindol-2-yl)-(2-(cyclobutylmethoxy-5-methanesulfonyl-phenyl)-methanone | 5-Chloro-6-morpholin-4-yl-2,3-dihydro-1H-isoindole hydrochloride example A44) and 2-Cyclobutylmethoxy-5-methanesulfonyl-benzoic acid (CAS: 845616-33-3) | 505.0 | 507.3 ($^{37}$Cl) 505.3 ($^{35}$Cl) |
| 250 | 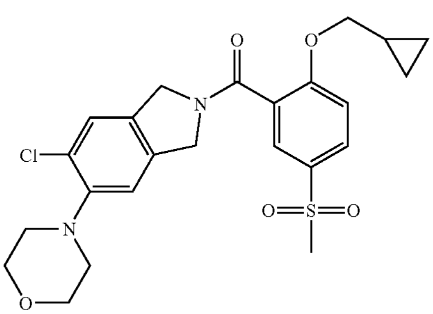 | (5-Chloro-6-morpholin-4-yl-1,3-dihydro-isoindol-2-yl)-(2-cyclopropylmethoxy-5-methanesulfonyl-phenyl)-methanone | 5-Chloro-6-morpholin-4-yl-2,3-dihydro-1H-isoindole hydrochloride (example A44) and 2-Cyclopropylmethoxy-5-methanesulfonyl-benzoic acid (CAS: 845616-03-7) | 491.0 | 493.3 ($^{37}$Cl) 491.3 ($^{35}$Cl) |
| 251 | 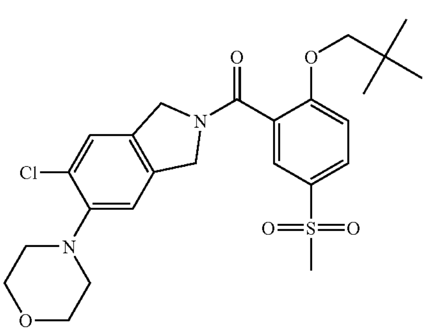 | (5-Chloro-6-morpholin-4-yl-1,3-dihydro-isoindol-2-yl)-[2-(2,2-dimethyl-propoxy)-5-methanesulfonyl-phenyl]-methanone | 5-Chloro-6-morpholin-4-yl-2,3-dihydro-1H-isoindole hydrochloride (example A44) and 2-(2,2-Dimethyl-propoxy)-5-methanesulfonyl-benzoic acid (CAS: 845616-85-5) | 507.0 | 509.4 ($^{37}$Cl) 507.3 ($^{35}$Cl) |

| Expl. No. | Structure | Systematic Name | Starting materials | MW Calc. | MW Found [M + H]+ |
|---|---|---|---|---|---|
| 252 | 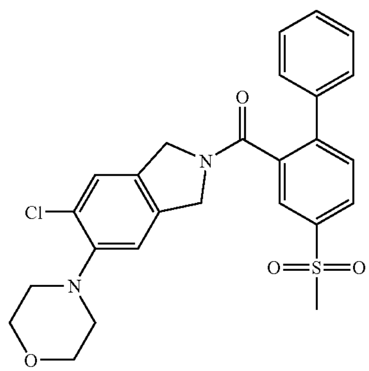 | (5-Chloro-6-morpholin-4-yl-1,3-dihydro-isoindol-2-yl)-(4-methanesulfonyl-biphenyl-2-yl)-methanone | 5-Chloro-6-morpholin-4-yl-2,3-dihydro-1H-isoindole hydrochloride (example A44) and 4-Methanesulfonyl-biphenyl-2-carboxylic acid (example B19) | 497.0 | 499.3 ($^{37}$Cl) 497.4 ($^{35}$Cl) |
| 253 | 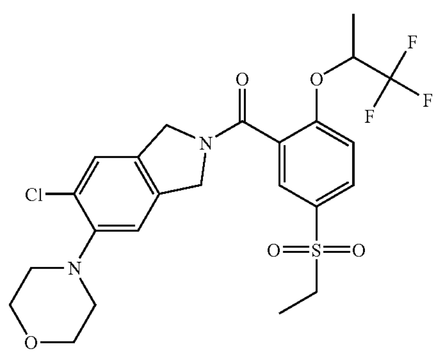 | rac-(5-Chloro-6-morpholin-4-yl-1,3-dihydro-isoindol-2-yl)-[5-ethanesulfonyl-2-(2,2,2-trifluoro-1-methyl-ethoxy)-phenyl]-methanone | 5-Chloro-6-morpholin-4-yl-2,3-dihydro-1H-isoindole hydrochloride (example A44) and rac-5-Ethanesulfonyl-2-(2,2,2-trifluoro-1-methyl-ethoxy)-benzoic acid (example B21) | 547.0 | 549.3 ($^{37}$Cl) 547.2 ($^{35}$Cl) |
| 254 | 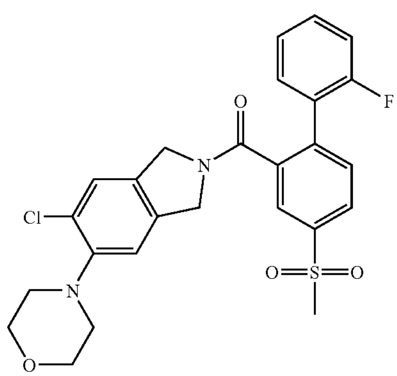 | (5-Chloro-6-morpholin-4-yl-1,3-dihydro-isoindol-2-yl)-(2'-fluoro-4-methanesulfonyl-biphenyl-2-yl)-methanone | 5-Chloro-6-morpholin-4-yl-2,3-dihydro-1H-isoindole hydrochloride (example A44) and 2'-Fluoro-4-methanesulfonyl-biphenyl-2-carboxylic acid (example B27) | 515.0 | 517.2 ($^{37}$Cl) 515.3 ($^{35}$Cl) |
| 255 | 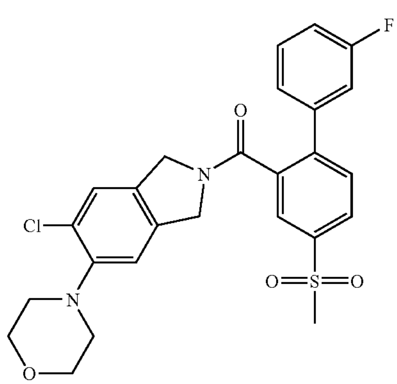 | (5-Chloro-6-morpholin-4-yl-1,3-dihydro-isoindol-2-yl)-(3'-fluoro-4-methanesulfonyl-biphenyl-2-yl)-methanone | 5-Chloro-6-morpholin-4-yl-2,3-dihydro-1H-isoindole hydrochloride (example A44) and 3'-Fluoro-4-methanesulfonyl-biphenyl-2-carboxylic acid (example B26) | 515.0 | 517.2 ($^{37}$Cl) 515.3 ($^{35}$Cl) |

-continued

| Expl. No. | Structure | Systematic Name | Starting materials | MW Calc. | MW Found [M + H]+ |
|---|---|---|---|---|---|
| 256 | 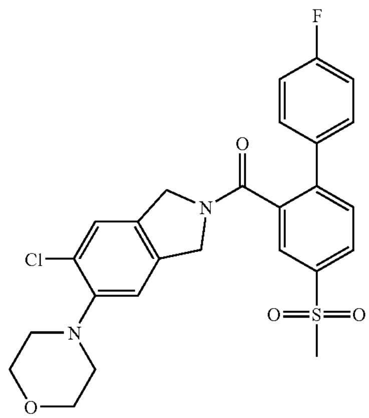 | (5-Chloro-6-morpholin-4-yl-1,3-dihydro-isoindol-2-yl)-(4'-fluoro-4-methanesulfonyl-biphenyl-2-yl)-methanone | 5-Chloro-6-morpholin-4-yl-2,3-dihydro-1H-isoindole hydrochloride (example A44) and 4'-Fluoro-4-methanesulfonyl-biphenyl-2-carboxylic acid (example B25) | 515.0 | 517.2 ($^{37}$Cl) 515.3 ($^{35}$Cl) |
| 257 | 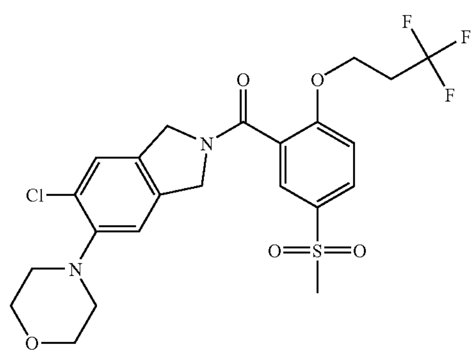 | (5-Chloro-6-morpholin-4-yl-1,3-dihydro-isoindol-2-yl)-[5-methanesulfonyl-2-(3,3,3-trifluoro-propoxy)-phenyl]-methanone | 5-Chloro-6-morpholin-4-yl-2,3-dihydro-1H-isoindole hydrochloride (example A44) and 5-Methanesulfonyl-2-(3,3,3-trifluoro-propoxy)-benzoic acid (CAS: 845616-30-0) | 533.0 | 535.3 ($^{37}$Cl) 533.2 ($^{35}$Cl) |
| 258 | 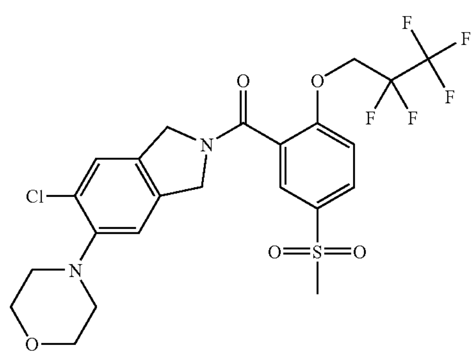 | (5-Chloro-6-morpholin-4-yl-1,3-dihydro-isoindol-2-yl)-[5-methanesulfonyl-2-(2,2,3,3,3-pentafluoro-propoxy)-phenyl]-methanone | 5-Chloro-6-morpholin-4-yl-2,3-dihydro-1H-isoindole hydrochloride (example A44) and 5-Methanesulfonyl-2-(2,2,3,3,3-pentafluoro-propoxy)-benzoic acid (CAS: 845616-42-4) | 568.9 | 571.2 ($^{37}$Cl) 569.2 ($^{35}$Cl) |
| 259 | 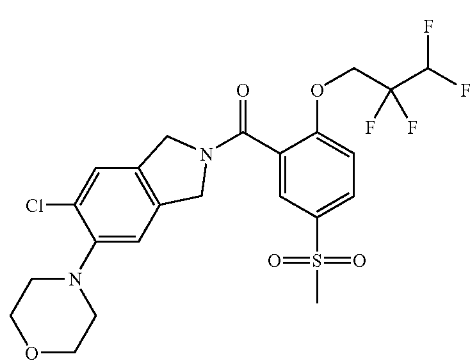 | (5-Chloro-6-morpholin-4-yl-1,3-dihydro-isoindol-2-yl)-[5-methanesulfonyl-2-(2,2,3,3-tetrafluoro-propoxy)-phenyl]-methanone | 5-Chloro-6-morpholin-4-yl-2,3-dihydro-1H-isoindole hydrochloride (example A44) and 5-Methanesulfonyl-2-(2,2,3,3-tetrafluoro-propoxy)-benzoic acid (CAS: 845616-52-6) | 551.0 | 553.1 ($^{37}$Cl) 551.3 ($^{35}$Cl) |

| Expl. No. | Structure | Systematic Name | Starting materials | MW Calc. | MW Found [M + H]+ |
|---|---|---|---|---|---|
| 260 | 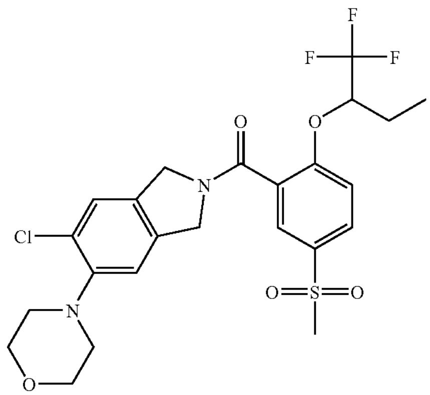 | rac-(5-Chloro-6-morpholin-4-yl-1,3-dihydro-isoindol-2-yl)-[5-methanesulfonyl-2-(1-trifluoromethyl-propoxy)-phenyl]-methanone | 5-Chloro-6-morpholin-4-yl-2,3-dihydro-1H-isoindole hydrochloride (example A44) and rac-5-Methanesulfonyl-2-(1-trifluoromethyl-propoxy)-benzoic acid (example B22) | 547.0 | 549.3 ($^{37}$Cl) 547.3 ($^{35}$Cl) |
| 261 | 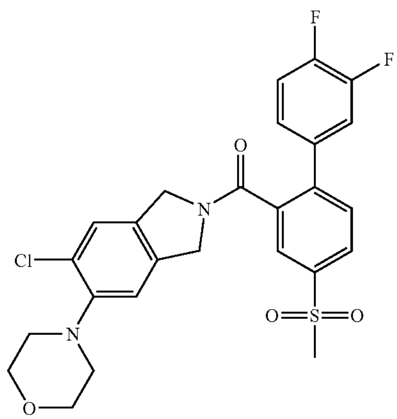 | (5-Chloro-6-morpholin-4-yl-1,3-dihydro-isoindol-2-yl)-(3',4'-difluoro-4-methanesulfonyl-biphenyl-2-yl)-methanone | 5-Chloro-6-morpholin-4-yl-2,3-dihydro-1H-isoindole hydrochloride (example A44) and 3',4'-Difluoro-4-methanesulfonyl-biphenyl-2-carboxylic acid (example B29) | 533.0 | 535.3 ($^{37}$Cl) 533.2 ($^{35}$Cl) |
| 262 | 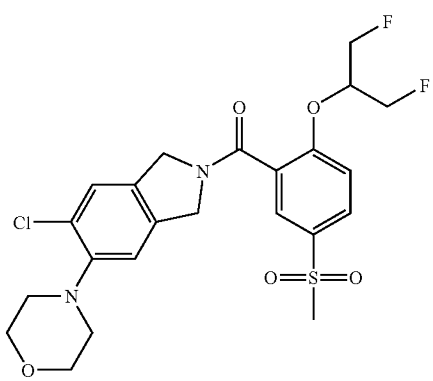 | (5-Chloro-6-morpholin-4-yl-1,3-dihydro-isoindol-2-yl)-[2-(2-fluoro-1-fluoromethyl-ethoxy)-5-methanesulfonyl-phenyl]-methanone | 5-Chloro-6-morpholin-4-yl-2,3-dihydro-1H-isoindole hydrochloride (example A44) and 2-(2-Fluoro-1-fluoromethyl-ethoxy)-5-methanesulfonyl-benzoic acid (CAS:845616-41-3) | 515.0 | 517.2 ($^{37}$Cl) 515.3 ($^{35}$Cl) |
| 263 | Chiral | (5-Ethyl-6-trifluoromethyl-1,3-dihydro-isoindol-2-yl)-[5-methanesulfonyl-2-((S)-2,2,2-trifluoro-1-methyl-ethoxy)-phenyl]-methanone | 5-Ethyl-6-trifluoromethyl-2,3-dihydro-1H-isoindole hydrochloride (example A45) and 5-Methanesulfonyl-2-((S)-2,2,2-trifluoro-1-methyl-ethoxy)-benzoic acid (example B3) | 509.5 | 510.4 |

-continued

| Expl. No. | Structure | Systematic Name | Starting materials | MW Calc. | MW Found [M + H]+ |
|---|---|---|---|---|---|
| 264 | Chiral 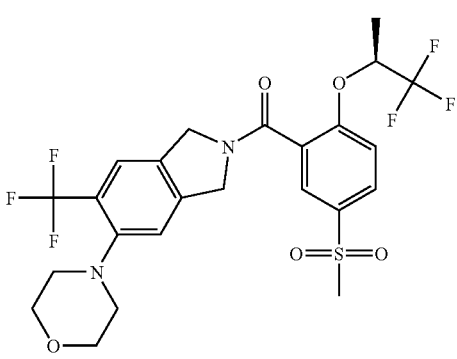 | [5-Methanesulfonyl-2-((S)-2,2,2-trifluoro-1-methyl-ethoxy)-phenyl]-(5-morpholin-4-yl-6-trifluoromethyl-1,3-dihydro-isoindol-2-yl)-methanone | 5-Morpholin-4-yl-6-trifluoromethyl-2,3-dihydro-1H-isoindole hydrochloride (example A46) and 5-Methanesulfonyl-2-((S)-2,2,2-trifluoro-1-methyl-ethoxy)-benzoic acid (example B3) | 566.5 | 567.2 |
| 265 | Chiral 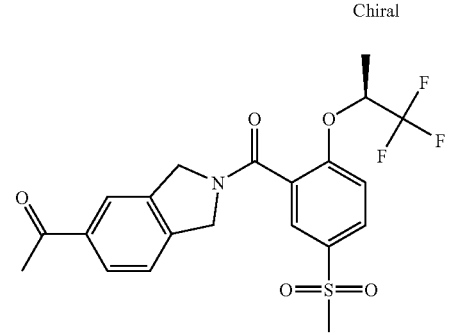 | 1-[2-[5-Methanesulfonyl-2-((S)-2,2,2-trifluoro-1-methyl-ethoxy)-benzoyl]-2,3-dihydro-1H-isoindol-5-yl]-ethanone | 1-(2,3-Dihydro-1H-isoindol-5-yl)-ethanone (example A47) and 5-Methanesulfonyl-2-((S)-2,2,2-trifluoro-1-methyl-ethoxy)-benzoic acid (example B3) | 455.4 | 456.4 |
| 266 | Chiral 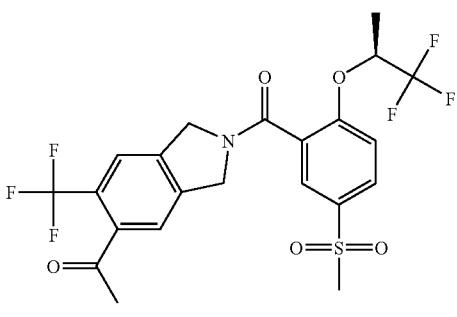 | 1-{2-[5-Methanesulfonyl-2-((S)-2,2,2-trifluoro-1-methyl-ethoxy)-benzoyl]-6-trifluoromethyl-2,3-dihydro-1H-isoindol-5-yl}-ethanone | 1-(6-Trifluoromethyl-2,3-dihydro-1H-isoindol-5-yl)-ethanone (example A48) and 5-Methanesulfonyl-2-((S)-2,2,2-trifluoro-1-methyl-ethoxy)-benzoic acid (example B3) | 523.4 | 524.2 |
| 267 | Chiral 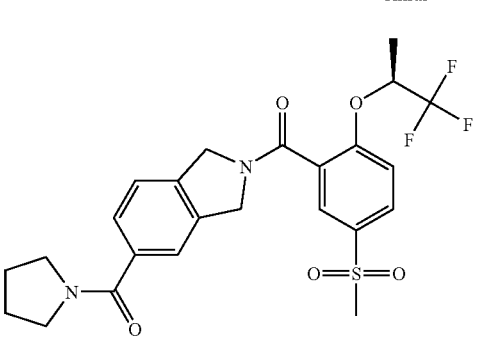 | [5-Methanesulfonyl-2-((S)-2,2,2-trifluoro-1-methyl-ethoxy)-phenyl]-[5-(pyrrolidine-1-carbonyl)-1,3-dihydro-isoindol-2-yl]-methanone | (2,3-Dihydro-1H-isoindol-5-yl)-pyrrolidin-1-yl-methanone hydrochloride (CAS: 685565-22-4) and 5-Methanesulfonyl-2-((S)-2,2,2-trifluoro-1-methyl-ethoxy)-benzoic acid (example B3) | 510.5 | 511.3 |

| Expl. No. | Structure | Systematic Name | Starting materials | MW Calc. | MW Found [M + H]+ |
|---|---|---|---|---|---|
| 268 | 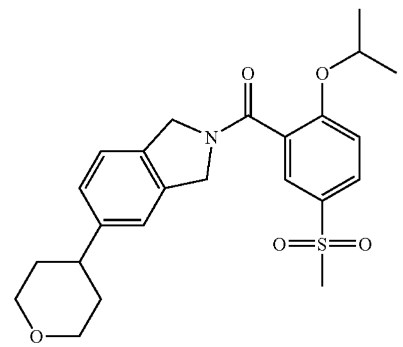 | (2-Isopropoxy-5-methanesulfonyl-phenyl)-[5-(tetrahydro-pyran-4-yl)-1,3-dihydro-isoindol-2-yl]-methanone | 5-(Tetrahydro-pyran-4-yl)-2,3-dihydro-1H-isoindole hydrochloride (example A49) and 2-Isopropoxy-5-methanesulfonyl-benzoic acid (example B1) | 443.6 | 444.3 |
| 269 | Chiral | [5-Methanesulfonyl-2-((S)-2,2,2-trifluoro-1-methyl-ethoxy)-phenyl]-[5-(tetrahydro-pyran-4-yl)-1,3-dihydro-isoindol-2-yl]-methanone | 5-(Tetrahydro-pyran-4-yl)-2,3-dihydro-1H-isoindole hydrochloride (example A49) and 5-Methanesulfonyl-2-((S)-2,2,2-trifluoro-1-methyl-ethoxy)-benzoic acid (example B3) | 497.5 | 498.3 |
| 270 | 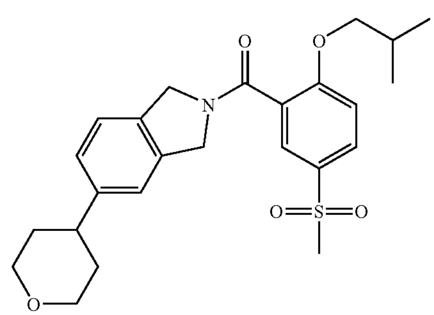 | (2-Isobutoxy-5-methanesulfonyl-phenyl)-[5-(tetrahydro-pyran-4-yl)-1,3-dihydro-isoindol-2-yl]-methanone | 5-(Tetrahydro-pyran-4-yl)-2,3-dihydro-1H-isoindole hydrochloride (example A49) and 2-Isobutoxy-5-methanesulfonyl-benzoic acid (example B11) | 457.6 | 458.4 |
| 271 | 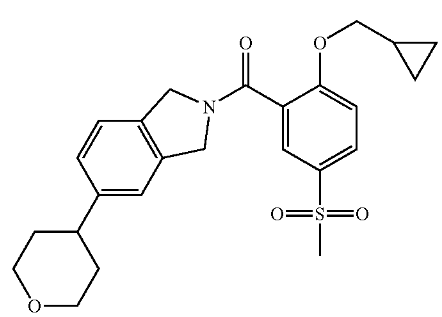 | (2-Cyclopropylmethoxy-5-methanesulfonyl-phenyl)-[5-(tetrahydro-pyran-4-yl)-1,3-dihydro-isoindol-2-yl]-methanone | 5-(Tetrahydro-pyran-4-yl)-2,3-dihydro-1H-isoindole hydrochloride (example A49) and 2-Cyclopropylmethoxy-5-methanesulfonyl-benzoic acid (CAS: 845616-03-7) | 455.6 | 456.5 |

-continued

| Expl. No. | Structure | Systematic Name | Starting materials | MW Calc. | MW Found [M + H]+ |
|---|---|---|---|---|---|
| 272 | 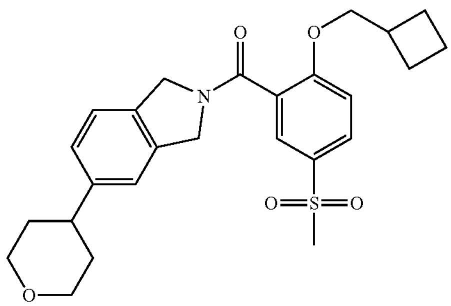 | (2-Cyclobutylmethoxy-5-methanesulfonyl-phenyl)-[5-(tetrahydro-pyran-4-yl)-1,3-dihydro-isoindol-2-yl]-methanone | 5-(Tetrahydro-pyran-4-yl)-2,3-dihydro-1H-isoindole hydrochloride (example A49) and 2-Cyclobutylmethoxy-5-methanesulfonyl-benzoic acid (CAS: 845616-33-3) | 469.6 | 470.4 |
| 273 | 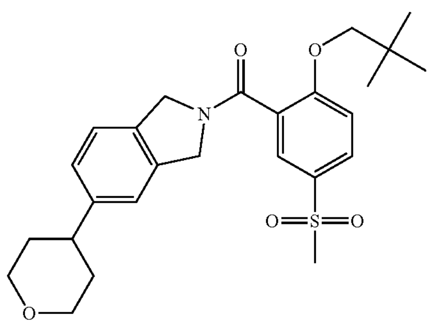 | [2-(2,2-Dimethyl-propoxy)-5-methanesulfonyl-phenyl]-[5-(tetrahydro-pyran-4-yl)-1,3-dihydro-isoindol-2-yl]-methanone | 5-(Tetrahydro-pyran-4-yl)-2,3-dihydro-1H-isoindole hydrochloride (example A49) and 2-(2,2-Dimethyl-propoxy)-5-methanesulfonyl-benzoic acid (CAS: 845616-85-5) | 471.6 | 472.4 |
| 274 | 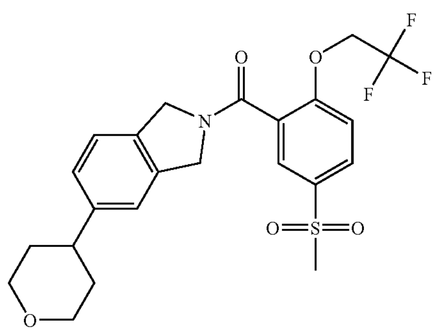 | [5-Methanesulfonyl-2-(2,2,2-trifluoro-ethoxy)-phenyl]-[5-(tetrahydro-pyran-4-yl)-1,3-dihydro-isoindol-2-yl]-methanone | 5-(Tetrahydro-pyran-4-yl)-2,3-dihydro-1H-isoindole hydrochloride (example A49) and 5-Methanesulfonyl-2-(2,2,2-trifluoro-ethoxy)-benzoic acid (example B10) | 483.5 | 484.5 |
| 275 | 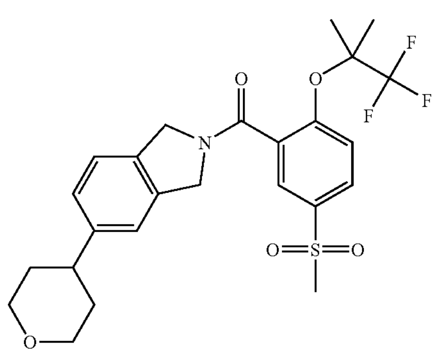 | [5-Methanesulfonyl-2-(2,2,2-trifluoro-1,1-dimethyl-ethoxy)-phenyl]-[5-(tetrahydro-pyran-4-yl)-1,3-dihydro-isoindol-2-yl]-methanone | 5-(Tetrahydro-pyran-4-yl)-2,3-dihydro-1H-isoindole hydrochloride (example A49) and 5-Methanesulfonyl-2-(2,2,2-trifluoro-1,1-dimethyl-ethoxy)-benzoic acid (CAS: 845618-01-1) | 511.6 | 512.4 |

| Expl. No. | Structure | Systematic Name | Starting materials | MW Calc. | MW Found [M + H]+ |
|---|---|---|---|---|---|
| 276 | 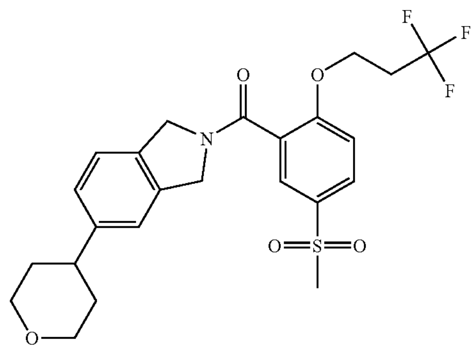 | [5-Methanesulfonyl-2-(3,3,3-trifluoro-propoxy)-phenyl]-[5-(tetrahydro-pyran-4-yl)-1,3-dihydro-isoindol-2-yl]-methanone | 5-(Tetrahydro-pyran-4-yl)-2,3-dihydro-1H-isoindole hydrochloride (example A49) and 5-Methanesulfonyl-2-(3,3,3-trifluoro-propoxy)-benzoic acid (CAS: 845616-30-0) | 497.5 | 498.5 |
| 277 | 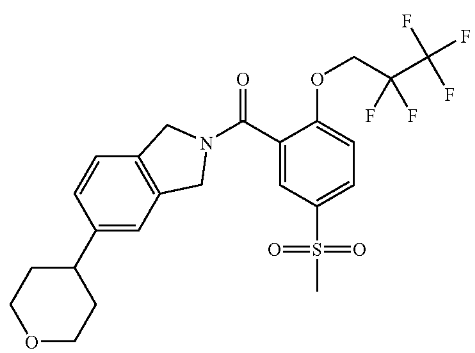 | [5-Methanesulfonyl-2-(2,2,3,3,3-pentafluoro-propoxy)-phenyl]-(5-(tetrahydro-pyran-4-yl)-1,3-dihydro-isoindol-2-yl]-methanone | 5-(Tetrahydro-pyran-4-yl)-2,3-dihydro-1H-isoindole hydrochloride (example A49) and 5-Methanesulfonyl-2-(2,2,3,3,3-pentafluoro-propoxy)-benzoic acid (CAS: 845616-42-4) | 533.5 | 534.3 |
| 278 | 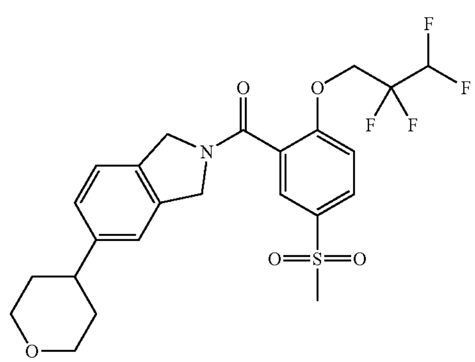 | [5-Methanesulfonyl-2-(2,2,3,3-tetrafluoro-propoxy)-phenyl]-[5-(tetrahydro-pyran-4-yl)-1,3-dihydro-isoindol-2-yl]-methanone | 5-(Tetrahydro-pyran-4-yl)-2,3-dihydro-1H-isoindole hydrochloride (example A49) and 5-Methanesulfonyl-2-(2,2,3,3-tetrafluoro-propoxy)-benzoic acid (CAS: 845616-52-6) | 515.5 | 516.3 |
| 279 | 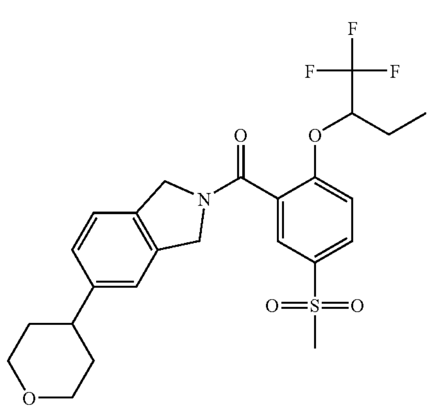 | rac-[5-Methanesulfonyl-2-(1-trifluoromethyl-propoxy)-phenyl]-[5-(tetrahydro-pyran-4-yl)-1,3-dihydro-isoindol-2-yl]-methanone | 5-(Tetrahydro-pyran-4-yl)-2,3-dihydro-1H-isoindole hydrochloride (example A49) and rac-5-Methanesulfonyl-2-(1-trifluoromethyl-propoxy)-benzoic acid (example B22) | 511.6 | 512.5 |

-continued

| Expl. No. | Structure | Systematic Name | Starting materials | MW Calc. | MW Found [M + H]+ |
|---|---|---|---|---|---|
| 280 | 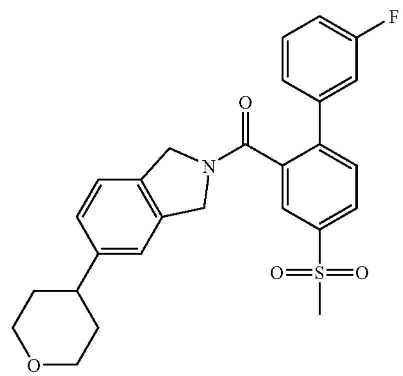 | (3'-Fluoro-4-methanesulfonyl-biphenyl-2-yl)-[5-(tetrahydro-pyran-4-yl)-1,3-dihydro-isoindol-2-yl]-methanone | 5-(Tetrahydro-pyran-4-yl)-2,3-dihydro-1H-isoindole hydrochloride (example A49) and 3'-Fluoro-4-methanesulfonyl-biphenyl-2-carboxylic acid (example B26) | 479.6 | 480.5 |
| 281 | 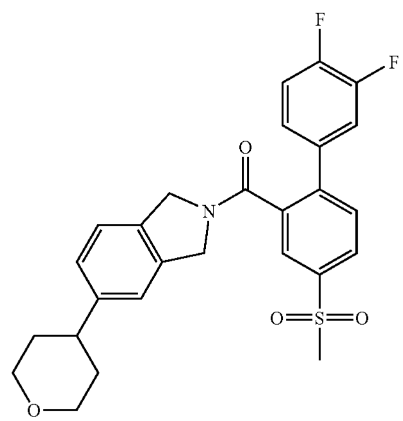 | (3',4'-Difluoro-4-methanesulfonyl-biphenyl-2-yl)-[5-(tetrahydro-pyran-4-yl)-1,3-dihydro-isoindol-2-yl]-methanone | 5-(Tetrahydro-pyran-4-yl)-2,3-dihydro-1H-isoindole hydrochloride (example A49) and 3',4'-Difluoro-4-methanesulfonyl-biphenyl-2-carboxylic acid (example B29) | 497.6 | 498.4 |
| 282 | 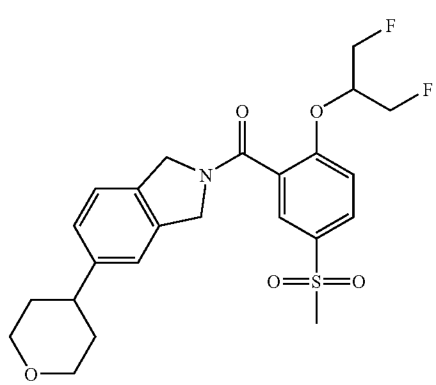 | [2-(2-Fluoro-1-fluoromethyl-ethoxy)-5-methanesulfonyl-phenyl]-[5-(tetrahydro-pyran-4-yl)-1,3-dihydro-isoindol-2-yl]-methanone | 5-(Tetrahydro-pyran-4-yl)-2,3-dihydro-1H-isoindole hydrochloride (example A49) and 2-(2-Fluoro-1-fluoromethyl-ethoxy)-5-methanesulfonyl-benzoic acid (CAS:845616-41-3) | 479.5 | 480.3 |

| Expl. No. | Structure | Systematic Name | Starting materials | MW Calc. | MW Found [M + H]+ |
|---|---|---|---|---|---|
| 283 | 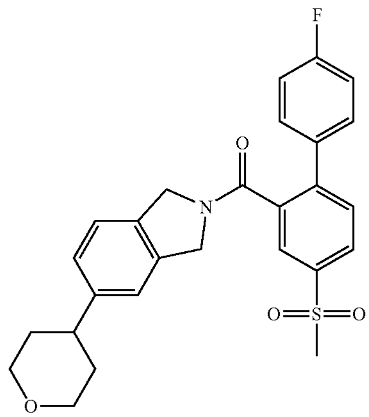 | (4-Fluoro-4-methanesulfonyl-biphenyl-2-yl)-[5-(tetrahydro-pyran-4-yl)-1,3-dihydro-isoindol-2-yl]-methanone | 5-(Tetrahydro-pyran-4-yl)-2,3-dihydro-1H-isoindole hydrochloride (example A49) and 4'-Fluoro-4-methanesulfonyl-biphenyl-2-carboxylic acid (example B25) | 479.6 | 480.1 |
| 284 | 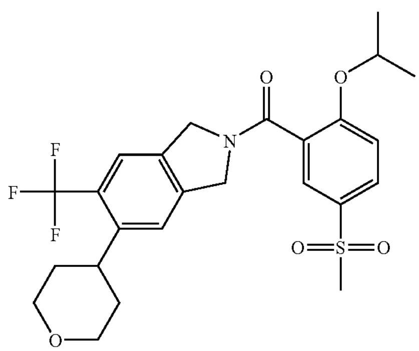 | (2-Isopropoxy-5-methanesulfonyl-phenyl)-[5-(tetrahydro-pyran-4-yl)-6-trifluoromethyl-1,3-dihydro-isoindol-2-yl]-methanone | 5-(Tetrahydro-pyran-4-yl)-6-trifluoromethyl-2,3-dihydro-1H-isoindole hydrochloride (example-A50) and Isopropoxy-5-methanesulfonyl-benzoic acid (example B1) | 511.6 | 512.5 |
| 285 | Chiral | [5-Methanesulfonyl-2-((S)-2,2,2-trifluoro-1-methyl-ethoxy)-phenyl]-[5-(tetrahydro-pyran-4-yl)-6-trifluoromethyl-1,3-dihydro-isoindol-2-yl]-methanone | 5-(Tetrahydro-pyran-4-yl)-6-trifluoromethyl-2,3-dihydro-1H-isoindole hydrochloride (example A50) and 5-Methanesulfonyl-2-((S)-2,2,2-trifluoro-1-methyl-ethoxy)-benzoic acid (example B3) | 565.5 | 566.5 |

| Expl. No. | Structure | Systematic Name | Starting materials | MW Calc. | MW Found [M + H]+ |
|---|---|---|---|---|---|
| 286 | 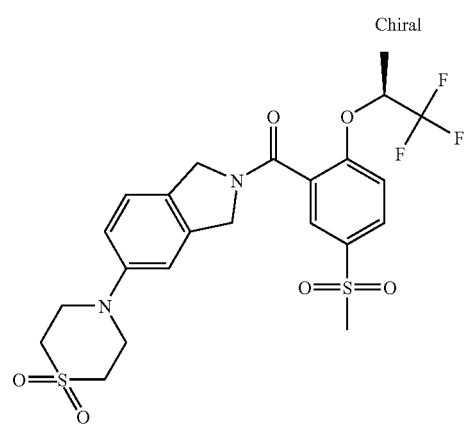 Chiral | [5-(1,1-Dioxo-1-thiomorpholin-4-yl)-1,3-dihydro-isoindol-2-yl]-[5-methanesulfonyl-2-((S)-2,2,2-trifluoro-1-methyl-ethoxy)-phenyl]-methanone | 5-(1,1-Dioxo-1-thiomorpholin-4-yl)-2,3-dihydro-1H-isoindole hydrochloride (example A51) and 5-Methanesulfonyl-2-((S)-2,2,2-trifluoro-1-methyl-ethoxy)-benzoic acid (example B3) | 546.6 | 547.2 |
| 287 | 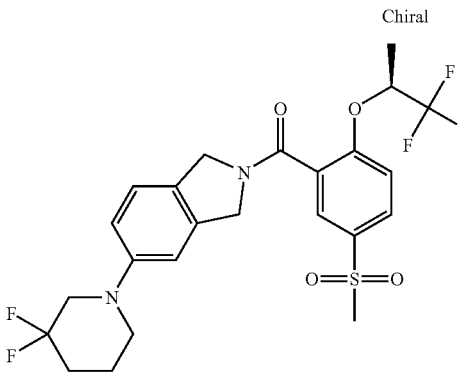 Chiral | [5-(3,3-Difluoro-piperidin-1-yl)-1,3-dihydro-isoindol-2-yl]-[5-methanesulfonyl-2-((S)-2,2,2-trifluoro-1-methyl-ethoxy)-phenyl]-methanone | 5-(3,3-Difluoro-piperidin-1-yl)-2,3-dihydro-1H-isoindole hydrochloride (example A52) and 5-Methanesulfonyl-2-((S)-2,2,2-trifluoro-1-methyl-ethoxy)-benzoic acid (example B3) | 532.5 | 533.3 |
| 288 | 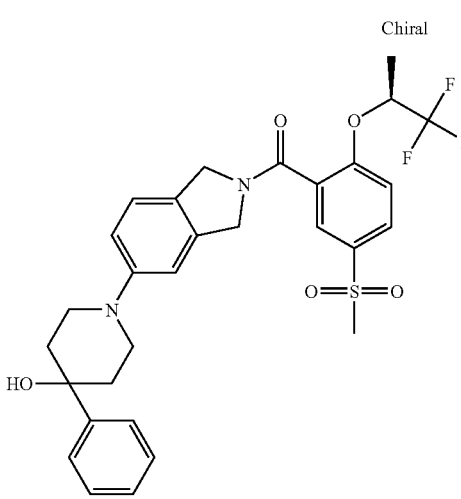 Chiral | [5-(4-Hydroxy-4-phenyl-piperidin-1-yl)-1,3-dihydro-isoindol-2-yl]-[5-methanesulfonyl-2-((S)-2,2,2-trifluoro-1-methyl-ethoxy)-phenyl]-methanone | 1-(2,3-Dihydro-1H-isoindol-5-yl)-4-phenyl-piperidin-4-ol hydrochloride (example A53) and 5-Methanesulfonyl-2-((S)-2,2,2-trifluoro-1-methyl-ethoxy)-benzoic acid (example B3) | 588.6 | 589.4 |

-continued

| Ex-pl. No. | Structure | Systematic Name | Starting materials | MW Calc. | MW Found [M + H]+ |
|---|---|---|---|---|---|
| 289 | Chiral | [5-Methanesulfonyl-2-((S)-2,2,2-trifluoro-1-methyl-ethoxy)-phenyl]-(5-methyl-6-morpholin-4-yl-1,3-dihydro-isoindol-2-yl)-methanone | 5-Methyl-6-morpholin-4-yl-2,3-dihydro-1H-isoindole hydrochloride (example A54) and 5-Methanesulfonyl-2-((S)-2,2,2-trifluoro-1-methyl-ethoxy)-benzoic acid (example B3) | 512.5 | 513.3 |
| 290 | Chiral | [5-Methanesulfonyl-2-((S)-2,2,2-trifluoro-1-methyl-ethoxy)-phenyl]-[5-(2,2,2-trifluoro-ethyl)-1,3-dihydro-isoindol-2-yl]-methanone | 5-(2,2,2-Trifluoro-ethyl)-2,3-dihydro-1H-isoindole hydrochloride (example A55) and 5-Methanesulfonyl-2-((S)-2,2,2-trifluoro-1-methyl-ethoxy)-benzoic acid (example B3) | 495.4 | 496.3 |
| 291 | Chiral | [5-Methanesulfonyl-2-((S)-2,2,2-trifluoro-1-methyl-ethoxy)-phenyl]-[5-(3-methoxy-azetidin-1-yl)-1,3-dihydro-isoindol-2-yl]-methanone | 5-(3-Methoxy-azetidin-1-yl)-2,3-dihydro-1H-isoindole trifluoro-acetate (example A56) and 5-Methanesulfonyl-2-((S)-2,2,2-trifluoro-1-methyl-ethoxy)-benzoic acid (example B3) | 498.5 | 499.4 |
| 292 | Chiral | [5-Methanesulfonyl-2-((S)-2,2,2-trifluoro-1-methyl-ethoxy)-phenyl]-[5-(4-methoxy-piperidin-1-yl)-1,3-dihydro-isoindol-2-yl]-methanone | 5-(4-Methoxy-piperidin-1-yl)-2,3-dihydro-1H-isoindole hydrochloride (example A57) and 5-Methanesulfonyl-2-((S)-2,2,2-trifluoro-1-methyl-ethoxy)-benzoic acid (example B3) | 526.6 | 527.2 |

-continued

| Expl. No. | Structure | Systematic Name | Starting materials | MW Calc. | MW Found [M + H]+ |
|---|---|---|---|---|---|
| 293 | Chiral | (5-Methanesulfonyl-2-((S)-2,2,2-trifluoro-1-methyl-ethoxy)-phenyl]-[(1S,4S)-5-(2-oxa-5-aza-bicyclo[2.2.1]hept-5-yl)-1,3-dihydro-isoindol-2-yl]-methanone | (1S,4S)-5-(2-Oxa-5-aza-bicyclo[2.2.1]hept-5-yl)-2,3-dihydro-1H-isoindole trifluoro-acetic acid (example A58) and 5-Methanesulfonyl-2-((S)-2,2,2-trifluoro-1-methyl-ethoxy)-benzoic acid (example B3) | 510.5 | 511.5 |
| 294 | Chiral | (2-Isopropoxy-5-methanesulfonyl-phenyl)-[(1S,4S)-5-(2-oxa-5-aza-bicyclo[2.2.1]hept-5-yl)-Isopropoxy-5-1,3-dihydro-isoindol-2-yl]-methanone | (1S,4S)-5-(2-Oxa-5-aza-bicyclo[2.2.1]hept-5-yl)-2,3-dihydro-1H-isoindole trifluoro-acetic acid (example A58) and 2-Isopropoxy-5-methanesulfonyl-benzoic acid (example B1) | 456.6 | 457.3 |
| 295 | Chiral | [5-Methanesulfonyl-2-((S)-2,2,2-trifluoro-1-methyl-ethoxy)-phenyl]-[(1R,5S)-5-(3-oxa-8-aza-bicyclo[3.2.1]oct-8-yl)-1,3-dihydro-isoindol-2-yl]-methanone | 8-(2,3-Dihydro-1H-isoindol-5-yl)-3-oxa-8-aza-bicyclo[3.2.1]octane trifluoro-acetate (example A59) and 5-Methanesulfonyl-2-((S)-2,2,2-trifluoro-1-methyl-ethoxy)-benzoic acid (example B3) | 524.6 | 525.3 |
| 296 | 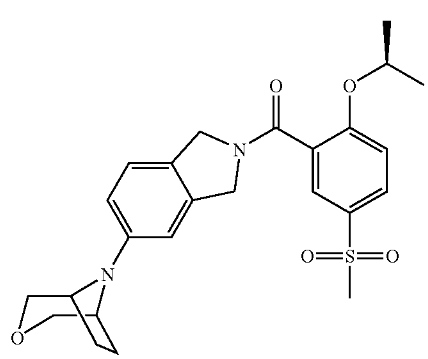 | (2-Isopropoxy-5-methanesulfonyl-phenyl)-[5-(3-oxa-8-aza-bicyclo[3.2.1]oct-8-yl)-1,3-dihydro-isoindol-2-yl]-methanone | '8-(2,3-Dihydro-1H-isoindol-5-yl)-3-oxa-8-aza-bicyclo[3.2.1]octane trifluoro-acetate (example A59) and 2-Isopropoxy-5-methanesulfonyl-benzoic acid (example B1) | 470.6 | 471.3 |

-continued

| Expl. No. | Structure | Systematic Name | Starting materials | MW Calc. | MW Found [M + H]+ |
|---|---|---|---|---|---|
| 297 | Chiral | (5-Cyclopropyl-6-morpholin-4-yl-1,3-dihydro-isoindol-2-yl)-[5-methanesulfonyl-2-((S)-2,2,2-trifluoro-1-methyl-ethoxy)-phenyl]-methanone | 5-Cyclopropyl-6-morpholin-4-yl-2,3-dihydro-1H-isoindole trifluoroacetate (example A60) and 5-Methanesulfonyl-2-((S)-2,2,2-trifluoro-1-methyl-ethoxy)-benzoic acid (example B3) | 538.6 | 539.3 |
| 298 | Chiral | [5-Cyclopropyl-6-(tetrahydro-pyran-4-yl)-1,3-dihydro-isoindol-2-yl]-[5-methanesulfonyl-2-((S)-2,2,2-trifluoro-1-methyl-ethoxy)-phenyl]-methanone | 5-Cyclopropyl-6-(tetrahydro-pyran-4-yl)-2,3-dihydro-1H-isoindole trifluoro-acetate (example A61) and 5-Methanesulfonyl-2-((S)-2,2,2-trifluoro-1-methyl-ethoxy)-benzoic acid (example B3) | 537.6 | 538.3 |
| 299 | Chiral | [5-(4-Hydroxy-tetrahydro-pyran-4-yl)-1,3-dihydro-isoindol-2-yl]-[5-methanesulfonyl-2-((S)-2,2,2-trifluoro-1-methyl-ethoxy)-phenyl]-methanone | 4-(2,3-Dihydro-1H-isoindol-5-yl)-tetrahydro-pyran-4-ol (example A62) and 5-Methanesulfonyl-2-((S)-2,2,2-trifluoro-1-methyl-ethoxy)-benzoic acid (example B3) | 513.5 | 514.5 |
| 300 | Chiral | [5-Methanesulfonyl-2-((S)-2,2,2-trifluoro-1-methyl-ethoxy)-phenyl]-[5-methyl-6-(tetrahydro-pyran-4-yl)-1,3-dihydro-isoindol-2-yl]-methanone | 5-Methyl-6-(tetrahydro-pyran-4-yl)-2,3-dihydro-1H-isoindole trifluoro-acetate (example A63) and 5-Methanesulfonyl-2-((S)-2,2,2-trifluoro-1-methyl-ethoxy)-benzoic acid (example B3) | 511.6 | 512.5 |

-continued

| Expl. No. | Structure | Systematic Name | Starting materials | MW Calc. | MW Found [M + H]+ |
|---|---|---|---|---|---|
| 301 | 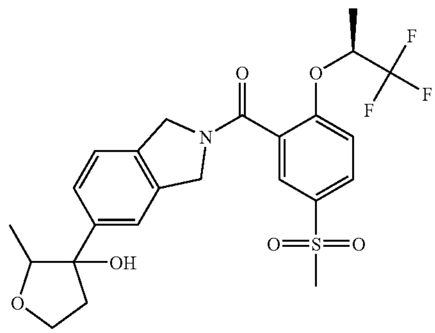 | [5-(3-Hydroxy-2-methyl-tetrahydro-furan-3-yl)-1,3-dihydro-isoindol-2-yl]-[5-methanesulfonyl-2-((S)-2,2,2-trifluoro-1-methyl-ethoxy)-phenyl]-methanone | 3-(2,3-Dihydro-1H-isoindol-5-yl)-2-methyl tetrahydro-furan-3-ol (example A64) and 5-Methanesulfonyl-2-((S)-2,2,2-trifluoro-1-methyl-ethoxy)-benzoic acid (example B3) | 513.5 | 514.2 |
| 302 | 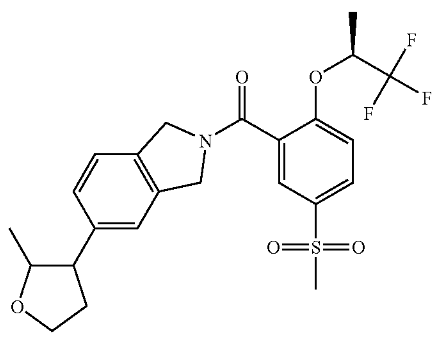 | [5-Methanesulfonyl-2-((S)-2,2,2-trifluoro-1-methyl-ethoxy)-phenyl]-[5-(2-methyl-tetrahydro-furan-3-yl)-1,3-dihydro-isoindol-2-yl]-methanone | 5-(2-Methyl-tetrahydro-furan-3-yl)-2,3-dihydro-1H-isoindole (example A65) and 5-Methanesulfonyl-2-((S)-2,2,2-trifluoro-1-methyl-ethoxy)-benzoic acid (example B3) | 497.5 | 498.4 |
| 303 | 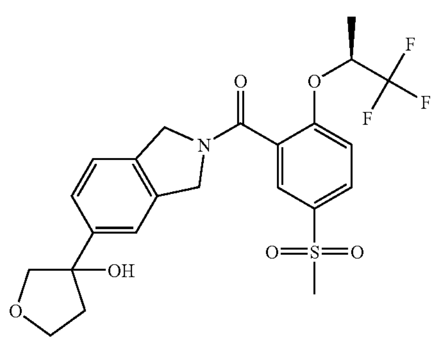 | [5-(3-Hydroxy-tetrahydro-furan-3-yl)-1,3-dihydro-isoindol-2-yl]-[5-methanesulfonyl-2-((S)-2,2,2-trifluoro-1-methyl-ethoxy)-phenyl]-methanone | 3-(2,3-Dihydro-1H-isoindol-5-yl)-tetrahydro-furan-3-ol (example A66) and 5-Methanesulfonyl-2-((S)-2,2,2-trifluoro-1-methyl-ethoxy)-benzoic acid (example B3) | 499.5 | 500.3 |
| 304 | 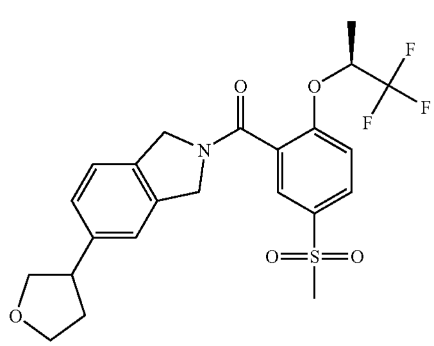 | [5-Methanesulfonyl-2-((S)-2,2,2-trifluoro-1-methyl-ethoxy)-phenyl]-[5-(tetrahydro-furan-3-yl)-1,3-dihydro-isoindol-2-yl]-methanone | 5-(Tetrahydro-furan-3-yl)-2,3-dihydro-1H-isoindole (example A67) and 5-Methanesulfonyl-2-((S)-2,2,2-trifluoro-1-methyl-ethoxy)-benzoic acid (example B3) | 483.5 | 484.5 |

-continued

| Expl. No. | Structure | Systematic Name | Starting materials | MW Calc. | MW Found [M + H]+ |
|---|---|---|---|---|---|
| 305 | Chiral 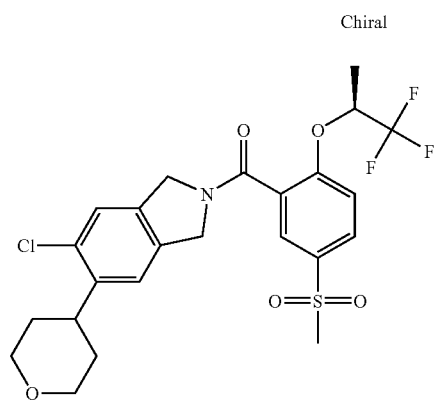 | [5-Chloro-6-(tetrahydro-pyran-4-yl)-1,3-dihydro-isoindol-2-yl]-[5-methanesulfonyl-2-((S)-2,2,2-trifluoro-1-methyl-ethoxy)-phenyl]-methanone | 5-Chloro-6-(tetrahydro-pyran-4-yl)-2,3-dihydro 1H-isoindole trifluoro acetate (example A68) and 5-Methanesulfonyl-2-((S)-2,2,2-trifluoro-1-methyl-ethoxy)-benzoic acid (example B3) | 532.0 | 534.1 ($^{37}$Cl) 532.0 ($^{35}$Cl) |
| 306 | Chiral 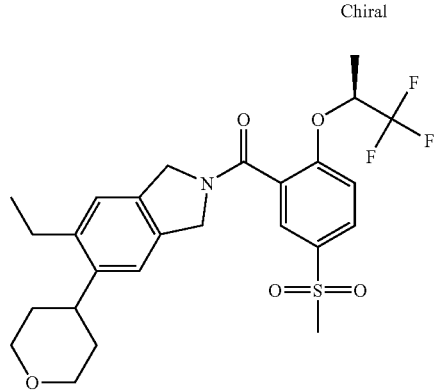 | [5-Ethyl-6-(tetrahydro-pyran-4-yl)-1,3-dihydro-isoindol-2-yl]-[5-methanesulfonyl-2-((S)-2,2,2-trifluoro-1-methyl-ethoxy)-phenyl]-methanone | 5-Ethyl-6-(tetrahydro-pyran-4-yl)-2,3-dihydro-1H-isoindole trifluoro-acetate (example A69) and 5-Methanesulfonyl-2-((S)-2,2,2-trifluoro-1-methyl-ethoxy)-benzoic acid (example B3) | 525.6 | 526.3 |
| 307 | Chiral 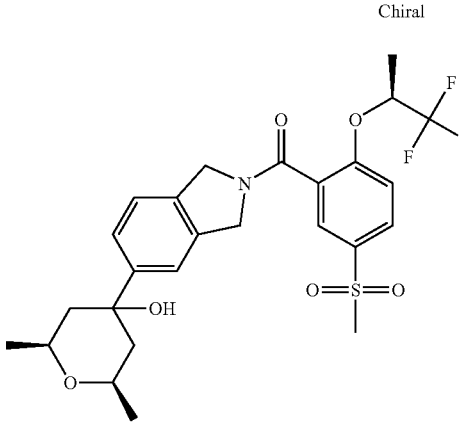 | [4-Hydroxy-2,6-dimethyl-tetrahydro-pyran-4-yl)-1,3-dihydro-isoindol-2-yl]-[5-methanesulfonyl-2-((S)-2,2,2-trifluoro-1-methyl-ethoxy)-phenyl]-methanone | 4-(2,3-Dihydro-1H-isoindol-5-yl)-2,6-dimethyl-tetrahydro pyran-4-ol (example A70) and 5-Methanesulfonyl-2-((S)-2,2,2-trifluoro-1-methyl-ethoxy)-benzoic acid (example B3) | 541.6 | 542.3 |

-continued

| Ex-pl. No. | Structure | Systematic Name | Starting materials | MW Calc. | MW Found [M + H]+ |
|---|---|---|---|---|---|
| 308 | Chiral | [2,6-Dimethyl-tetrahydro-pyran-4-yl)-1,3-dihydro-isoindol-2-yl]-[5-methanesulfonyl-2-((S)-2,2,2-trifluoro-1-methyl-ethoxy)-phenyl]-methanone | 2,6-Dimethyl-tetrahydro-pyran-4-yl)-2,3-dihydro-1H-isoindole (example A71) and 5-Methanesulfonyl-2-((S)-2,2,2-trifluoro-1-methyl-ethoxy)-benzoic acid (example B3) | 525.6 | 526.3 |
| 309 | 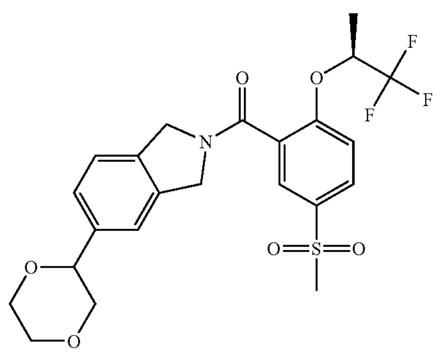 | (5-[1,4]Dioxan-2-yl-1,3-dihydro-isoindol-2-yl)-[5-methanesulfonyl-2-((S)-2,2,2-trifluoro-1-methyl-ethoxy)-phenyl]-methanone | rac-5-[1,4]Dioxan-2-yl-2,3-dihydro-1H-isoindole (example A72) and 5-Methanesulfonyl-2-((S)-2,2,2-trifluoro-1-methyl-ethoxy)-benzoic acid (example B3) | 499.5 | 500.4 |
| 310 | 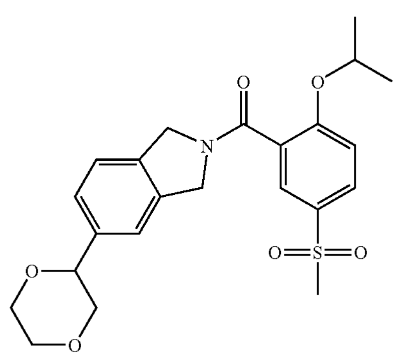 | (5-[1,4]Dioxan-2-yl-1,3-dihydro-isoindol-2-yl)-(2-isopropoxy-5-methanesulfonyl-phenyl)-methanone | rac-5-[1,4]Dioxan-2-yl-2,3-dihydro-1H-isoindole (example A72) and 2-Isopropoxy-5-methanesulfonyl-benzoic acid (example B1) | 445.5 | 446.3 |
| 311 | 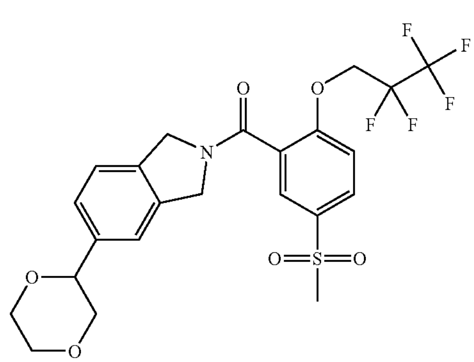 | (5-[1,4]Dioxan-2-yl-1,3-dihydro-isoindol-2-yl)-[5-methanesulfonyl-2-(2,2,3,3,3-pentafluoro-propoxy)-phenyl]-methanone | rac-5-[1,4]Dioxan-2-yl-2,3-dihydro-1H-isoindole (example A72) and 5-Methanesulfonyl-2-(2,2,3,3,3-pentafluoro-propoxy)-benzoic acid (CAS: 845616-42-4) | 535.5 | 536.3 |

| Ex-pl. No. | Structure | Systematic Name | Starting materials | MW Calc. | MW Found [M + H]+ |
|---|---|---|---|---|---|
| 312 | 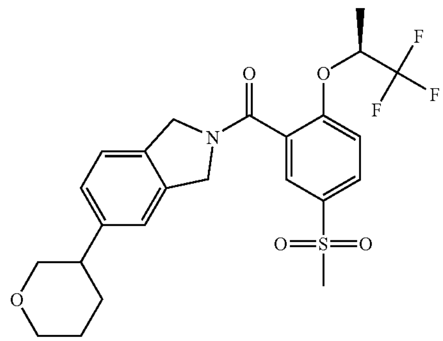 | [5-Methanesulfonyl-2-((S)-2,2,2-trifluoro-1-methyl-ethoxy)-phenyl]-[5-(tetrahydro-pyran-3-yl)-1,3-dihydro-isoindol-2-yl]-methanone | rac-5-(Tetrahydro-pyran-3-yl)-2,3-dihydro-1H-isoindole (example A73) and 5-Methanesulfonyl-2-((S)-2,2,2-trifluoro-1-methyl-ethoxy)-benzoic acid (example B3) | 497.5 | 498.3 |

EXAMPLE 313

[5-Methanesulfonyl-2-((S)-2,2,2-trifluoro-1-methyl-ethoxy)-phenyl]-(2-pyridin-4-yl-5,7-dihydro-pyrrolo[3,4-b]pyridin-6-yl)-methanone

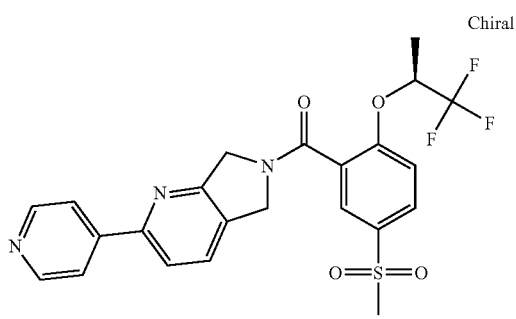

Prepared in analogy to Example A54(a) from (2-chloro-5,7-dihydro-pyrrolo[3,4-b]pyridin-6-yl)-[5-methanesulfonyl-2-((S)-2,2,2-trifluoro-1-methyl-ethoxy)-phenyl]-methanone (Example C4) and 4-tributylstannanylpyridine. White solid. MS (m/e): 492.1 [M+H]+, 100%).

EXAMPLE 314

[5-Methanesulfonyl-2-((S)-2,2,2-trifluoro-1-methyl-ethoxy)-phenyl]-[2-(tetrahydro-pyran-4-yl)-5,7-dihydro-pyrrolo[3,4-b]pyridin-6-yl]-methanone (a) [2-(3,6-Dihydro-2H-pyran-4-yl)-5,7-dihydro-pyrrolo[3,4-b]pyridin-6-yl]-[5-methanesulfonyl-2-(((S)-2,2,2-trifluoro-1-methyl-ethoxy)-phenyl]-methanone

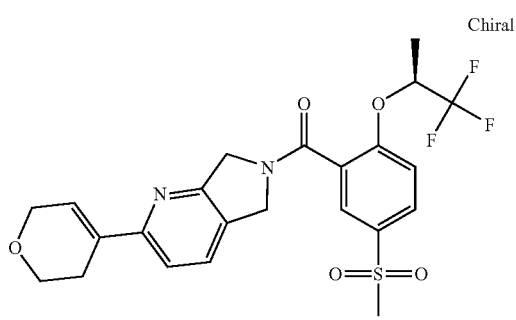

Prepared in analogy to Example A54(a) from (2-chloro-5,7-dihydro-pyrrolo[3,4-b]pyridin-6-yl)-[5-methanesulfonyl-2-((S)-2,2,2-trifluoro-1-methyl-ethoxy)-phenyl]-methanone (Example C4) and tributyl-(3,6-dihydro-2H-pyran-4-yl)-stannane. White solid. MS (m/e): 497.4 [M+H]+, 100%).

(b) [5-Methanesulfonyl-2-((S)-2,2,2-trifluoro-1-methyl-ethoxy)-phenyl]-[2-(tetrahydro-pyran-4-yl)-5,7-dihydro-pyrrolo[3,4-b]pyridin-6-yl]-methanone

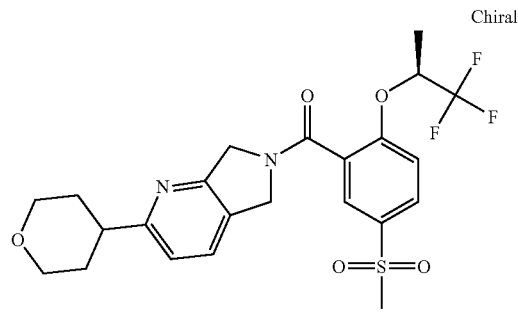

Prepared in analogy to Example A49(b) from [2-(3,6-dihydro-2H-pyran-4-yl)-5,7-dihydro-pyrrolo[3,4-b]pyridin-6-yl]-[5-methanesulfonyl-2-((S)-2,2,2-trifluoro-1-methyl-ethoxy)-phenyl]-methanone and ammonium formate. White solid. MS (m/e): 499.3 [M+H]+, 100%).

In analogy to Example A4(a), compounds 315 to 320 of the following table were prepared from (5-Iodo-1,3-dihydro-isoindol-2-yl)-[5-methanesulfonyl-2-((S)-2,2,2-trifluoro-1-methyl-ethoxy)-phenyl]-methanone (Example C3) and organostananne derivative:

| Expl. No. | Structure | Systematic Name | Starting materials | MW Calc. | MW Found [M + H]+ |
|---|---|---|---|---|---|
| 315 | 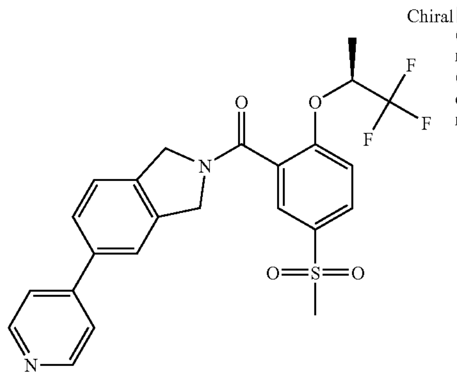 | [5-Methanesulfonyl-2-((S)-2,2,2-trifluoro-1-methyl-ethoxy)-phenyl]-(5-pyridin-4-yl-1,3-dihydro-isoindol-2-yl)-methanone | 4-tributylstannylpyridine | 490.5 | 491.2 |
| 316 | 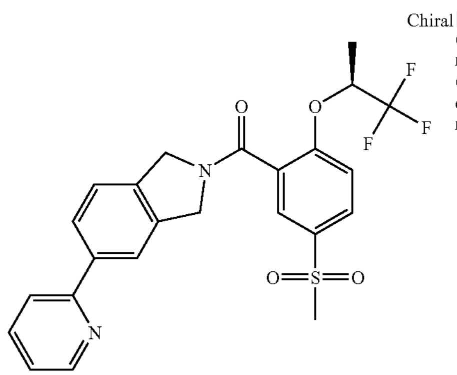 | [5-Methanesulfonyl-2-((S)-2,2,2-trifluoro-1-methyl-ethoxy)-phenyl]-(5-pyridin-2-yl-1,3-dihydro-isoindol-2-yl)-methanone | 2-tributylstannylpyridine | 490.5 | 491.3 |
| 317 | 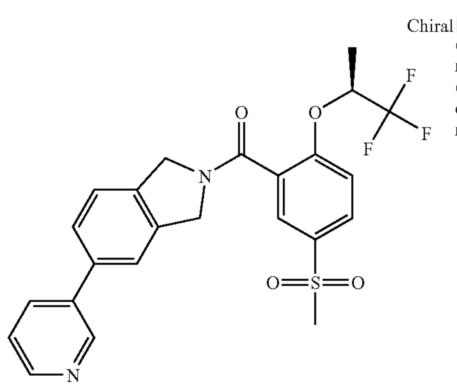 | [5-Methanesulfonyl-2-((S)-2,2,2-trifluoro-1-methyl-ethoxy)-phenyl]-(5-pyridin-3-yl-1,3-dihydro-isoindol-2-yl)-methanone | 3-tributylstannylpyridine | 490.5 | 491.2 |

| Expl. No. | Structure | Systematic Name | Starting materials | MW Calc. | MW Found [M + H]+ |
|---|---|---|---|---|---|
| 318 | 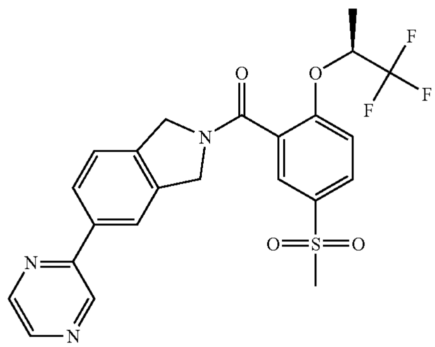 | Chiral [5-Methanesulfonyl-2-((S)-2,2,2-trifluoro-1-methyl-ethoxy)-phenyl]-(5-pyrazin-2-yl-1,3-dihydro-isoindol-2-yl)-methanone | 2-tributyistannylpyrazine | 491.5 | 492.1 |
| 319 | 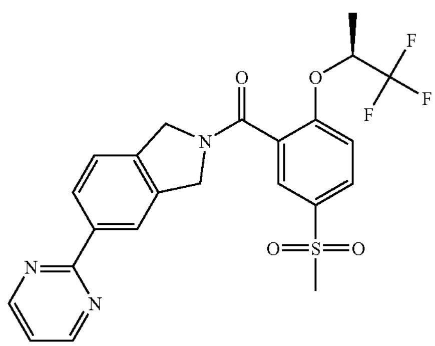 | Chiral [5-Methanesulfonyl-2-((S)-2,2,2-trifluoro-1-methyl-ethoxy)-phenyl]-(5-pyrimidin-2-yl-1,3-dihydro-isoindol-2-yl)-methanone | 2-tributylstannylpyrimidine | 491.5 | 492.1 |
| 320 | 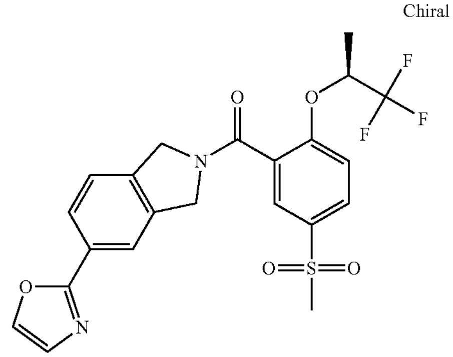 | Chiral [5-Methanesulfonyl-2-((S)-2,2,2-trifluoro-1-methyl-ethoxy)-phenyl]-(5-oxazol-2-yl-1,3-dihydro-isoindol-2-yl)-methanone | 2-Tributyistannanyl-oxazole (GAS: 145214-05-7) | 480.5 | 481.1 |

EXAMPLE 321

[6-(4-Fluoro-phenyl)-1,3-dihydro-pyrrolo[3,4-c]pyridin-2-yl]-[5-methanesulfonyl-2-((S)-2,2,2-trifluoro-1-methyl-ethoxy)-phenyl]-methanone

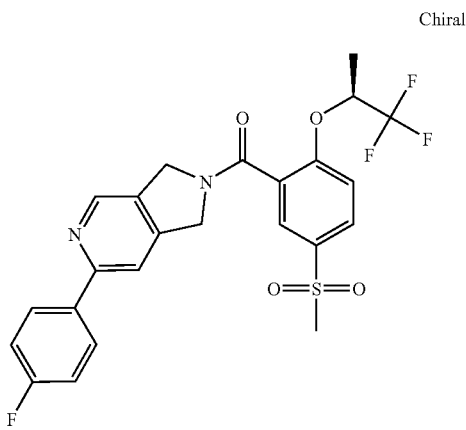

In a glass tube were placed 0.07 mmol 6-Chloro-1,3-dihydro-pyrrolo[3,4-c]pyridin-2-yl)-[5-methanesulfonyl-2-((S)-2,2,2-trifluoro-1-methyl-ethoxy)-phenyl]-methanone (Example 167), 0.07 mmol 4-fluorophenyl boronic acid, 0.2 mmol sodium carbonate, 0.003 mmol Pd(OAc)$_2$, 0.07 mmol tetrabutylammonium bromide, 0.15 ml water and a magnetic stir bar. The vessel was sealed with a septum and placed into the microwave cavity. The temperature was ramped from room temperature to 150° C. Once 150° C. was reached, the reaction mixture was held at this temperature for 5 minutes. After the mixture was allowed to cool to room temperature, the reaction vessel was opened and the contents were poured into a separating funnel. Water and dichloromethane were added, and the aqueous layer was extracted 3 times with dichloromethane. The solvent was removed in vacuo. The residue was purified on a 5.0 g Flashpack cartridge: Eluent: Heptane/AcOEt to provide the title compound (50%). White solid. MS (m/e): 509.3 [M+H]$^+$, 100%).

EXAMPLE 322

[3-(4-Fluoro-phenyl)-5,7-dihydro-pyrrolo[3,4-b]pyridin-6-yl]-[5-methanesulfonyl-2-((S)-2,2,2-trifluoro-1-methyl-ethoxy)-phenyl]-methanone

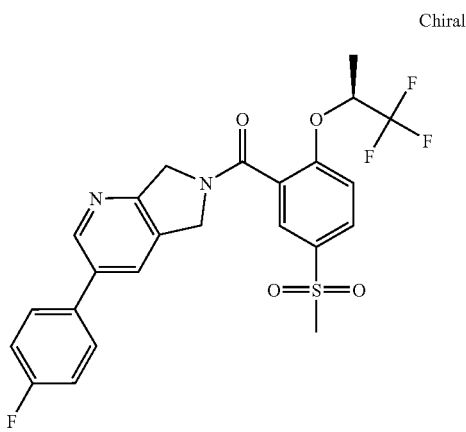

Prepared in analogy to Example 321 from (3-Bromo-5,7-dihydro-pyrrolo[3,4-b]pyridin-6-yl)-[5-methanesulfonyl-2-((S)-2,2,2-trifluoro-1-methyl-ethoxy)-phenyl]-methanone (example 22) and 4-fluorophenyl boronic acid. White solid. MS (m/e): 509.2 [M+H]$^+$, 100%).

EXAMPLE 323

[5-Methanesulfonyl-2-((S)-2,2,2-trifluoro-1-methyl-ethoxy)-phenyl]-(5-phenyl-1,3-dihydro-isoindol-2-yl)-methanone

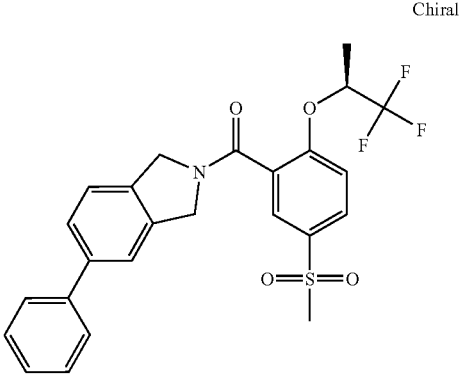

To a solution of 0.19 mmol (5-Iodo-1,3-dihydro-isoindol-2-yl)-[5-methanesulfonyl-2-((S)-2,2,2-trifluoro-1-methyl-ethoxy)-phenyl]-methanone (Example C3) in 1 ml DMF under argon was added successively 0.018 mmol tetrakistriphenylphosphine, 0.28 mmol phenyl boronic acid and 0.56 mmol potassium carbonate. The reaction mixture was heated at 120° C. for 2 hours then cooled to room temperature and filtered. The filtrate was evaporated to dryness and the residue was treated with sat. NaCl. The resulting mixture was extracted 3 times with dichloromethane. The organics phases were dried over sodium sulfate and evaporated. The crude compound was purified on a 10 g of Si-Amine cartridge: n-Heptane/Ethylacetate to provide the title compound (50%). Off-white solid. MS (m/e): 490.0 [M+H]$^+$, 100%).

In analogy to Example 323, compounds 324 to 346 of the following table were prepared from (5-Iodo-1,3-dihydro-isoindol-2-yl)-[5-methanesulfonyl-2-((S)-2,2,2-trifluoro-1-methyl-ethoxy)-phenyl]-methanone (Example C3) and boronic acid derivative:

| Expl. No. | Structure | Systematic Name | Starting materials | MW Calc. | MW Found [M + H]+ |
|---|---|---|---|---|---|
| 324 | Chiral | [5-(2-Chloro-phenyl)-1,3-dihydro-isoindol-2-yl]-[5-methanesulfonyl-2-(2,2,2-trifluoro-1-methyl-ethoxy)-phenyl]-methanone | (5-Iodo-1,3-dihydro-isoindol-2-yl)-[5-methanesulfonyl-2-((S)-2,2,2-trifluoro-1-methyl-ethoxy)-phenyl]-methanone (Example C3) and 2-chloro-phenylboronic acid | 524.0 | 524.3 |
| 325 | Chiral | [5-(3-Chloro-phenyl)-1,3-dihydro-isoindol-2-yl]-[5-methanesulfonyl-2-(2,2,2-trifluoro-1-methyl-ethoxy)-phenyl]-methanone | (5-Iodo-1,3-dihydro-isoindol-2-yl)-[5-methanesulfonyl-2-((S)-2,2,2-trifluoro-1-methyl-ethoxy)-phenyl]-methanone (Example C3) and 3-chloro-phenylboronic acid | 524.0 | 524.3 |
| 326 | Chiral | [5-Methanesulfonyl-2-(2,2,2-trifluoro-1-methyl-ethoxy)-phenyl]-[5-(4-methoxy-phenyl)-1,3-dihydro-isoindol-2-yl]-methanone | (5-Iodo-1,3-dihydro-isoindol-2-yl)-[5-methanesulfonyl-2-((S)-2,2,2-trifluoro-1-methyl-ethoxy)-phenyl]-methanone (Example G3) and 4-methoxy-phenylboronic acid | 519.6 | 520.1 |

-continued

| Expl. No. | Structure | Systematic Name | Starting materials | MW Calc. | MW Found [M + H]+ |
|---|---|---|---|---|---|
| 327 | Chiral | [5-Methanesulfonyl-2-(2,2,2-trifluoro-1-methyl-ethoxy)-phenyl]-(5-p-tolyl-1,3-dihydro-isoindol-2-yl)-methanone | (5-Iodo-1,3-dihydro-isoindol-2-yl)-[5-methanesulfonyl-2-((S)-2,2,2-trifluoro-1-methyl-ethoxy)-phenyl]-methanone (Example C3) and 4-methyl-phenylboronic acid | 503.5 | 504.0 |
| 328 | Chiral | [5-(3,4-Dichloro-phenyl)-1,3-dihydro-isoindol-2-yl]-[5-methanesulfonyl-2-(2,2,2-trifluoro-1-methyl-ethoxy)-phenyl]-methanone | (5-Iodo-1,3-dihydro-isoindol-2-yl)-[5-methanesulfonyl-2-((S)-2,2,2-trifluoro-1-methyl-ethoxy)-phenyl]-methanone (Example C3) and 3,4-dichloro-phenylboronic acid | 558.4 | 557.9 |
| 329 | Chiral | [5-(4-Chloro-phenyl)-1,3-dihydro-isoindol-2-yl]-[5-methanesulfonyl-2-(2,2,2-trifluoro-1-methyl-ethoxy)-phenyl]-methanone | (5-Iodo-1,3-dihydro-isoindol-2-yl)-[5-methanesulfonyl-2-((S)-2,2,2-trifluoro-1-methyl-ethoxy)-phenyl]-methanone (Example G3) and 4-chloro-phenylboronic acid | 524.0 | 524.3 |

-continued

| Expl. No. | Structure | Systematic Name | Starting materials | MW Calc. | MW Found [M + H]+ |
|---|---|---|---|---|---|
| 330 | Chiral | [5-Methanesulfonyl-2-(2,2,2-trifluoro-1-methyl-ethoxy)-phenyl]-(5-thiophen-3-yl-1,3-dihydro-isoindol-2-yl)-methanone | (5-Iodo-1,3-dihydro-isoindol-2-yl)-[5-methanesulfonyl-2-((S)-2,2,2-trifluoro-1-methyl-ethoxy)-phenyl]-methanone (Example C3) and 3-thienyl-boronic acid | 595.5 | 496.1 |
| 331 | Chiral | [5-Methanesulfonyl-2-(2,2,2-trifluoro-1-methyl-ethoxy)-phenyl]-[5-(4-methyl-thiophen-2-yl)-1,3-dihydro-isoindol-2-yl]-methanone | (5-Iodo-1,3-dihydro-isoindol-2-yl)-[5-methanesulfonyl-2-((S)-2,2,2-trifluoro-1-methyl-ethoxy)-phenyl]-methanone (Example C3) and 4-methylthiophene-2-boronic acid | 509.6 | 510.1 |
| 332 | Chiral | [5-Methanesulfonyl-2-(2,2,2-trifluoro-1-methyl-ethoxy)-phenyl]-[5-(3-methyl-thiophen-2-yl)-1,3-dihydro-isoindol-2-yl]-methanone | (5-Iodo-1,3-dihydro-isoindol-2-yl)-[5-methanesulfonyl-2-((S)-2,2,2-trifluoro-1-methyl-ethyoxy)-phenyl]-methanone (Example C3) and 3-methylthiophene-2-boronic acid | 509.6 | 510.1 |
| 333 | Chiral | [5-(4-Fluoro-phenyl)-1,3-dihydro-isoindol-2-yl]-[5-methanesulfonyl-2-(2,2,2-trifluoro-1-methyl-ethoxy)-phenyl]-methanone | (5-Iodo-1,3-dihydro-isoindol-2-yl)-[5-methanesulfonyl-2-((S)-2,2,2-trifluoro-1-methyl-ethyoxy)-phenyl]-methanone (Example C3) and 4-fluoro-phenylboronic acid | 507.5 | 508.1 |

-continued

| Expl. No. | Structure | Systematic Name | Starting materials | MW Calc. | MW Found [M + H]+ |
|---|---|---|---|---|---|
| 334 | 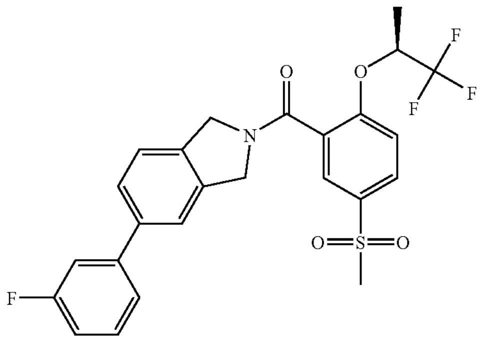 | Chiral [5-(3-Fluoro-phenyl)-1,3-dihydro-isoindol-2-yl]-[5-methanesulfonyl-2-(2,2,2-trifluoro-1-methyl-ethoxy)-phenyl]-methanone | (5-Iodo-1,3-dihydro-isoindol-2-yl)-[5-methanesulfonyl-2-((S)-2,2,2-trifluoro-1-methyl-ethoxy)-phenyl]-methanone (Example G3) and 3-fluoro-phenylboronic acid | 507.5 | 508.1 |
| 335 | 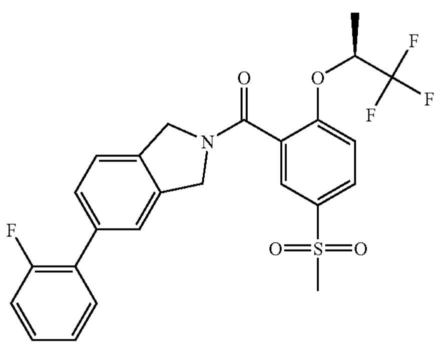 | Chiral [5-(2-Fluoro-phenyl)-1,3-dihydro-isoindol-2-yl]-[5-methanesulfonyl-2-(2,2,2-trifluoro-1-methyl-ethoxy)-phenyl]-methanone | (5-Iodo-1,3-dihydro-isoindol-2-yl)-[5-methanesulfonyl-2-((S)-2,2,2-trifluoro-1-methyl-ethoxy)-phenyl]-methanone (Example G3) and 2-fluoro-phenylboronic acid | 507.5 | 508.1 |
| 336 | 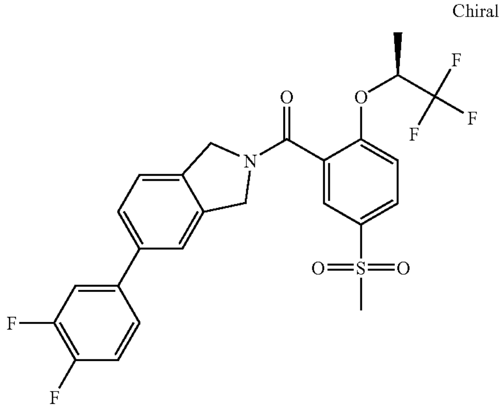 | Chiral [5-(3,4-Difluoro-phenyl)-1,3-dihydro-isoindol-2-yl]-[5-methanesulfonyl-2-(2,2,2-trifluoro-1-methyl-ethoxy)-phenyl]-methanone | (5-Iodo-1,3-dihydro-isoindol-2-yl)-[5-methanesulfonyl-2-((S)-2,2,2-trifluoro-1-methyl-ethoxy)-phenyl]-methanone (Example C3) and 3,4-difluoro-phenylboronic acid | 525.5 | 526.2 |

-continued

| Expl. No. | Structure | Systematic Name | Starting materials | MW Calc. | MW Found [M + H]+ |
|---|---|---|---|---|---|
| 337 | 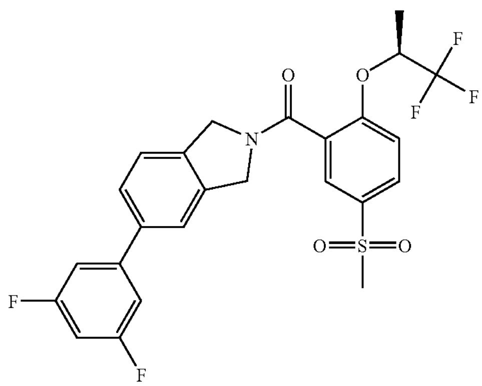 | Chiral [5-(3,5-Difluoro-phenyl)-1,3-dihydro-isoindol-2-yl]-[5-methanesulfonyl-2-2,2,2-trifluoro-1-methyl-ethoxy)-phenyl]-methanone | (5-Iodo-1,3-dihydro-isoindol-2-yl)-[5-methanesulfonyl-2-((S)-2,2,2-trifluoro-1-methyl-ethoxy)-phenyl]-methanone (Example C3) and 3,5-difluoro-phenylboronic acid | 525.5 | 526.2 |
| 338 | 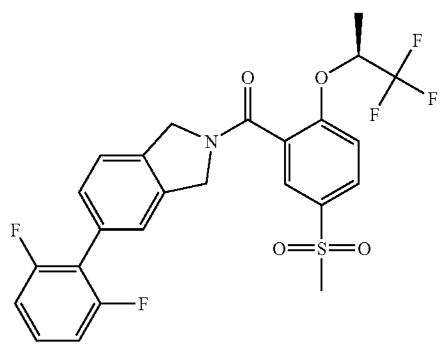 | Chiral [5-(2,6-Difluoro-phenyl)-1,3-dihydro-isoindol-2-yl]-[5-methanesulfonyl-2-(2,2,2-trifluoro-1-methyl-ethoxy)-phenyl]-methanone | (5-Iodo-1,3-dihydro-isoindol-2-yl)-[5-methanesulfonyl-2-((S)-2,2,2-trifluoro-1-methyl-ethoxy)-phenyl]-methanone (Example C3) and 2,6-difluoro-phenylboronic acid | 525.5 | 526.2 |
| 339 | 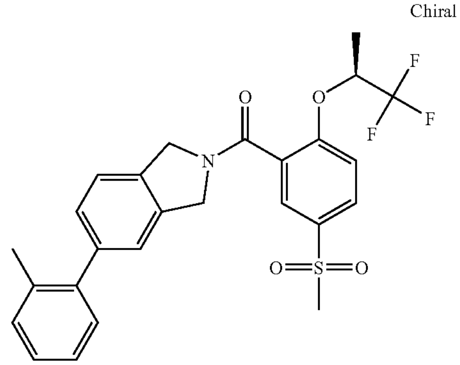 | Chiral [5-Methanesulfonyl-2-(2,2,2-trifluoro-1-methyl-ethoxy)-phenyl]-(5-o-tolyl-1,3-dihydro-isoindol-2-yl)-methanone | (5-Iodo-1,3-dihydro-isoindol-2-yl)-[5-methanesulfonyl-2-((S)-2,2,2-trifluoro-1-methyl-ethoxy)-phenyl]-methanone (Example C3) and 2-methyl-phenylboronic acid | 503.5 | 504.0 |
| 340 | 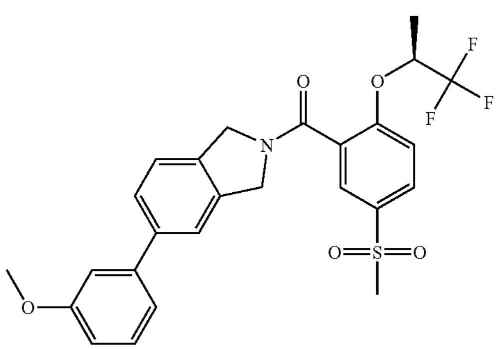 | Chiral [5-Methanesulfonyl-2-(2,2,2-trifluoro-1-methyl-ethoxy)-phenyl]-[5-(3-methoxy-phenyl)-1,3-dihydro-isoindol-2-yl]-methanone | (5-Iodo-1,3-dihydro-isoindol-2-yl)-[5-methanesulfonyl-2-((S)-2,2,2-trifluoro-1-methyl-ethoxy)-phenyl]-methanone (Example C3) and 3-methoxy-phenylboronic acid | 519.5 | 520.1 |

-continued

| Expl. No. | Structure | Systematic Name | Starting materials | MW Calc. | MW Found [M + H]+ |
|---|---|---|---|---|---|
| 341 | Chiral | [5-(2,6-Dimethyl-phenyl)-1,3-dihydro-isoindol-2-yl]-[5-methanesulfonyl-2-(2,2,2-trifluoro-1-methyl-ethoxy)-phenyl]-methanone | (5-Iodo-1,3-dihydro-isoindol-2-yl)-[5-methanesulfonyl-2-((S)-2,2,2-trifluoro-1-methyl-ethoxy)-phenyl]-methanone (Example C3) and 2,6-dimethyl-phenylboronic acid | 517.6 | 518.2 |
| 342 | Chiral | [5-Methanesulfonyl-2-(2,2,2-trifluoro-1-methyl-ethoxy)-phenyl]-(5-m-tolyl-1,3-dihydro-isoindol-2-yl)-methanone | (5-Iodo-1,3-dihydro-isoindol-2-yl)-[5-methanesulfonyl-2-((S)-2,2,2-trifluoro-1-methyl-ethoxy)-phenyl]-methanone (Example C3) and 3-methyl-phenylboronic acid | 503.5 | 504.0 |
| 343 | Chiral | [5-Methanesulfonyl-2-(2,2,2-trifluoro-1-methyl-ethoxy)-phenyl]-[5-(2-methoxy-phenyl)-1,3-dihydro-isoindol-2-yl]-methanone | (5-Iodo-1,3-dihydro-isoindol-2-yl)-[5-methanesulfonyl-2-((S)-2,2,2-trifluoro-1-methyl-ethoxy)-phenyl]-methanone (Example C3) and 2-methoxy-phenylboronic acid | 519.5 | 520.1 |
| 344 | Chiral | [5-Methanesulfonyl-2-((S)-2,2,2-trifluoro-1-methyl-ethoxy)-phenyl]-(5-thiophen-2-yl-1,3-dihydro-isoindol-2-yl)-methanone | (5-Iodo-1,3-dihydro-isoindol-2-yl)-[5-methanesulfonyl-2-((S)-2,2,2-trifluoro-1-methyl-ethoxy)-phenyl]-methanone (Example C3) and 2-thienyl-boronic acid | 495.5 | 496.0 |

-continued

| Expl. No. | Structure | Systematic Name | Starting materials | MW Calc. | MW Found [M + H]+ |
|---|---|---|---|---|---|
| 345 | Chiral | [5-Methanesulfonyl-2-((S)-2,2,2-trifluoro-1-methyl-ethoxy)-phenyl]-[5-(4-methyl-thiophen-3-yl)-1,3-dihydro-isoindol-2-yl]-methanone | (5-Iodo-1,3-dihydro-isoindol-2-yl)-[5-methanesulfonyl-2-((S)-2,2,2-trifluoro-1-methyl-ethoxy)-phenyl]-methanone (Example C3) and 4-Methyl-3-thiopheneboronic acid | 509.6 | 510.1 |
| 346 | Chiral | [5-Methanesulfonyl-2-((S)-2,2,2-trifluoro-1-methyl-ethoxy)-phenyl]-[5-(5-methyl-thiophen-2-yl)-1,3-dihydro-isoindol-2-yl]-methanone | (5-Iodo-1,3-dihydro-isoindol-2-yl)-[5-methanesulfonyl-2-((S)-2,2,2-trifluoro-1-methyl-ethoxy)-phenyl]-methanone (Example C3) and 5-Methylthiophene-2-boronic acid | 509.6 | 510.2 |

In analogy to Example B32(a), compounds 347 to 352 of the following table were prepared from (5-Iodo-1,3-dihydro-isoindol-2-yl)-[5-methanesulfonyl-2-((S)-2,2,2-trifluoro-1-methyl-ethoxy)-phenyl]-methanone (Example C3) and heterocyclic derivatives in the presence of the mentioned ligand:

| Expl. No. | Structure | Systematic Name | Starting materials | MW Calc. | MW Found [M + H]+ |
|---|---|---|---|---|---|
| 347 | Chiral | [5-Methanesulfonyl-2-((S)-2,2,2-trifluoro-1-methyl-ethoxy)-phenyl]-(5-pyrazol-1-yl-1,3-dihydro-isoindol-2-yl)-methanone | (5-Iodo-1,3-dihydro-isoindol-2-yl)-[5-methanesulfonyl-2-((S)-2,2,2-trifluoro-1-methyl-ethoxy)-phenyl]-methanone (Example C3) and pyrazole and with trans-1,2-diaminocyclohexane as ligand | 479.5 | 480.0 |

-continued

| Expl. No. | Structure | Systematic Name | Starting materials | MW Calc. | MW Found [M + H]+ |
|---|---|---|---|---|---|
| 348 | Chiral | [5-Methanesulfonyl-2-((S)-2,2,2-trifluoro-1-methyl-ethoxy)-phenyl]-(5-[1,2,4]triazol-1-yl-1,3-dihydro-isoindol-2-yl)-methanone | (5-Iodo-1,3-dihydro-isoindol-2-yl)-[5-methanesulfonyl-2-((S)-2,2,2-trifluoro-1-methyl-ethoxy)-phenyl]-methanone (Example C3) and 1,2,4-triazole and (1R,2R)-Diaminomethylcyclohexane as ligand | 480.5 | 481.1 |
| 349 | Chiral | [5-Methanesulfonyl-2-((S)-2,2,2-trifluoro-1-methyl-ethoxy)-phenyl]-[5-(4-methyl-imidazol-1-yl)-1,3-dihydro-isoindol-2-yl]-methanone | (5-Iodo-1,3-dihydro-isoindol-2-yl)-[5-methanesulfonyl-2-((S)-2,2,2-trifluoro-1-methyl-ethoxy)-phenyl]-methanone (Example C3) and 4-methylimidazole and 1,10-phenanthroline as ligand | 493.5 | 494.1 |
| 350 | Chiral | (5-Imidazol-1-yl-1,3-dihydro-isoindol-2-yl)-[5-methanesulfonyl-2-((S)-2,2,2-trifluoro-1-methyl-ethoxy)-phenyl]-methanone | (5-Iodo-1,3-dihydro-isoindol-2-yl)-[5-methanesulfonyl-2-((S)-2,2,2-trifluoro-1-methyl-ethoxy)-phenyl]-methanone (Example C3) and imidazole and 1,10-phenanthroline as ligand | 479.5 | 480.0 |
| 351 | Chiral | [5-Methanesulfonyl-2-((S)-2,2,2-trifluoro-1-methyl-ethoxy)-phenyl]-[5-(4-methyl-pyrazol-1-yl)-1,3-dihydro-isoindol-2-yl]-methanone | (5-Iodo-1,3-dihydro-isoindol-2-yl)-[5-methanesulfonyl-2-((S)-2,2,2-trifluoro-1-methyl-ethoxy)-phenyl]-methanone (Example C3) and Methylpyrazole and 1,10-phenanthroline as ligand | 493.5 | 494.1 |

| Expl. No. | Structure | Systematic Name | Starting materials | MW Calc. | MW Found [M + H]+ |
|---|---|---|---|---|---|
| 352 | 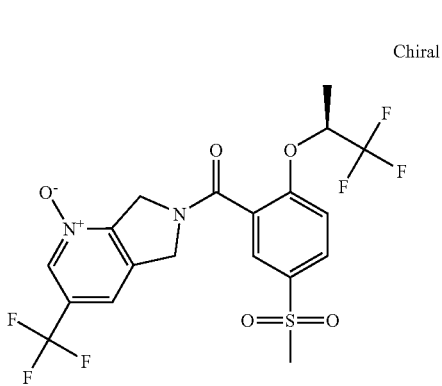 Chiral | [5-Methanesulfonyl-2-((S)-2,2,2-trifluoro-1-methyl-ethoxy)-phenyl]-[5-(2-methyl-imidazol-1-yl)-1,3-dihydro-isoindol-2-yl]-methanone | (5-Iodo-1,3-dihydro-isoindol-2-yl)-[5-methanesulfonyl-2-((S)-2,2,2-trifluoro-1-methyl-ethoxy)-phenyl]-methanone (Example C3) and 2-Methylimidazole and 1,10-phenanthroline as ligand | 493.5 | 494.4 |

EXAMPLE 353

[5-Methanesulfonyl-2-((S)-2,2,2-trifluoro-1-methyl-ethoxy)-phenyl]-(1-oxy-3-trifluoromethyl-5,7-dihydro-pyrrolo[3,4-b]pyridin-6-yl)-methanone

EXAMPLE 354

6-Chloro-2-(2-isopropoxy-5-methanesulfonyl-benzoyl)-2,3-dihydro-isoindol-1-one

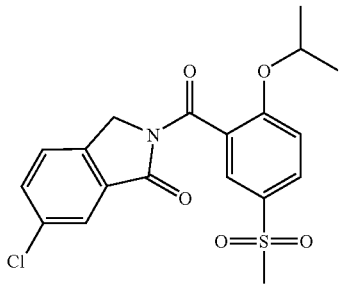

To a solution of 0.21 mmol [5-Methanesulfonyl-2-((S)-2,2,2-trifluoro-1-methyl-ethoxy)-phenyl]-(3-trifluoromethyl-5,7-dihydro-pyrrolo[3,4-b]pyridin-6-yl)-methanone (example 61) in 2 ml dichloromethane was added 0.31 mmol 3-chloroperbenzoic acid. The mixture was stirred at room temperature for 72 hours. The mixture was diluted with dichloromethane. The solution was washed twice with a sat. bicarbonate solution and once with a 10% sodium carbonate solution to destroy any residual peroxides, dried over sodium sulfate, filtered and the solvent was removed in vacuo. The crude solid was purified on a 5 g Flashpack cartridge. Eluent: Heptane/ethylacetate to provide the title compound (92%). White foam. MS (m/e): 516.1 [M+NH4]+, 100%).

0.4 mmol 6-chloro-1-isoindolinone (CAS: 58083-59-3) was dissolved in 3 nml of pyridine. 0.05 mmol of 4-dimethylaminopyridine was added, followed by slow addition of a solution of 0.5 mmol 2-isopropoxy-5-methanesulfonyl-benzoyl chloride (prepared from example B1 and oxalyl chloride in dichloromethane) in 2 ml dichloromethane at room temperature. The reaction mixture is stirred for 10 minutes at room temperature, then the dichloromethane is stripped off in the rotatory evaporator. The remaining solution was then refluxed for 3 hours. The dark red solution was quenched with water, acidified by addition of diluted hydrochloric acid and extracted 3 times with ethyl acetate. The organic phase is dried and concentrated. Chromatography (silica gel; ethyl acetate/heptane) gave the title compound as a slightly yellowish solid. Yield=55%. MS (m/e): 408.2 [M+H]+, 100%).

EXAMPLE 355

[5-Methanesulfonyl-2-((S)-2,2,2-trifluoro-1-methyl-ethoxy)-phenyl]-(4-morpholin-4-yl-2,3-dihydro-indol-1-yl)-methanone

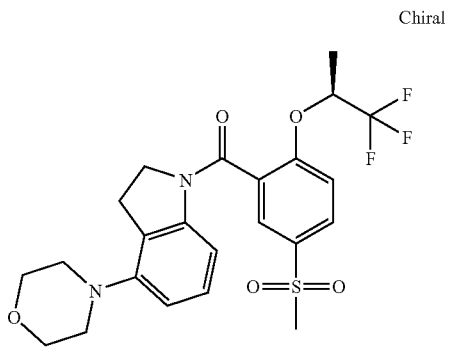

A mixture of 0.2 mmol (4-Bromo-2,3-dihydro-indol-1-yl)-[5-methanesulfonyl-2-((S)-2,2,2-trifluoro-1-methyl-ethoxy)-phenyl]-methanone (example 211), 0.4 mmol morpholine, 0.3 mmol sodium tert-butylate, 2.5 mg rac.BINAP and 2.0 mg tris-(dibenzylidenaceton)-dipalladium chloroform complex in 5 ml toluene is heated at 80° C. for 3 hours. Fresh morpholine (0.4 mmol) is added and the mixture hold at 80° overnight. The reaction mixture is concentrated. Chromatography of the residue (silica gel; ethyl acetate/heptane) yields the title compound as a slightly yellow solid. Yield=57%. MS (m/e): 499.3 [M+H]$^+$, 100%).

EXAMPLE 356

[5-Methanesulfonyl-2-((S)-2,2,2-trifluoro-1-methyl-ethoxy)-phenyl]-(6-morpholin-4-yl-1,3-dihydro-pyrrolo[3,4-c]pyridin-2-yl)-methanone

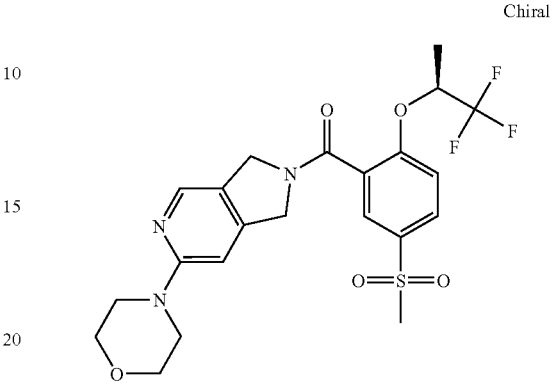

A mixture of 0.33 mmol (6-Chloro-1,3-dihydro-pyrrolo[3,4-c]pyridin-2-yl)-[5-methanesulfonyl-2-((S)-2,2,2-trifluoro-1-methyl-ethoxy)-phenyl]-methanone (example 167), 0.67 mmol morpholine in 2 ml dimethylacetamide is heated at 180° C. for 30 minutes in a microwave oven. The solvent was removed in vacuo. Chromatography of the residue (silica gel; ethyl acetate/heptane) yields the title compound as a white solid. Yield=13%. MS (m/e): 500.1 [M+H]$^+$, 100%).

In analogy to Example 1, compounds 357 to 380 of the following table were prepared from the acid derivatives and amine derivatives:

| Expl. No. | Structure | Systematic Name | Starting materials | MW Calc. | MW Found [M + H]$^+$ |
|---|---|---|---|---|---|
| 357 | Chiral | [5-Methanesulfonyl-2-((S)-2,2,2-trifluoro-1-methyl-ethoxy)-phenyl]-[5-(2,2,2-trifluoro-ethoxy)-1,3-dihydro-isoindol-2-yl]-methanone | 5-(2,2,2-Trifluoro-ethoxy)-2,3-dihydro-1H-isoindole hydrochloride (example A74) and 5-Methanesulfonyl-2-((S)-2,2,2-trifluoro-1-methyl-ethoxy)-benzoic acid (example B3) | 511.4 | 512.2 |
| 358 | 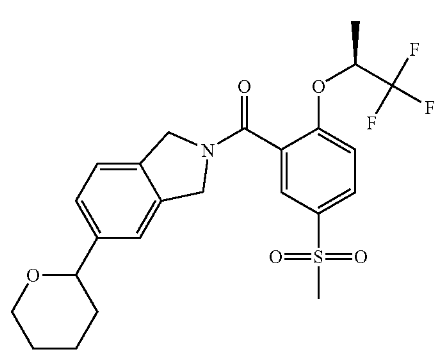 | [5-Methanesulfonyl-2-((S)-2,2,2-trifluoro-1-methyl-ethoxy)-phenyl]-[5-(tetrahydro-pyran-2-yl)-1,3-dihydro-isoindol-2-yl]-methanone | rac-5-(Tetrahydro-pyran-2-yl)-2,3-dihydro-1H-isoindole (example A75) and 5-Methanesulfonyl-2-((S)-2,2,2-trifluoro-1-methyl-ethoxy)-benzoic acid (example B3) | 497.5 | 498.5 |

-continued

| Expl. No. | Structure | Systematic Name | Starting materials | MW Calc. | MW Found [M + H]+ |
|---|---|---|---|---|---|
| 359 | 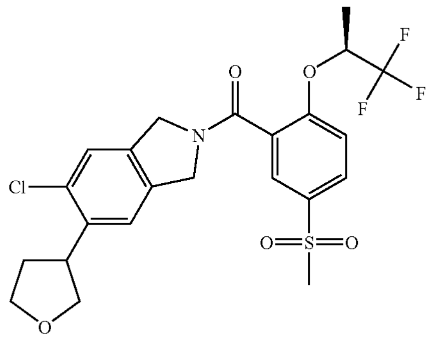 | [5-Chloro-6-(tetrahydro-furan-3-yl)-1,3-dihydro-isoindol-2-yl]-[5-methanesulfonyl-2-((S)-2,2,2-trifluoro-1-methyl-ethoxy)-phenyl]-methanone | rac-5-Chloro-6-(tetrahydro-furan-3-yl)-2,3-dihydro-1H-isoindole trifluoroacetate (example A76) and 5-Methanesulfonyl-2-((S)-2,2,2-trifluoro-1-methyl-ethoxy)-benzoic acid (example B3) | 518.0 | 520.1 ($^{37}$Cl) 518.2 ($^{35}$Cl) |
| 360 | 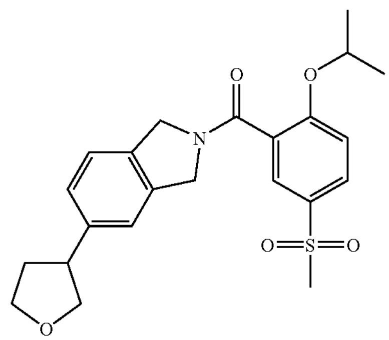 | rac-(2-Isopropoxy-5-methanesulfonyl-phenyl)-[5-(tetrahydro-furan-3-yl)-1,3-dihydro-isoindol-2-yl]-methanone | rac-5-(Tetrahydro-furan-3-yl)-2,3-dihydro-1H-isoindole (example A67) and 2-Isopropoxy-5-methanesulfonyl-benzoic acid (example B1) | 429.5 | 430.0 |
| 361 | 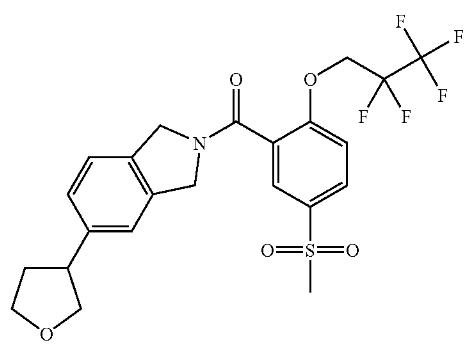 | rac-[5-Methanesulfonyl-2-(2,2,3,3,3-pentafluoro-propoxy)-phenyl]-[5-(tetrahydro-furan-3-yl)-1,3-dihydro-isoindol-2-yl]-methanone | rac-5-(Tetrahydro-furan-3-yl)-2,3-dihydro-1H-isoindole (example A67) and 5-Methanesulfonyl-2-(2,2,3,3,3-pentafluoro-propoxy)-benzoic acid (CAS: 845616-42-4) | 519.5 | 520.0 |
| 362 | 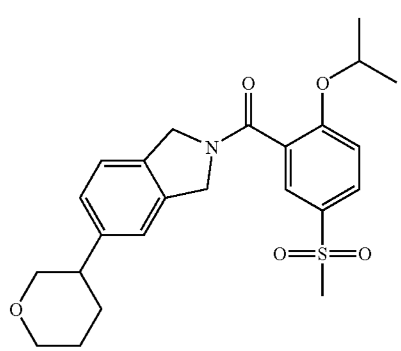 | rac-(2-Isopropoxy-5-methanesulfonyl-phenyl)-[5-(tetrahydro-pyran-3-yl)-1,3-dihydro-isoindol-2-yl]-methanone | rac-5-(Tetrahydro-pyran-3-yl)-2,3-dihydro-1H-isoindole (example A73) and 2-Isopropoxy-5-methanesulfonyl-benzoic acid (example B1) | 443.6 | 444.3 |

-continued

| Expl. No. | Structure | Systematic Name | Starting materials | MW Calc. | MW Found [M + H]+ |
|---|---|---|---|---|---|
| 363 | 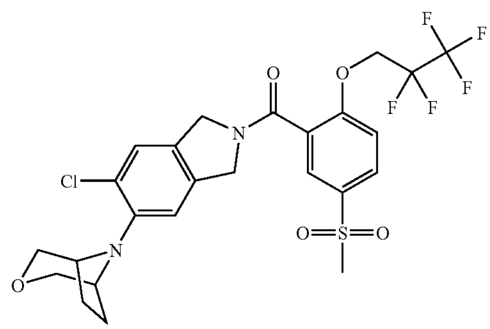 | [5-Chloro-6-(3-oxa-8-aza-bicyclo[3.2.1]oct-8-yl)-1,3-dihydro-isoindol-2-yl]-[5-methanesulfonyl-2-(2,2,3,3,3-pentafluoro-propoxy)-phenyl]-methanone | 8-(6-Chloro-2,3-dihydro-1H-isoindol-5-yl)-3-oxa-8-aza-bicyclo [3.2.1]octane trifluoroacetate (example A77) and 5-Methanesulfonyl-2-(2,2,3,3,3-pentafluoro-propoxy)-benzoic acid (GAS: 845616-42-4) | 595.0 | 597.2 ($^{37}$Cl) 595.1 ($^{35}$Cl) |
| 364 | 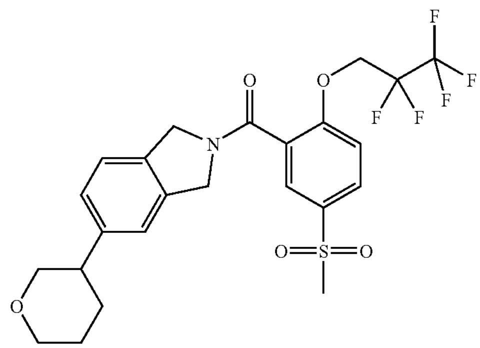 | rac-[5-Methanesulfonyl-2-(2,2,3,3,3-pentafluoro-propoxy)-phenyl]-[5-(tetrahydro-pyran-3-yl)-1,3-dihydro-isoindol-2-yl]-methanone | rac-5-(Tetrahydro-pyran-3-yl)-2,3-dihydro-1H-isoindole (example A73) and 5-Methanesulfonyl-2-(2,2,3,3,3-pentafluoro-propoxy)-benzoic acid (CAS: 845616-42-4) | 533.5 | 534.3 |
| 365 | Chiral | ((1S,4S)-5-Chloro-6-2-oxa-5-aza-bicyclo[2.2.1]hept-5-yl-1,3-dihydro-isoindol-2-yl)-[5-methanesulfonyl-2-((S)-2,2,2-trifluoro-1-methyl-ethoxy)-phenyl]-methanone | 5-Chloro-6-(1S,4S)-2-oxa-5-aza-bicyclo[2.2.1]hept-5-yl-2,3-dihydro-1H-isoindole trifluoroacetate (example A78) and 5-Methanesulfonyl-2-((S)-2,2,2-trifluoro-1-methyl-ethoxy)-benzoic acid (example B3) | 545.0 | 547.2 ($^{37}$Cl) 545.3 ($^{35}$Cl) |
| 366 | Chiral | [5-Fluoro-6-(tetrahydro-pyran-4-yl)-1,3-dihydro-isoindol-2-yl]-[5-methanesulfonyl-2-((S)-2,2,2-trifluoro-1-methyl-ethoxy)-phenyl]-methanone | 5-Fluoro-6-(tetrahydro-pyran-4-yl)-2,3-dihydro-1H-isoindole (example A79) and 5-Methanesulfonyl-2-((S)-2,2,2-trifluoro-1-methyl-ethoxy)-benzoic acid (example B3) | 515.5 | 516.3 |

-continued

| Expl. No. | Structure | Systematic Name | Starting materials | MW Calc. | MW Found [M + H]+ |
|---|---|---|---|---|---|
| 367 | Chiral | [5-Methanesulfonyl-2-((S)-2,2,2-trifluoro-1-methyl-ethoxy)-phenyl]-[5-(tetrahydro-pyran-4-yloxy)-1,3-dihydro-isoindol-2-yl]-methanone | 5-(Tetrahydro-pyran-4-yloxy)-2,3-dihydro-1H-isoindole trifluoroacetate (example A80) and 5-Methanesulfonyl-2-((S)-2,2,2-trifluoro-1-methyl-ethoxy)-benzoic acid (example B3) | 513.5 | 514.5 |
| 368 | Chiral | [5-(3-Fluoro-oxetan-3-yl)-1,3-dihydro-isoindol-2-yl]-[5-methanesulfonyl-2-((S)-2,2,2-trifluoro-1-methyl-ethoxy)-phenyl]-methanone | 5-(3-Fluoro-oxetan-3-yl)-2,3-dihydro-1H-isoindole (example A81) and 5-Methanesulfonyl-2-((S)-2,2,2-trifluoro-1-methyl-ethoxy)-benzoic acid (example B3) | 487.5 | 488.0 |
| 369 | Chiral | (5-Cyclopropylmethoxy-1,3-dihydro-isoindol-2-yl)-[5-methanesulfonyl-2-((S)-2,2,2-trifluoro-1-methyl-ethoxy)-phenyl]-methanone | 5-Cyclopropylmethoxy-2,3-dihydro-1H-isoindole trifluoroacetate (example A82) and 5-Methanesulfonyl-2-((S)-2,2,2-trifluoro-1-methyl-ethoxy)-benzoic acid (example B3) | 483.5 | 484.3 |
| 370 | Chiral | [5-Methanesulfonyl-2-((S)-2,2,2-trifluoro-1-methyl-ethoxy)-phenyl]-[5-(3,3,3-trifluoro-propoxy)-1,3-dihydro-isoindol-2-yl]-methanone | 5-(3,3,3-Trifluoro-propoxy)-2,3-dihydro-1H-isoindole trifluoroacetate (example A83) and 5-Methanesulfonyl-2-((S)-2,2,2-trifluoro-1-methyl-ethoxy)-benzoic acid (example B3) | 525.5 | 526.2 |

-continued

| Expl. No. | Structure | Systematic Name | Starting materials | MW Calc. | MW Found [M + H]+ |
|---|---|---|---|---|---|
| 371 | Chiral | (5-Fluoro-6-morpholin-4-yl-1,3-dihydro-isoindol-2-yl)-[5-methanesulfonyl-2-((S)-2,2,2-trifluoro-1-methyl-ethoxy)-phenyl]-methanone | 5-Fluoro-6-morpholin-4-yl-2,3-dihydro-1H-isoindole trifluoroacetate (example A84) and 5-Methanesulfonyl-2-((S)-2,2,2-trifluoro-1-methyl-ethoxy)-benzoic acid (example B3) | 516.5 | 517.3 |
| 372 | 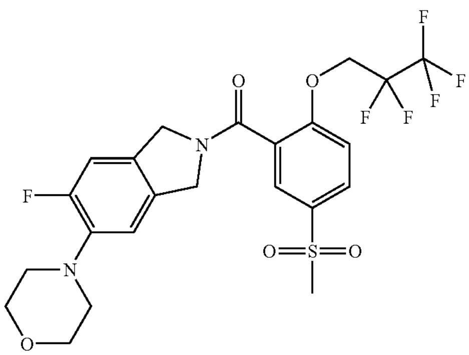 | (5-Fluoro-6-morpholin-4-yl-1,3-dihydro-isoindol-2-yl)-[5-methanesulfonyl-2-(2,2,3,3,3-pentafluoro-propoxy)-phenyl]-methanone | 5-Fluoro-6-morpholin-4-yl-2,3-dihydro-1H-isoindole trifluoroacetate (example A84) and 5-Methanesulfonyl-2-(2,2,3,3,3-pentafluoro-propoxy)-benzoic acid (CAS: 845616-42-4) | 552.5 | 553.3 |
| 373 | 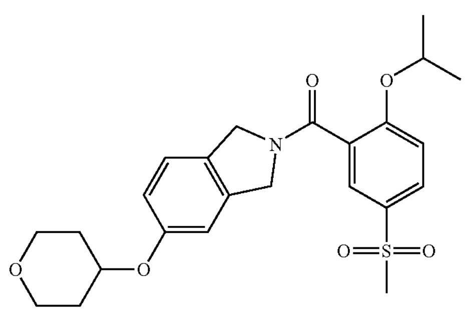 | (2-Isopropoxy-5-methanesulfonyl-phenyl)-[5-(tetrahydro-pyran-4-yloxy)-1,3-dihydro-isoindol-2-yl]-methanone | 5-(Tetrahydro-pyran-4-yloxy)-2,3-dihydro-1H-isoindole trifluoroacetate (example A80) and 2-Isopropoxy-5-methanesulfonyl-benzoic acid (example B1) | 459.6 | 460.1 |
| 374 | 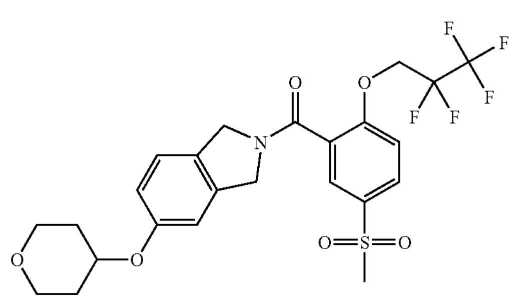 | [5-Methanesulfonyl-2-(2,2,3,3,3-pentafluoro-propoxy)-phenyl]-[5-(tetrahydro-pyran-4-yloxy)-1,3-dihydro-isoindol-2-yl]-methanone | 5-(Tetrahydro-pyran-4-yloxy)-2,3-dihydro-1H-isoindole trifluoroacetate (example A80) and 5-Methanesulfonyl-2-(2,2,3,3,3-pentafluoro-propoxy)-benzoic acid (CAS: 845616-42-4) | 549.5 | 550.2 |

-continued

| Expl. No. | Structure | Systematic Name | Starting materials | MW Calc. | MW Found [M + H]+ |
|---|---|---|---|---|---|
| 375 | Chiral | [5-Chloro-6-(tetrahydro-pyran-4-yloxy)-1,3-dihydro-isoindol-2-yl]-[5-methanesulfonyl-2-((S)-2,2,2-trifluoro-1-methyl-ethoxy)-phenyl]-methanone | 5-Chloro-6-(tetrahydro-pyran-4-yloxy)-2,3-dihydro-1H-isoindole trifluoroacetate (example A85) and 5-Methanesulfonyl-2-((S)-2,2,2-trifluoro-1-methyl-ethoxy)-benzoic acid (example B3) | 548.0 | 550.2 ($^{37}$Cl) 548.1 ($^{35}$Cl) |
| 376 | 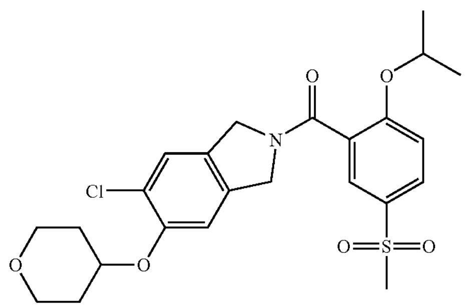 | [5-Chloro-6-(tetrahydro-pyran-4-yloxy)-1,3-dihydro-isoindol-2-yl]-(2-isopropoxy-5-methanesulfonyl-phenyl)-methanone | 5-Chloro-6-(tetrahydro-pyran-4-yloxy)-2,3-dihydro-1H-isoindole trifluoroacetate (example A85) and 2-Isopropoxy-5-methanesulfonyl-benzoic acid (example B1) | 494.0 | 496.1 ($^{37}$Cl) 494.1 ($^{35}$Cl) |
| 377 | Chiral | [5-Fluoro-6-(tetrahydro-pyran-4-yloxy)-1,3-dihydro-isoindol-2-yl]-[5-methanesulfonyl-2-((S)-2,2,2-trifluoro-1-methyl-ethoxy)-phenyl]-methanone | 5-Fluoro-6-(tetrahydro-pyran-4-yloxy)-2,3-dihydro-1H-isoindole trifluoroacetate (example A86) and 5-Methanesulfonyl-2-((S)-2,2,2-trifluoro-1-methyl-ethoxy)-benzoic acid (example B3) | 531.5 | 532.0 |
| 378 | 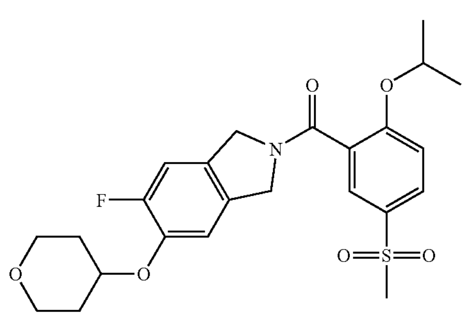 | [5-Fluoro-6-(tetrahydro-pyran-4-yloxy)-1,3-dihydro-isoindol-2-yl]-(2-isopropoxy-5-methanesulfonyl-phenyl)-methanone | 5-Fluoro-6-(tetrahydro-pyran-4-yloxy)-2,3-dihydro-1H-isoindole trifluoroacetate (example A86) and 2-Isopropoxy-5-methanesulfonyl-benzoic acid (example B1) | 477.6 | 478.0 |

| Expl. No. | Structure | Systematic Name | Starting materials | MW Calc. | MW Found [M + H]+ |
|---|---|---|---|---|---|
| 379 | 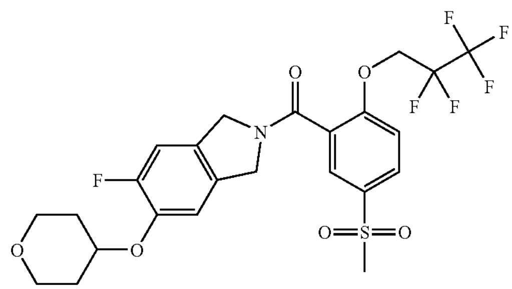 | [5-Fluoro-6-(tetrahydro-pyran-4-yloxy)-1,3-dihydro-isoindol-2-yl]-[5-methanesulfonyl-2-(2,2,3,3,3-pentafluoro-propoxy)-phenyl]-methanone | 5-Fluoro-6-(tetrahydro-pyran-4-yloxy)-2,3-dihydro-1H-isoindole trifluoroacetate (example A86) and 5-Methanesulfonyl-2-(2,2,3,3,3-pentafluoro-propoxy)-benzoic acid (CAS: 845616-42-4) | 567.5 | 568.2 |
| 380 | 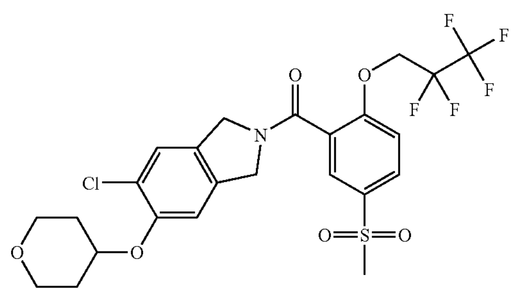 | [5-Chloro-6-(tetrahydro-pyran-4-yloxy)-1,3-dihydro-isoindol-2-yl]-[5-methanesulfonyl-2-(2,2,3,3,3-pentafluoro-propoxy)-phenyl]-methanone | 5-Chloro-6-(tetrahydro-pyran-4-yloxy)-2,3-dihydro-1H-isoindole trifluoroacetate (example A85) and 5-Methanesulfonyl-2-(2,2,3,3,3-pentafluoro-propoxy)-benzoic acid (CAS: 845616-42-4) | 584.0 | 586.1 ($^{37}Cl$) 584.0 ($^{35}Cl$) |

EXAMPLE 381

[5-Methanesulfonyl-2-((S)-2,2,2-trifluoro-1-methyl-ethoxy)-phenyl]-[2-(3-trifluoromethyl-phenyl)-5,7-dihydro-pyrrolo[3,4-b]pyridin-6-yl]-methanone

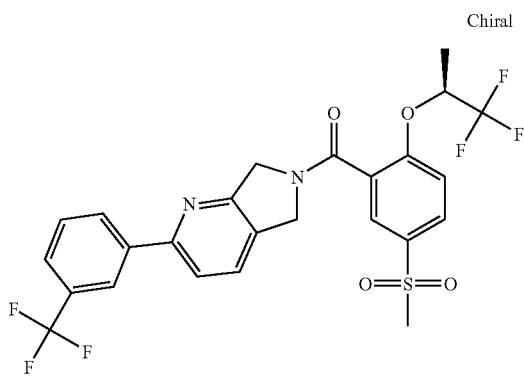

Prepared in analogy to Example A54(a) from (2-chloro-5,7-dihydro-pyrrolo[3,4-b]pyridin-6-yl)-[5-methanesulfonyl-2-((S)-2,2,2-trifluoro-1-methyl-ethoxy)-phenyl]-methanone (Example C4) and tributyl-[3-(trifluoromethyl)phenyl]-stannane. White solid. MS (m/e): 559.2 [M+H]+, 100%).

EXAMPLE 382

[2-(4-Fluoro-phenyl)-5,7-dihydro-pyrrolo[3,4-b]pyridin-6-yl]-[5-methanesulfonyl-2-((S)-2,2,2-trifluoro-1-methyl-ethoxy)-phenyl]-methanone

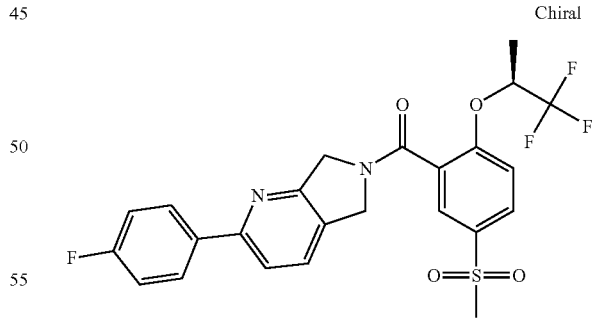

Prepared in analogy to Example A54(a) from (2-chloro-5,7-dihydro-pyrrolo[3,4-b]pyridin-6-yl)-[5-methanesulfonyl-2-((S)-2,2,2-trifluoro-1-methyl-ethoxy)-phenyl]-methanone (Example C4) and tributyl(4-fluorophenyl)stannane. White solid. MS (m/e): 509.1 [M+H]+, 100%).

The invention claimed is:
1. A compound of formula I

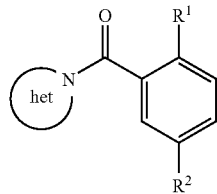

I wherein
R$^1$ is halogen, —OR$^{1'}$, —SR$^{1'''}$, morpholin, heterocycloalkyl, aryl or 5-or 6-membered heteroaryl;
R$^{1'}$ and R$^{1'''}$ are each independently hydrogen, lower alkyl, lower alkyl substituted by halogen, —(CH$_2$)$_x$-cycloalkyl or —(CH$_2$)$_x$-aryl;
R$^2$ is —S(O)$_2$-lower alkyl, —S(O)$_2$NH-lower alkyl, or CN;

is an aromatic or partially aromatic bicyclic amine, having one or two additional N-atoms selected from the group consisting of

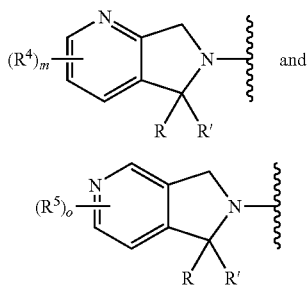

and wherein one additional N-ring atom of the aromatic or partially aromatic bicyclic amine can be available in form of its oxide

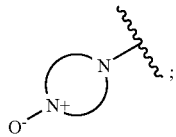

R$^3$ to R$^{10}$ are each independently hydrogen, hydroxy, halogen, =O, lower alkyl, cycloalkyl, heterocycloalkyl, lower alkoxy, CN, NO$_2$, NH$_2$, aryl, 5- or 6-membered heteroaryl containing one, two or three heteroatoms selected from the group consisting of oxygen, sulphur and nitrogen, —NH-lower alkyl, —N(lower alkyl)$_2$, cyclic amide, —C(O)-cyclic amide, S-lower alkyl, —S(O)$_2$-lower alkyl, lower alkyl substituted by halogen, lower alkoxy substituted by halogen, lower alkyl substituted by hydroxy, —O—(CH$_2$)$_y$-lower alkoxy, —O(CH$_2$)$_y$C(O)N(lower alkyl)$_2$, —C(O)-lower alkyl, —O—(CH$_2$)$_x$-aryl, —O—(CH$_2$)$_x$-cycloalkyl, —O—(CH$_2$)$_x$-heterocycloalkyl, —C(O)O-lower alkyl, —C(O)—NH-lower alkyl, —C(O)—N(lower alkyl)$_2$, 2-oxy-5-aza-bicyclo[2.2.1]hept-5-yl or 3-oxa-8-aza-bicyclo[3.2.1]oct-8-yl;
R and R', are each independently hydrogen or lower alkyl;
wherein heteroaryl is selected from the group consisting of furanyl, thienyl, pyrrolyl, imidazolyl, pyrazolyl, triazolyl, thiazolyl, isothiazolyl, isoxazolyl, pyridinyl, pyrazinyl, and pyrimidinyl; and
heterocycloalkyl is selected from the group consisting of tetrahydropyran-2, 3 or 4-yl, tetrahydrofuran-2 or 3-yl, oxetan-3-yl, and [1,4]dioxin-2-yl;
and wherein all aryl-, morpholin, heterocycloalkyl- or 5 or 6 membered heteroaryl groups as defined for R$^1$, R$^{1'}$, R$^{1'''}$ and R$^3$ to R$^{10}$ are unsubstituted or substituted by one or more substituents selected from the group consisting of hydroxy, =O, halogen, lower alkyl, phenyl, lower alkyl substituted by halogen and lower alkoxy;
n, m, o, p, q, r, s and t are each independently 1 or 2;
x is 0, 1 or 2; and
y is 1 or 2;
or a pharmaceutically acceptable acid addition salt thereof.
2. A compound of claim 1, having formula IB

IB wherein
R$^1$ is halogen, —OR$^{1'}$, —SR$^{1'''}$, morpholin, heterocycloalkyl, aryl or 5- or 6-membered heteroaryl;
R$^{1'}$ and R$^{1'''}$ are each independently hydrogen, lower alkyl, lower alkyl substituted by halogen, —(CH$_2$)$_x$-cycloalkyl or —(CH$_2$)$_x$-aryl;
R$^2$ is —S(O)$_2$-lower alkyl, —S(O)$_2$NH-lower alkyl, or CN;
and wherein the additional N-ring atom of the bicyclic amine can be available in form of its oxide R$^4$ is hydrogen, hydroxy, halogen, =O, lower alkyl, cycloalkyl, heterocycloalkyl, lower alkoxy, CN, NO$_2$, NH$_2$, aryl, 5- or 6-membered heteroaryl containing one, two or three heteroatoms selected from the group consisting of oxygen, sulphur and nitrogen, —NH-lower alkyl, —N(lower alkyl)$_2$, cyclic amide, —C(O)-cyclic amide, S-lower alkyl, —S(O)$_2$-lower alkyl, lower alkyl substituted by halogen, lower alkoxy substituted by halogen, lower alkyl substituted by hydroxy, —O—(CH$_2$)$_y$-lower alkoxy, —O(CH$_2$)$_y$C(O)N(lower alkyl)$_2$, —C(O)-lower alkyl, —O—(CH$_2$)$_x$-aryl, —O—(CH$_2$)$_x$-cycloalkyl, —O—(CH$_2$)$_x$-heterocycloalkyl, —C(O)O- lower alkyl, —C(O)—NH-lower alkyl, —C(O)—N(lower alkyl)$_2$, 2-oxy-5-aza-bicyclo[2.2.1]hept-5-yl or 3-oxa-8-aza-bicyclo[3.2.1]oct-8-yl;

R and R' are each independently hydrogen or lower alkyl;

wherein heteroaryl is selected from the group consisting of furanyl, thienyl, pyrrolyl, imidazolyl, pyrazolyl, triazolyl, thiazolyl, isothiazolyl, isoxazolyl, pyridinyl, pyrazinyl, and pyrimidinyl; and heterocycloalkyl is selected from the group consisting of tetrahydropyran-2, 3 or 4-yl, tetrahydrofuran-2 or 3-yl, oxetan-3-yl, and [1,4]dioxin-2-yl;

and wherein all aryl-, morpholin, heterocycloalkyl- or 5 or 6 membered heteroaryl groups as defined for $R^1$, $R^{1'}$, $R^{1'''}$ and $R^4$ are unsubstituted or substituted by one or more substituents selected from the group consisting of hydroxy, =O, halogen, lower alkyl, phenyl, lower alkyl substituted by halogen and lower alkoxy;

m is 1 or 2;

x is 0, 1 or 2; and y is 1 or 2;

or a pharmaceutically acceptable acid addition salt thereof.

3. A compound of claim 2, selected from the group consisting of (2-cyclobutylmethoxy-5-methanesulfonyl-phenyl)-(3-trifluoromethyl-5,7-dihydro-pyrrolo[3,4-b]pyridin-6-yl)-methanone, (2-isobutoxy-5-methanesulfonyl-phenyl)-(3-trifluoromethyl-5,7-dihydro-pyrrolo[3,4-b]pyridin-6-yl)-methanone,

[5-methanesulfonyl-2-((R)-2,2,2-trifluoro-1-methyl-ethoxy)-phenyl]-(3-trifluoromethyl-5,7-dihydro-pyrrolo[3,4-b]pyridin-6-yl)-methanone, (4'-fluoro-4-methanesulfonyl-biphenyl-2-yl)-(3-trifluoromethyl-5,7-dihydro-pyrrolo[3,4-b]pyridin-6-yl)-methanone, (3',4'-difluoro-4-methanesulfonyl-biphenyl-2-yl)-(3-trifluoromethyl-5,7-dihydro-pyrrolo[3,4-b]pyridin-6-yl)-methanone,

[5-methanesulfonyl-2-(2,2,3,3,3-pentafluoro-propoxy)-phenyl]-(3-trifluoromethyl-5,7-dihydro-pyrrolo [3,4-b]pyridin-6-yl)-methanone,

[5-methanesulfonyl-2-(2,2,3,3-tetrafluoro-propoxy)-phenyl]-(3-trifluoromethyl-5,7-dihydro-pyrrolo [3,4-b]pyridin-6-yl)-methanone,

[5-methanesulfonyl-2-((S)-2,2,2-trifluoro-1-methyl-ethoxy)-phenyl]-(2-methyl-3-trifluoromethyl-5,7-dihydro-pyrrolo[3,4-b]pyridin-6-yl)-methanone,

[3-(4-fluoro-phenyl)-5,7-dihydro-pyrrolo[3,4-b]pyridin-6-yl]-[5-methanesulfonyl-2-((S)-2,2,2-trifluoro-1-methyl-ethoxy)-phenyl]-methanone,

[5-methanesulfonyl-2-((S)-2,2,2-trifluoro-1-methyl-ethoxy)-phenyl]-(3-trifluoromethyl-5,7-dihydro-pyrrolo[3,4-b]pyridin-6-yl)-methanone and

[2-(4-fluoro-phenyl)-5,7-dihydro-pyrrolo[3,4-b]pyridin-6-yl]-[5-methanesulfonyl-2-((S)-2,2,2-trifluoro-1-methyl-ethoxy)-phenyl]-methanone.

4. A compound of claim 1, having formula IC

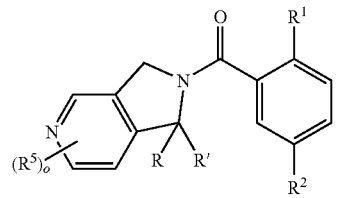

IC wherein $R^1$ is halogen, —$OR^{1'}$, —$SR^{1'''}$, morpholin, heterocycloalkyl, aryl or 5- or 6-membered heteroaryl;

$R^{1'}$ and $R^{1'''}$ are each independently hydrogen, lower alkyl, lower alkyl substituted by halogen, —(CH$_2$)$_x$-cycloalkyl or —(CH$_2$)$_x$-aryl;

$R^2$ is —S(O)$_2$-lower alkyl, —S(O)$_2$NH-lower alkyl, or CN;

and wherein the additional N-ring atom of the bicyclic amine can be available in form of its oxide

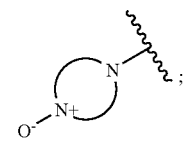

$R^5$ is hydrogen, hydroxy, halogen, =O, lower alkyl, cycloalkyl, heterocycloalkyl, lower alkoxy, CN, NO$_2$, NH$_2$, aryl, 5- or 6-membered heteroaryl containing one, two or three heteroatoms selected from the group consisting of oxygen, sulphur and nitrogen, —NH-lower alkyl, —N(lower alkyl)$_2$, cyclic amide, —C(O)-cyclic amide, S-lower alkyl, —S(O)$_2$-lower alkyl, lower alkyl substituted by halogen, lower alkoxy substituted by halogen, lower alkyl substituted by hydroxy, —O—(CH$_2$)$_y$-lower alkoxy, —O(CH$_2$)$_y$C(O)N(lower alkyl)$_2$, —C(O)-lower alkyl, —O—(CH$_2$)$_x$-aryl, —O—(CH$_2$)$_x$-cycloalkyl, —O—(CH$_2$)$_x$-heterocycloalkyl, —C(O)O-lower alkyl, —C(O)—NH-lower alkyl, —C(O)—N(lower alkyl)$_2$, 2-oxy-5-aza-bicyclo[2.2.1]hept-5-yl or 3-oxa-8-aza-bicyclo[3.2.1]oct-8-yl;

R and R' are each independently hydrogen or lower alkyl;

wherein heteroaryl is selected from the group consisting of furanyl, thienyl, pyrrolyl, imidazolyl, pyrazolyl, triazolyl, thiazolyl, isothiazolyl, isoxazolyl, pyridinyl, pyrazinyl, and pyrimidinyl; and heterocycloalkyl is selected from the group consisting of tetrahydropyran-2, 3 or 4-yl, tetrahydrofuran-2 or 3-yl, oxetan-3-yl, and [1,4]dioxin-2-yl;

and wherein all aryl-, cycloalkyl-, cyclic amide, heterocycloalkyl- or 5 or 6 membered heteroaryl groups as defined for $R^1$, $R^{1'}$, $R^{1'''}$ and $R^5$ are unsubstituted or substituted by one or more substituents selected from the group consisting of hydroxy, =O, halogen, lower alkyl, phenyl, lower alkyl substituted by halogen and lower alkoxy;

o is 1 or 2;

x is 0, 1 or 2; and y is 1 or 2;

or a pharmaceutically acceptable acid addition salt thereof.

5. A compound of claim 4, selected from the group consisting of (2-cyclobutylmethoxy-5-methanesulfonyl-phenyl)-(6-trifluoromethyl-1,3-dihydro-pyrrolo[3,4-c]pyridin-2-yl)-methanone, (4'-fluoro-4-methanesulfonyl-biphenyl-2-yl)-(6-trifluoromethyl-1,3-dihydro-pyrrolo[3,4-c]pyridin-2-yl)-methanone, (3',4'-difluoro-4-methanesulfonyl-biphenyl-2-yl)-(6-trifluoromethyl-1,3-dihydro-pyrrolo[3,4-c]pyridin-2-yl)-methanone,

[5-methanesulfonyl-2-(2,2,3,3,3-pentafluoro-propoxy)-phenyl]-(6-trifluoromethyl-1,3-dihydro-pyrrolo[3,4-c]pyridin-2-yl)-methanone,

[5-methanesulfonyl-2-(2,2,3,3-tetrafluoro-propoxy)-phenyl]-(6-trifluoromethyl-1,3-dihydro-pyrrolo [3,4-c]pyridin-2-yl)-methanone,

[6-(4-fluoro-phenyl)-1,3-dihydro-pyrrolo[3,4-c]pyridin-2-yl]-[5-methanesulfonyl-2-((S)-2,2,2-trifluoro-1-methyl-ethoxy)-phenyl]-methanone and

[5-methanesulfonyl-2-((S)-2,2,2-trifluoro-1-methyl-ethoxy)-phenyl]-(6-morpholin-4-yl-1,3-dihydro-pyrrolo[3,4-c]pyridin-2-yl)-methanone.

6. A pharmaceutical composition comprising a therapeutically effective amount of a compound of formula I

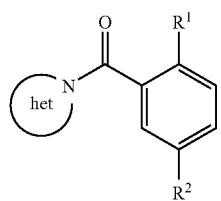

I wherein $R^1$ is halogen, —$OR^{1'}$, —$SR^{1''}$, morpholin, heterocycloalkyl, aryl or 5- or 6-membered heteroaryl;

$R^{1'}$ and $R^{1''}$ are each independently hydrogen, lower alkyl, lower alkyl substituted by halogen, —$(CH_2)_x$-cycloalkyl or —$(CH_2)_x$-aryl;

$R^2$ is —$S(O)_2$-lower alkyl, —$S(O)_2NH$-lower alkyl, or CN;

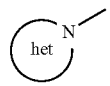

is an aromatic or partially aromatic bicyclic amine, having one or two additional N-atom selected from the group consisting of

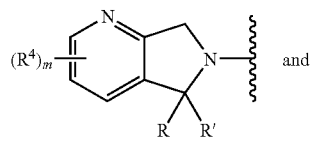
b)

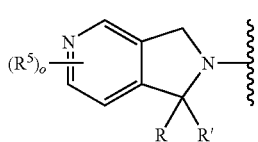
c)

and wherein one additional N-ring atom of the aromatic or partially aromatic bicyclic amine can be available in form of its oxide

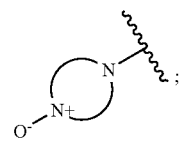

$R^3$ to $R^{10}$ are each independently hydrogen, hydroxy, halogen, =O, lower alkyl, cycloalkyl, heterocycloalkyl, lower alkoxy, CN, $NO_2$, $NH_2$, aryl, 5- or 6-membered heteroaryl containing one, two or three heteroatoms selected from the group consisting of oxygen, sulphur and nitrogen, —NH-lower alkyl, —N(lower alkyl)$_2$, cyclic amide, —C(O)-cyclic amide, S-lower alkyl, —$S(O)_2$-lower alkyl, lower alkyl substituted by halogen, lower alkoxy substituted by halogen, lower alkyl substituted by hydroxy, —O—$(CH_2)_y$-lower alkoxy, —$O(CH_2)_yC(O)N$(lower alkyl)$_2$, —C(O)-lower alkyl, —O—$(CH_2)_x$-aryl, —O—$(CH_2)_x$-cycloalkyl, —O—$(CH_2)_x$-heterocycloalkyl, —C(O)O-lower alkyl, —C(O)—NH-lower alkyl, —C(O)—N(lower alkyl)$_2$, 2-oxy-5-aza-bicyclo[2.2.1]hept-5-yl or 3-oxa-8-aza-bicyclo[3.2.1]oct-8-yl;

R, R', are each independently hydrogen or lower alkyl;

wherein heteroaryl is selected from the group consisting of furanyl, thienyl, pyrrolyl, imidazolyl, pyrazolyl, triazolyl, thiazolyl, isothiazolyl, isoxazolyl, pyridinyl, pyrazinyl, and pyrimidinyl; and heterocycloalkyl is selected from the group consisting of tetrahydropyran-2, 3 or 4-yl, tetrahydrofuran-2 or 3-yl, oxetan-3-yl, and [1,4]dioxin-2-yl;

and wherein all aryl-, morpholin, heterocycloalkyl- or 5 or 6 membered heteroaryl groups as defined for $R^1$, $R^{1'}$, $R^{1''}$ and $R^3$ to $R^{10}$ are unsubstituted or substituted by one or more substituents selected from the group consisting of hydroxy, =O, halogen, lower alkyl, phenyl, lower alkyl substituted by halogen and lower alkoxy;

n, m, o, p, q, r, s and t are each independently 1 or 2;

x is 0, 1 or 2; and y is 1 or 2;

or a pharmaceutically acceptable acid addition salt thereof and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,557,114 B2 | Page 1 of 1 |
| APPLICATION NO. | : 11/343365 | |
| DATED | : July 7, 2009 | |
| INVENTOR(S) | : Jolidon et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 236 days.

Signed and Sealed this
Third Day of May, 2011

David J. Kappos
*Director of the United States Patent and Trademark Office*